(12) United States Patent
Kasher et al.

(10) Patent No.: US 11,819,411 B2
(45) Date of Patent: Nov. 21, 2023

(54) ANNULOPLASTY AND TISSUE ANCHOR TECHNOLOGIES

(71) Applicant: Edwards Lifesciences Innovation (Israel) Ltd., Caesarea (IL)

(72) Inventors: Yuval Kasher, Kfar Shmuel (IL); Tomer Shoham, Kibbutz Einat (IL); Or Cohen, Modi'in (IL); Tal Benshahar, Mazkeret Batya (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 207 days.

(21) Appl. No.: 17/145,258

(22) Filed: Jan. 8, 2021

(65) Prior Publication Data

US 2021/0145584 A1    May 20, 2021

Related U.S. Application Data

(63) Continuation of application No. PCT/IB2020/060044, filed on Oct. 27, 2020.
(Continued)

(51) Int. Cl.
*A61F 2/24* (2006.01)
*A61B 17/04* (2006.01)

(52) U.S. Cl.
CPC ........ *A61F 2/2466* (2013.01); *A61B 17/0469* (2013.01); *A61F 2/2445* (2013.01);
(Continued)

(58) Field of Classification Search
CPC .................. A61F 2/2466; A61F 2/2445; A61F 2220/0016; A61F 2230/0091;
(Continued)

(56) References Cited

U.S. PATENT DOCUMENTS 3,604,488 A    9/1971  Wishart et al.
3,656,185 A    4/1972  Carpentier
(Continued)

FOREIGN PATENT DOCUMENTS

CN    113331995 A    9/2021
EP    1034753 A1    9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Keri J Nelson
*Assistant Examiner* — Rebecca Lynee Zimmerman
(74) *Attorney, Agent, or Firm* — Anya Adams

(57) ABSTRACT

Apparatus comprising a tissue anchor for use with an anchor driver. The anchor comprises a head, and a tissue-engaging element coupled to a proximal end of the head. The tissue-engaging element defines a central longitudinal axis of the anchor, and has a sharpened distal tip, configured to be driven into tissue of a subject. The head comprises a driver interface, configured to be reversibly engaged by the anchor driver, and an eyelet, disposed laterally from the central longitudinal axis, defining an aperture on an aperture plane, the aperture having a length along a long axis of the aperture and a width along a short axis of the aperture, the long axis and the short axis disposed on the aperture plane. The eyelet is mounted such that the aperture plane is slanted at a fixed angle with respect to the central longitudinal axis. Other applications are also described.

32 Claims, 75 Drawing Sheets

Related U.S. Application Data

(60) Provisional application No. 62/949,392, filed on Dec. 17, 2019, provisional application No. 62/927,624, filed on Oct. 29, 2019.

(52) U.S. Cl.
CPC ............... *A61B 2017/0409* (2013.01); *A61B 2017/0441* (2013.01); *A61F 2220/0016* (2013.01); *A61F 2230/0091* (2013.01)

(58) Field of Classification Search
CPC ............ A61F 2/2418; A61F 2220/0091; A61F 2/2442; A61B 17/0469; A61B 2017/0409; A61B 2017/0441; A61B 17/0487; A61B 17/0467; A61B 17/0482; A61B 17/07292; A61B 17/50; A61B 2017/00911; A61B 2017/0406; A61B 2017/0414; A61B 2017/0488; A61B 2017/0496; A61B 2090/061; A61B 2090/065; A61B 2090/08021; A61B 2090/0807; A61B 17/0401; A61B 2090/3966; A61B 90/06; A61B 90/08; A61B 90/39

See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup III |
| 5,601,572 A | 2/1997 | Middleman et al. |
| 5,626,609 A | 5/1997 | Zvenyatsky et al. |
| 5,626,613 A | 5/1997 | Schmieding |
| 5,643,317 A | 7/1997 | Pavonik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser |
| 6,626,917 B1 | 9/2003 | Craig |
| 6,626,930 B1 | 9/2003 | Allen et al. |

(56) References Cited

U.S. PATENT DOCUMENTS

| | | |
|---|---|---|
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoen et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |

(56) References Cited

U.S. PATENT DOCUMENTS

| | | |
|---|---|---|
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,853,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,343 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |

(56) References Cited

U.S. PATENT DOCUMENTS

| | | |
|---|---|---|
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |

(56) References Cited

U.S. PATENT DOCUMENTS

| | | |
|---|---|---|
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0094355 A1* | 4/2010 | Trenhaile ............ A61B 17/0401 606/232 |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0245632 A1 | 9/2012 | Tsai et al. |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |

(56) References Cited

U.S. PATENT DOCUMENTS

| | | |
|---|---|---|
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1* | 5/2014 | Gross .................. A61F 2/2466 623/2.37 |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0151054 A1 | 6/2017 | Stone et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |

(56) References Cited

FOREIGN PATENT DOCUMENTS

| WO | 2022101817 A2 | 5/2022 |
|---|---|---|
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon 36.06 (1988): 313-319.
Ahmadi, Ali et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum p. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology 52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischernic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results 04yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

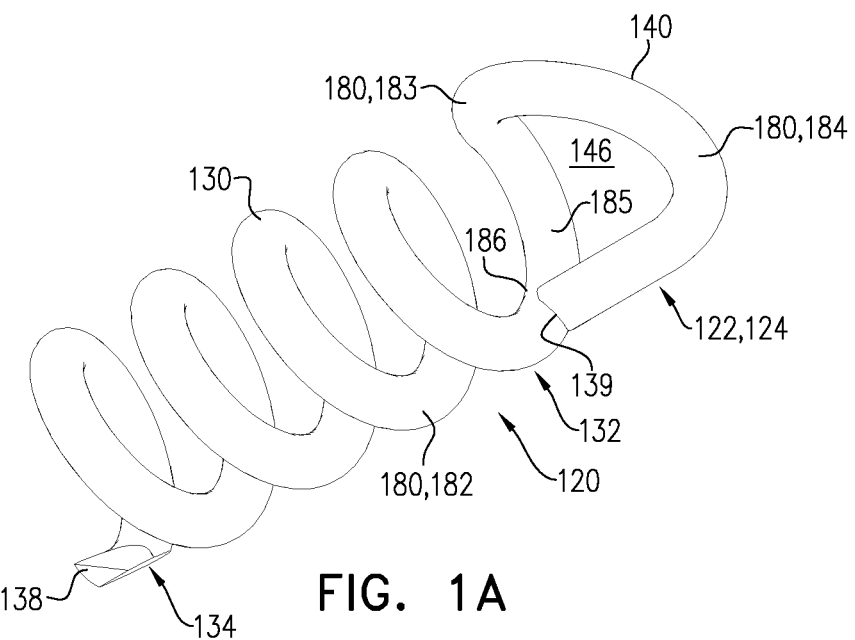
FIG. 1A
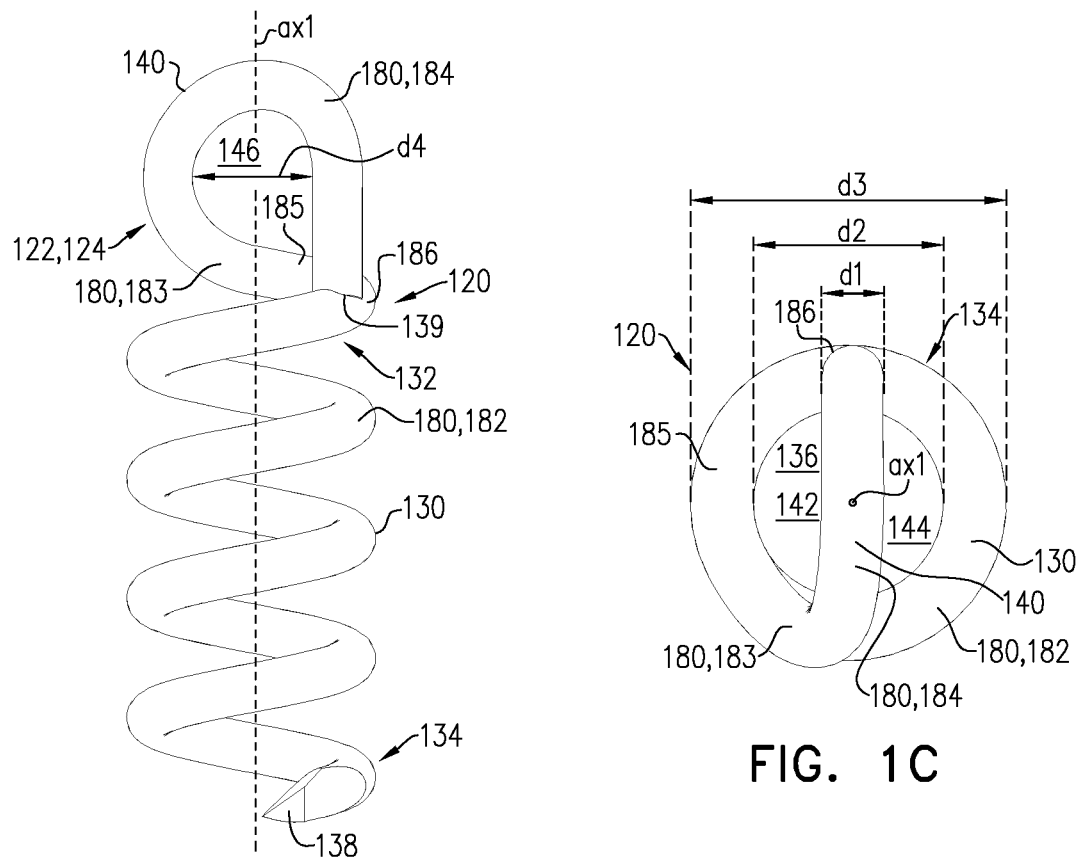
FIG. 1B
FIG. 1C

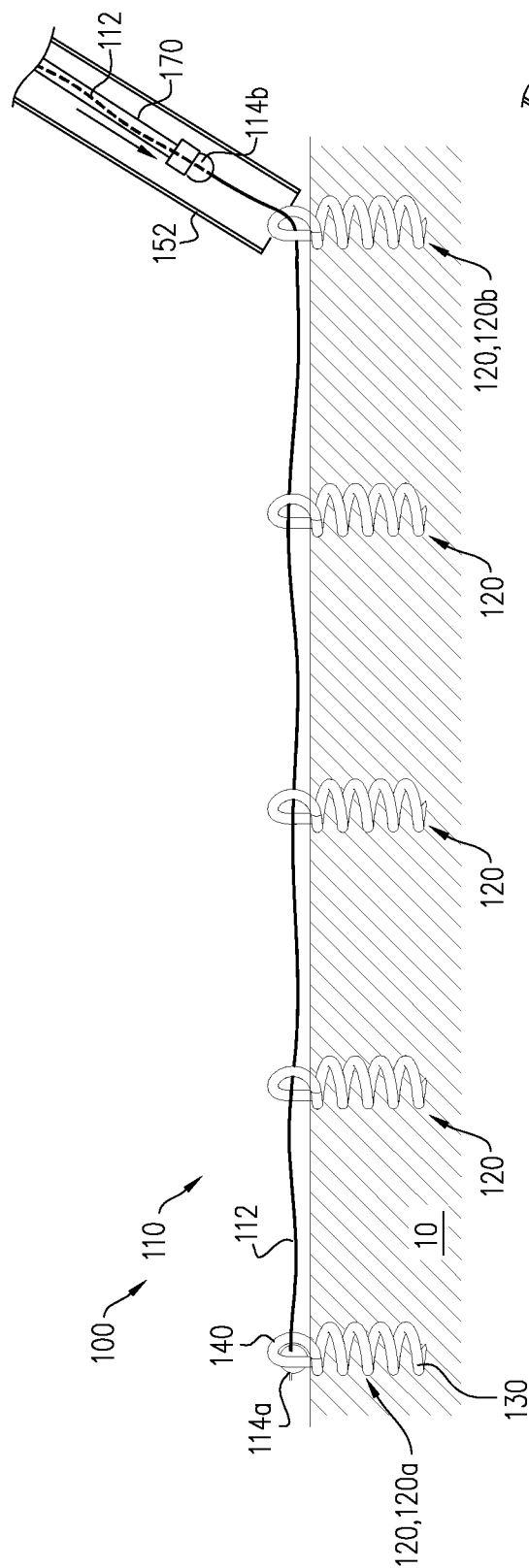
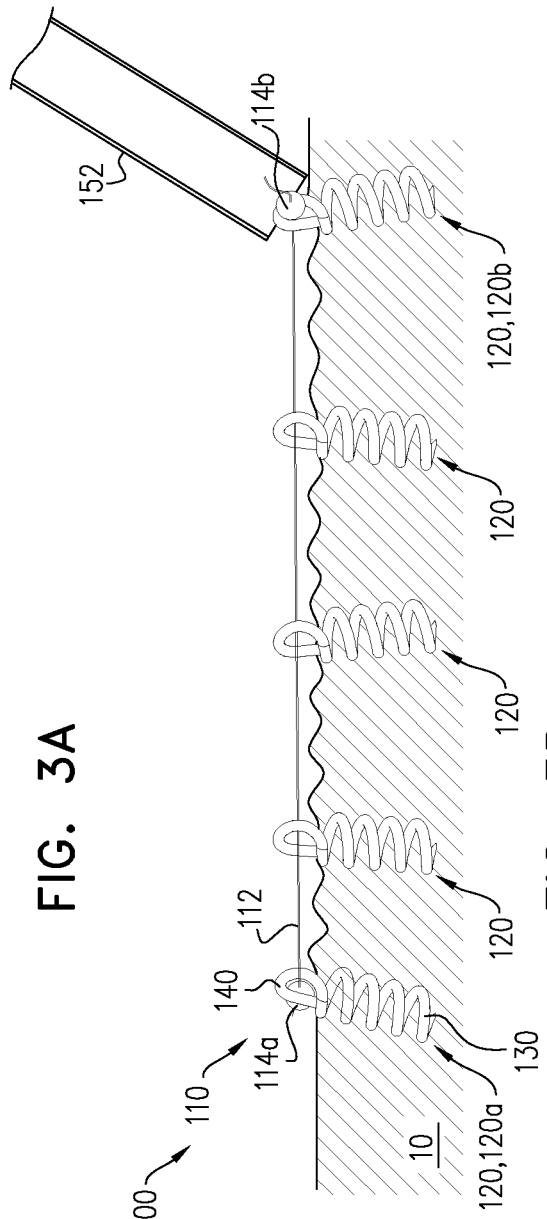

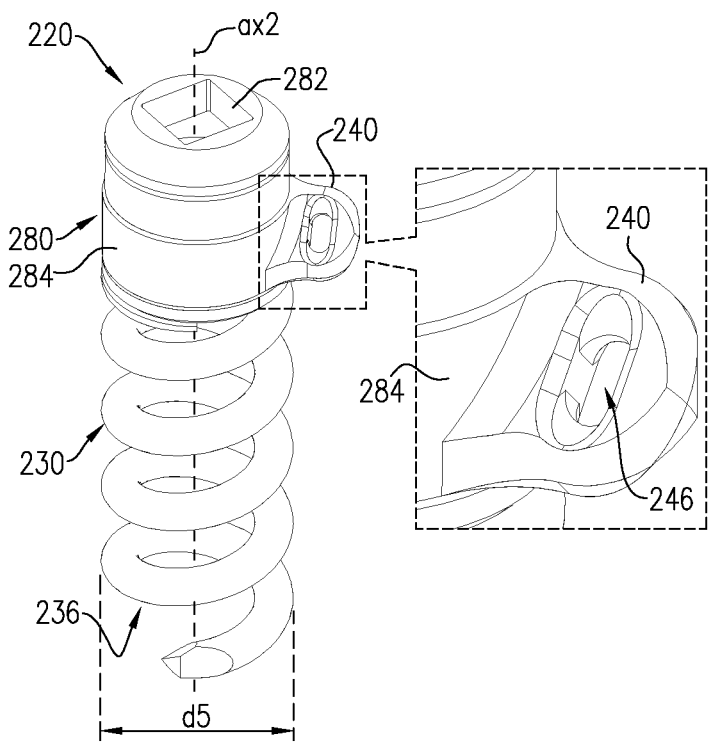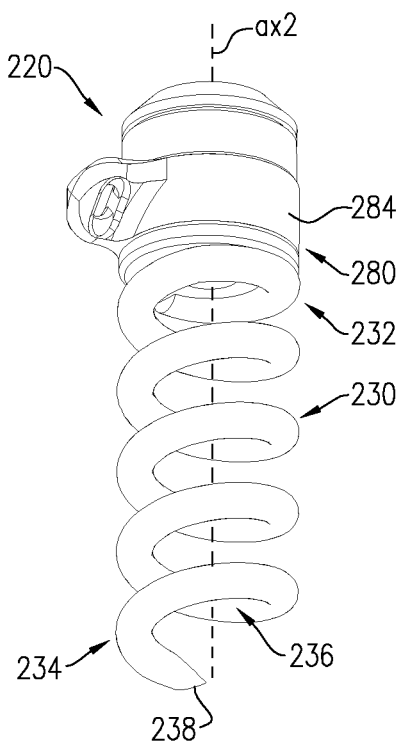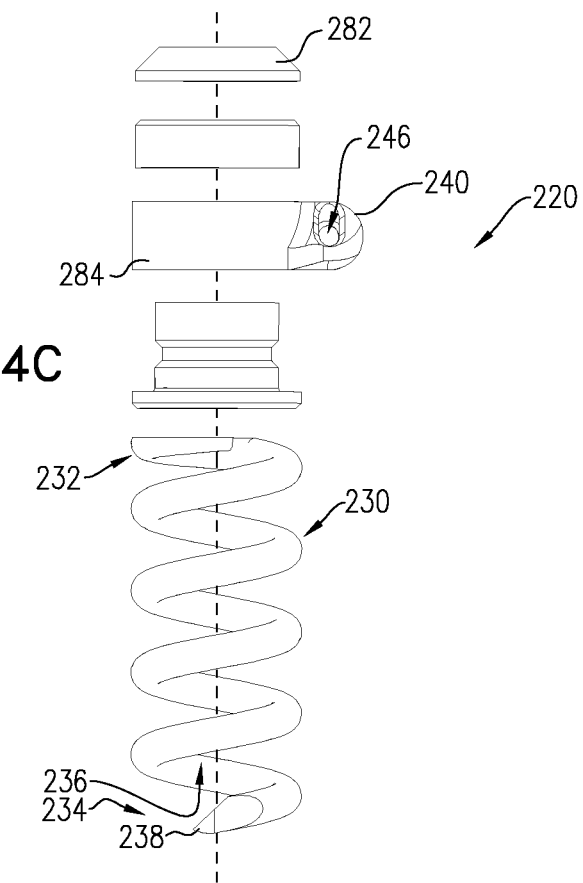
FIG. 4A
FIG. 4B
FIG. 4C

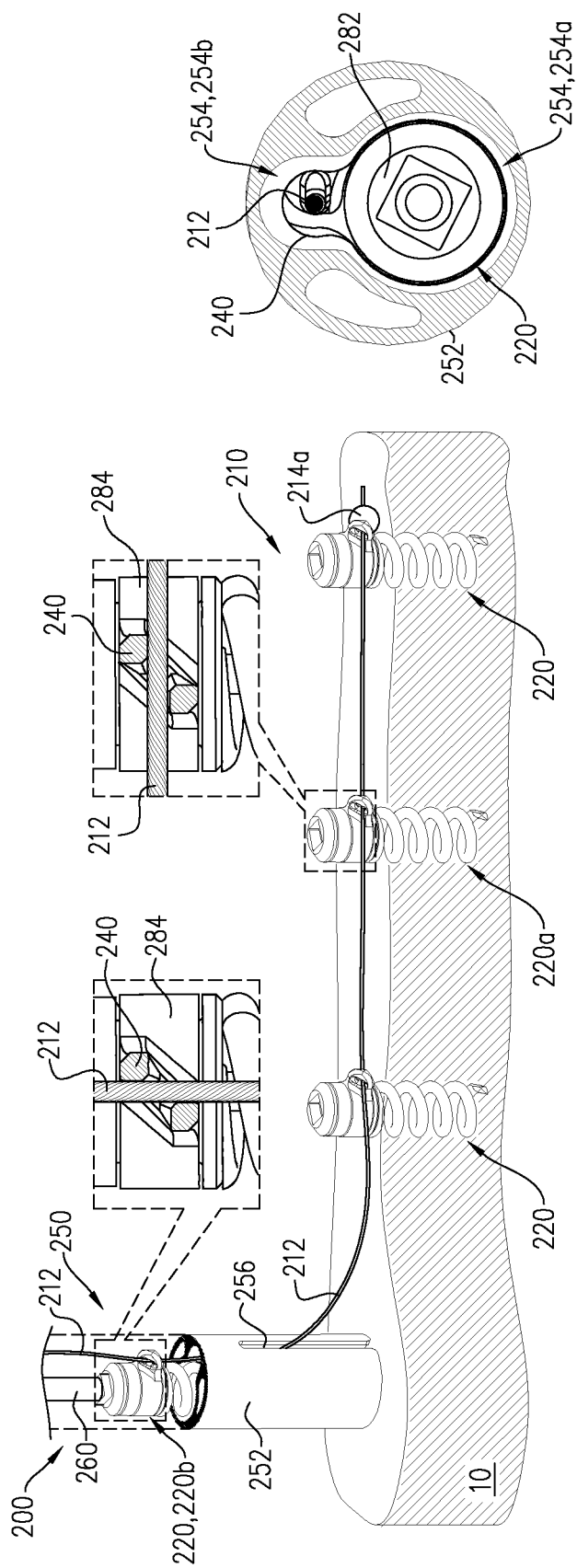
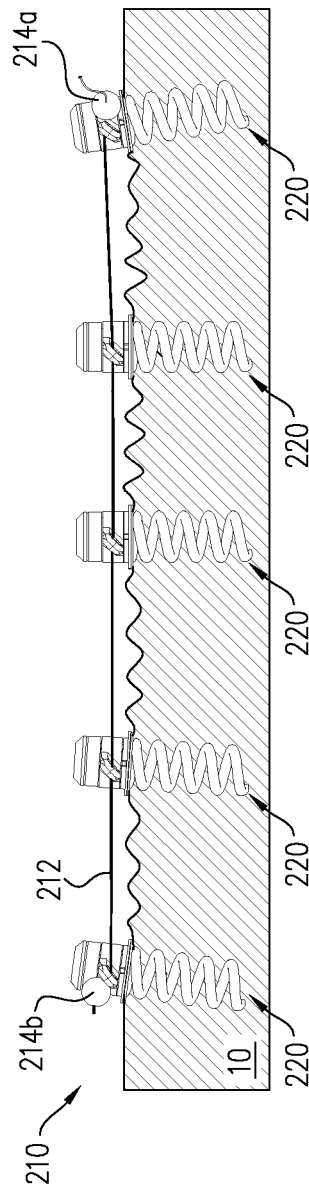
FIG. 5A
FIG. 5B
FIG. 5C

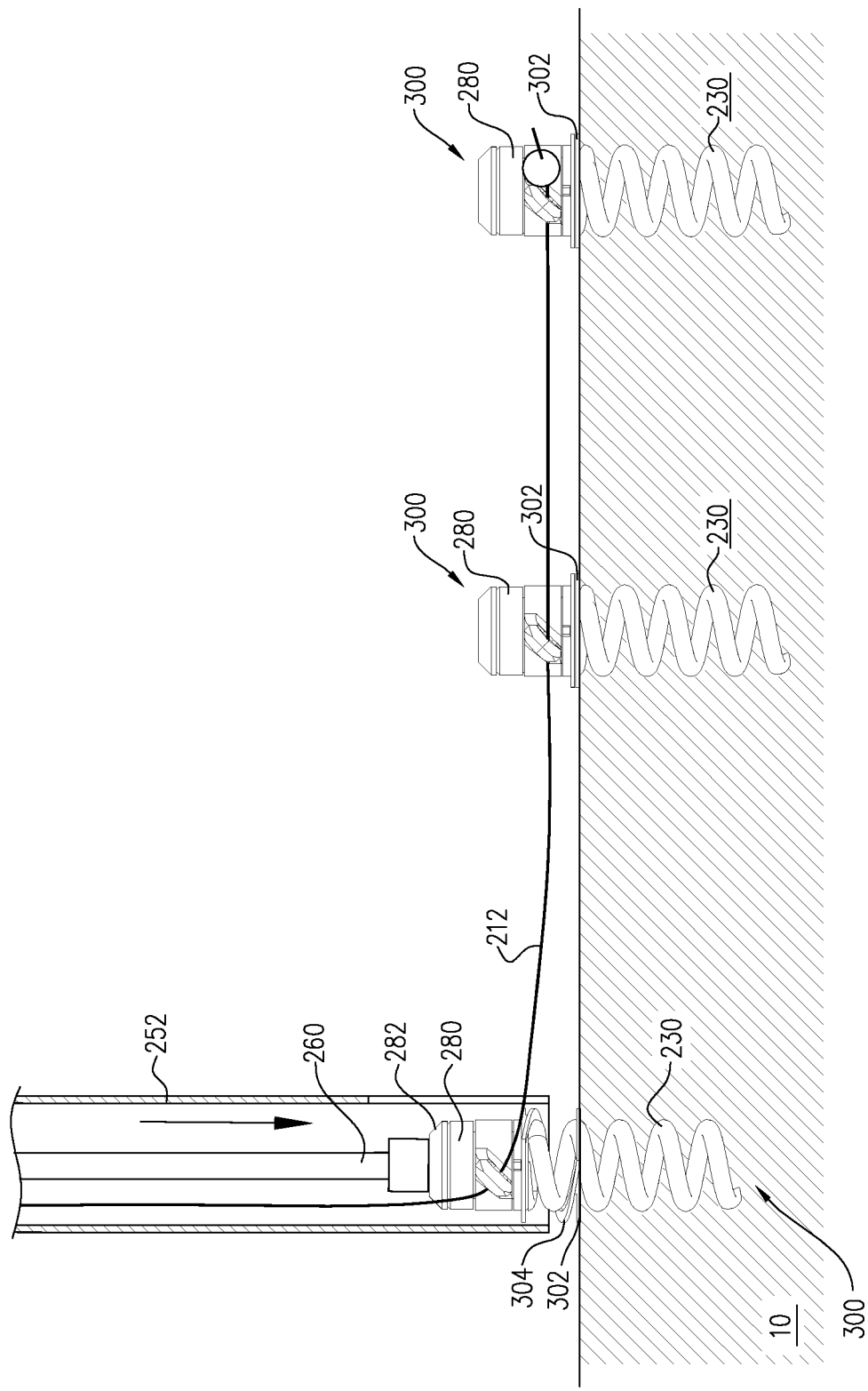

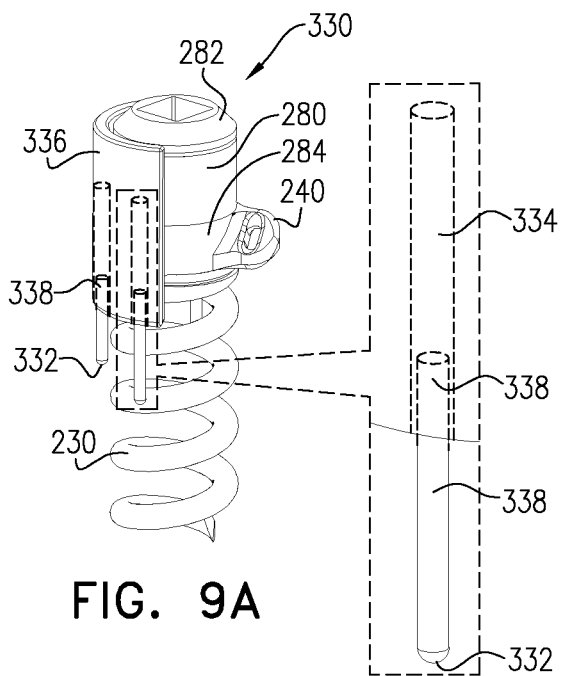
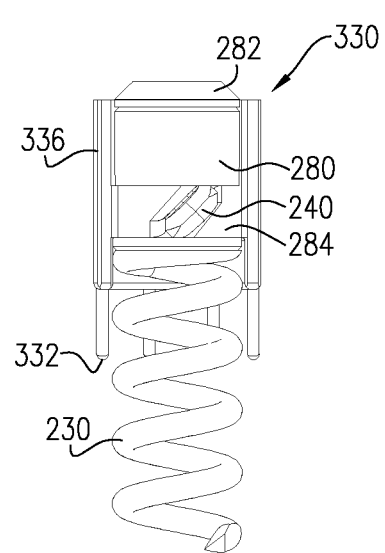
FIG. 9A
FIG. 9B
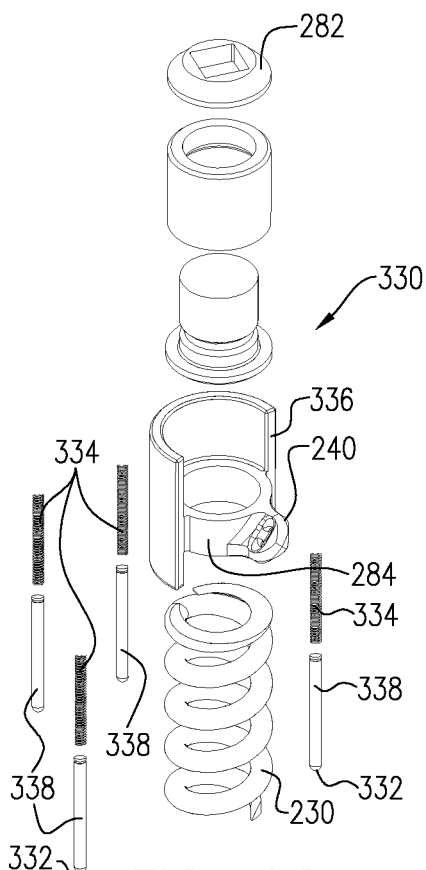
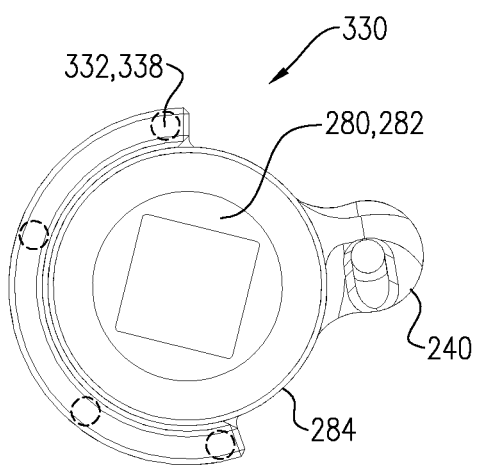
FIG. 9C
FIG. 9D

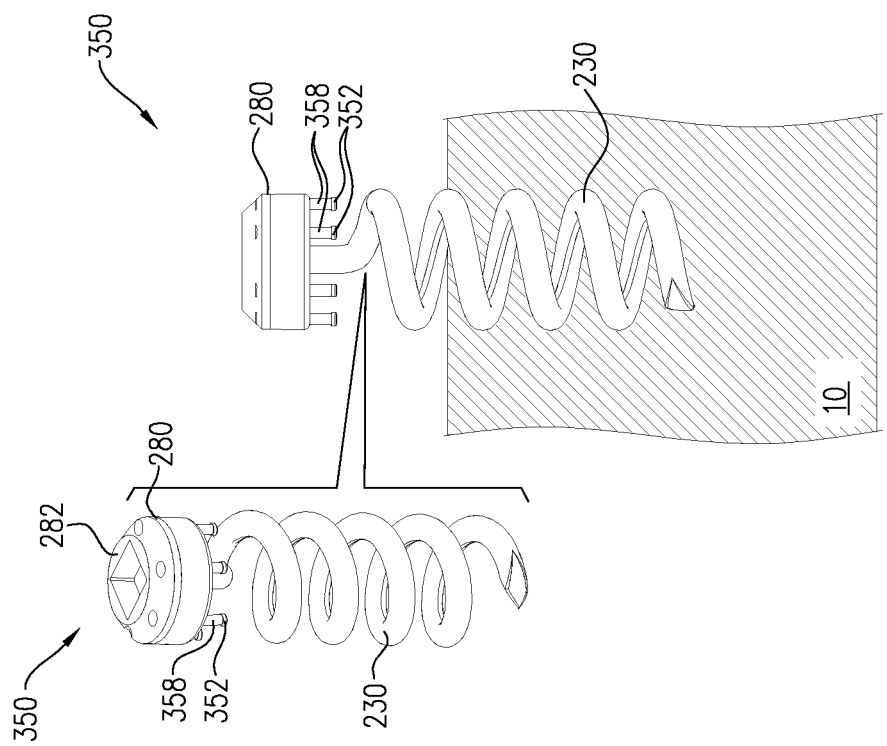
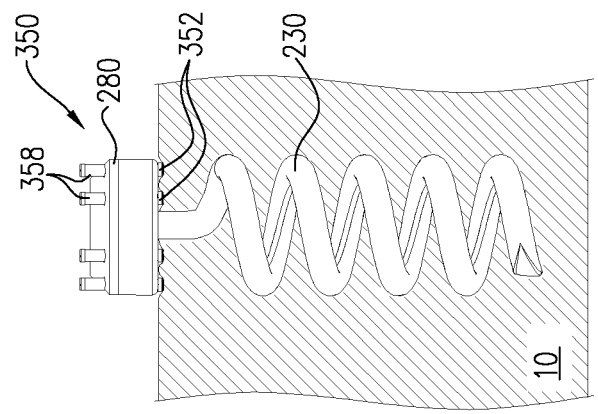
FIG. 11A
FIG. 11B

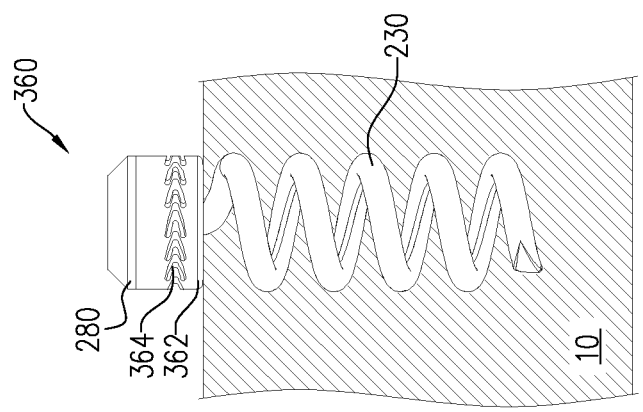
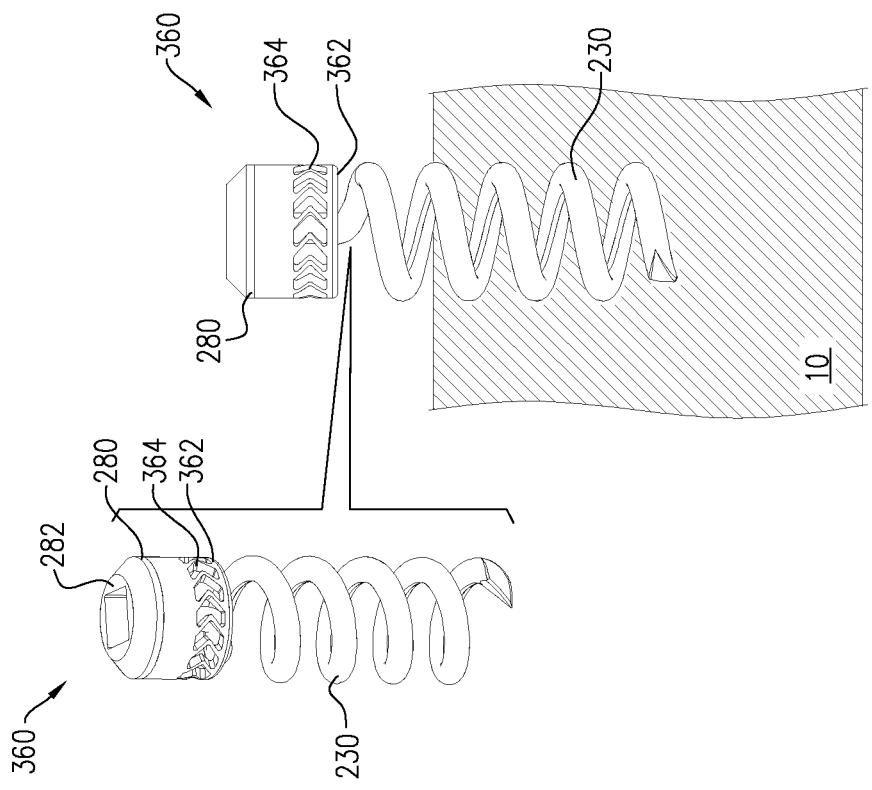
FIG. 12A
FIG. 12B

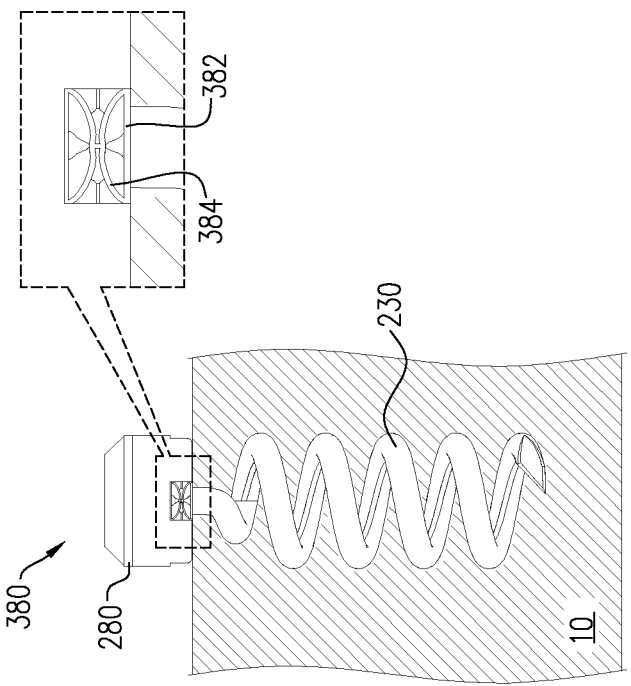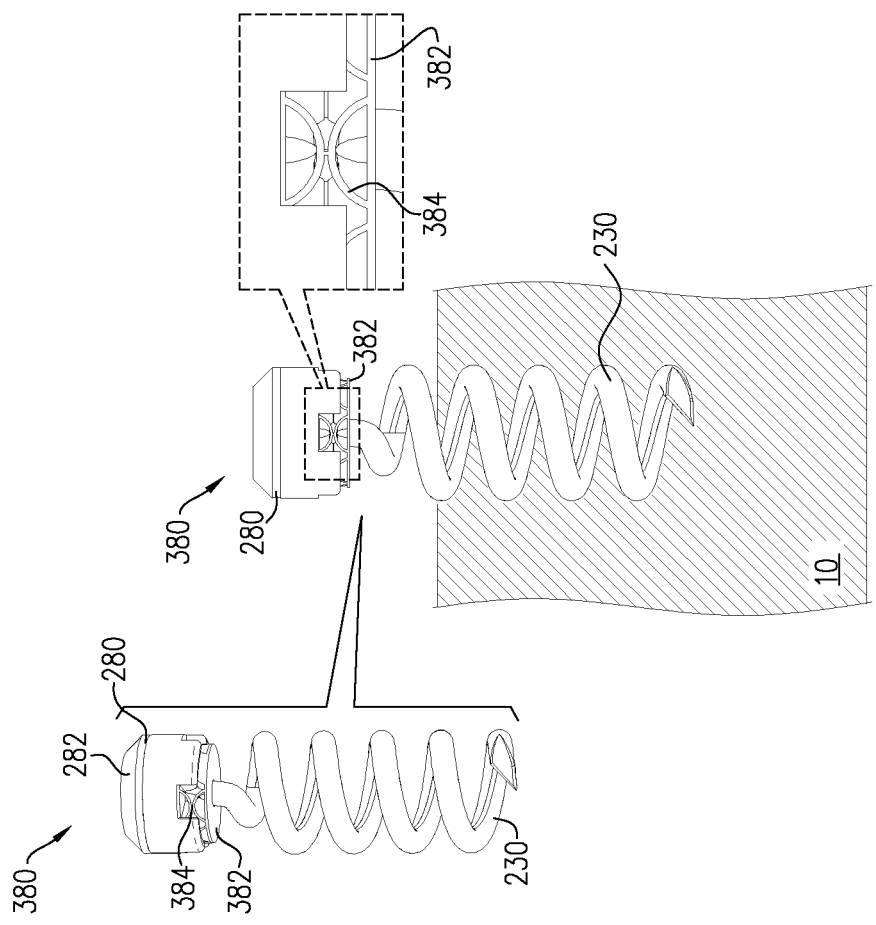
FIG. 14B
FIG. 14A

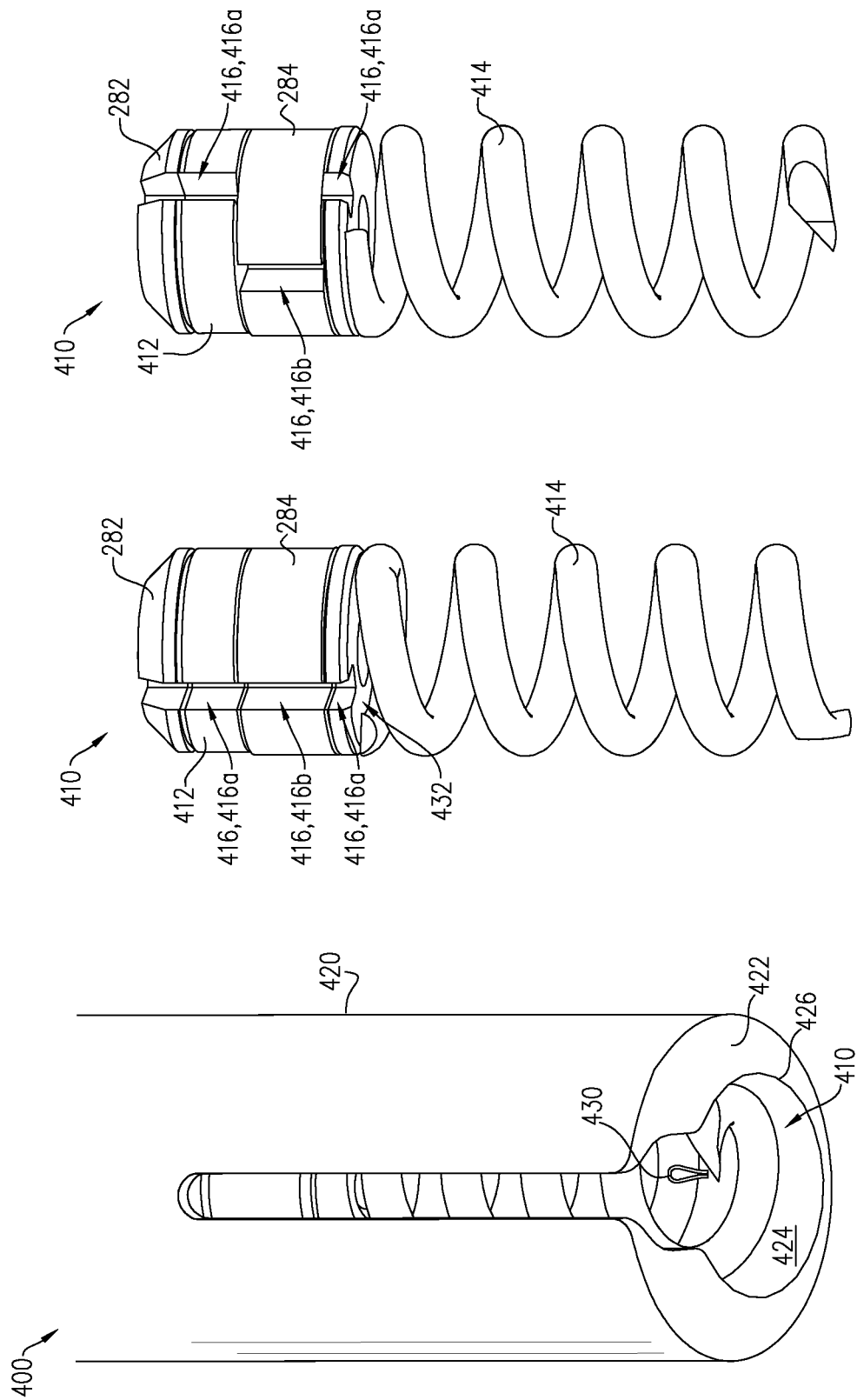

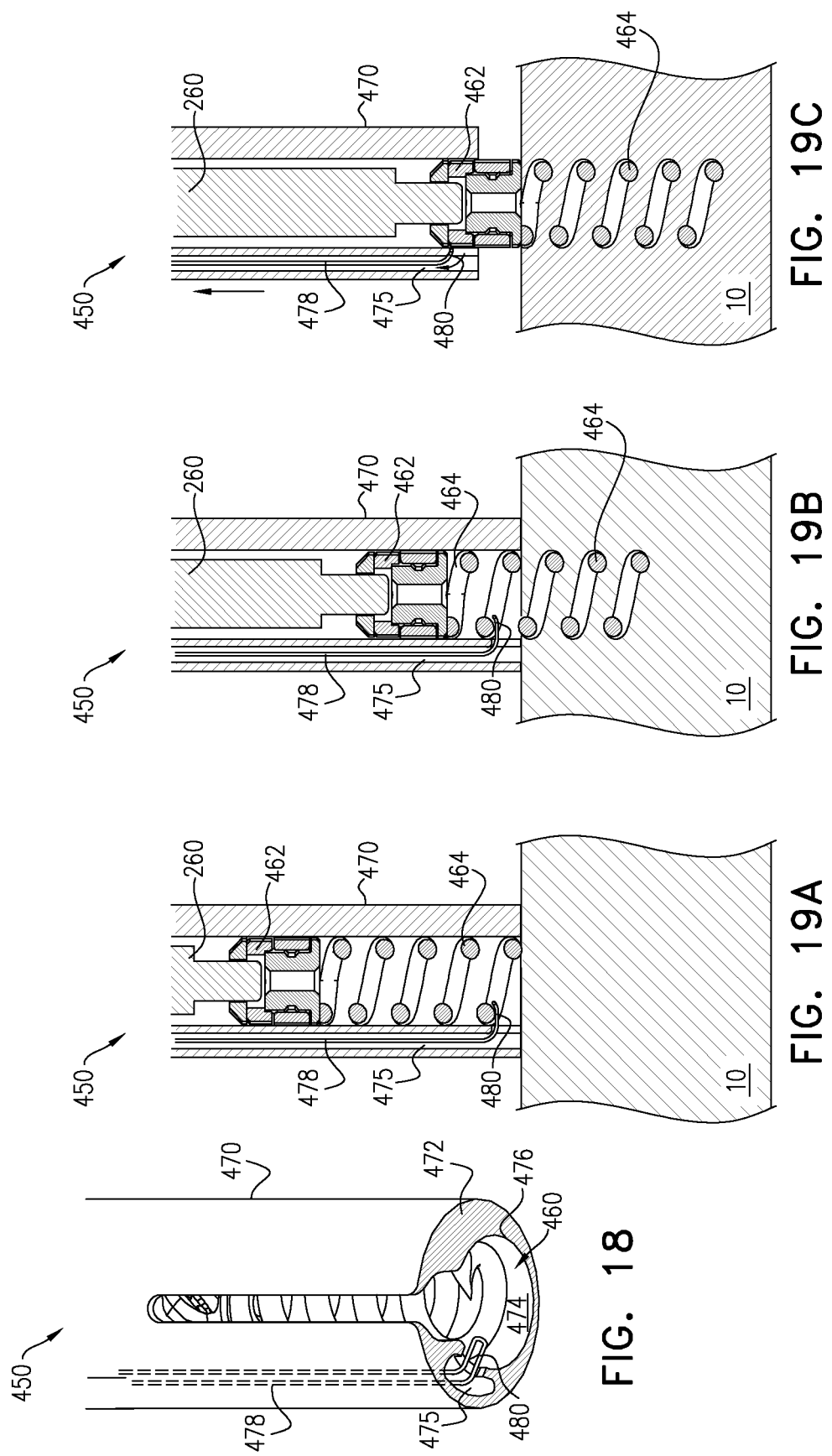

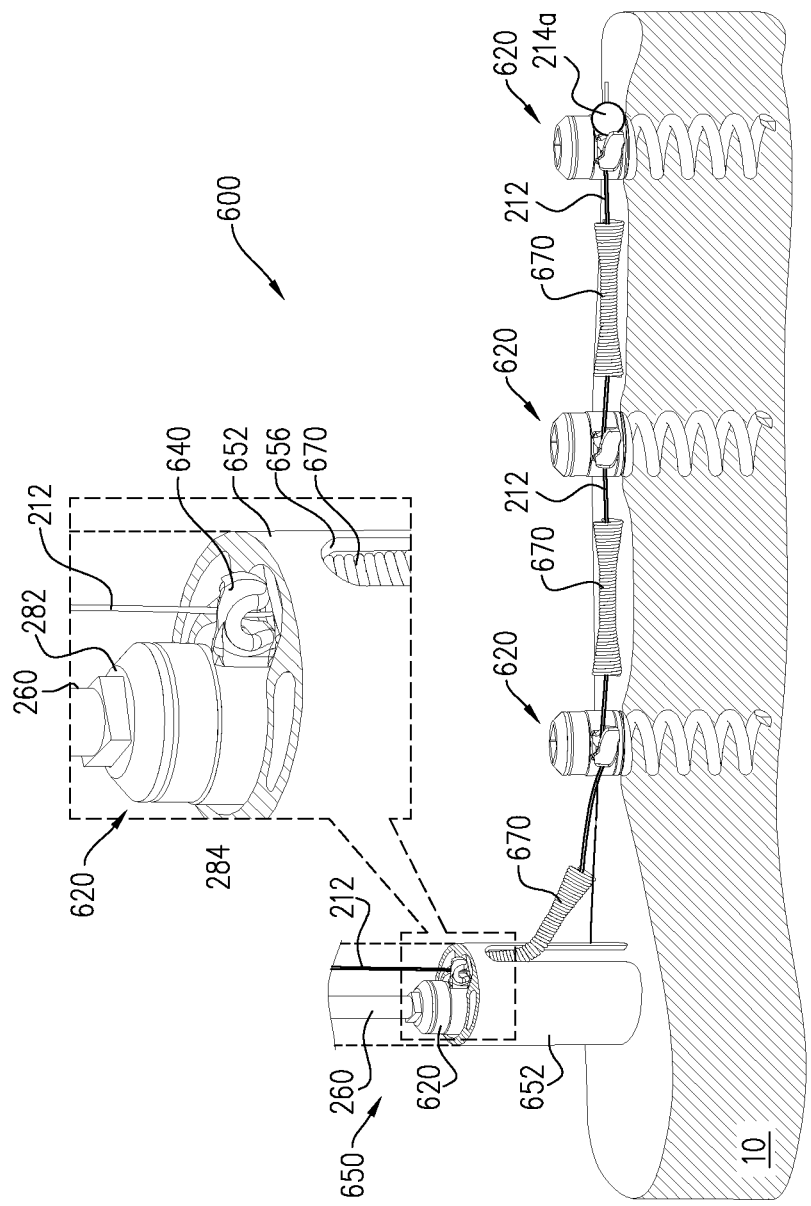
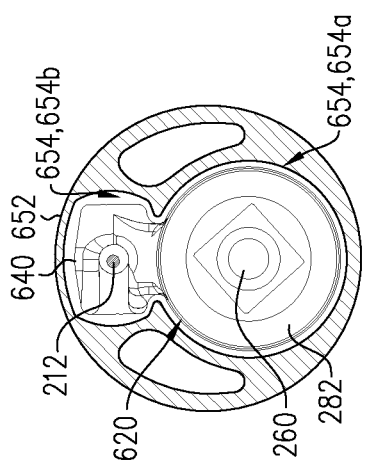
FIG. 22B
FIG. 22A

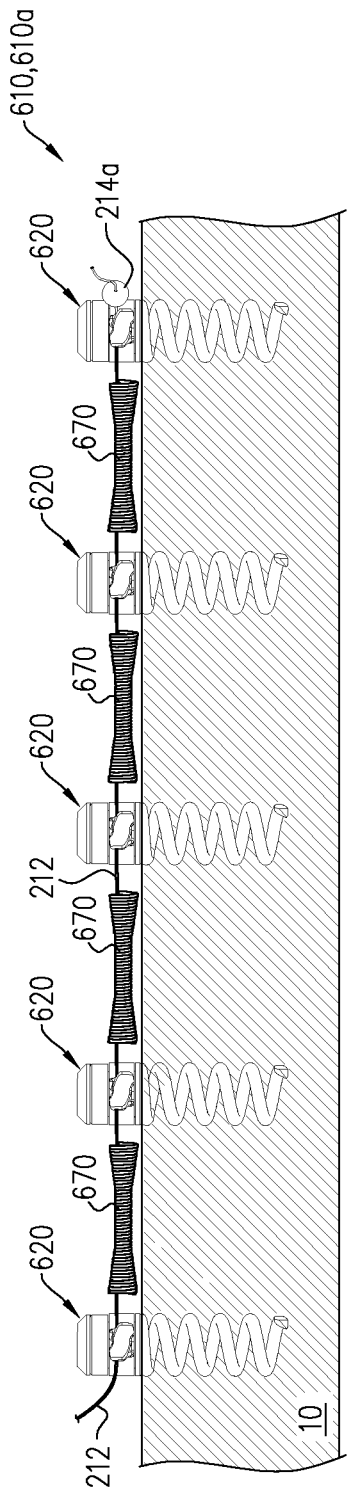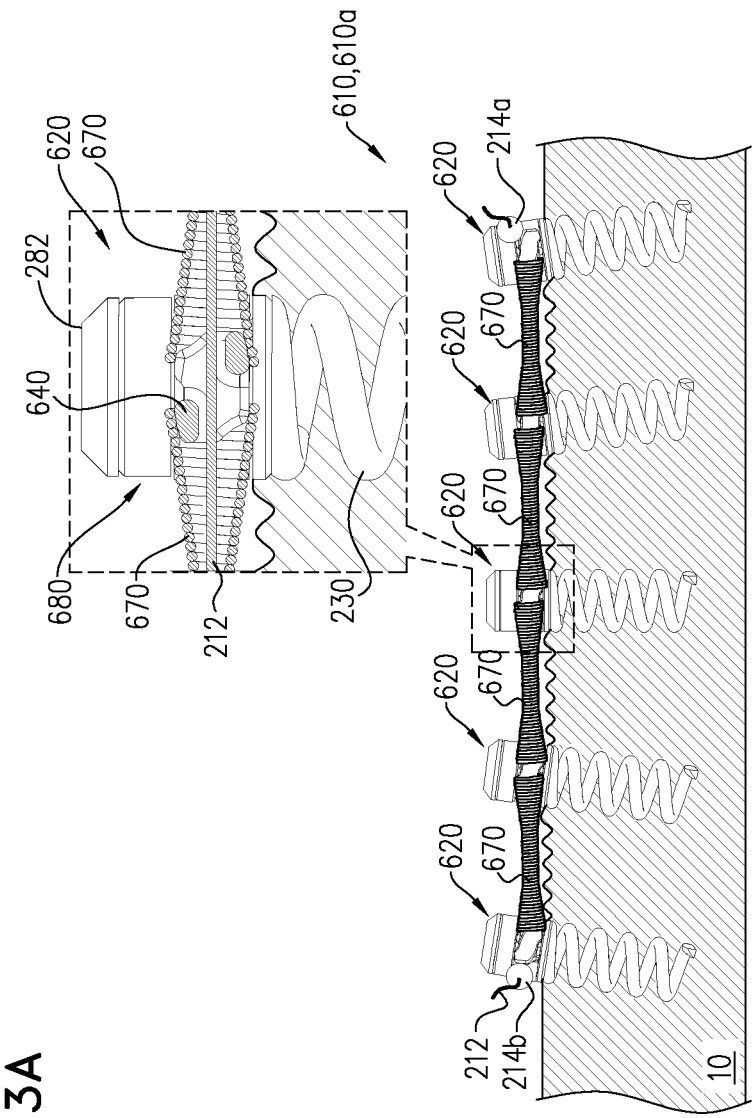
FIG. 23A
FIG. 23B

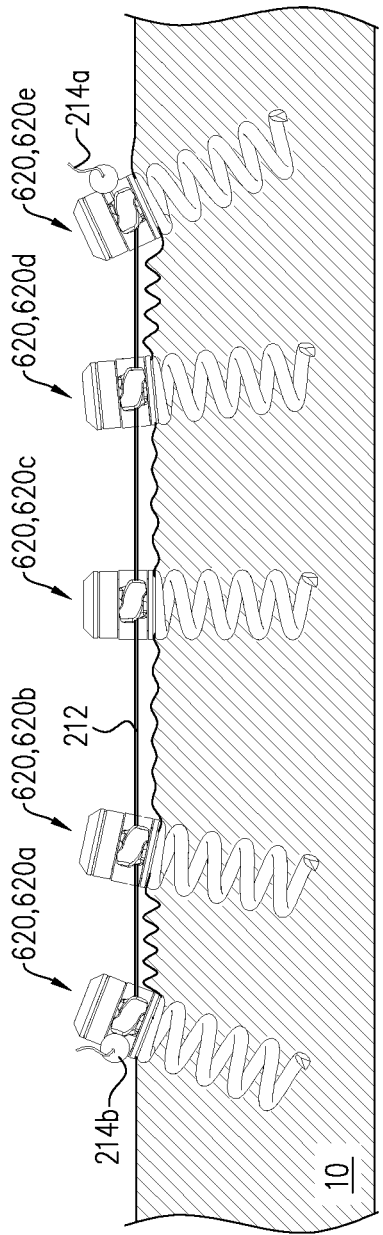
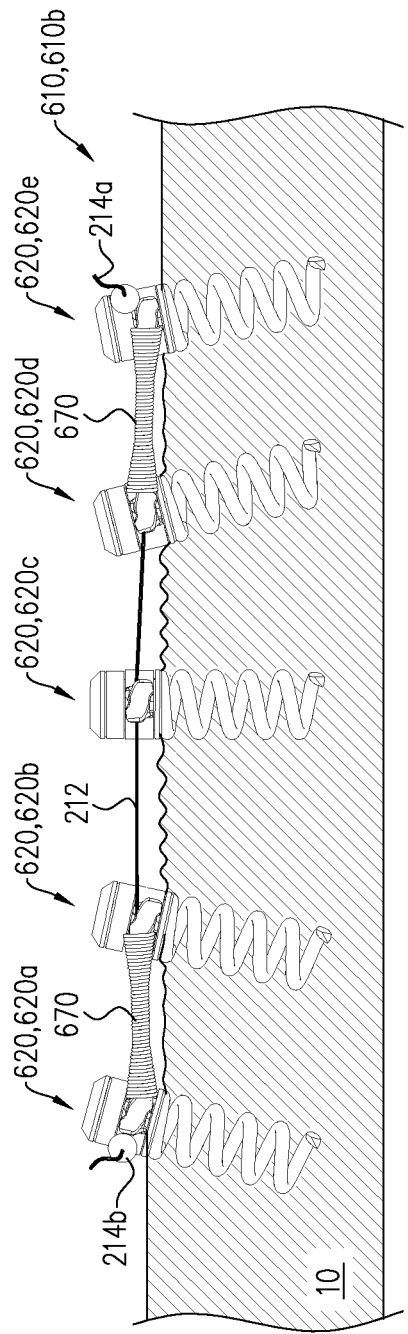
FIG. 24
FIG. 25

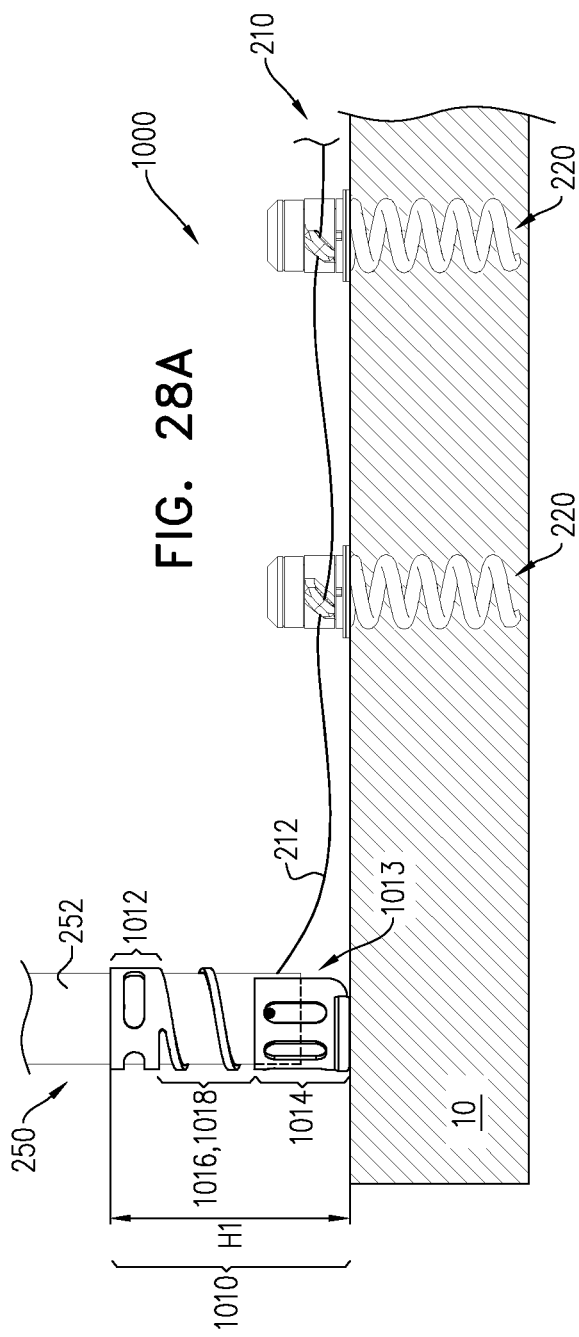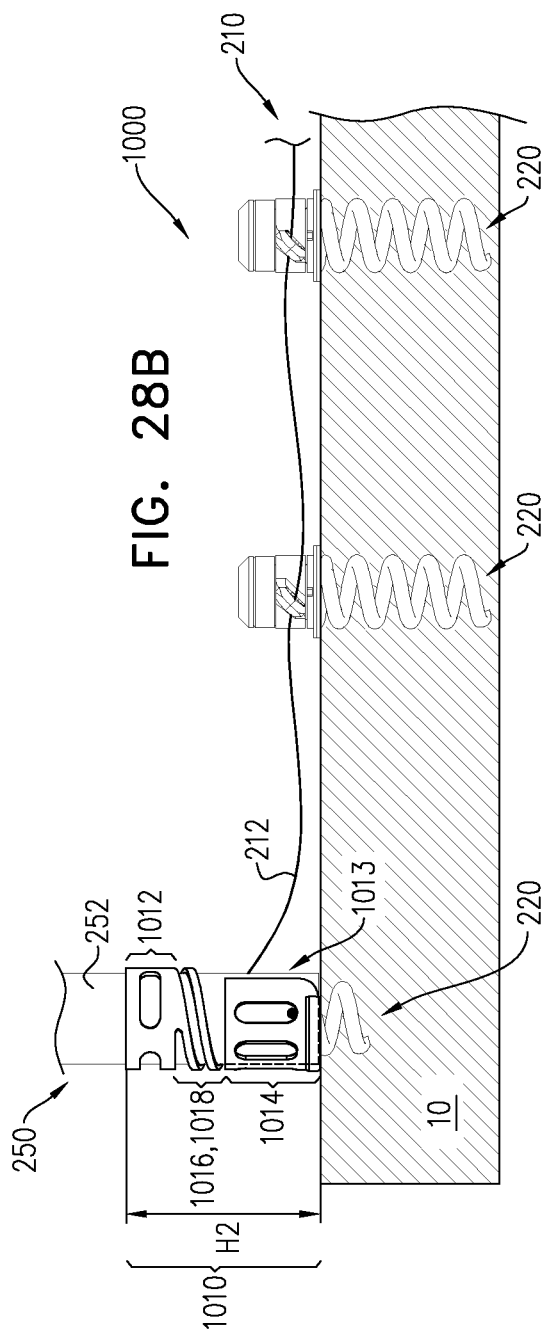

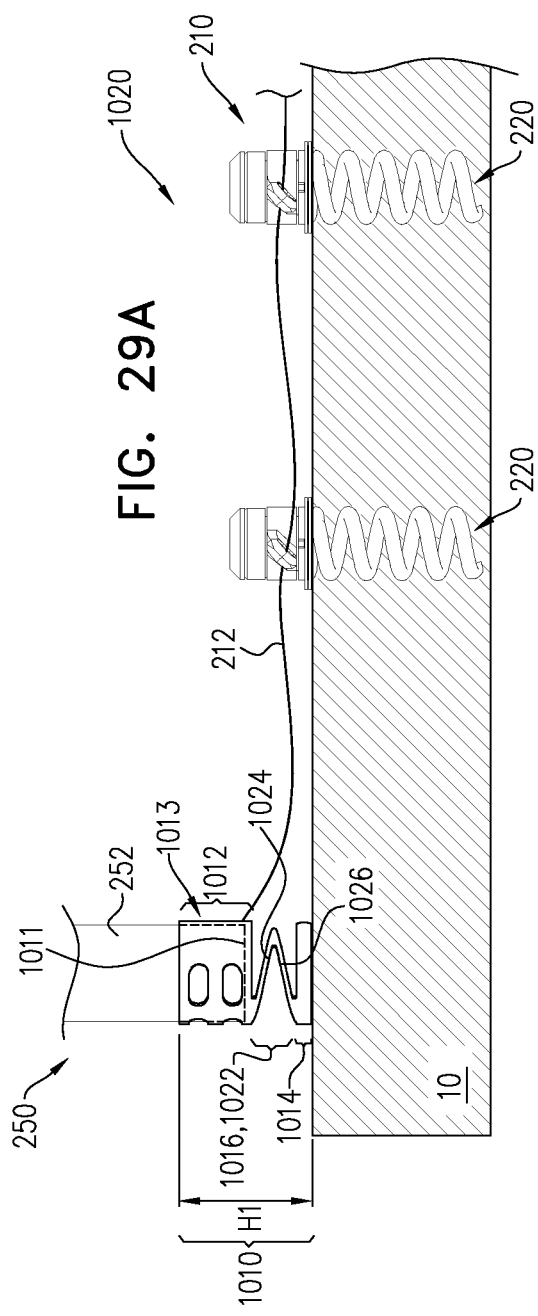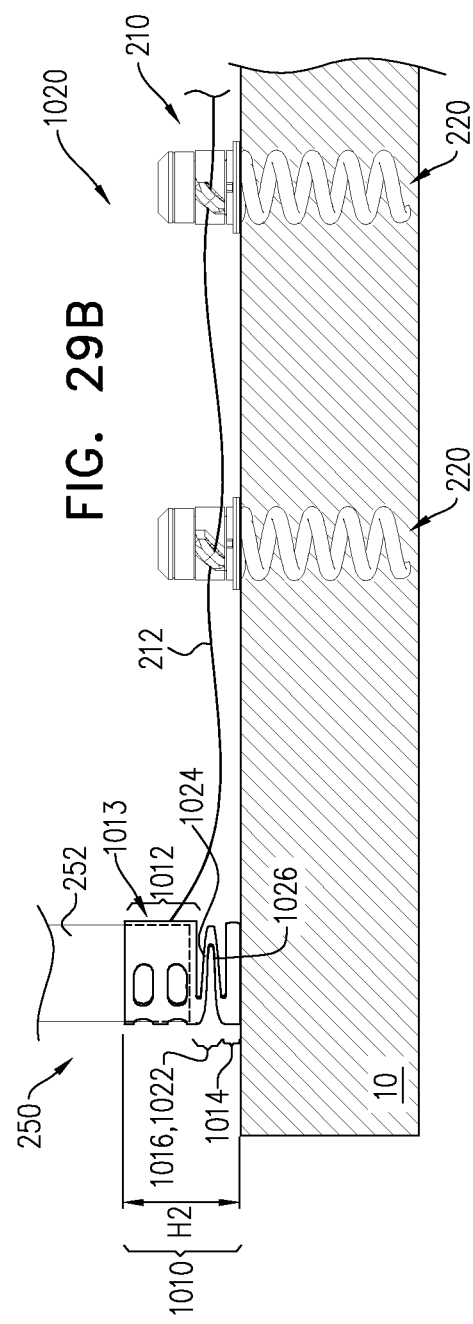

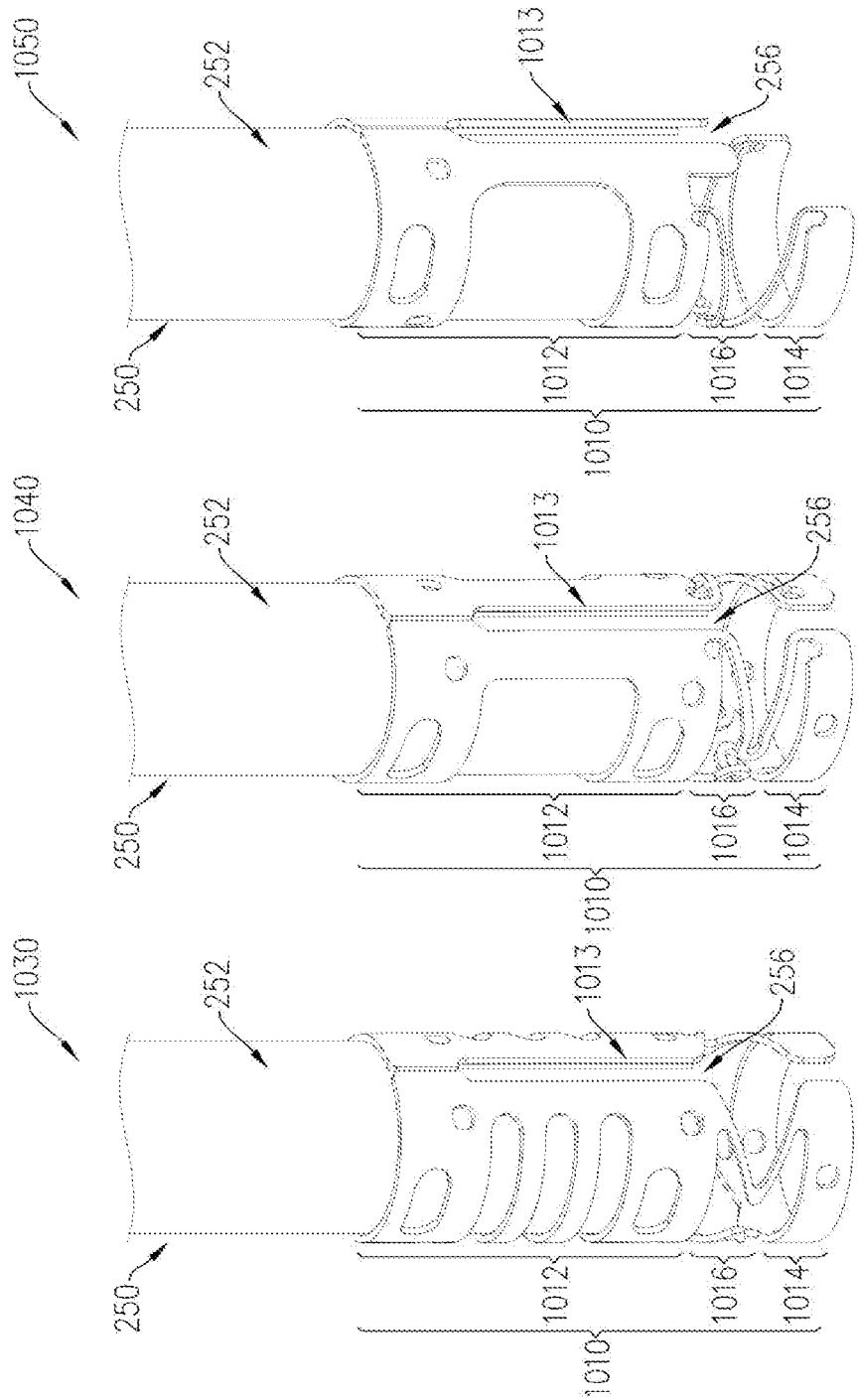

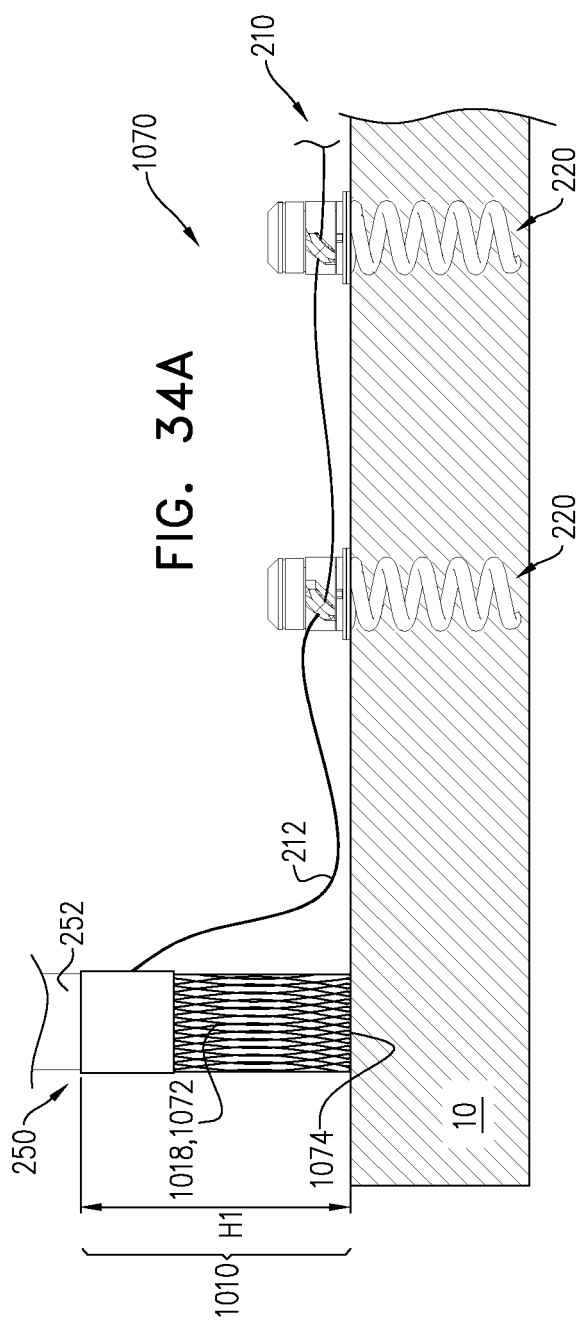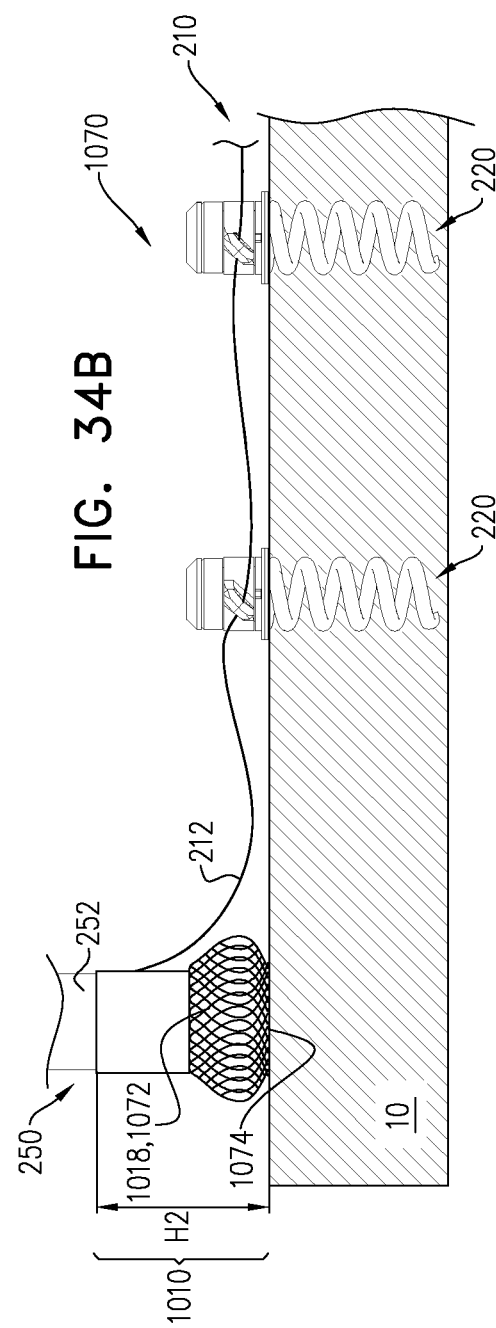

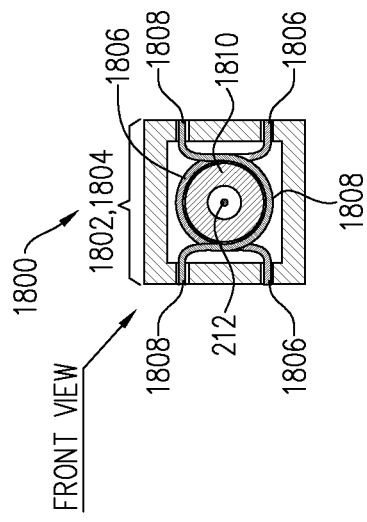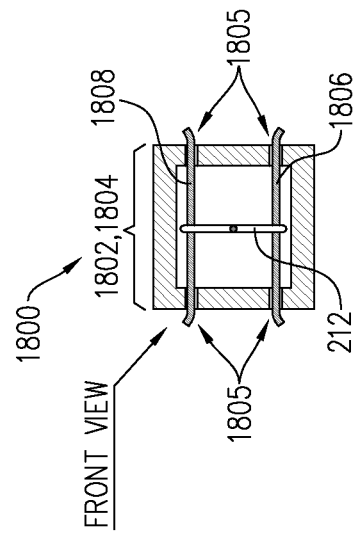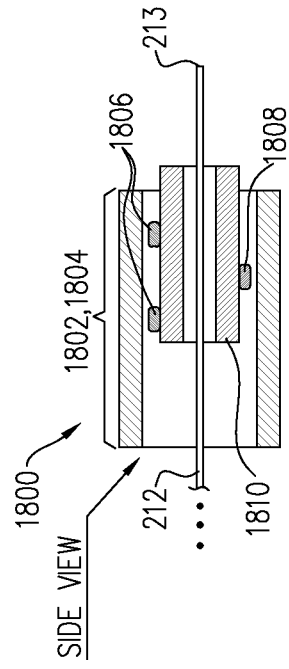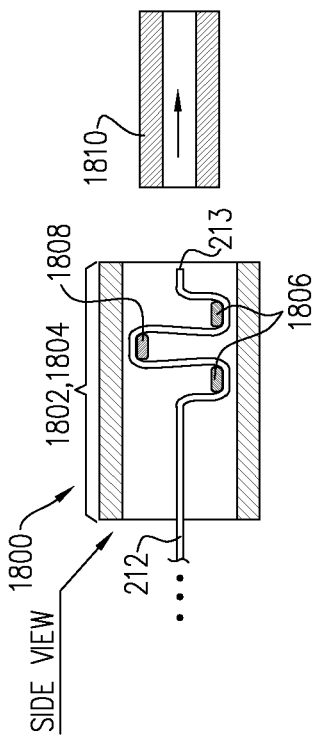
FIG. 44A
FIG. 44B

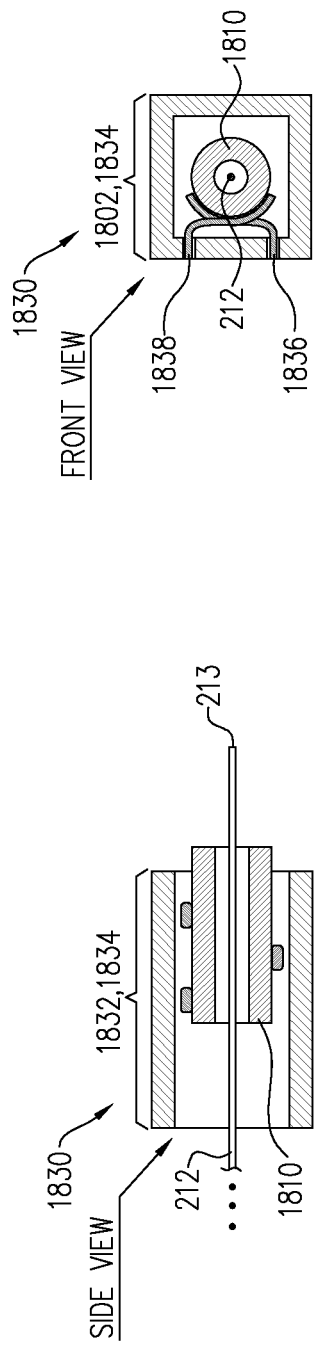
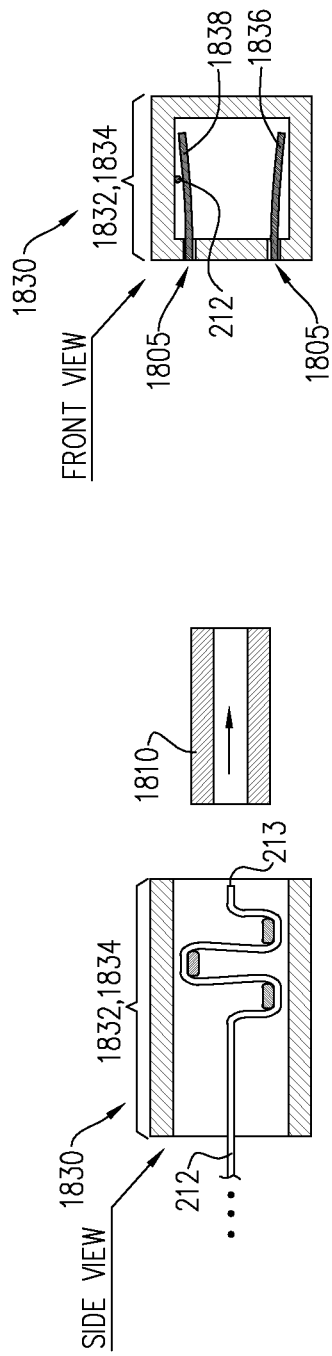
FIG. 46A
FIG. 46B

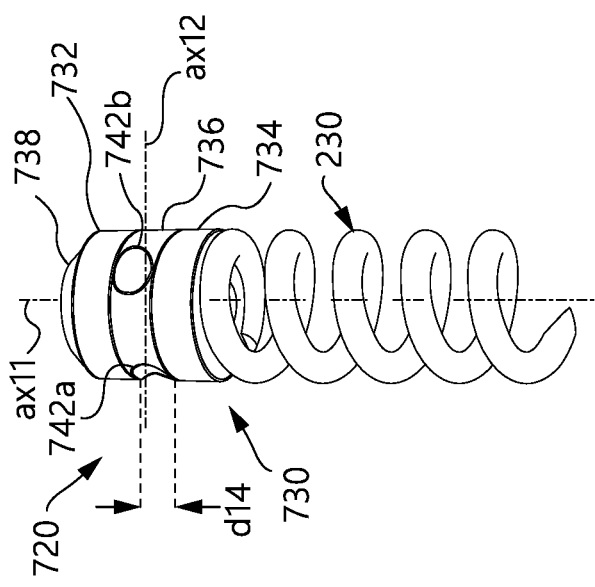
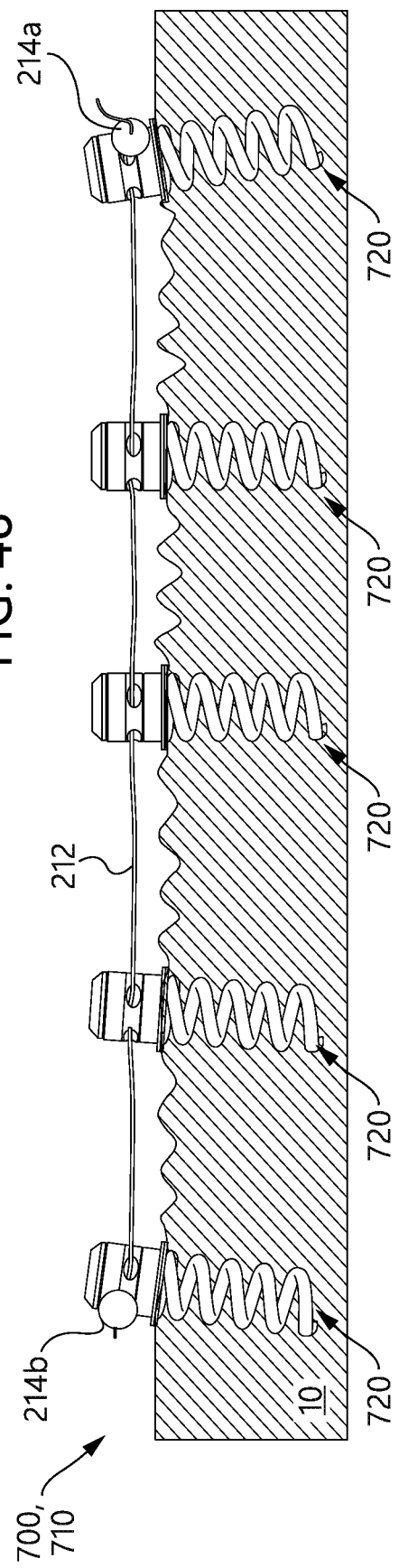
FIG. 48
FIG. 49

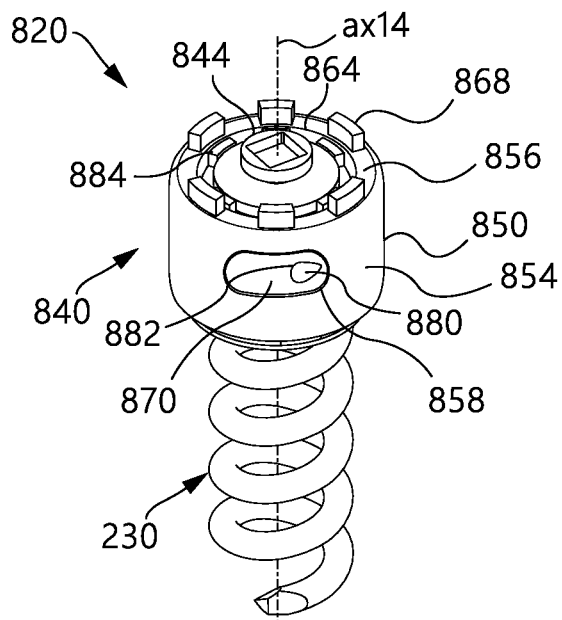
FIG. 52A
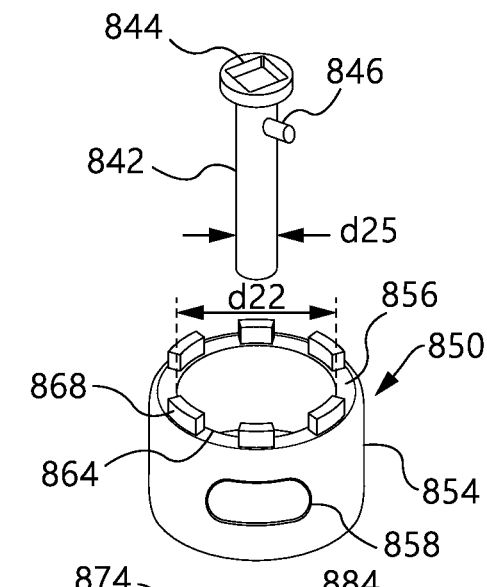
FIG. 52B
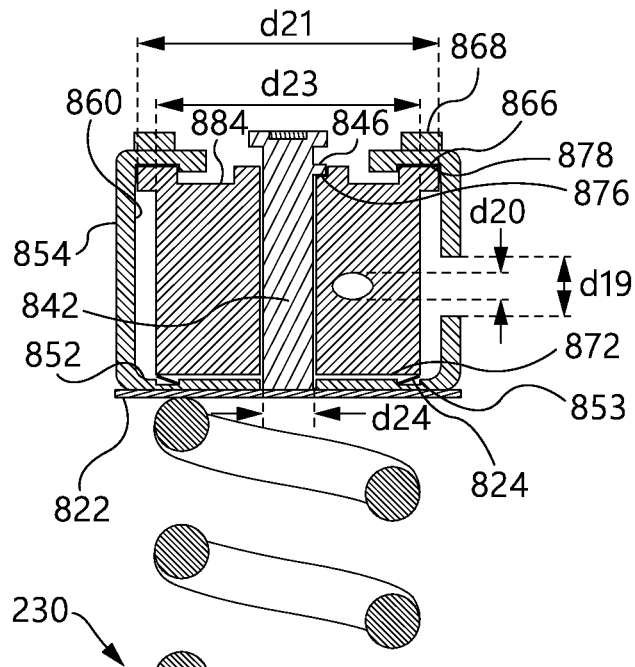
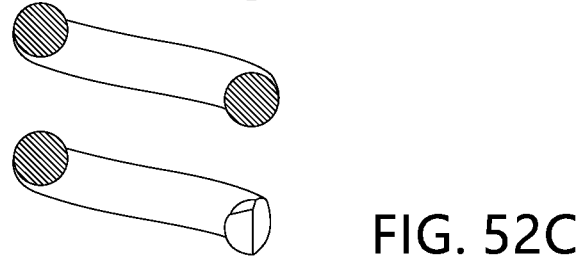
FIG. 52C

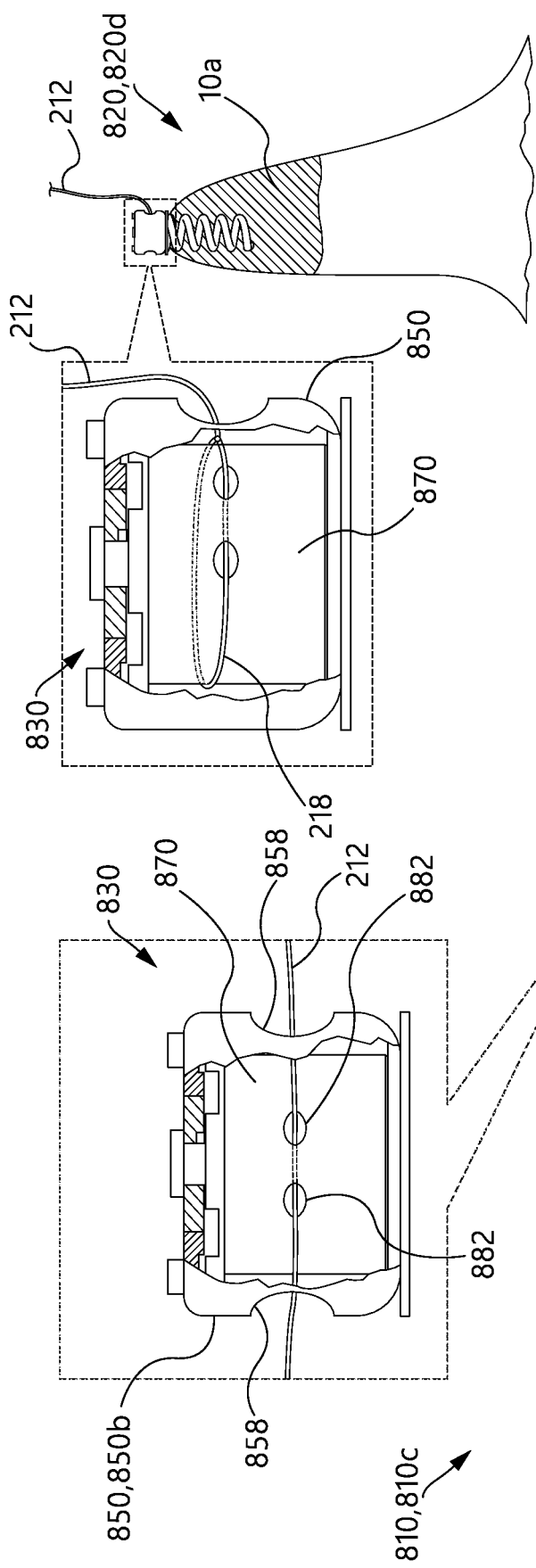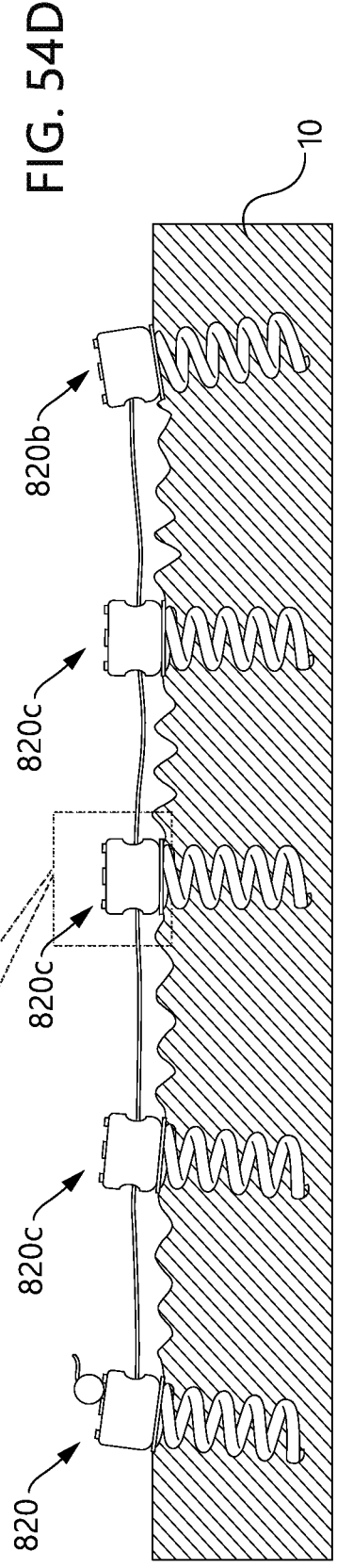
FIG. 54D
FIG. 54C

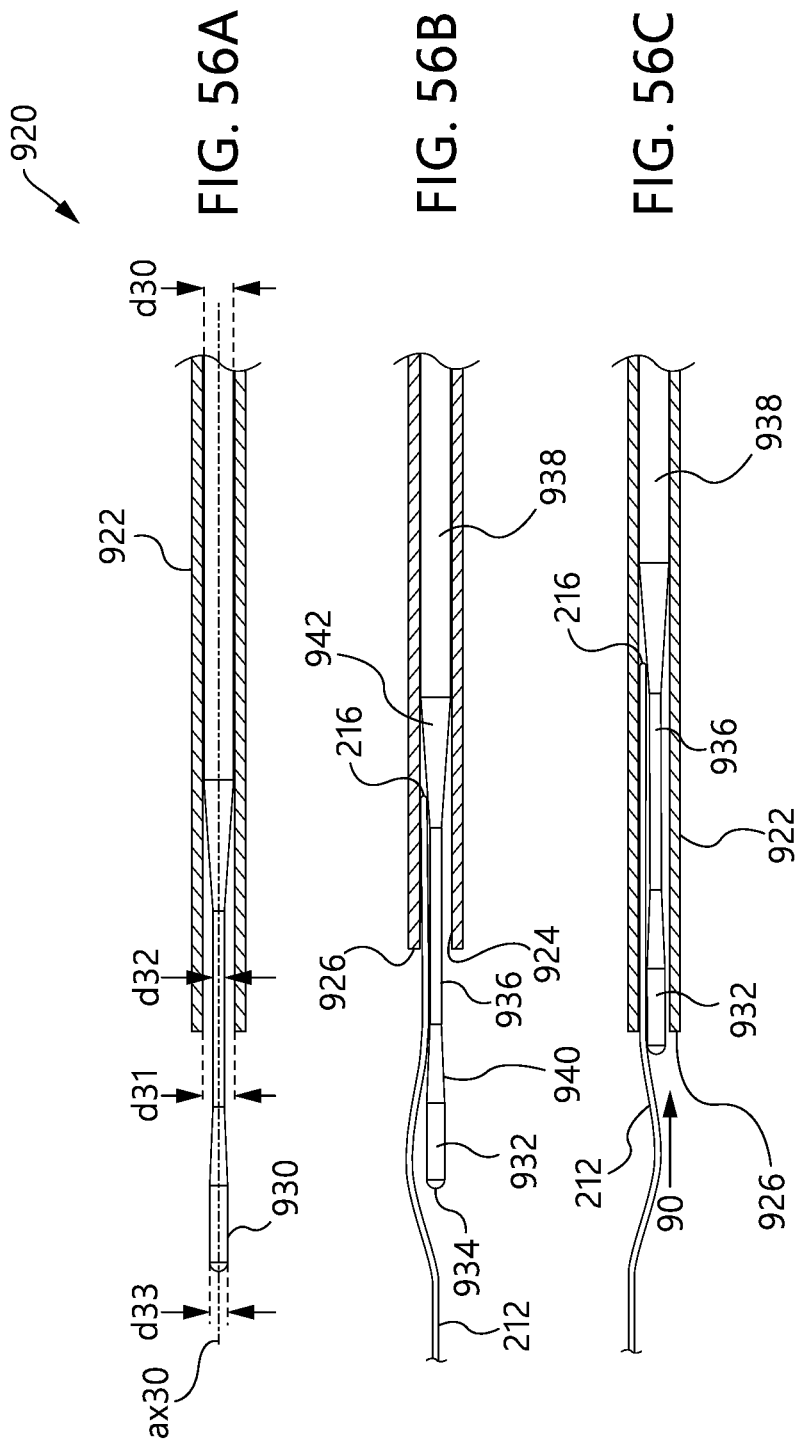

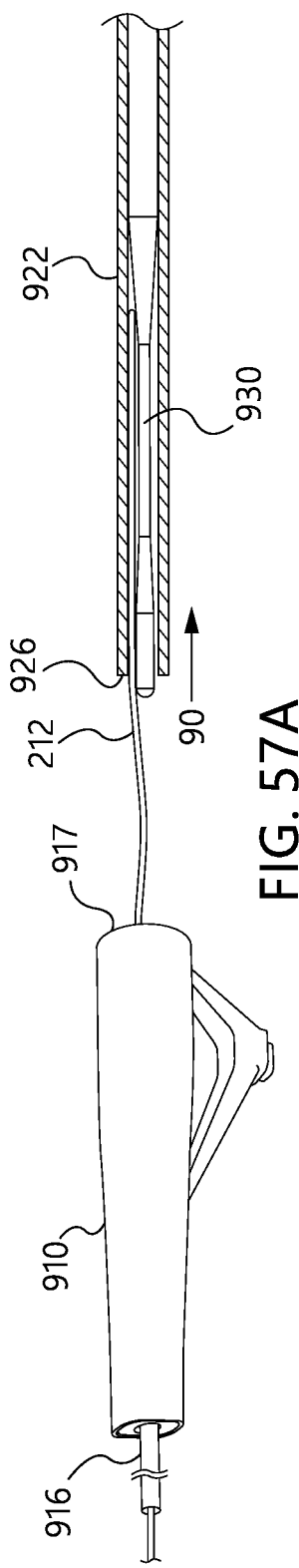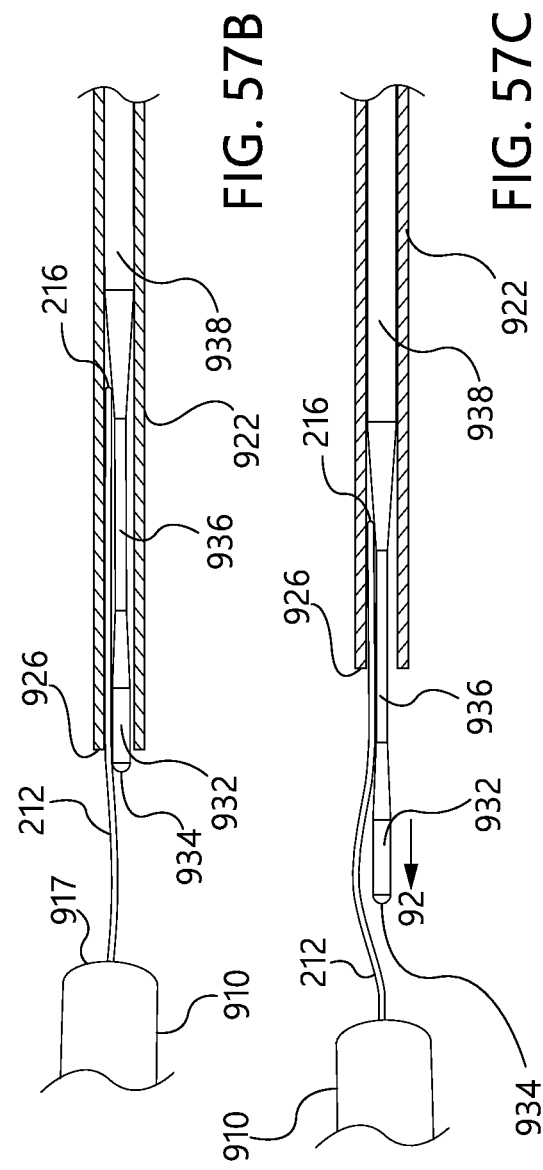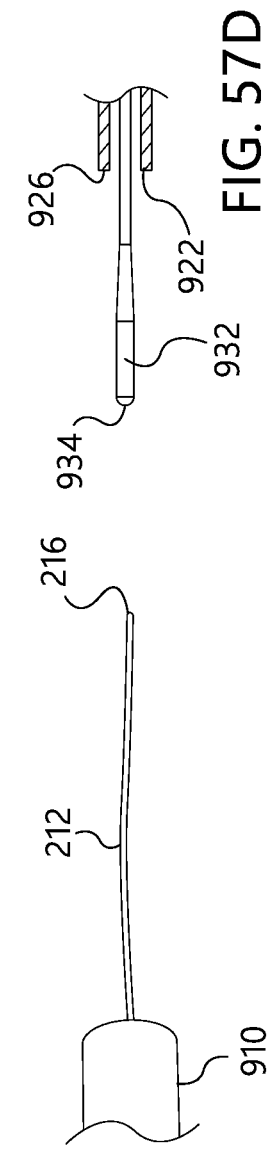

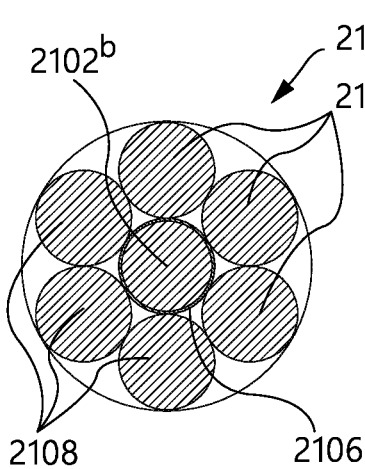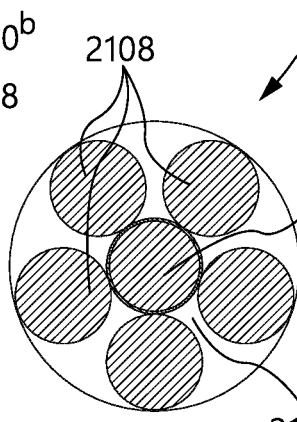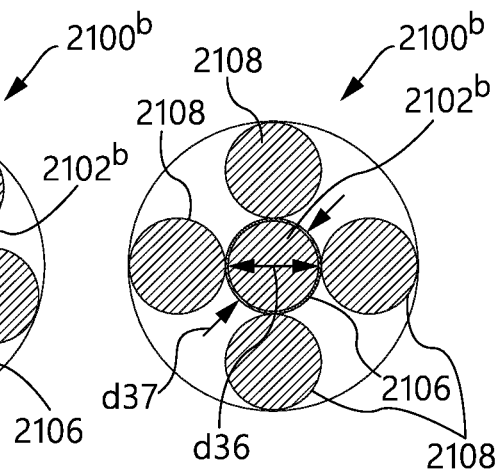
FIG. 65A    FIG. 65B    FIG. 65C
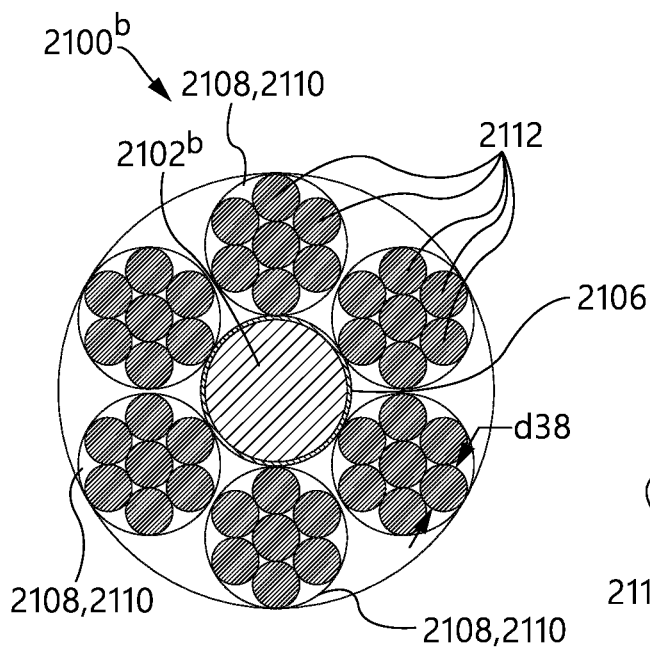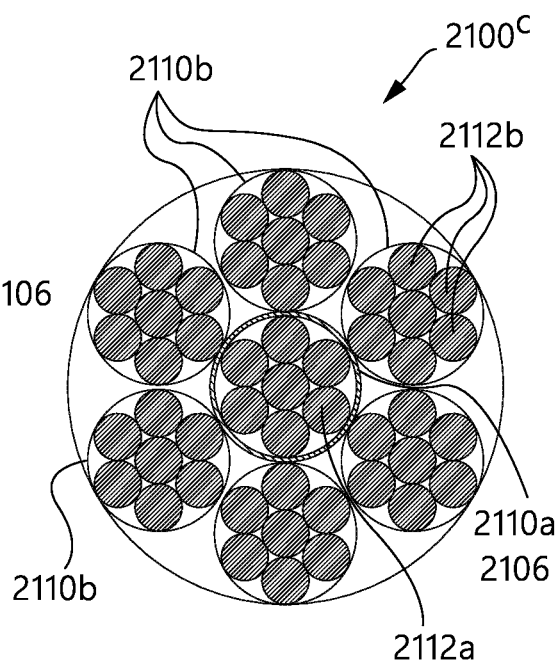
FIG. 66A    FIG. 66B

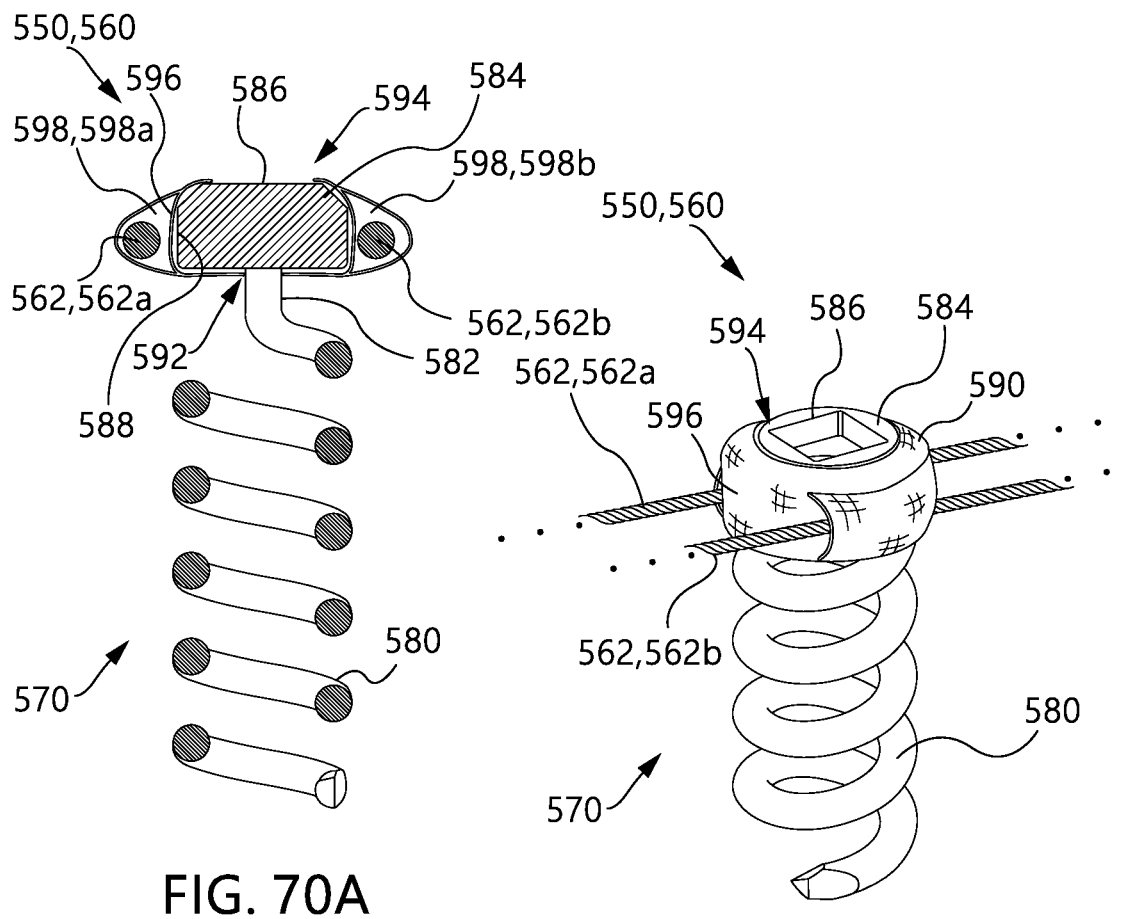
FIG. 70A
FIG. 70B
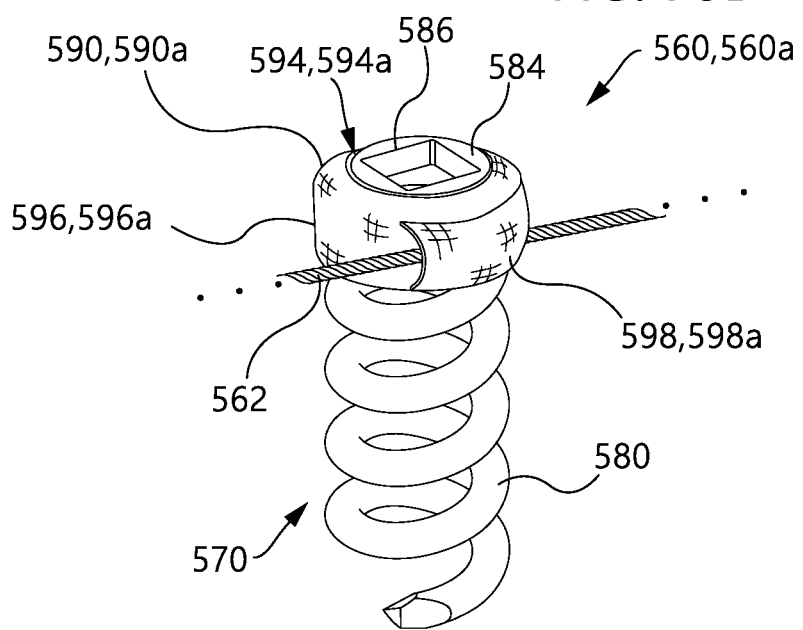
FIG. 70C

ANNULOPLASTY AND TISSUE ANCHOR TECHNOLOGIES

CROSS-REFERENCES TO RELATED APPLICATIONS

The present application is a Continuation of International Patent Application PCT/IB2020/060044 to Kasher et al, filed Oct. 27, 2020, which claims priority to:

U.S. Provisional Patent Application 62/927,624 to Kasher et al, filed Oct. 29, 2019, and entitled "Annuloplasty and Tissue Anchor Technologies;" and U.S. Provisional Patent Application 62/949,392 to Kasher et al, filed Dec. 17, 2019, and entitled "Annuloplasty and Tissue Anchor Technologies."

The above-referenced applications are incorporated herein by reference for all purposes.

BACKGROUND

Annuloplasty involves remodeling tissue of an annulus. This can be done by pulling tissue about the annulus to a new shape. Tissue anchors can be used to facilitate medical procedures including annuloplasty, other remodeling of tissues, and securing implants. In some instances, tissue anchors can be used as an alternative to sutures. For example, a tissue anchor may be used for a procedure in which there is no line-of-sight to the target.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

Some applications relate to tissue anchors that are configured (e.g, shaped) to be slidable along a wire, line, contracting member, etc. both (i) while aligned (i.e., parallel or coaxial) with the wire, and (ii) while oriented orthogonal to the wire, line, contracting member, etc. This is believed to facilitate, inter alia, (i) advancement of the anchor along the wire, line, contracting member, etc. while aligned with the wire, line, contracting member, etc. during transcatheter delivery, and (ii) subsequent sliding of the wire, line, contracting member, etc. with respect to the anchor after implantation, e.g, while the wire, line, contracting member, etc. is orthogonal to the anchor.

The tissue anchor can comprise (i) a tissue-engaging element, (ii) and a head at a proximal end of the tissue-engaging element. The head can define an eyelet that defines an aperture therethrough.

A variety of different tissue-engagement element configurations are possible. For some applications, the tissue-engaging element is shaped as a helix having an axis and defines a central lumen along the axis. For some applications, the tissue-engaging element can be pushed axially into tissue, and in some circumstances, can include barbs or barbed portions to hold the tissue-engaging element in tissue. Other tissue-engaging elements or portions of anchors are also possible.

For some applications, the central lumen of a helical-shaped tissue engaging element is open at both ends, and the tissue anchor provides a straight channel along the entirety of the tissue anchor, aligned with the axis of the helix. For such applications, the eyelet faces orthogonal to the axis of the helix. During delivery, the wire, line, contracting member, etc. is aligned with the anchor, and extends through the anchor by extending distally past (not through) the eyelet, through the lumen of the helix, and out of a distal end of the lumen. In this state, the anchor is smoothly slidable along the wire, line, contracting member, etc. while aligned with the wire, line, contracting member, etc. The anchor is anchored by rotation. As the helical tissue-engaging element rotates, it captures the portion of the wire, line, contracting member, etc. at the distal end of the lumen, and draws it proximally toward the head, such that eventually the wire, line, contracting member, etc. no longer extends through the lumen of the helix, but instead extends through the eyelet. In this state, the anchor is smoothly slidable along the wire, line, contracting member, etc. while orthogonal to the wire, line, contracting member, etc.

For some applications, the eyelet has a particular shape that facilitates smooth sliding along the wire, line, contracting member, etc. both (i) when the anchor is parallel with the wire, line, contracting member, etc, and (ii) when the anchor is in an orthogonal orientation with respect to the wire, line, contracting member, etc. In each of these orientations, the eyelet defines a respective clear, straight pathway through the aperture of the eyelet for the wire, line, contracting member, etc. to pass through. For some such applications, the shape and orientation of the eyelet is such that, both (i) when viewed in an orientation parallel to the axis of the anchor, and (ii) when viewed in an orientation orthogonal to the axis of the anchor, the aperture defined by the eyelet appears to be circular.

For some applications, one or more spacers are threaded on the wire, line, contracting member, etc. between anchors. For some such applications, the spacers have flared ends and the eyelets of the anchors have one or more tapered portions, such that the flared ends and the tapered portions mate in order to provide secure and stable spacing of the anchors and/or force distribution between the anchors.

Some applications relate to systems, apparatuses, and methods for determining successful (e.g, complete) anchoring to a tissue that is not in line-of-sight, such as during percutaneous (e.g, transluminal) techniques.

In some applications, the tissue anchor comprises a tissue-engaging element and a head. An anchor driver can engage the anchor at the head (e.g, reversibly attaching to the head), and drives the tissue-engaging element into the tissue. Often, successful anchoring includes the tissue-engaging element becoming fully embedded in the tissue, e.g, such that the head abuts the surface of the tissue.

For some applications, the tissue anchor undergoes a conformational change upon successful anchoring, e.g, passively in response to the head pressing against the tissue. For some such applications, the conformational change is visible using imaging techniques such as fluoroscopy. For example, a radiopaque element may change shape and/or change position with respect to another part of the anchor, and this can be identified using imaging.

For some applications, one or more systems and/or apparatuses are provided which facilitate a determination of successful (e.g, complete) anchoring to a tissue that is not in line-of-sight. Respective tissue-indicating devices are coupled to a distal tubular end portion of a flexible tube of a delivery tool used for implantation of the implant which undergo conformational changes upon contact with tissue from a resting state into a compressed state. The conformational change is visible using imaging techniques such as fluoroscopy. For example, a radiopaque element may change shape responsively to contact of the flexible tube with tissue, and this can be identified using imaging.

For some applications, one or more systems and/or apparatuses are provided which comprise respective contracting-member-covering devices that are each couplable to the contracting member (e.g, wire, line, suture, etc.) coupled to the tissue anchors of the implant. The contracting-member-covering devices comprise fasteners which are configured to lock in place the contracting member after annuloplasty is performed by cinching. For some applications, the contracting-member-covering devices described herein are configured to expand to cover the excess portions of the contracting member as well as the free end of contracting member. For some applications, the contracting-member-covering devices described herein are configured to change shape to cover the excess portions of the contracting member as well as the free end of contracting member. For some applications, the contracting-member-covering devices described herein are configured to cover the excess portions of the contracting member as well as the free end of contracting member by drawing the excess portions of the contracting member as well as the free end of contracting member within a housing of the contracting-member-covering device.

For some applications, one or more systems and/or apparatuses are provided which comprise respective locking mechanisms comprising fasteners configured to be couplable to the contracting member in a vicinity of terminal tissue anchor of the plurality of tissue anchors. The fastener, in a closed state thereof, is configured to restrict movement of the contracting member with respect to the plurality of tissue anchors. For some applications, the locking mechanism is integrated with a cutting tool configured to sever the contracting member.

There is therefore provided, in accordance with an application, a system and/or an apparatus, for use with an anchor driver, the system and/or apparatus including a wire, line, contracting member, etc. and a first anchor and a second anchor. Each of the first and second anchors can be configured to include a tissue-engaging element defining a central longitudinal axis of the anchor, having a sharpened distal tip, and configured to be driven into tissue of a subject; and a head, coupled to a proximal end of the tissue-engaging element. In some applications, the head includes a driver interface, configured to be reversibly engaged by the anchor driver, and an eyelet defining an aperture through which the wire, line, contracting member, etc. is threaded. The eyelet can be disposed laterally from the central longitudinal axis and be shaped to facilitate smooth sliding of the eyelet over the wire, line, contracting member, etc. along a slide-axis of the eyelet while the wire, line, contracting member, etc. is aligned with the slide-axis. In some applications, the eyelet also has an external shape that defines a tapered portion that tapers away from the aperture along the slide-axis. In some applications, the tapered portion tapers over a distance of between 0.25 mm to 3 mm, between 0.5 mm to 2 mm, or about 1 mm. The taper can be in one direction or multiple (e.g., 2 or more) directions, e.g, tapering from larger (e.g, wider, larger radius, etc.) center to smaller (e.g, thinner, smaller radius, etc.) ends.

In an application, the external shape of the eyelet defines the tapered portion as a first tapered portion that tapers away from the aperture in a first taper-direction along the slide-axis, and a second tapered portion that tapers away from the aperture in a second taper-direction along the slide-axis, the second taper-direction being opposite to the first taper-direction.

In an application, for the eyelet of each of the first and second anchors the slide-axis is a second slide-axis. For example, in some applications, the eyelet has a first slide-axis that is parallel with the central longitudinal axis with the second slide-axis being orthogonal to the first slide-axis. In some applications, the eyelet is shaped to facilitate smooth sliding of the eyelet over the wire, line, contracting member, etc. both (i) along the first slide-axis while the wire, line, contracting member, etc. is aligned with the first slide-axis, and (ii) along the second slide-axis while the wire, line, contracting member, etc. is aligned with the second slide-axis.

In an application, the wire, line, contracting member, etc. has a thickness that is more than 70 percent as great as the width of the aperture. In an application, the thickness of the wire, line, contracting member, etc. is less than 90 percent as great as a length of the aperture.

In an application, the system and/or apparatus further includes a spacer that is tubular, has a first spacer-end, a second spacer-end, and a mid-portion therebetween. In some applications, the spacer defines a spacer-lumen between the first spacer-end and the second spacer-end, and the wire, line, contracting member, etc. is threaded through the spacer-lumen, such that the spacer is threaded on the wire, line, contracting member, etc. between the first anchor and the second anchor, with the first spacer-end facing the first anchor, and the second spacer-end facing the second anchor. In some applications, the spacer-lumen widens from the mid-portion toward the first spacer-end, thereby being shaped to snugly receive the tapered portion of the eyelet of the first anchor, and the spacer-lumen widens from the mid-portion toward the second spacer-end, thereby being shaped to snugly receive the tapered portion of the eyelet of the second anchor.

In an application, the spacer is configured to limit a proximity between the first anchor and the second anchor. In an application, the spacer is elastically flexible in deflection.

In an application, the spacer is generally not compressible axially. In an application, the spacer is defined by a helical wire shaped as closed coil that defines the spacer-lumen.

In an application, the spacer has: a first flared zone in which the spacer-lumen widens from the mid-portion toward the first spacer-end, and in which an outer diameter of the spacer increases from the mid-portion toward the first spacer-end; and a second flared zone in which the spacer-lumen widens from the mid-portion toward the second spacer-end, and in which an outer diameter of the spacer increases from the mid-portion toward the second spacer-end.

In an application, the tissue-engaging element is helical, defines the central longitudinal axis by extending in a helix around and along the central longitudinal axis, and is configured to be screwed into the tissue of the subject.

In an application, the tissue-engaging element has a high-friction surface, such as a knurled surface, textured surface, barbed surface, etc.

In an application, the eyelet defines the aperture on an aperture plane, and the aperture has a length along a long axis of the aperture and a width along a short axis of the aperture. In an application, the long axis and the short axis are disposed on the aperture plane, and the length is orthogonal to the width and greater than the width. The eyelet can also be mounted such that the aperture plane is slanted at a fixed angle with respect to the central longitudinal axis.

In an application, the tissue-engaging element is helical, defines the central longitudinal axis by extending in a helix around and along the central longitudinal axis, and is configured to be screwed into the tissue of the subject, and the helix slants in the same direction as the aperture plane with respect to the central longitudinal axis. Other tissue-engaging elements, e.g, hooks, barbs, etc, and other shapes are also possible.

In an application, the eyelet is shaped and oriented such that both (i) when viewed along a first view-line that is parallel with the central longitudinal axis, and (ii) when viewed along a second view-line that is orthogonal to the first view-line, the aperture appears circular.

In an application, the aperture is shaped like a stadium. In an application, the eyelet defines a rim around the aperture, the rim having greater beveling on the long axis than on the short axis.

In an application, the short axis is orthogonal to, and extends radially from, the central longitudinal axis.

In an application, the driver interface is disposed on the central longitudinal axis of the anchor.

In an application, the length of the aperture is at least 1.4 times as great as the width of the aperture. In an application, the length of the aperture is 1.4-5 times as great as the width of the aperture. In an application, the length of the aperture is 1.4-3 times as great as the width of the aperture. In an application, the length of the aperture is 1.5-2.5 times as great as the width of the aperture. In an application, the length of the aperture is 1.6-2.2 times as great as the width of the aperture. In an application, the length of the aperture is 1.6-2 times as great as the width of the aperture. In an application, the length of the aperture is 1.6-1.8 times as great as the width of the aperture.

In an application, the eyelet is mounted such that the aperture plane is slanted at 30-60 degrees with respect to the central longitudinal axis. In an application, the eyelet is mounted such that the aperture plane is slanted at 40-50 degrees with respect to the central longitudinal axis. In an application, the eyelet is mounted such that the aperture plane is slanted at 45 degrees with respect to the central longitudinal axis.

In an application, the system and/or apparatus further includes the anchor driver.

In an application, the system and/or apparatus includes a delivery tool that includes the anchor driver and a percutaneously-advanceable tube (e.g., catheter, etc.), and for each of the first and second anchors, while the anchor driver is engaged with the anchor, the anchor driver and the anchor are slidable through the tube.

In an application, the tube defines an internal channel that has an orthogonal cross-section that defines a major channel region and a minor channel region in communication with the major channel region. The major channel-region generally has a larger cross-sectional area than does the minor channel region. In some applications, each of the first and second anchors is slidable through the channel with the tissue-engaging element and the driver interface sliding through the major channel region, and the eyelet sliding through the minor channel region.

In an application, the tissue-engaging element fits snugly within the major channel region, and the eyelet fits snugly within the minor channel region.

In an application, the eyelet is shaped to facilitate smooth sliding of the eyelet simultaneously (i) snugly though the minor channel region, and (ii) over the wire, line, contracting member, etc, while the wire, line, contracting member, etc. is disposed within the minor channel region and is parallel with the central longitudinal axis.

In an application, each of the anchors is advanceable out of a distal opening of the tube. In some applications, the tube defines a lateral slit into the minor channel region and the lateral slit is continuous with, and extends proximally from, the distal opening of the tube. The lateral slit is generally dimensioned to allow the wire, line, contracting member, etc, but not the first or second anchor, to exit the tube laterally via the slit.

In an application, the system and/or apparatus further includes a tubular spacer that is threaded on the wire, line, contracting member, etc. between the first anchor and the second anchor, such that when the first anchor and the second anchor are disposed in the internal channel of the tube, the spacer is disposed in the minor channel region.

In an application, the lateral slit is dimensioned to allow the tubular spacer to exit the tube laterally via the slit.

In an application, the orthogonal cross-section of the channel is keyhole-shaped.

In an application, the orthogonal cross-section of the channel has a double-lobed shape.

In an application, in orthogonal cross-section, the channel has a narrowed neck between the major channel region and the minor channel region.

In an application, the system and/or apparatus further includes a tubular spacer that is threaded on the wire, line, contracting member, etc. between the first anchor and the second anchor, such that when the first anchor and the second anchor are disposed in the internal channel of the tube, the spacer is disposed in the minor channel region.

In an application, the narrowed neck is dimensioned to inhibit the spacer from entering the major channel region.

In an application, the eyelet is mounted to be revolvable or rotatable around the central longitudinal axis.

In an application, each of the first and second anchors is configured such that, for each of the first and second anchors, while the anchor driver is engaged with the anchor inside the internal channel, the driver interface is rotatable by the anchor driver while the eyelet remains disposed in the minor channel region.

In an application, the eyelet is mounted to be revolvable or rotatable around the central longitudinal axis while the aperture remains at a fixed angle with respect to the central longitudinal axis.

In an application, the head includes a ring that circumscribes the central longitudinal axis, and is rotatably coupled to the tissue-engaging element, and the eyelet is mounted on the ring, and is revolvable or rotatable around the central longitudinal axis by rotation of the ring about the central longitudinal axis.

There is further provided, in accordance with an application, a system and/or an apparatus, including an anchor including a driver interface and an anchor driver. The anchor driver includes a shaft and a driver head, coupled to a distal end of the shaft, and configured to reversibly engage the driver interface.

In some applications, the anchor includes a helical tissue-engaging element defining a central longitudinal axis of the anchor by extending helically around the central longitudinal axis, having a sharpened distal tip, and configured to be driven into tissue of a subject, and an anchor head, coupled to a proximal end of the tissue-engaging element. The anchor head can include the driver interface. In some applications, other types, shapes, and configurations of anchors are also possible.

In some applications, the system and/or apparatus further includes a tube, such as a catheter. In some applications, the catheter is shaped to define a channel from a proximal portion of the catheter to a distal portion of the catheter, and a distal opening at the distal portion of the catheter, the channel ending at the distal opening. In some applications, the anchor driver configured to advance the anchor through the channel and out of the distal opening, and to drive the tissue-engaging element into the tissue, e.g, by rotating the anchor, pushing the anchor into tissue, etc.

In some applications, there is a spur at the distal portion of the catheter, the spur protruding medially into the channel so as to (i) obstruct the tissue-engaging element from passing the spur distally in the absence of rotation of the tissue-engaging element, and (ii) allow the tissue-engaging element to screw past the spur distally.

In an application, the anchor head is dimensioned such that, in at least one rotational position of the head with respect to the catheter, the spur obstructs the anchor head from passing the spur axially.

In an application, the anchor head is dimensioned such that, in at least one other rotational position of the head with respect to the catheter, the anchor head is slidable past the spur axially.

In an application, the anchor head defines a groove in an outer surface of the head, the groove being parallel with the central longitudinal axis of the anchor, and being dimensioned such that, in the other rotational position of the head with respect to the catheter, the spur can slide along the groove as the anchor head is slid past the spur axially.

In an application, the catheter includes a lateral wall that defines the channel.

In some applications, the spur is reversibly transitionable between (i) an extended state in which the spur protrudes medially from the lateral wall into the channel, and (ii) a retracted state in which the spur is at least partly retracted into the lateral wall. The spur, in the extended state, obstructs the anchor head from passing the spur distally, and the spur, in the retracted state, allows the anchor head to pass the spur distally.

In an application, the catheter further includes a pullwire that is coupled to the spur and extends proximally from the spur along the lateral wall, and the spur is retractable into the lateral wall by pulling on the pullwire.

There is further provided, in accordance with an application, a system and/or an apparatus, usable or for use with an anchor driver, the system and/or apparatus including an annuloplasty structure that includes a wire, a plurality of anchors, and a plurality of connectors.

A variety of anchor configurations are possible. Each of the anchors of the plurality of anchors includes a tissue-engaging element and a head. In some applications, the tissue-engaging element defines a central longitudinal axis of the anchor, having a sharpened distal tip, and configured to be driven into tissue of a subject. In some applications, the tissue-engaging element can be pushed axially into tissue, and in some circumstances, can include barbs or barbed portions to hold the tissue-engaging element in tissue. Other tissue-engaging elements or portions of anchors are also possible. The head can be coupled to the tissue-engaging element via a neck. The head can include a driver interface configured to be reversibly engaged by the anchor driver.

In some applications, each of the plurality of connectors slidably couple a respective anchor of the plurality of anchors to the wire, line, contracting member, etc. In some applications, each of the plurality of connectors comprise or include a flexible sheet. In some applications, the flexible sheet is shaped to define a hole through which the neck of the respective anchor extends, such that (i) the head of the respective anchor is disposed on a first side of the sheet, (ii) the tissue-engaging element of the respective anchor is on a second, opposite, side of the sheet, and (iii) the respective anchor is rotatable, around the central longitudinal axis, with respect to the sheet by the neck of the respective anchor rotating within the hole.

In some applications, each of the plurality of connectors includes an eyelet, aperture, or other opening through which the wire, line, contracting member, etc. is threaded, thereby slidably coupling the connector to the wire, line, contracting member, etc. In an application, the eyelet is defined by a hem stitched in the flexible sheet.

In an application, the flexible sheet is a flexible sheet of a fabric, but other materials are also possible.

In an application, the wire, line, contracting member, etc. is a first wire, and the annuloplasty structure includes a second wire, each of the connectors slidably coupling the respective one of the anchors to the first wire and to the second wire.

In an application, the first wire and the second wire are generally parallel with each other.

In an application, for each connector the eyelet is a first eyelet, the first wire is threaded through the first eyelet, thereby slidably coupling the connector to the first wire. In an application, the sheet is also shaped to define a second eyelet through which the second wire is threaded, thereby slidably coupling the connector to the second wire. In an application, the flexible sheet is shaped to define hole between the first eyelet and the second eyelet, such that the respective anchor is disposed between the first wire and the second wire.

There is further provided, in accordance with an application, a system and/or an apparatus including a tissue anchor usable with or for use with an anchor driver. The anchor includes a tissue-engaging element. The tissue-engaging element can be configured to define a central longitudinal axis of the anchor, having a sharpened distal tip, and to be driven into tissue of a subject. For some applications, the tissue-engaging element is configured to be pushed axially into tissue. For some applications, the tissue-engaging element is hook-shaped. For some applications, the tissue-engaging element can include barbs or barbed portions to hold the tissue-engaging element in tissue. Other tissue-engaging elements or portions of anchors are also possible.

The tissue anchor also includes a head coupled to a proximal end of the tissue-engaging element. The head can include a driver interface, configured to be reversibly engaged by the anchor driver, and an eyelet or other connector (e.g, connectable to a wire, line, contracting member, tether, suture, etc.). The head can be paired with a variety of different tissue-engaging element configurations.

In some applications, the eyelet or other connector defines an aperture on an aperture plane. In some applications, the aperture has a length along a long axis of the aperture and a width along a short axis of the aperture, the long axis and the short axis disposed on the aperture plane, and the length being orthogonal to the width and greater than the width. The eyelet/connector and/or aperture can be disposed laterally from the central longitudinal axis and mounted such that the aperture plane is slanted at a fixed angle with respect to the central longitudinal axis.

In an application, the system and/or apparatus comprises an implant that includes the anchor, and a wire, line, contracting member, etc. threaded through the aperture. In some applications, the eyelet/connector defines the aperture such that the eyelet has a first slide-axis that is parallel with the central longitudinal axis, and a second slide-axis that is orthogonal to the first slide-axis. In some applications, the eyelet is shaped to facilitate smooth sliding of the eyelet (i) over the wire, line, contracting member, etc. along the first slide-axis while the wire, line, contracting member, etc. is aligned with the first slide-axis, and (ii) over the wire, line, contracting member, etc. along the second slide-axis while the wire, line, contracting member, etc. is aligned with the second slide-axis.

In an application, the eyelet has an external shape that defines a tapered portion that tapers away from the aperture along the second slide-axis.

In an application, the implant further includes a spacer that is tubular, that has a first spacer-end, a second spacer-end, and a mid-portion therebetween, and that defines a spacer-lumen between the first spacer-end and the second spacer-end. The wire, line, contracting member, etc. is threaded through the spacer-lumen. In some applications, the spacer-lumen widens from the mid-portion toward the first spacer-end, thereby being shaped to snugly receive the tapered portion of the eyelet.

In an application, the spacer is elastically flexible in deflection. In an application, the spacer is generally not compressible axially.

In an application, the spacer is defined by a helical wire shaped as closed coil that defines the spacer-lumen.

In an application, the spacer has a flared zone in which the spacer-lumen widens from the mid-portion toward the first spacer-end, and in which an outer diameter of the spacer increases from the mid-portion toward the first spacer-end.

In an application, the anchor is a first anchor of the implant, the implant further includes a second anchor that includes an eyelet that defines an aperture and has an external shape that defines a tapered portion, and the wire, line, contracting member, etc. is threaded through an aperture of an eyelet of the second anchor such that the spacer is disposed, on the wire, line, contracting member, etc, between the tapered portion of the eyelet of the first anchor and the tapered portion of the eyelet of the second anchor, with the first spacer-end facing the first anchor, and the second spacer-end facing the second anchor.

In an application, the spacer-lumen widens from the mid-portion toward the second spacer-end, thereby being shaped to snugly receive the tapered portion of the eyelet of the second anchor.

In an application, the spacer is configured to limit a proximity between the first anchor and the second anchor.

In an application, the external shape of the eyelet defines the tapered portion as a first tapered portion that tapers away from the aperture in a first taper-direction along the second slide-axis, and a second tapered portion that tapers away from the aperture in a second taper-direction along the second slide-axis, the second taper-direction being opposite to the first taper-direction.

In an application, the spacer is a first spacer of the implant, and the implant further includes a second spacer that is tubular, that has a first spacer-end, a second spacer-end, and a mid-portion therebetween, and that defines a spacer-lumen between the first spacer-end and the second spacer-end. The wire, line, contracting member, etc. is threaded through the spacer-lumen of the second spacer such that the eyelet is disposed, on the wire, line, contracting member, etc, between the first spacer-end of the first spacer and the second spacer-end of the second spacer. In some applications, the spacer-lumen of the second spacer widens from the mid-portion of the second spacer toward the second spacer-end of the second spacer, thereby being shaped to snugly receive the second tapered portion of the eyelet.

In an application, the eyelet is shaped and oriented such that both (i) when viewed along a first view-line that is parallel with the central longitudinal axis, and (ii) when viewed along a second view-line that is orthogonal to the first view-line, the aperture appears circular.

In an application, the aperture is shaped like a stadium. In an application, the eyelet defines a rim around the aperture, the rim having greater beveling on the long axis than on the short axis.

In an application, the short axis is orthogonal to, and extends radially from, the central longitudinal axis. In an application, the driver interface is disposed on the central longitudinal axis of the anchor.

In an application, the length of the aperture is at least 1.4 times as great as the width of the aperture. In an application, the length of the aperture is 1.4-5 times as great as the width of the aperture. In an application, the length of the aperture is 1.4-3 times as great as the width of the aperture. In an application, the length of the aperture is 1.5-2.5 times as great as the width of the aperture. In an application, the length of the aperture is 1.6-2.2 times as great as the width of the aperture. In an application, the length of the aperture is 1.6-2 times as great as the width of the aperture. In an application, the length of the aperture is 1.6-1.8 times as great as the width of the aperture.

In an application, the eyelet is mounted such that the aperture plane is slanted at 30-60 degrees with respect to the central longitudinal axis. In an application, the eyelet is mounted such that the aperture plane is slanted at 40-50 degrees with respect to the central longitudinal axis. In an application, the eyelet is mounted such that the aperture plane is slanted at 45 degrees with respect to the central longitudinal axis.

In an application, the eyelet is mounted to be revolvable or rotatable around the central longitudinal axis while the aperture plane remains slanted at the fixed angle with respect to the central longitudinal axis.

In an application, the head includes a ring that circumscribes the central longitudinal axis, and is rotatably coupled to the tissue-engaging element, and the eyelet is mounted on the ring, and is revolvable or rotatable around the central longitudinal axis by rotation of the ring about the central longitudinal axis.

In an application, the system and/or apparatus further includes the anchor driver.

In an application, the system and/or apparatus includes a delivery tool that includes the anchor driver and a percutaneously-advanceable tube, and while the anchor driver is engaged with the anchor, the anchor driver and the anchor are slidable through the tube.

In an application, the tube defines an internal channel that has a keyhole-shaped orthogonal cross-section that defines a major channel region and a minor channel region, the major channel-region has a larger cross-sectional area than does the minor channel region, and the anchor is slidable through the channel with the tissue-engaging element sliding snugly through the major channel region, and the eyelet sliding snugly through the minor channel region.

In an application, the system and/or apparatus includes an implant that includes a wire, line, contracting member, etc. and the tissue anchor, the eyelet is shaped to facilitate smooth sliding of the eyelet simultaneously (i) snugly though the minor channel region, and (ii) over the wire, line, contracting member, etc, while the wire, line, contracting member, etc. is disposed within the minor channel region and is parallel with the central longitudinal axis.

In an application, the eyelet is shaped to facilitate smooth sliding of the eyelet over the wire, line, contracting member, etc. while the wire, line, contracting member, etc. is oriented orthogonal to the central longitudinal axis.

In an application, the anchor is advanceable out of a distal end of the tube, the tube defines a lateral slit extending proximally from the distal end of the tube, the slit is adjacent to the minor channel region, and the slit allows the wire, line, contracting member, etc, but not the anchor, to exit the tube laterally, proximally from the distal end of the tube.

In an application, the system and/or apparatus includes an implant including a wire, line, contracting member, etc. and the tissue anchor, and the eyelet is shaped to facilitate smooth sliding of the wire, line, contracting member, etc. through the aperture both (i) while the wire, line, contracting member, etc. is parallel with the central longitudinal axis, and (ii) while the wire, line, contracting member, etc. is oriented orthogonal to the central longitudinal axis.

In an application, the wire, line, contracting member, etc. has a thickness that is more than 70 percent as great as the width of the aperture. In an application, the thickness of the wire, line, contracting member, etc. is less than 90 percent as great as the length of the aperture.

In an application, the tissue-engaging element is helical, defines the central longitudinal axis by extending in a helix around and along the central longitudinal axis, and is configured to be screwed into the tissue of the subject. But other tissue-engaging element configurations are also possible.

In an application, the helix slants in the same direction as the aperture plane with respect to the central longitudinal axis.

There is also provided, in accordance with an application, a system and/or an apparatus including a tissue anchor usable with or for use with an anchor driver, the tissue anchor including a tissue-engaging element and a head coupled to a proximal end of the tissue-engaging element.

In some applications, the tissue-engaging element defines a central longitudinal axis of the anchor, has a sharpened distal tip, and is configured to be driven into tissue of a subject.

In some applications, the head includes a driver interface, configured to be reversibly engaged by the anchor driver, and an eyelet or other connector. The eyelet or connector can be configured to define an aperture, can be disposed laterally from the central longitudinal axis, and can be mounted such that the aperture is at a fixed angle with respect to the central longitudinal axis. The eyelet/connector and aperture can be shaped to define (i) a first clear straight pathway through the aperture along a first line that is parallel to the central longitudinal axis, and (ii) a second clear straight pathway through the aperture along a second line that is orthogonal to the first line.

In an application, the eyelet is shaped such that both (i) when viewed along the first line, and (ii) when viewed along second line, the aperture appears circular.

In an application, the eyelet is mounted so as to be revolvable or rotatable around the central longitudinal axis while remaining at the fixed angle with respect to the central longitudinal axis.

In an application, the fixed angle is slanted with respect to the central longitudinal axis, and the eyelet defines the aperture on an aperture plane that is slanted at the fixed angle with respect to the central longitudinal axis.

In an application, the aperture has a length along a long axis of the aperture and a width along a short axis of the aperture, the long axis and the short axis disposed on the aperture plane, and length is orthogonal to the width and greater than the width.

In an application, the length of the aperture is at least 1.4 times as great as the width of the aperture. In an application, the length of the aperture is 1.4-5 times as great as the width of the aperture. In an application, the length of the aperture is 1.4-3 times as great as the width of the aperture. In an application, the length of the aperture is 1.5-2.5 times as great as the width of the aperture. In an application, the length of the aperture is 1.6-2.2 times as great as the width of the aperture. In an application, the length of the aperture is 1.6-2 times as great as the width of the aperture. In an application, the length of the aperture is 1.6-1.8 times as great as the width of the aperture.

In an application, the eyelet is mounted such that the aperture plane is slanted at 30-60 degrees with respect to the central longitudinal axis. In an application, the eyelet is mounted such that the aperture plane is slanted at 40-50 degrees with respect to the central longitudinal axis. In an application, the eyelet is mounted such that the aperture plane is slanted at 45 degrees with respect to the central longitudinal axis.

There is further provided, in accordance with an application, a system and/or an apparatus including a tissue anchor usable with or for use with an anchor driver, the tissue anchor including a tissue-engaging element and a head coupled to a proximal end of the tissue-engaging element. In some applications, the tissue-engaging element defines a central longitudinal axis of the anchor, has a sharpened distal tip, and is configured to be driven into tissue of a subject. In some applications, the tissue-engaging element is configured to be pushed into tissue, not rotated. In some applications, the tissue-engaging element is hook-shaped, straight, angled, and/or another configuration. For some applications, the tissue-engaging element can include barbs or barbed portions to hold the tissue-engaging element in tissue. Other tissue-engaging elements or portions of anchors are also possible.

In some applications, the head includes a driver interface, configured to be reversibly engaged by the anchor driver. In some applications, a protrusion protrudes distally away from the head, such that driving the tissue-engaging element into the tissue presses the protrusion against the tissue. In some applications, the protrusion is fixed in place. In some applications, the protrusion is configured to move with respect to the head automatically in response to being pressed against the tissue.

In an application, the driver interface is rigidly coupled to the tissue-engaging element.

In an application, the protrusion is configured to move proximally with respect to the head automatically in response to being pressed against the tissue. In an application, the protrusion is configured to move elastically with respect to the head automatically in response to being pressed against the tissue.

In an application, the protrusion extends distally past at least the proximal end of the tissue-engaging element and is disposed laterally outward from the tissue-engaging element. In an application, the protrusion extends distally past at least the proximal end of the tissue-engaging element and extends circumferentially at least partway around the tissue-engaging element. In an application, the protrusion extends distally past at least the proximal end of the tissue-engaging element and is disposed medially from the tissue-engaging element.

In an application, the tissue-engaging element is helical, and extends helically around the protrusion. In some applications, the tissue-engaging element is configured to be at least one of rotated into tissue and/or pushed into tissue. In some applications, the tissue-engaging element is hook-shaped, straight, angled, and/or another configuration. In some applications, the tissue-engaging element can include barbs or barbed portions to hold the tissue-engaging element in tissue. Other tissue-engaging elements or portions of anchors are also possible.

In an application, the protrusion is radiopaque.

In an application, the protrusion is configured to bend automatically in response to being pressed against the tissue.

In an application, the tissue-engaging element is helical, defines the central longitudinal axis by extending helically around and along the central longitudinal axis, and is configured to be screwed into the tissue of the subject. In some applications, the tissue-engaging element is configured to be at least one of rotated into tissue and/or pushed into tissue. In some applications, the tissue-engaging element is hook-shaped, straight, angled, and/or another configuration. In some applications, the tissue-engaging element can include barbs or barbed portions to hold the tissue-engaging element in tissue. Other tissue-engaging elements or portions of anchors are also possible.

In an application, the protrusion is configured to move reversibly in response to being pressed against the tissue.

In an application, the protrusion includes a spring. In an application, the spring is a helical compression spring that extends helically around at least part of the tissue-engaging element. In an application, the helical compression spring defines a plurality of turns around the part of the tissue-engaging element.

In an application, the helical compression spring defines no more than one complete turn, and in response to being pressed against the tissue, a first end of the helical compression spring becomes aligned, along the central longitudinal axis, with a second end of the helical compression spring.

In an application, the system and/or apparatus further includes a spring coupled functionally between the protrusion and the head so as to bias or configure the protrusion to move reversibly in response to the protrusion being pressed against the tissue.

In an application, the tissue anchor includes a cuff, extending at least partway around the head and the central longitudinal axis, a distal portion of the cuff protruding distally away from the head to define the protrusion, and the spring functionally couples the cuff to the head such that the cuff is configured to move proximally with respect to the head automatically in response to the distal portion of the cuff being pressed against the tissue.

In an application, the spring includes a plurality of chevron-shaped spring elements pointing circumferentially around the central longitudinal axis.

In an application, the tissue anchor is configured to be used with a wire, line, contracting member, etc. In an application, the tissue anchor further includes a ring and an eyelet the ring circumscribes the central longitudinal axis and is rotatably coupled to the tissue-engaging element. The eyelet/connector can be configured to facilitate sliding of the wire/line/etc. therethrough, can be mounted on the ring, and can be revolvable or rotatable around the central longitudinal axis by rotation of the ring about the central longitudinal axis. The cuff can be coupled to the ring.

In an application, a proximal portion of the head protrudes proximally from the cuff, and the cuff is dimensioned such that the moving of the cuff proximally with respect to the head obscures the proximal portion of the head with a proximal portion of the cuff.

In an application, the cuff is radiopaque.

In an application, the system and/or apparatus further includes one or more radiopaque indicators extending proximally from the cuff, and the cuff is dimensioned such that the moving of the cuff proximally with respect to the head moves the one or more indicators proximally past a proximal portion of the head.

In an application, the protrusion includes a post configured to axially slide proximally with respect to the head in response to being pressed against the tissue.

In an application, the post includes a first post, and the spring includes a first spring, and the system and/or apparatus further includes a second post configured to axially slide proximally with respect to the head in response to being pressed against the tissue.

In an application, the system and/or apparatus further includes the anchor driver. The anchor driver is configured, while reversibly engaged to the driver interface, to drive the tissue-engaging element into the tissue. In some applications, the anchor driver includes a pressure sensor at a distal end of the anchor driver. The protrusion can include a post configured to, in response to being pressed against the tissue, move proximally with respect to the head and press the pressure sensor. The pressure sensor is configured to provide a signal in response to being pressed.

In an application, the anchor driver includes a wire extending from the pressure sensor to a proximal portion of the anchor driver, and the pressure sensor is configured to transmit the signal via the wire.

In an application, the post is configured to axially slide proximally with respect to the head in response to being pressed against the tissue.

There is further provided, in accordance with an application, a system and/or an apparatus, including a tissue anchor having an eyelet. In some applications, the tissue anchor includes a helical tissue-engaging element. In some applications, a helical tissue-engaging element has a proximal end and a distal end and defines a central lumen along a central longitudinal axis of the tissue anchor. In some applications, the eyelet is configured such that it spans laterally across the proximal end of the tissue-engaging element and extends proximally away from the tissue-engaging element, thereby defining a bilaterally-facing aperture proximal from the tissue-engaging element.

In an application, the tissue anchor is a first tissue anchor of a plurality of tissue anchors, and the system and/or apparatus includes an annuloplasty implant including the plurality of tissue anchors, and a wire, line, contracting member, etc. threaded therethrough.

In an application, the system and/or apparatus includes an implant including a wire, line, contracting member, etc. and the tissue anchor, and the system and/or apparatus further includes a delivery tool for percutaneous implantation of the implant, the delivery tool including an anchor driver. In some applications, the system and/or apparatus has a delivery state in which:

the anchor driver is reversibly coupled to the eyelet, the wire, line, contracting member, etc. extends longitudinally through the lumen such that the anchor is freely slidable along the wire, line, contracting member, etc, and the delivery tool and the implant are percutaneously advanceable into a subject, In some applications, the delivery tool is configured to transition the system and/or apparatus into an implanted state by the anchor driver rotating the tissue anchor such that the tissue-engaging element becomes driven into tissue of the subject, and the wire, line, contracting member, etc. becomes drawn proximally along the helical element until the wire, line, contracting member, etc. exits the lumen and extends laterally through the aperture.

In an application, the tissue anchor is a first tissue anchor of a plurality of tissue anchors, the implant includes the plurality of tissue anchors, and the wire, line, contracting member, etc. extends longitudinally through the lumen of each tissue anchor of the plurality of tissue anchors, such that each of the tissue anchors is freely slidable along the wire, line, contracting member, etc.

In an application, the tissue anchor includes a rod that has a sharpened distal tip; a first portion extending from the distal tip to a transition site of the rod; and a second portion, continuous with the first portion, and extending from the transition site to a second tip of the rod. In some applications, the tissue-engaging element is defined by the first portion of the rod extending helically around and along the central longitudinal axis of the anchor, and the eyelet is defined at least in part by the second portion of the rod defining an arch that spans laterally across the proximal end of the tissue-engaging element and arches proximally away from the tissue-engaging element.

In an application, the system and/or apparatus includes an implant including a wire, line, contracting member, etc. and the tissue anchor, and the system and/or apparatus further includes a delivery tool for percutaneous implantation of the implant, the delivery tool including a tube and an anchor driver. In some applications, the anchor driver is reversibly coupled/couplable to the eyelet, the anchor is disposed in the tube, the wire, line, contracting member, etc. extends through the tube, and longitudinally through the lumen such that the anchor is freely slidable by the anchor driver along the wire, line, contracting member, etc. The delivery tool and the implant are percutaneously advanceable into a subject.

In an application, the rod is shaped such that the eyelet and a proximal-most turn of the helical tissue-engaging element collectively define a closed loop, and the wire, line, contracting member, etc. extends distally through the closed loop and through the lumen such that the anchor is freely slidable by the anchor driver along the wire, line, contracting member, etc.

In an application, the eyelet has a lateral thickness that is less than two thirds as great as a lateral diameter of the lumen.

In an application, the eyelet is defined at least in part by the second tip of the rod being attached to an attachment site of the rod, the attachment site being within the first portion of the rod.

In an application, the tissue-engaging element includes a plurality of helical turns of the rod. In an application, the plurality of helical turns of the rod include a distal-most helical turn distally delimited by the distal tip of the rod, and a proximal-most helical turn proximally delimited by the transition site. In an application, the second tip of the rod is attached to an attachment site of the rod, the attachment site being partway around the proximal-most helical turn.

In an application, the second tip of the rod is attached to an attachment site of the rod, the attachment site being at least one third around the proximal-most helical turn.

There is further provided, in accordance with an application, a system and/or an apparatus, including an anchor-delivery tube having a distal tubular end portion and a tissue-indicating device coupled to the distal tubular end portion of the anchor-delivery tube. In some applications, the tissue-indicating device includes a radiopaque material shaped to define a tubular body having a central longitudinal axis and configured for placement in contact with an annulus of a native heart valve of a subject, the tubular body including a compressible element. In some applications, the tissue-indicating device is compressible into a compressed state responsively to contact with tissue of the native heart valve, and expandable from the compressed state in an absence of force applied to the tissue-indicating device.

The system can also include one or more tissue anchors or at least one tissue anchor for implantation along the annulus of the valve of the subject.

In some applications, the tissue-indicating device is configured to provide a guide for implantation of the tissue anchor along the annulus during implantation of the tissue anchor and is retrievable following the implantation of the tissue anchor.

In an application, the tissue-indicating device is shaped to define a tubular stent body.

In an application, the tissue-indicating device includes a superelastic material. In an application, the compressible element includes a coiled element. In an application, the compressible element includes a spring. In an application, the compressible element includes a strut element compressible along a longitudinal axis of the anchor-delivery tube.

In an application, the tissue-indicating device includes:
a proximal tube element,
a distal tube element, and
   a linking element coupling together the proximal and distal tube elements, the distal tube element is spaced at a first distance from the proximal tube element during a resting state of the tissue-indicating device, and the distal tube element is spaced at a second distance from the proximal tube element during the compressed state of the tissue-indicating device, the second distance being shorter than the first distance.

In an application, the proximal tube element is fixedly coupled to the distal tubular end portion of the anchor-delivery tube.

In an application, the linking element includes a coiled element. In an application, the linking element includes a spring. In an application, the linking element includes a strut element.

In an application, the linking element includes first and second scaffolding elements, at least respective parts of the first and second scaffolding elements are spaced apart from each other during the resting state of the tissue-indicating device, and the respective parts of the first and second scaffolding elements are moved closer together other during the compressed state of the tissue-indicating device.

In an application, during a resting state of the tissue-indicating device, the tissue-indicating device assumes a first height, and during the compressed state, the tissue-indicating device assumes a second height that is shorter than the first height.

In an application, the proximal tube element and the linking element surround the distal tubular end portion of the anchor-delivery tube, and the linking element is compressible longitudinally proximally along the distal tubular end portion of the anchor-delivery tube to draw the distal tube element toward the proximal tube element.

In an application, the proximal tube element is fixedly coupled to the distal tubular end portion of the anchor-delivery tube.

In an application, proximal tube element surrounds the distal tubular end portion of the anchor-delivery tube, and the linking element is disposed distally to a distal end of the anchor-delivery tube and is compressible longitudinally proximally to draw the distal tube element toward the proximal tube element.

In an application, the proximal tube element is fixedly coupled to the tubular distal end portion of the anchor-delivery tube.

In an application, the compressible element includes a plurality of struts arranged in a braided arrangement in which, during a resting state of the tissue-indicating device, the tissue-indicating device assumes a first height, and during the compressed state, the tissue-indicating device assumes a second height that is shorter than the first height.

In an application, during the compressed state, the tissue-indicating device shortens longitudinally and expands radially.

In an application, the plurality of struts includes a subset of rounded struts at a distal end of the tissue-indicating device.

In an application, the at least one tissue anchor includes a plurality of tissue anchors, and the system and/or apparatus further includes a contracting member (e.g, wire, line, suture, etc.) slidably coupled to the plurality of tissue anchors, and each the plurality of tissue anchors and the contracting member are configured for delivery through the anchor-delivery tube.

In an application, the distal tubular end portion of the anchor-delivery tube is shaped so as to define a lateral slit extending proximally from a distal end of the anchor-delivery tube, and the slit allows the contracting member, but not the tissue anchors, to exit the anchor-delivery tube laterally, proximally from the distal end of the tube.

In an application, the tissue-indicating device is shaped so as to define a slit which is disposed in alignment with the lateral slit of the anchor-delivery tube.

There is further provided, in accordance with an application, a system and/or an apparatus, including a plurality of tissue anchors, a contracting member (e.g, wire, line, suture, etc.) slidably coupled to the plurality of tissue anchors, and a fastener configured to be couplable to the contracting member in a vicinity of a terminal tissue anchor of the plurality of tissue anchors. The fastener, in a closed state or locked state thereof, is configured to restrict movement of the contracting member with respect to the plurality of tissue anchors.

In some applications, the system and/or apparatus includes a contracting-member-covering device that is couplable to the contracting member in the vicinity of the terminal tissue anchor, the contracting-member-covering device being configured to cover excess portions of the contracting member following (a) implantation of the terminal anchor, (b) transitioning the fastener into the closed/locked state, and (c) cutting of the contracting member proximally to the terminal anchor.

In an application, the fastener is separate from the contracting-member-covering device.

In an application, the contracting member includes a metal wire. In an application, the contracting-member-covering device is configured to cover a free end of the contracting member.

In an application, the contracting-member-covering device includes a housing and the contracting member passes longitudinally through the housing. In some applications, the housing includes at least first and second deflectable wires passing transversely through the housing and alongside a portion of the contracting member, the first and second wires being (1) in a first position in which the first and second deflectable wires do not engage the contracting member, and (2) transitionable into a second position in which the first and second wires deflect to assume a configuration which changes a conformation of the portion of the contracting member in a manner which draws additional portions of the contracting member into the housing.

In an application, the system and/or apparatus further includes a tube positionable between the contracting member and the first and second deflectable wires in the first position, the tube being (1) configured to restrict the first and second deflectable wires from transitioning to the second position, and (2) removable from within the housing to allow for the first and second deflectable wires to transition to the second position.

In an application, in the first position: at least a majority of the first deflectable wire is disposed above the portion of the contracting member, and at least a majority of the second deflectable wire is disposed below the portion of the contracting member.

In an application, in the second position: the at least the majority of the first deflectable wire pushes down on the portion of the contracting member, and the at least the majority of the second deflectable wire pushes upwardly against the portion of the contracting member.

In an application, in the first position, the first and second deflectable wires assume a loaded configuration in which each of the first and second deflectable wires assumes a curved configuration, and, in the second position, the first and second deflectable wires assume a straight configuration.

In an application, in the second position, the first and second deflectable wires each assume a length that is greater than a width of the housing, and the first and second deflectable wires each define at least one crimping region configured to shorten the length of the first and second deflectable wires in the second position.

In an application, the contracting-member-covering device includes a housing, and the contracting-member passes through the housing and through an opening in the housing.

In an application, the contracting-member-covering device includes an expandable fabric that is coupled to the housing in a vicinity of the opening, and the expandable fabric is configured to expand to cover the excess portions of the contracting member exiting the housing via the opening.

In an application, the contracting-member-covering device includes a spring coupled to the housing in a vicinity of the opening, and the spring is configured to expand to cover the excess portions of the contracting member exiting the housing via the opening.

In an application, the spring includes a metal spring that is covered with fabric.

In an application, the spring includes first and second scaffolding elements which are disposed opposite each other, and the first and second scaffolding elements are configured to expand laterally away from a wall of the housing that defines the opening.

In an application, the system and/or apparatus further includes a delivery tool configured to deliver the housing, and, when the delivery tool is coupled to the housing, the delivery tool applies a force to the housing to compress the spring, and when the delivery tool is decoupled from the housing, the spring is allowed to expand.

In an application, the fastener is disposed within the housing.

In an application, the fastener includes a clamping structure that (a) is biased toward assuming the closed state in which the clamping structure is configured to clamp onto the contracting member passed through the housing, and (b) can be flexed to an open state in which the contracting member is movable with respect to the housing.

In an application, the system and/or apparatus further includes a delivery tool configured to deliver the housing, and the delivery tool further includes a stop removably coupled to the fastener and configured to maintain the fastener in the open state.

In an application, the system and/or apparatus further includes a contracting-member-cutting tool including a moveable cutting element having a sharp edge, and movement of the stop hammers the stop against the moveable cutting element such that movement of the moveable cutting element severs the contracting member.

In an application, the contracting-member-covering device is configured to draw the excess portions of the contracting member within the housing.

In an application, the contracting-member-covering device includes a spiral spring movable along a path, the contracting member passes alongside an end of the spiral spring, and the spiral spring is moveable in a spiral to push the contracting member with the end of the spiral spring along the path and away from the opening of the housing.

In an application, the end of the spiral spring includes a cross-beam, and the cross-beam is configured to push the contracting member along the path.

In an application, the fastener is disposed within the housing, and the system and/or apparatus further includes a delivery tool configured to deliver the housing. In some applications, the delivery tool further includes a stop removably coupled to the fastener, the stop being configured to (a) maintain the fastener in the open state when the delivery tool is coupled to the housing and (b) maintain the cross-beam in a position in which the cross-beam does not engage the contracting member, and the cross-beam is configured to push the contracting member along the path in an absence of the stop.

In an application, the contracting-member-covering device includes a flap that is disposed external to the housing, and the flap is moveable from (1) an open state in which the flap is distanced from the housing, to (2) a closed state in which the flap is disposed alongside the housing in a manner in which the flap pushes the excess portions of the contracting member exiting the housing via the opening and an end of the contracting member, against an external surface of the housing.

In an application, the flap includes two metal scaffolding beams disposed opposite each other.

In an application, a piece of fabric is coupled to and extends between the two metal scaffolding beams in a manner in which, in the closed state of the flap, the fabric covers the excess portions of the contracting member and the end of the contracting member.

In an application, the flap further includes a cross-beam extending between the two metal scaffolding beams, and, in the closed state of the flap, the cross-beam pushes the excess portions of the contracting member exiting the housing via the opening and the end of the contracting member, against the external surface of the housing.

There is further provided, in accordance with an application, a system and/or an apparatus, including a plurality of tissue anchors, a contracting member (e.g, wire, line, suture, etc.) slidably coupled to the plurality of tissue anchors, and a fastener configured to be couplable to the contracting member in a vicinity of a terminal tissue anchor of the plurality of tissue anchors, the fastener, in a closed state thereof, being configured to restrict movement of the contracting member with respect to the plurality of tissue anchors.

In some applications, the fastener includes a housing shaped so as to define (a) a first lumen for passage therethrough of the contracting member, the first lumen being along a longitudinal axis of the housing, and (b) a second lumen disposed at a nonzero angle with respect to the first lumen. In some applications, a locking ball is moveable within the second lumen from a first position in which the locking ball does not apply pressure to the contracting member, to a second position in which the locking ball applies pressure to the contracting member so as to restrict movement of the contracting member.

In some applications, an advancement pin disposed within the second lumen proximally to the locking ball, the advancement pin being configured to advance the locking ball from the first position to the second position. In an application, in the second position, the locking ball is configured to contact a portion of the contracting member.

In an application, the second lumen is in fluid communication with a portion of the first lumen.

In an application, the second lumen has a threaded surface, the advancement pin has a threaded outer surface, and the threaded surfaces facilitate locking of the locking ball in the second position.

In an application, the second lumen has a first sublumen sized to accommodate the advancement pin, and a second sublumen sized to accommodate the locking ball, and the first sublumen is disposed proximally to the second sublumen.

In an application, the system and/or apparatus further includes a delivery tool configured to deliver the fastener along the contracting member and to apply torque to the advancement pin.

There is further provided, in accordance with an application, a system and/or an apparatus, including: a plurality of tissue anchors; a contracting member (e.g, wire, line, suture, etc.) slidably coupled to the plurality of tissue anchors; and a fastener configured to be couplable to the contracting member in a vicinity of a terminal tissue anchor of the plurality of tissue anchors, the fastener, in a closed state thereof, being configured to restrict movement of the contracting member with respect to the plurality of tissue anchors.

In some applications, the fastener includes: a housing shaped so as to define a lumen for passage therethrough of the contracting member, and a contracting-member-lock-and-cutter element slidable within the lumen of the housing. In some applications, the contracting-member-lock-and-cutter element includes first and second arms coupled together at respective distal portions thereof at a distal portion of the contracting-member-lock-and-cutter element, the first and second arms being compressible toward each other when the contracting-member-lock-and-cutter element is advanced within the lumen of the housing such that the contracting-member-lock-and-cutter element assumes a closed state.

In some applications, the first and second arms each are shaped to as to define respective cutting elements at respective proximal ends of the first and second arms, and respective protrusions at respective middle portions of the first and second arms.

In some applications, there is also a pusher shaped so as to push the contracting-member-lock-and-cutter element within the lumen of the housing. In some applications, the contracting member passes through the lumen of the housing, through an opening defined by the distal portion of the contracting-member-lock-and-cutter element, and through an opening defined by the pusher.

In some applications, a wall of the lumen of the housing pushes against the first and second arms of the contracting-member-lock-and-cutter element such that they compress toward each other when the contracting-member-lock-and-cutter element is pushed within the lumen of the housing. In some applications, in the closed state, (a) the respective cutting elements of the contracting-member-lock-and-cutter element come together in order to cut the contracting member, and, at the same time, (b) the respective protrusions of the contracting-member-lock-and-cutter element come together in order to compress the contracting member therebetween and facilitate locking of the contracting member by restricting movement of the contracting member.

In an application, the housing is configured to cover a free end of the contracting member following cutting by the cutting elements.

There is further provided, in accordance with an application, a system and/or an apparatus, including a plurality of tissue anchors; a contracting member (e.g, wire, line, suture, etc.) slidably coupled to the plurality of tissue anchors; and a fastener configured to be couplable to the contracting member in a vicinity of a terminal tissue anchor of the plurality of tissue anchors. The fastener, in a closed state thereof, is configured to restrict movement of the contracting member with respect to the plurality of tissue anchors.

In some applications, the fastener includes a housing including an inner wall shaped so as to define (a) a lumen for passage therethrough of the contracting member, (b) a distal conical surface, and (c) a proximal portion of the inner wall that is threaded. In some applications, the fastener also includes a threaded screwing element having a threaded surface that is engageable with the threaded proximal portion of the inner wall of the housing and longitudinally screwable within the lumen of the housing.

In some applications, a contracting-member lock is coupled to the threaded screwing element and moveable within the lumen of the housing responsively to screwing of the threaded screwing element. In some applications, the contracting-member lock includes first and second gripping elements disposed on either side of the contracting member, each of the first and second gripping elements defining a tapered surface configured to (1) fit within the distal conical surface of the housing responsively to pushing of the contracting-member lock distally by distal screwing of the threaded screwing element, and thereby (2) compress the contracting member passing through the first and second gripping elements.

In an application, the housing is configured to cover a free end of the contracting member following cutting of the contracting member.

There is further provided, in accordance with an application, a system and/or an apparatus, including a plurality of tissue anchors; a contracting member (e.g, wire, line, suture, etc.) slidably coupled to the plurality of tissue anchors; and a fastener configured to be couplable to the contracting member in a vicinity of a terminal tissue anchor of the plurality of tissue anchors. The fastener, in a closed state thereof, is configured to restrict movement of the contracting member with respect to the plurality of tissue anchors.

In some applications, the fastener includes a housing including an inner wall shaped so as to define a lumen for passage therethrough of the contracting member. The lumen can be shaped in part so as to define a conical surface having a wide proximal portion and a narrow distal portion having a narrow surface at a distal end of the conical surface.

In some applications, the fastener includes a distal spring-coupling element at a distal end of the lumen, and a proximal spring-coupling element at a proximal end of the lumen and disposed proximally to the conical surface. A spring can be coupled to the distal and proximal spring-coupling elements.

In some applications, at least one inwardly-compressible element is coupled to the spring at a site along the spring that is disposed within a space defined by the conical surface, the at least one inwardly-compressible element being disposed alongside the contracting member.

In some applications, in an open state of the fastener, the proximal spring-coupling element is in a proximal position in which the spring is pulled into a stretched state between the proximal and distal spring-coupling elements in which the at least one inwardly-compressible element is disposed in a space defined by the wide portion of the conical surface and does not apply inward pressure to the contracting member.

In some applications, in a closed state of the fastener, the proximal spring-coupling element is in a distal position in which the spring assumes a relaxed state in which the at least one inwardly-compressible element is disposed in the narrow portion of the conical surface and applies inward pressure to the contracting member responsively to pressure applied to the at least one inwardly-compressible element by the narrow surface of the conical surface.

In an application, the proximal spring-coupling element is shaped so as to define a threaded coupling site for coupling thereto of a tool which maintains the fastener in the open state, and upon decoupling of the tool from the proximal spring-coupling element by unscrewing, the spring returns to its resting state and the fastener assumes the closed state.

In an application, the spring is shaped so as to define at least one slit for inward movement of the at least one inwardly-compressible element.

In an application, the at least one inwardly-compressible element includes a plurality of inwardly-compressible spheres surrounding the contracting member.

In an application, the housing is configured to cover a free end of the contracting member following cutting of the contracting member.

There is further provided, in accordance with an application, a method, including positioning an anchor-delivery tube having a distal tubular end portion against tissue of an annulus of a valve of a subject, the distal tubular end portion being coupled to a tissue-indicating device. In some applications, the tissue-indicating device includes a radiopaque material shaped to define a tubular body having a central longitudinal axis and configured for placement in contact with an annulus of a native heart valve of the subject. The tubular body can include a compressible element.

In some applications, the tissue-indicating device is compressible into a compressed state responsively to contact with tissue of the native heart valve, and expandable from the compressed state in an absence of force applied to the tissue-indicating device.

In some applications, the method further includes determining a presence of tissue by pressing the compressible element against the tissue and imaging the compressed state of the compressible element.

In some applications, the method includes, responsively to the determining, implanting at least one tissue anchor along the annulus of the valve of the subject while using the tissue-indicating device as a guide for implantation of the tissue anchor along the annulus.

In some applications, the method also includes retrieving the tissue-indicating device the implanting of the tissue anchor.

In some applications, implanting at least one tissue anchor includes implanting at least two tissue anchors coupled together by a contracting member (e.g, wire, line, suture, etc.), and the method further includes allowing the contracting member, but not the tissue anchors, to exit the anchor-delivery tube laterally, proximally from the distal end of the tube via a lateral slit extending proximally from a distal end of the anchor-delivery tube. The above method(s) can be performed on a living animal or on a simulation, such as on a cadaver, cadaver heart, simulator (e.g. with the body parts, heart, tissue, etc. being simulated), etc.

There is further provided, in accordance with an application, a method, including implanting at an annulus of a heart of a patient an implant including (1) a plurality of tissue anchors, and (2) a contracting member (e.g, wire, line, suture, etc.) slidably coupled to the plurality of tissue anchors.

In some applications, the method also includes restricting movement of the contracting member with respect to the plurality of tissue anchors by coupling a fastener to the contracting member in a vicinity of a terminal tissue anchor of the plurality of tissue anchors.

In some applications, the method includes cutting the contracting member subsequently to the restricting of the movement.

In some applications, the method includes covering excess portions of the contracting member by coupling a contracting-member-covering device to the contracting member in the vicinity of the terminal tissue anchor.

In some applications, covering excess portions of the contracting member includes covering a free end of the contracting member.

In some applications, the contracting-member-covering device includes the fastener, and restricting movement of the contracting member includes restricting movement by the coupling of the restricting movement of the contracting member to the contracting member. The above method(s) can be performed on a living animal or on a simulation, such as on a cadaver, cadaver heart, simulator (e.g. with the body parts, heart, tissue, etc. being simulated), etc.

There is further provided, in accordance with an application, a tissue anchor usable with or for use with an anchor driver. The anchor includes a tissue-engaging element. In some applications, the tissue-engaging element can be helical and configured to define a central longitudinal axis of the anchor, having a rod with a sharpened distal tip, and to be driven into tissue of a subject. The anchor also includes a head coupled to a proximal end of the tissue-engaging element. The head can include a driver interface, configured to be reversibly engaged by the anchor driver, and an eyelet or other connector (e.g, connectable to a wire, line, contracting member, tether, suture, etc.). The eyelet can define an aperture through which a wire may be threaded. The rod has a height across a first sectional axis, and a width across a second sectional axis orthogonal to the first sectional axis, wherein the width of the rod is greater that its height.

In some applications, the rod has an elliptic cross-sectional profile. In an application, the width of the rod is 1.3-5 times as great as the height of the rod. In an application, the width of the rod is 1.4-3 times as great as the height of the rod. In an application, the width of the rod is 1.5-2.5 times as great as the height of the rod. In an application, the width of the rod is 1.5-2.1 times as great as the height of the rod. In an application, the width of the rod is 1.6-2 times as great as the height of the rod. In an application, the first sectional axis is parallel to the central longitudinal axis. In some applications, the first sectional axis is angled with respect to the central longitudinal axis.

There is further provided, in accordance with an application, a system and/or an apparatus including a tissue anchor usable with or for use with an anchor driver. The anchor includes a tissue-engaging element. In some applications, the tissue-engaging element can be helical and be configured to define a central longitudinal axis of the anchor, having a sharpened distal tip, and to be driven into tissue of a subject. Other tissue-engaging element configurations are also possible. The anchor also includes a head coupled to a proximal end of the tissue-engaging element. The head can include a driver interface, configured to be reversibly engaged by the anchor driver, and a ring comprising a channel. The channel defines a channel axis which is orthogonal to an axis that is parallel to the central longitudinal axis. The ring circumscribes and is rotatable about the central longitudinal axis. The channel axis is offset from the central longitudinal axis, forming a gap between an innermost edge of the channel and the central longitudinal axis.

In some applications, the head further comprises a proximal head segment that includes the driver interface and is positioned proximal to the ring, wherein the proximal head segment is immovable with respect to the tissue-engaging element.

In some applications, the head further comprises a distal head segment positioned distal to the ring, wherein the distal head segment is immovable with respect to the tissue-engaging element.

In some applications, the tissue anchor is a first tissue anchor of a plurality of tissue anchors, and the system and/or apparatus further includes an annuloplasty implant comprising the plurality of tissue anchors, and a wire extending through the channels of the plurality of tissue anchors. In an application, the diameter of the channel is not greater than 5 percent of the thickness of the wire.

There is further provided, in accordance with an application, a system and/or an apparatus including a tissue anchor usable with or for use with an anchor driver. The anchor includes a tissue-engaging element. The tissue-engaging element can be helical and be configured to define a central longitudinal axis of the anchor, having a sharpened distal tip, and to be driven into tissue of a subject. Other tissue-engaging element configurations are also possible. The anchor also includes a head coupled to a proximal end of the tissue-engaging element. The head can include a driver interface, configured to be reversibly engaged by the anchor driver, and a stem having a stem outer diameter, wherein the stem is coaxial with the central longitudinal axis. The head also includes a ring defining a ring inner diameter. The ring is disposed around the stem, is rotatable about the central longitudinal axis, and is laterally movable with respect to the stem.

In an application, the ring inner diameter is at least 1.3 times as great as the stem outer diameter. In an application, the ring inner diameter is 1.3-5 times as great as the stem outer diameter. In an application, the ring inner diameter is 1.4-3 times as great as the stem outer diameter. In an application, the ring inner diameter is 1.5-2.5 times as great as the stem outer diameter. In an application, the ring inner diameter is 1.5-2.1 times as great as the stem outer diameter. In an application, the ring inner diameter is 1.6-2 times as great as the stem outer diameter.

In some applications, the head further comprises a proximal head segment that includes the driver interface and is positioned proximal to the ring, and a distal head segment positioned distal to the ring, wherein the proximal head segment and the distal head segment are immovable with respect to the tissue-engaging element.

In some applications, the proximal head segment comprises a proximal groove, wherein the distal head segment comprises a distal groove, and wherein the proximal groove and the distal groove are aligned with each other, and are parallel to the central longitudinal axis.

In some applications, the tissue anchor is a first tissue anchor of a plurality of tissue anchors, and the system and/or apparatus further includes an annuloplasty implant comprising the plurality of tissue anchors, and a wire threaded through the rings of the plurality of tissue anchors.

In some applications, the proximal groove and the distal groove are configured to accommodate at least a portion of the wire.

In some applications, the head has an outer diameter that is greater than an outer diameter of the tissue-engaging element. In some applications, the difference between the outer diameter of the head and the outer diameter of the tissue-engaging element is at least as great as twice the thickness of the wire.

In some applications, the system and/or apparatus further includes a delivery tube comprising a flexible tube that defined a tube inner diameter, wherein the tube inner diameter is no more than 20 percent greater than an outer diameter of the ring. In an application, the tube inner diameter is no more than 10 percent greater than the outer diameter of the ring. In an application, the tube inner diameter is no more than 5 percent greater than the outer diameter of the ring.

There is further provided, in accordance with an application, a system and/or an apparatus including a tissue anchor usable with or for use with an anchor driver. The anchor includes a tissue-engaging element. The tissue-engaging element can be configured in a variety of ways. For example, the tissue-engaging element can be configured to define a central longitudinal axis of the anchor, having a sharpened distal tip, and to be driven into tissue of a subject. The anchor also includes a head coupled to a proximal end of the tissue-engaging element. The head includes a wire tensioning mechanism for applying tension to a wire. The wire tensioning mechanism can include a housing and a spool.

The housing includes a housing base portion, a housing top portion defining a top opening, a sidewall extending between the housing base portion and the housing top portion, and an inner chamber defined between the housing base portion, the sidewall. The housing top portion includes a complementary locking interface. The sidewall includes at least one side opening. The inner chamber has an inner chamber diameter.

The spool is disposed within the inner chamber and has a spool diameter. The spool includes a spool base facing the housing base portion, a spool top portion facing the housing top portion, a spool central lumen which is coaxial with the central longitudinal axis, and a channel defining a channel axis which is orthogonal to an axis parallel to the central longitudinal axis. The spool top portion includes a spool locking interface configured to releasably engage with the complementary locking interface, and a spool driving interface facing the top opening. The channel axis is offset from the spool central lumen.

The wire tensioning mechanism also includes a spring disposed between the housing and the spool. The housing can include a driver interface, configured to be reversibly engaged by the anchor driver, and a stem extending through the spool central lumen between the tissue-engaging element and the driver interface.

The wire tensioning mechanism is configured to transition between a locked configuration, in which the spool locking interface is engaged with the complementary locking interface, thereby preventing the spool from rotating relative to the housing, and an unlocked configuration, in which the spool locking interface is released from the complementary locking interface, thereby allowing the spool to be rotated relative to the housing. The spring is configured, in a free state thereof, to bias the spool to engage with the housing to form a locked configuration of the wire tensioning mechanism.

In some applications, the spring is disposed between the housing base portion and the spool base. In some applications, the housing base portion comprises a base groove, and wherein the spring is positioned within the base groove. In an application, the spring is a disc spring.

In some applications, the housing top portion further comprises a housing top interface.

In some applications, the system and/or apparatus further comprises a wire, wherein the wire extends through the at least one side opening and through the channel. In an application, the difference between the inner chamber diameter and the spool diameter is at least 200% greater than the diameter of wire. In an application, the difference between the inner chamber diameter and the spool diameter is at least 250% greater than the diameter of wire. In an application, the difference between the inner chamber diameter and the spool diameter is at least 300% greater than the diameter of wire. In an application, the difference between the inner chamber diameter and the spool diameter is at least 400% greater than the diameter of wire. In an application, the diameter of the channel is no more than 5 percent greater than the outer diameter of the ring.

In some applications, the system and/or apparatus further comprises a stopper attached to an end of the wire and disposed between the channel and the sidewall, wherein the stopper has a diameter greater than the diameter of the channel. In some applications, the wire is attached to the spool via a closed loop extending through the channel and around a portion of spool.

In some applications, the spool further comprises a spool side recess, and the stem further comprises a protrusion configured to engage with the spool side recess in the locked configuration, thereby preventing rotational movement of the tissue-engaging element with respect to the spool, and to disengage therefrom in the unlocked configuration, thereby allowing the tissue-engaging element to rotate with respect to the spool.

In some applications, the housing is rotatable about the central longitudinal axis with respect to the tissue-engaging element.

In some applications, the anchor further comprises a flange disposed around the proximal end of the tissue engaging element and configured to support the housing.

In some applications, the at least one side opening comprises two side openings, opposite to each other.

In some applications, the tissue anchor is one of a plurality of tissue anchors. In some applications, the tissue anchor is a primary tissue anchor, and wherein the apparatus further comprises at least one secondary tissue anchor for use with the anchor driver. The secondary tissue anchor can be similar to the primary tissue anchor in that the secondary tissue anchor also includes a tissue-engaging element, that can be referred to as a secondary tissue-engaging element.

The secondary tissue-engaging element can similarly have a secondary sharpened distal tip and can be similarly configured to be driven into tissue of a subject. Similarly, the secondary anchor also includes a secondary head coupled to a proximal end of the secondary tissue-engaging element, wherein the head can include driver interface configured to be reversibly engaged by the anchor drive. However, the secondary tissue anchor may differ from the primary anchor in that the secondary anchor is devoid of a wire tensioning mechanism that includes a spool.

In some applications, the system also includes an adjustment tool that comprises an adjustment interface. The adjustment interface is configured to engage with the spool driving interface. The adjustment tool is configured to push the spool against the spring to transition the wire tensioning mechanism to the unlocked configuration and is also configured to rotate the spool about the central longitudinal axis in the unlocked configuration. In some applications, the system also includes a retainment tool that comprises a retainment interface. The retainment interface is configured to engage with the housing top interface.

There is further provided, in accordance with an application, a system and/or an apparatus including a wire uptake assembly. The wire uptake assembly includes a sleeve defining a central longitudinal axis, and a gripper which is at least partially disposed within the sleeve. The sleeve comprises a sleeve lumen having a lumen diameter. The gripper includes a gripper distal portion having a gripper distal diameter, and a gripper narrow portion having a narrow diameter. The gripper is axially movable with respect to the sleeve. The gripper distal diameter is smaller than the lumen diameter. The narrow diameter is smaller than the gripper distal diameter.

In some applications, the gripper distal portion comprises a rounded gripper distal end. In some applications, the gripper distal portion comprises a tapering gripper distal end.

In some applications, the gripper distal portion and the gripper narrow portion are symmetrically disposed around the central longitudinal axis. In some applications, the gripper distal portion and the gripper neck portion are asymmetrically disposed around the central longitudinal axis.

In some applications, the system and/or apparatus further includes a wire having a free state wire diameter. In an application, the wire is compressible to at least 95% of its free state wire diameter. In an application, the wire is compressible to at least 90% of its free state wire diameter. In an application, the wire is compressible to at least 80% of its free state wire diameter. In an application, the wire is compressible to at least 60% of its free state wire diameter.

In an application, the difference between the lumen diameter and the gripper distal diameter is smaller than the wire diameter. In an application, the difference between the lumen diameter and the gripper distal diameter is smaller than 90% of the wire diameter. In an application, the difference between the lumen diameter and the gripper distal diameter is smaller than 70% of the wire diameter. In an application, the difference between the lumen diameter and the gripper distal diameter is smaller than 30% of the wire diameter. In an application, the difference between the lumen diameter and the gripper distal diameter is smaller than 10% of the wire diameter.

In an application, the difference between the lumen diameter and the narrow diameter is at least as great as the wire diameter. In an application, the difference between the lumen diameter and the narrow diameter is greater than 110% of the wire diameter. In an application, the difference between the lumen diameter and the narrow diameter is greater than 120% of the wire diameter. In an application, the difference between the lumen diameter and the narrow diameter is greater than 130% of the wire diameter. In an application, the difference between the lumen diameter and the narrow diameter is greater than 150% of the wire diameter. In an application, the difference between the lumen diameter and the narrow diameter is greater than 200% of the wire diameter.

In some applications, the gripper further comprises a gripper proximal portion having a gripper proximal diameter, wherein the lumen diameter is at least as great as the gripper proximal diameter, and wherein the gripper distal diameter is smaller than the gripper proximal diameter.

In an application, the difference between the lumen diameter and the gripper proximal diameter is smaller than the wire diameter. In an application, the difference between the lumen diameter and the gripper proximal diameter is not greater than 95% of the wire diameter. In an application, the difference between the lumen diameter and the gripper proximal diameter is not greater than 90% of the wire diameter. In an application, the difference between the lumen diameter and the gripper proximal diameter is not greater than 85% of the wire diameter. In an application, the difference between the lumen diameter and the gripper proximal diameter is not greater than 80% of the wire diameter.

In some applications, the system and/or apparatus further includes a catheter defining a catheter lumen, wherein the wire uptake assembly is at least partially disposed within the catheter lumen, and wherein at least one component of the wire uptake assembly is axially movable with respect to the catheter.

There is further provided, in accordance with an application, a method, including inserting a wire into a sleeve lumen of a sleeve of a wire uptake assembly. The wire uptake assembly comprises the sleeve having a sleeve distal end and a gripper. The gripper comprises a gripper distal portion disposed distal to a sleeve distal end, and a gripper narrow portion that is partially disposed within the sleeve lumen and is partially exposed out of the sleeve.

In some applications, the method further includes pulling the gripper until the gripper distal portion at least partially extends into the sleeve lumen, and is pressing the wire between the gripper distal portion and the sleeve so as to restrict axial movement of the wire with respect to the sleeve. In some applications, the method further includes pulling the wire uptake assembly, thereby pulling the wire attached thereto.

In some applications, inserting the wire into the sleeve lumen is performed such that the wire is inserted until it is blocked from further advancement by a gripper proximal portion of the gripper, which is disposed within the sleeve lumen. The gripper proximal portions has a gripper proximal diameter such that the difference between the diameter of the sleeve lumen and the gripper proximal diameter, is smaller than the diameter of the wire.

In some applications, the method further includes pushing the gripper distally, until the wire is released from the wire uptake assembly.

There is further provided, in accordance with an application, a method, including implanting, at an annulus of a heart of a patient, a docking apparatus comprising an implant. The implant includes (1) a plurality of tissue anchors, and (2) a contracting member (e.g, wire, line, suture, etc.) slidably coupled to the plurality of tissue anchors.

The method further includes contracting the implant so as to reduce the size of the annulus of the heart valve. The method further includes delivering a prosthetic valve of the heart valve in a crimped state thereof. The method further includes expanding the prosthetic valve against the annulus, so as to anchor it to the annulus against the docking apparatus under pressure under pressure.

In some applications, each one of the plurality of anchors comprises a tissue-engaging element having a sharpened distal tip, wherein implanting the plurality of anchors includes sequentially driving the anchors into the tissue of the annulus.

In some applications, each one of the plurality of anchors comprises a head comprising a driving interface. In some applications, driving each anchor into the tissue of the annulus comprises engaging an anchor driver with the driving interface, and rotating the anchor driver so as to rotate the anchor about a central longitudinal axis defined by its tissue-engaging element. In some applications, the head of at least two anchors comprises an eyelet, and wherein the contracting member is threaded through the eyelets.

In an application, the heart valve is the mitral valve. In an application, the heart valve is the tricuspid valve.

There is further provided, in accordance with an application, a system and/or an apparatus including a plurality of tissue anchors usable with or for use with an anchor driver, and a wire assembly. Each anchor includes a tissue-engaging element. The tissue-engaging element can be configured in a variety of ways, for example, to define a central longitudinal axis of the anchor, having a sharpened distal tip, and to be driven into tissue of a subject. The anchor also includes a head coupled to a proximal end of the tissue-engaging element. The head can include a driver interface, configured to be reversibly engaged by the anchor driver. The wire assembly extends through openings formed in the heads of the plurality of anchors. The wire assembly includes a main wire comprising a plurality of alternating portions coated by radiopaque coating, and a plurality of alternating radiolucent portions.

In some applications, the opening of the head of an anchor is an eyelet. In some applications, the opening of the head of an anchor is a channel.

In some applications, the main wire is formed of a metal material, selected from titanium, nitinol, platinum, stainless steel, and/or alloys and/or combinations thereof.

In some applications, the radiopaque coating comprises at least one biocompatible metal material, selected from: gold, platinum, titanium, silver, tantalum, barium, bismuth, iridium, tungsten, rhenium, osmium, iridium, palladium, and biocompatible oxides, and/or combinations thereof.

There is further provided, in accordance with an application, a system and/or an apparatus including a plurality of tissue anchors usable with or for use with an anchor driver, and a wire assembly. Each anchor includes a tissue-engaging element. The tissue-engaging element can be configured in a variety of ways, for example, to define a central longitudinal axis of the anchor, having a sharpened distal tip, and to be driven into tissue of a subject. The anchor also includes a head coupled to a proximal end of the tissue-engaging element. The head can include a driver interface, configured to be reversibly engaged by the anchor driver. The wire assembly extends through openings formed in the heads of the plurality of anchors. The wire assembly includes a main wire, and a plurality of additional wires woven around the main wire. At least one portion of the main wire is coated by a radiopaque coating.

In some applications, the opening of the head of an anchor is an eyelet. In some applications, the opening of the head of an anchor is a channel.

In some applications, the main wire comprises a plurality of alternating portions coated by radiopaque coating and a plurality of alternating portions which are radiolucent portions. In some applications, the plurality of additional wires is radiolucent.

In some applications, the main wire and each one of the plurality of additional wires is formed of a metal material, selected from titanium, nitinol, platinum, stainless steel, and/or alloys and/or combinations thereof.

In some applications, plurality of additional wires comprises at least six additional wires, woven around the main wire. In some applications, each one of the plurality of additional wires comprises an inner wire assembly, wherein each inner wire assembly comprise a plurality of inner wires. In some applications, each plurality of inner wires comprises at least seven inner wires.

In some applications, each inner wire is formed of a metal material, selected from titanium, nitinol, stainless steel, and/or combinations thereof.

In some applications, the main wire comprises a central inner wire assembly comprising a plurality of central inner wires. In some applications, at least one portion of the central inner wire assembly is coated by the radiopaque coating along an outer diameter thereof. In some applications, the plurality of central inner wires comprises at least seven central inner wires.

There is further provided, in accordance with an application, a system and/or an apparatus including a plurality of tissue anchors usable with or for use with an anchor driver, and a wire assembly. Each anchor includes a tissue-engaging element. The tissue-engaging element can be configured in a variety of ways, for example, to define a central longitudinal axis of the anchor, having a sharpened distal tip, and to be driven into tissue of a subject. The anchor also includes a head coupled to a proximal end of the tissue-engaging element. The head can include a driver interface, configured to be reversibly engaged by the anchor driver. The wire assembly extends through openings formed in the heads of the plurality of anchors. The wire assembly includes a main wire, at least one additional wire, and at least one composite tube comprising at least one radiopaque material, wherein the at least one additional wire and the at least one composite tube are woven around the main wire.

In some applications, the opening of the head of an anchor is an eyelet. In some applications, the opening of the head of an anchor is a channel.

In some applications, the at least one composite tube includes an inner core comprising at least one first material, and an outer sheath comprising at least one layer comprising at least one second material, wherein the inner core is disposed within a lumen of the outer sheath.

In some applications, the first material is selected from: gold, platinum, titanium, silver, tantalum, palladium, nitinol, and/or combinations and/or alloys thereof. In some applications, the first material is radiopaque, and the second material is radiolucent.

In some applications, each one of the main wire and the at least one additional wire are radiolucent and are formed of a metal material, selected from titanium, nitinol, platinum, stainless steel, and/or alloys and/or combinations thereof.

In some applications, the at least one additional wire comprises at least five additional wires, and the at least five additional wires and the at least one composite tube are woven around the main wire. In some applications, the at least one additional wire comprises at least four additional wires, the at least one composite tube comprises at least two composite tubes, and the at least four additional wires and the at least two composite tubes are woven around the main wire.

There is further provided, in accordance with an application, a system and/or an apparatus including a plurality of tissue anchors usable with or for use with an anchor driver, and a wire assembly. Each anchor includes a tissue-engaging element. The tissue-engaging element can be configured in a variety of ways, for example, to define a central longitudinal axis of the anchor, having a sharpened distal tip, and to be driven into tissue of a subject. The anchor also includes a head coupled to a proximal end of the tissue-engaging element. The head can include a driver interface, configured to be reversibly engaged by the anchor driver. The wire assembly extends through openings formed in the heads of the plurality of anchors. The wire assembly includes a main wire, at least one additional wire, and at least one composite tube comprising at least one radiopaque material, wherein the at least one additional wire, the at least one composite tube, and the main wire are woven or interlaced around each other.

In some applications, the opening of the head of an anchor is an eyelet. In some applications, the opening of the head of an anchor is a channel.

In some applications, the at least one composite tube includes an inner core comprising at least one first material, and an outer sheath comprising at least one layer comprising at least one second material, wherein the inner core is disposed within a lumen of the outer sheath.

In some applications, the first material is selected from: gold, platinum, titanium, silver, tantalum, palladium, nitinol, and/or combinations and/or alloys thereof. In some applications, the first material is radiopaque, and the second material is radiolucent.

In some applications, each one of the main wire and the at least one additional wire are radiolucent and are formed of a metal material, selected from titanium, nitinol, platinum, stainless steel, and/or alloys and/or combinations thereof.

In some applications, the at least one additional wire comprises at least five additional wires, and the at least five additional wires. In some applications, the at least one additional wire comprises at least four additional wires, the at least one composite tube comprises at least two composite tubes, and the at least four additional wires.

There is further provided, in accordance with an application, a system and/or an apparatus, usable or for use with an anchor driver, the system and/or apparatus including an annuloplasty structure that includes a wire, a plurality of anchors, and a plurality of flexible sleeves. A variety of anchor configurations are possible. Each of the anchors of the plurality of anchors includes a tissue-engaging element. In some applications, the tissue-engaging element defines a central longitudinal axis of the anchor, having a sharpened distal tip, and configured to be driven into tissue of a subject and a head. The head can be coupled to the tissue-engaging element via a neck. The head can include a driver interface configured to be reversibly engaged by the anchor driver. The head also defines a head circumferential surface around the longitudinal central axis.

Each of the plurality of flexible sleeves slidably couple a respective anchor of the plurality of anchors to the wire, line, contracting member, etc. In some applications, each of the plurality of flexible sleeves includes a sleeve circumferential portion, a proximal opening dimensioned to expose the driver interface, and a distal opening through which the neck extends. The sleeve circumferential portion is snugly disposed around the head circumferential surface. The anchor is rotatable, around the central longitudinal axis, with respect to the sleeve. Each flexible sleeve also includes at least one an eyelet through which the wire is threaded, thereby slidably coupling the connector to the wire. In some applications, the flexible sleeve comprises a fabric.

In some applications, the eyelet is defined by a patch coupled to the sleeve at upper and lower portions of the patch.

In some applications, the wire is a first wire, and the annuloplasty structure comprises a second wire, each of the sleeves slidably coupling the respective one of the anchors to the first wire and to the second wire. In some applications, the first wire and the second wire are generally parallel with each other.

In an application, for each sleeve, the eyelet is a first eyelet, the first wire is threaded through the first eyelet, thereby slidably coupling the sleeve to the first wire, and the sleeve comprises a second eyelet through which the second wire is threaded, thereby slidably coupling the sleeve to the second wire.

The present invention will be more fully understood from the following detailed description of applications thereof, taken together with the drawings, in which:

BRIEF DESCRIPTION OF THE DRAWINGS

FIGS. 1A-C, 2A-B, and 3A-B are schematic illustrations of examples of a tissue anchor, an implant comprising the anchor, a system comprising the implant, and techniques for use therewith, in accordance with some applications;

FIGS. 4A-H and 5A-C are schematic illustrations of examples of a tissue anchor, an implant comprising the tissue anchor, a system comprising the implant, and techniques for use therewith, in accordance with some applications;

FIGS. 6A-E, 7A-E, 8A-E, 9A-E, 10A-E, 11A-B, 12A-B, 13A-B, and 14A-B are schematic illustrations of examples of tissue anchors, and techniques for use therewith, that are configured to facilitate determination of successful anchoring to a tissue that is not in line-of-sight, in accordance with some applications;

FIGS. 16A-C, 17A-C, 18, and 19A-C are schematic illustrations of example systems for facilitating controlled anchoring of an anchor to tissue, in accordance with some applications;

FIGS. 21A-G, 22A-B, 23A-B, 24, 25, 26, and 27 are schematic illustrations of examples of a tissue anchor, an implant comprising the tissue anchor, a system comping the implant, and techniques for use therewith, in accordance with some applications;

FIGS. 28A-B, 29A-B, 30, 31A-B, 32, 33, and 34A-B are schematic illustrations of examples of respective systems for facilitating a determination of successful (e.g, complete) anchoring to a tissue that is not in line-of-sight, in accordance with some applications;

FIGS. 44A-B, 45A-B, and 46A-B are schematic illustrations of examples of respective systems for covering excess contracting member after the contracting member has been cut following cinching, in accordance with some applications.

FIGS. 48 and 49 are schematic illustrations of an example tissue anchor, and an implant comprising the tissue anchor, in accordance with some applications;

FIGS. 52A-C, 53A-C, and 54A-D are schematic illustrations of examples of a wire tensioning mechanism, tissue anchors comprising the wire tensioning mechanism, implants comprising such tissue anchor, and techniques for use therewith, in accordance with some applications;

FIGS. 55, 56A-C, 57A-D, 58A-C, and 59A-C are schematic illustrations of a wire uptake assembly, a system comprising the wire uptake assembly, and techniques for use therewith, in accordance with some applications;

FIGS. 63, 64, 65A-C, 66A-B, 67A-C, 68A-C, and 69A-B are schematic illustrations of examples of wire assemblies, and implant comprising the wire assemblies, in accordance with some applications; and FIGS. 70A-C are schematic illustrations of examples of systems comprising an implant, in accordance with some applications.

DETAILED DESCRIPTION OF EMBODIMENTS

Figure 2A:
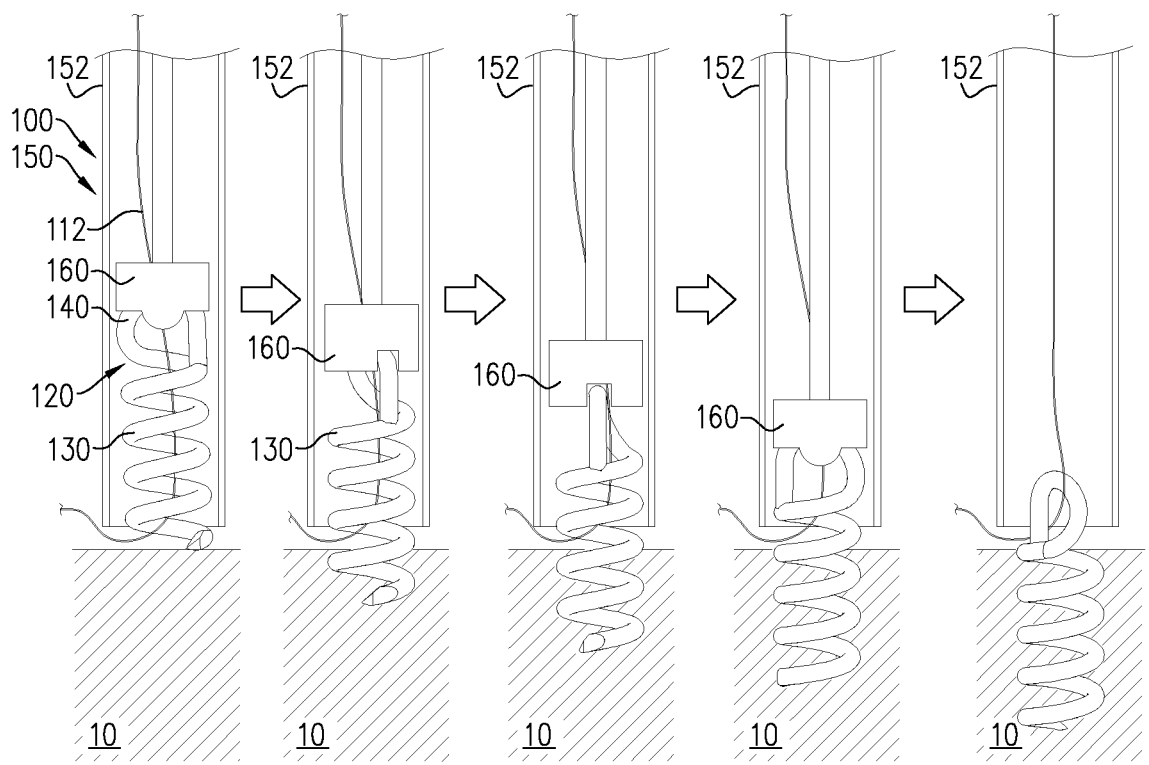

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

Reference is made to FIGS. 1A-C, 2A-B, and 3A-B, which are schematic illustrations of examples of a tissue anchor 120, an implant 110 comprising the anchor, a system 100 comprising the implant, and techniques for use therewith, in accordance with some applications. System 100 is a tissue-adjustment system and can be used for adjusting a dimension of a tissue structure. For example, system 100 can be an annuloplasty system, and implant 110 can be an annuloplasty structure (e.g., an annuloplasty ring, an annulus adjustment device, etc.).

FIG. 1A shows an isometric view of example anchor 120, FIG. 1B shows a side view of the anchor, and FIG. 1C shows an end view of the anchor as viewed distally along a central longitudinal axis ax1 of the anchor. Anchor 120 comprises a tissue-engaging element 130 and an eyelet 140. Tissue-engaging element 130 has a proximal end 132, a distal end 134, and defines central longitudinal axis ax1 of anchor 120. At distal end 134, tissue-engaging element 130 has a sharpened distal tip 138.

Tissue-engaging element 130 is helical and defines a central lumen 136 along axis ax1, the lumen having a lateral diameter d2 (i.e., d2 is the inner diameter of the helix defined by the tissue-engaging element). The helix defined by tissue-engaging element 130 has an outer diameter d3. Other tissue-engaging element configurations are also possible.

Eyelet 140 is coupled to proximal end 132 of tissue-engaging element 130. Eyelet 140 spans laterally across the proximal end of the tissue-engaging element—e.g, across a proximal end of lumen 136.

As described in more detail hereinbelow, anchor 120 (e.g, eyelet 140 thereof) is configured to facilitate sliding of the anchor along a wire (or sliding of the wire through the anchor) while the anchor is aligned with the wire—e.g, while axis ax1 is parallel with the wire. (For some applications, such alignment may mean axis ax1 is coaxial with the wire.) In some applications, a lateral thickness d1 of eyelet 140 is sufficiently smaller than diameter d2 to allow the wire to pass smoothly, in a straight line parallel with axis ax1, past eyelet 140 and through lumen 136. For example, lateral thickness d1 can be less than two thirds as great (e.g, less than half as great, such as less than a third as great) as diameter d2. For some applications, such sufficient space exists on either side of eyelet 140, although as described and explained hereinbelow, the wire often passes the eyelet on one particular side. Often, and as shown in FIG. 1C, eyelet 140 (or at least a proximal portion thereof) passes through axis ax1.

As also described in more detail hereinbelow, anchor 120 (e.g, connector or eyelet 140 thereof) is configured to facilitate sliding of the anchor along the wire (or sliding of the wire through the anchor) while the anchor is oriented orthogonal to the wire—i.e., while axis ax1 is orthogonal to the wire. Eyelet 140 extends proximally away from tissue-engaging element 130, thereby defining a bilaterally-facing aperture 146 that is proximal from the tissue-engaging element. Eyelet 140 (or at least a proximal portion thereof) extends sufficiently far proximally to provide aperture 146 with a height along axis ax1 that is sufficient for the wire to pass smoothly, in a straight line orthogonal with axis ax1, through the 146.

For some applications, aperture 146 has a greatest width d4 (orthogonal to axis ax1) that is at least 90 percent as great as diameter d2. In some applications, connector or eyelet 140 does not extend laterally past the lateral extent of tissue-engaging element 130 (e.g, the greatest outer width of eyelet 140 is smaller than diameter d3 of tissue-engaging element 130), or at most extends laterally by a distance that is no more than 10 percent of diameter d3 (e.g., the greatest outer width of eyelet 140 is no more than 10 percent greater than diameter d3). It is hypothesized by the inventors that these dimensions advantageously provide a large aperture 146 while not significantly increasing the overall width of anchor 120, for transcatheter delivery.

System 100 comprises an implant 110 that comprises a wire 112 and at least one anchor 120. System 100 further comprises a delivery tool 150 for percutaneous (e.g., transluminal, such as transfemoral) implantation of implant 110. Tool 150 comprises a flexible anchor driver 160 that is configured to reversibly engage eyelet 140. Driver 160 often comprises an elongate and flexible shaft 162, and a driver head 164 coupled to the distal end of the shaft. Driver head 164 is the component of anchor driver 160 that reversibly engages eyelet 140. Via this engagement, driver 160 is configured to drive tissue-engaging element 130 into tissue, e.g., by rotating (and distally pushing) anchor 120. Tool 150 can further comprise a flexible tube 152 via which anchor 120 (engaged with driver 160) is advanceable to the tissue to which the anchor is to be anchored.

In some applications, the width d4 and the height of the aperture, are each at least 50 percent greater than (e.g., twice as great as) the thickness of wire 112. In some applications, the lateral distance (measured orthogonally to axis ax1) between eyelet 140 and tissue-engaging element 130 on side 142 is at least 50 percent greater than the thickness of wire 112.

The term "wire" (as used in the specification and the claims) can refer to a single metallic strand, but also encompasses other elongate structures that can serve a similar function, such as a line, a tether, a cable, a thread, a suture, a braid, contracting member, a ribbon, etc. While a "wire," "line", etc. can be formed of a metal material, this is not necessary, and a "wire," "line," etc. herein can be formed of one or more of a variety of different materials.

Figure 2B:
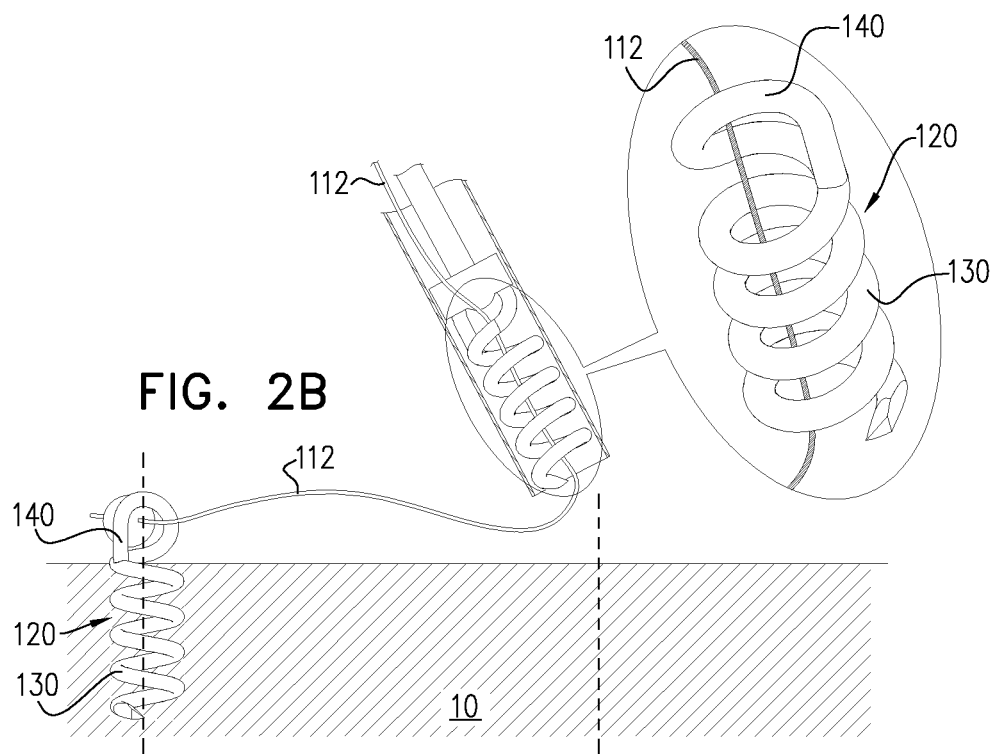

In a delivery state of system 100, anchor driver 160 is reversibly engaged with eyelet 140, and wire 112 extends longitudinally through lumen 136 such that the anchor is freely slidable along the wire (e.g., as shown in the first frame of FIG. 2A, and in FIG. 2B). In this context, the term longitudinally (including the specification and the claims) means generally parallel with central longitudinal axis ax1 of anchor 120. Although anchor 120 is described hereinabove as facilitating smooth sliding while the wire is straight and parallel with axis ax1, in actual use the wire may not be perfectly straight or parallel with axis ax1.

System 100 is configured such that, when in the delivery state, rotation of the helix of tissue-engaging element 130 draws wire 112 proximally along the helix of the tissue-engaging element until the wire eventually exits lumen 136 at proximal end 132 and is left threaded through aperture 146 of eyelet 140. This is illustrated in FIG. 2A, in which tool 150 is anchoring anchor 120 to tissue 10 of a subject. By anchoring anchor 120, tool 150 transitions the system and/or apparatus from the delivery state into an implanted state by rotating the anchor such that (i) tissue-engaging element 130 becomes driven into the tissue, and (ii) wire 112 becomes drawn proximally along the helix of the tissue-engaging element until the wire exits lumen 136 and extends laterally through aperture 146 of eyelet 140.

As described hereinabove, once wire 112 extends laterally through aperture 146, the wire can slide smoothly through the aperture while orthogonal to axis ax1. This is hypothesized by the inventors to be useful, inter alia, for applications in which wire 112 is tensioned in order to adjust anatomical dimensions, such as annuloplasty. FIGS. 3A-B show such an application, in which tissue 10 represents tissue of the annulus of a native heart valve, such as the mitral valve, and implant 110 is an annuloplasty structure comprising wire 112 and multiple anchors 120.

In FIG. 3A, multiple anchors 120 have been anchored to tissue 10. As described hereinabove, each anchor 120 (except possibly a first anchor 120a to be anchored) was delivered to the tissue in the delivery state with wire 112 extending longitudinally through lumen 136, and then during anchoring was transitioned into the implanted state shown, in which wire 112 extends laterally through aperture 146 of eyelet 140. After a desired number of anchors 120 have been anchored, an adjustment tool 170 is introduced, which can be over and along a proximal portion of wire 112, and is used to facilitate tensioning of the wire. A reference force is provided (e.g., against a last anchor 120b to be anchored) by tool 170 and/or tube 152, while wire 112 is pulled proximally. A first end of wire 112 cannot slide out of first anchor 120a (e.g., is fixed to the first anchor), e.g., due to the presence of a first stopper 114a. Therefore, the tensioning of wire 112 draws anchors 120 (e.g., anchors 120a and 120b) closer together, thereby contracting the tissue to which the anchors are anchored (FIG. 3B). This is facilitated by eyelets 140 providing smooth sliding of wire 112 through apertures 146 while the wire is orthogonal to the anchors, as described hereinabove. The tension is locked into implant 110, such as by fixing a second stopper 114b to wire 112 proximal to last anchor 120b. Excess wire 112 can then be cut and removed from the subject.

For simplicity, FIGS. 3A-B show implant 110 in a linear configuration. However, for annuloplasty, implant 110 is often implanted in a curve (or even a complete ring) around the valve annulus, such that the contraction reduces the size (e.g., reduces a radius, etc.) of the valve annulus, improving coaptation of the valve leaflets.

In some applications, anchor driver 160 drives anchor 120 via its engagement with eyelet 140. Therefore, as well as facilitating sliding along wire 112, eyelet 140 also serves as a driver interface 124 of anchor 120. To facilitate this, eyelet 140 can be rigidly coupled to tissue-engaging element 130.

Reference is again made to FIGS. 1A-C. For some applications, anchor 120 comprises a single monolithic rod 180 that has a sharpened distal tip 138 and a second tip 139, and is shaped to define all of the components of the anchor described hereinabove. For such applications, rod 180 can be described as having (i) a first portion 182 that is shaped to define tissue-engaging element 130, and (ii) a second portion 184 that is continuous with the first portion, and that is shaped to define eyelet 140. First portion 182 extends between (i.e., is delimited by) distal tip 138 and a transition site 183 of the rod. Second portion 184 extends between (i.e., is delimited by) transition site 183 and second tip 139 of the rod. Tissue-engaging element 130 is defined by first portion 182 extending helically around and along central longitudinal axis ax1 of anchor 120. Eyelet 140 is defined at least in part (e.g., at least a proximal portion of the eyelet is defined) by second portion 184 defining an arch that spans laterally across proximal end 132 of tissue-engaging element 130, and that arches proximally away from the tissue-engaging element.

In some applications, eyelet 140 is defined at least in part by second tip 139 being attached to an attachment site 186 of rod 180. Attachment site 186 is often within first portion 182 of rod 180—i.e., between distal tip 138 and transition site 183. For some applications, and as shown, tissue-engaging element 130 can comprise a plurality of helical turns of rod 180, including (i) a distal-most helical turn that is distally delimited by the distal tip of the rod, and (ii) a proximal-most helical turn proximally delimited by transition site 183, and attachment site 186 can be partway around the proximal-most helical turn. For some such applications, and as is shown in FIG. 1C, attachment site 186 can be at least one third (i.e., at least 120 degrees) of the way around (e.g., about halfway around) the proximal-most helical turn from transition site 183.

As described hereinabove, in the delivery state, wire 112 extends past eyelet 140 and through lumen 136, and then is drawn proximally by rotation of the helix of element 130 until it exits the lumen and becomes disposed through aperture 146 of eyelet 140. In order to facilitate this behavior, in the delivery state, wire 112 extends past a particular side of eyelet 140. The formation of eyelet 140 (e.g, from rod 180) can form a closed loop comprising (i) the arch formed by second portion 184 of the rod, and (ii) a part 185 of second portion 182 (e.g, the part of the proximal-most helical turn) that is disposed between transition site 183 and attachment site 186. In the delivery state, wire 112 can extend past eyelet 140 on the side 142 of the eyelet in which the wire extends through this closed loop. The part of wire 112 that is drawn proximally along the helix arrives at the opposite side 144 of eyelet 140, thereby resulting in the wire being disposed through aperture 146 of eyelet 140, under the arch formed by portion 184. Another way to describe this arrangement, is that (i) the helix of tissue-engaging element 130 leads to one side (side 144) of eyelet 140, and (ii) in the delivery state, wire 112 extends past eyelet 140 on the other side (side 142) of the eyelet and into lumen 136.

For some applications, anchor 120 and/or implant 110 can be used in combination with apparatuses, systems, and/or implanted using methods/techniques, described in one or more of the following references, mutatis mutandis, each of which is incorporated herein by reference in its entirety for all purposes:

U.S. patent application Ser. No. 14/437,373 to Sheps et al, which published as US 2015/0272734 (now U.S. Pat. No. 9,949,828)

U.S. patent application Ser. No. 15/782,687 to Iflah et al, which published as US 2018/0049875

PCT Patent Application PCT/IL2019/050777 to Brauon et al, which published as WO/2020/012481

U.S. Provisional Patent Application 62/811,693 to Brauon et al.

Reference is made to FIGS. 4A-H and 5A-C, which are schematic illustrations of examples of a tissue anchor 220, an implant 210 comprising the tissue anchor, a system 200 comprising the implant, and techniques for use therewith, in accordance with some applications. System 200 is a tissue-adjustment system and can be used for adjusting a dimension of a tissue structure. For example, system 200 can be an annuloplasty system, and implant 210 can be an annuloplasty structure (e.g, an annuloplasty ring, annuloplasty implant, etc.).

Figure 4D:
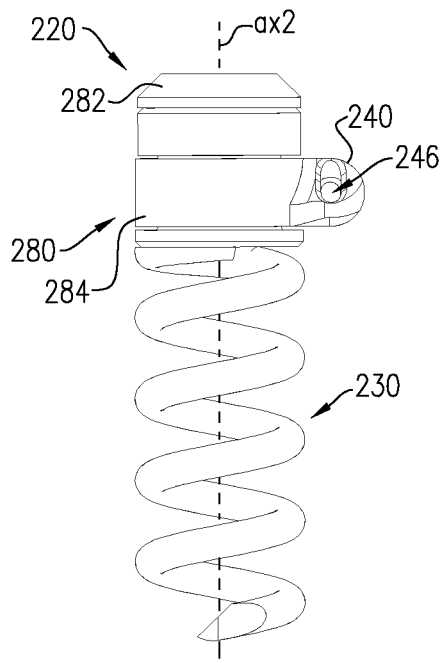
Figure 4E:
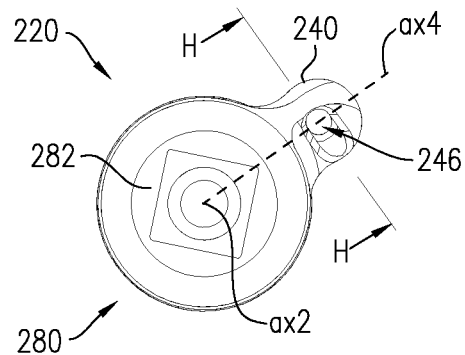
Figure 4F:
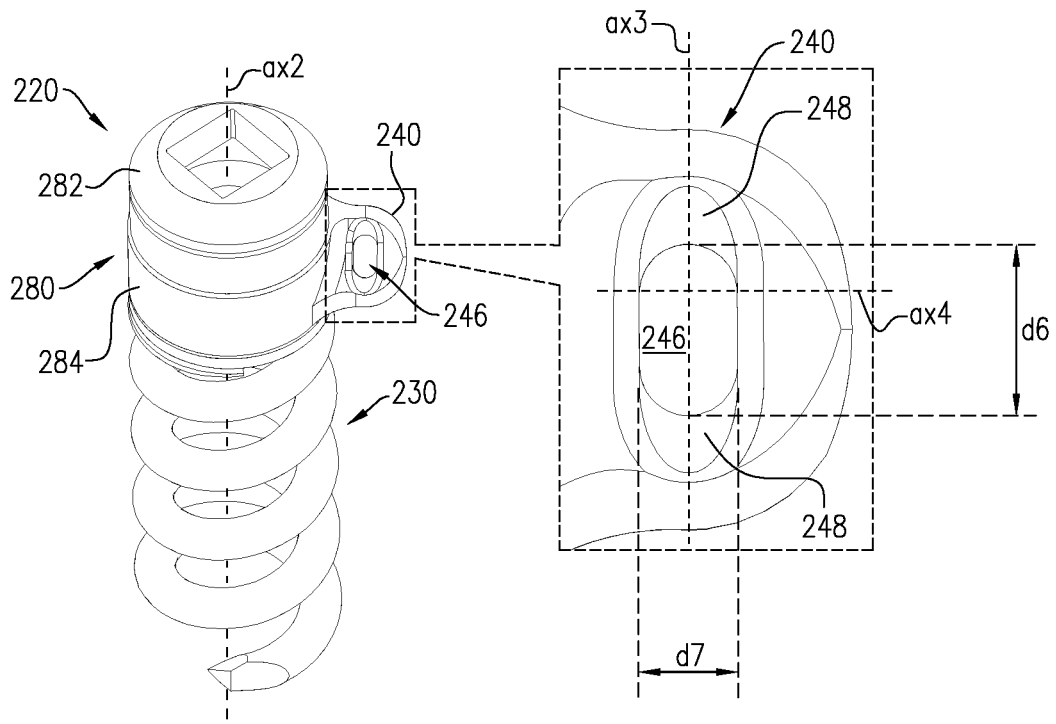
Figure 4H:
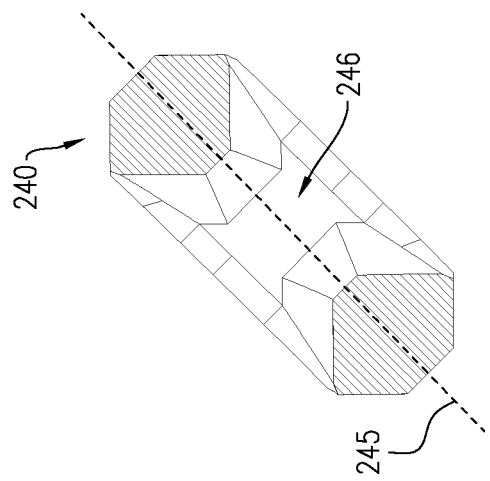
Figure 4G:
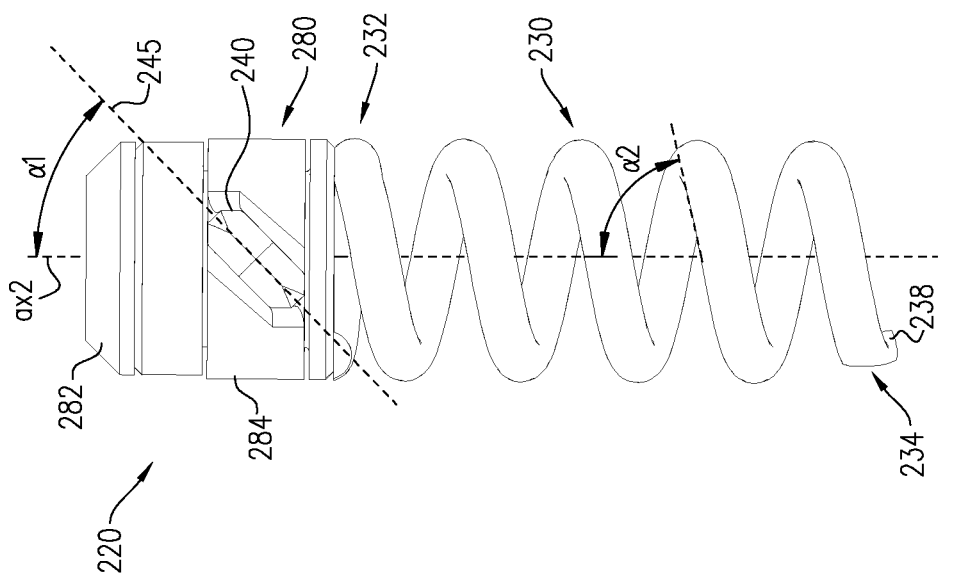
Figure 6A:
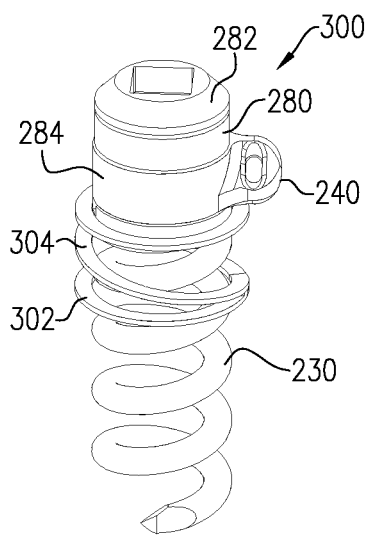
Figure 6B:
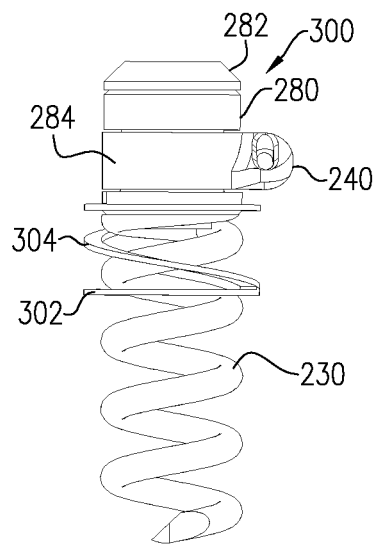
Figure 6C:
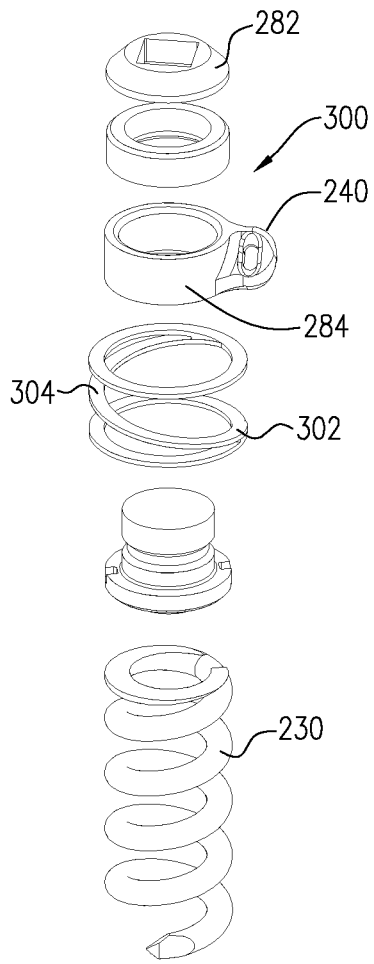
Figure 6D:
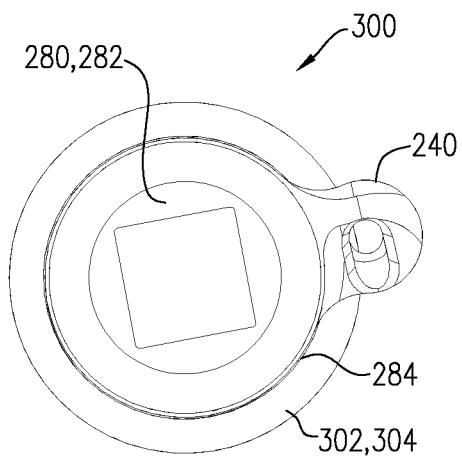

FIGS. 4A, 4B, and 4F show respective isometric views of anchor 220, FIGS. 4D and 4G show respective side views of the anchor, FIG. 4E shows an end view of the anchor as viewed distally along a central longitudinal axis ax2 of the anchor, and FIG. 4C shows an exploded view of the anchor. FIG. 4H shows a cross-section of an eyelet 240 of anchor 220 (the position and orientation of the cross-section is indicated in FIG. 4E).

Anchor 220 comprises a tissue-engaging element 230 and a head 280. The tissue-engaging element can be configured in a variety of ways. In some applications, as shown in FIGS. 4A-4G, the tissue-engaging element has a proximal end 232, a distal end 234, and defines central longitudinal axis ax2 of anchor 220. At distal end 234, tissue-engaging element 230 has a sharpened distal tip 238, and the tissue-engaging element is configured to be driven (e.g, screwed, pushed, etc.) into tissue of the subject. For some applications, and as shown, tissue-engaging element 230 is helical and defines a central lumen 236 along axis ax2. Optionally, tissue-engaging element 230 can be another type of tissue-engaging element, such as a dart or a staple. In some applications, the tissue-engaging element can be hook-shaped, straight, angled, and/or another configuration. In some applications, the tissue-engaging element can include barbs or barbed portions to hold the tissue-engaging element in tissue.

Tissue-engaging element 230 has a lateral width d5. For applications in which tissue-engaging element 230 is helical, width d5 is an outer diameter of the helix. Head 280 is coupled to proximal end 232 of tissue-engaging element 230 and comprises a driver interface 282 and an eyelet 240 that defines an aperture 246 therethrough. Driver interface 282 is configured to be reversibly engaged by an anchor driver 260. Driver 260 often comprises an elongate and flexible shaft 261, and a driver head 264 coupled to a distal end of the shaft. Driver head 264 is the component of anchor driver 260 that reversibly engages driver interface 282. Driver interface 282 can be rigidly coupled to tissue-engaging element 230.

In some applications, and as shown, driver interface 282 is disposed on central longitudinal axis ax2, and eyelet 240 is disposed laterally from axis ax2.

As described in more detail hereinbelow, and for the same reasons described for anchor 120, mutatis mutandis, anchor 220 (e.g, connector or eyelet 240 thereof) is configured to facilitate sliding of the anchor along a wire (or sliding of the wire through the anchor) while the anchor is aligned with the wire—e.g, while axis ax2 is parallel with the wire. As also described in more detail hereinbelow, anchor 220 (e.g, connector or eyelet 240 thereof) is configured to facilitate sliding of the anchor along the wire (or sliding of the wire through the anchor) while the anchor is oriented orthogonal to the wire—i.e., while axis ax2 is orthogonal to the wire. This is achieved at least partly due to the shape and dimensions of connector or eyelet 240.

Eyelet 240 defines aperture 246 on an aperture plane 245 and is mounted such that the aperture plane is slanted at a fixed angle alpha_1 (see FIG. 4G) with respect to axis ax2. In some applications, angle alpha_1 is 30-60 degrees (e.g, 40-50 degrees, such as at 45 degrees).

FIG. 4F, and in particular the inset image thereof, shows eyelet 240 head-on, as viewed orthogonal to aperture plane 245. Aperture 246 has a length d6 along a long axis ax3 of the aperture, and a width d7 along a short axis ax4 of the aperture, the long axis and the short axis both disposed on aperture plane 245. Length d6 is orthogonal to width d7 and is often greater than width d7. For example, length d6 can be at least 1.4 times as great as width d7. For example, length d6 can be 1.4-5 times as great as width d7, e.g, 1.4-3 times as great, e.g, 1.5-2.5 times as great, e.g, 1.6-2.2 times as great, e.g, 1.6-2 times as great, such as 1.6-1.8 times as great.

In some applications, and as shown (e.g, in FIG. 4F), the ends of aperture 246 are rounded. For some applications, aperture 246 is shaped as a noncircular ellipse. For some applications, and as shown (e.g, in FIG. 4F), aperture 246 is shaped as a stadium—i.e., having rounded ends, and straight sides (e.g, parallel with long axis ax3).

In some applications, and as shown (e.g, in FIG. 4F), short axis ax4 is orthogonal to, and extends radially from, the central longitudinal axis.

In some applications, eyelet 240 is shaped to define (i) a first clear straight pathway through aperture 246 along a first line that is parallel to axis ax2 (e.g., as shown in FIG. 4E), and (ii) a second clear straight pathway through the aperture along a second line that is orthogonal to the first line (e.g, as shown in FIG. 4D). It is hypothesized that this shape advantageously allows sliding of eyelet 240 along a wire in either of these mutually-orthogonal orientations. It is noted that these pathways are not discrete, and the shape of eyelet 240 similarly facilitates its sliding along a wire when in an orientation that is partway between these mutually-orthogonal orientations.

Despite the actual shape of aperture 246, described hereinabove, eyelet 240 can be shaped and dimensioned such that both (i) when viewed along the first line (i.e., a first view-line) that is parallel to axis ax2 (e.g, as shown in FIG. 4E), and (ii) when viewed along the second line (i.e., a second view-line) that is orthogonal to the first view line (e.g, as shown in FIG. 4D), aperture 246 appears to be circular. It is hypothesized by the inventors that this shape advantageously allows smooth sliding of eyelet 240 along a wire in either of these orientations (and typically also in a continuum of orientations therebetween). Thus, these view lines can be considered to be first and second slide axes of anchor 220 (e.g, of eyelet 240 thereof). It is further hypothesized by the inventors that this shape advantageously allows such sliding even when the wire is more than 50 percent as great (e.g, more than 70 percent as great, such as more than 90 percent as great) as the diameter of the apparent circular shape of aperture 246 (i.e., as width d7).

To further facilitate smooth sliding of a wire through aperture 246, eyelet 240 defines a beveled rim around the aperture. For some applications, and as shown, beveling 248 is greater on long axis ax3 (i.e., at the ends of the aperture) than on short axis ax4 (i.e., at the sides of the aperture). For some applications, on each face of eyelet 240 (i.e., on each side of aperture 246), the eyelet defines a bathtub-shaped cavity, with the bottoms of the bathtubs meeting to form aperture 246.

For some applications, and as shown, eyelet 240 is mounted to be revolvable or rotatable around axis ax2 while aperture plane 245 remains slanted at its fixed angle with respect to the central longitudinal axis. Optionally, eyelet 240 can be revolvable or rotatable around another axis. For example, head 280 can comprise a ring 284 on which eyelet 240 is mounted. Ring 284 circumscribes and is rotatable about axis ax2, e.g, by being rotatably coupled to tissue-engaging element 230, such as by being rotatably coupled to another component of head 280 (e.g, driver interface 282) that is fixedly coupled to the tissue-engaging element.

For some applications in which tissue-engaging element 230 is helical, on the side of anchor 220 on which eyelet 240 is disposed, the helix of the tissue-engaging element slants in the same direction as aperture plane 245 with respect to axis ax2, e.g, as can be seen in FIG. 4G. However, the lead angle alpha_2 of the helix of tissue-engaging element 230 can be different from angle alpha_1 of aperture plane 245. For example, and as shown, angle alpha_2 can be greater (e.g, more than 50% greater) than angle alpha_1. Other tissue-engaging element configurations are also possible.

As described hereinabove, anchor 220 (e.g, eyelet 240 thereof) is configured to facilitate sliding of the anchor along a wire (or sliding of the wire through the anchor) while the anchor is aligned with the wire—e.g, while axis ax2 is parallel with the wire. This is hypothesized by the inventors to facilitate transcatheter advancement of anchor 220 along the wire. As also described hereinabove, anchor 220 (e.g, eyelet 240 thereof) is configured to facilitate sliding of the anchor along the wire (or sliding of the wire through the anchor) while the anchor is oriented orthogonal to the wire—i.e., while axis ax2 is orthogonal to the wire. This is hypothesized by the inventors to be useful, inter alia, for applications in which the wire is tensioned after implantation in order to adjust anatomical dimensions, such as annuloplasty. FIGS. 5A-C show such an application, in which tissue 10 represents tissue of the annulus of a native heart valve, such as the mitral valve, and implant 210 is an annuloplasty structure comprising a wire 212 and multiple anchors 220.

FIGS. 5A-C show system 200, which comprises implant 210, and a delivery tool 250 for percutaneous (e.g, transluminal, such as transfemoral) implantation of the implant. Tool 250 comprises a flexible anchor driver 260 that is configured to reversibly engage driver interface 282 of anchor 220. Via this engagement, driver 260 is configured to drive tissue-engaging element 230 into tissue, e.g, by rotating (and distally pushing) anchor 220. In some applications, tool 250 further comprises a flexible tube 252 (e.g, a transluminal catheter) via which each anchor 220, engaged with driver 260, is advanceable to the tissue to which the anchor is to be anchored.

In FIG. 5A, multiple anchors 220 have been anchored to tissue 10. Each anchor 220 was delivered to the tissue in a delivery state in which wire 212 extends through aperture 246 of eyelet 240 while generally parallel to axis ax2. This is illustrated for an anchor 220b that is shown in FIG. 5A as being currently delivered. The inset image of anchor 220b illustrates the clear straight path that it is possible for wire 212 to take through aperture 246 of eyelet 240.

As subsequent anchors 220 are anchored to the same tissue, wire 212 becomes oriented laterally with respect to the anchors. Due to the configuration of eyelet 240, despite this reorientation of wire 212, the wire can still take a clear straight path through aperture 246 of eyelet 240. This is illustrated in the inset image of anchor 220a.

After a desired number of anchors 220 have been anchored, an adjustment tool is introduced (e.g, over and along a proximal portion of wire 212), and is used to facilitate tensioning of the wire, e.g, as described for implant 110 hereinabove, mutatis mutandis. Therefore, the tensioning of wire 212 draws anchors 220 closer together, thereby contracting the tissue to which the anchors are anchored (FIG. 5C). This is facilitated by eyelets 240 providing smooth sliding of wire 212 through apertures 246 while the wire is orthogonal to the anchors, as described hereinabove. A first stopper 214a and a second stopper 214b can be used, e.g, as described for implant 110 hereinabove, mutatis mutandis. Excess wire 212 can then be cut and removed from the subject.

For simplicity, FIGS. 5A and 5C show implant 210 in a linear configuration. However, for annuloplasty, implant 210 is often implanted in a curve (or even a complete ring) around the valve annulus, such that the contraction reduces the size of the valve annulus, improving coaptation of the valve leaflets.

As described hereinabove, for some applications, eyelet 240 is mounted to be revolvable or rotatable around axis ax2. This therefore provides independence between the rotational position of the eyelet and that of tissue-engaging element 230. It is hypothesized that, for applications in which tissue-engaging element 230 is helical, this independence advantageously allows the tissue-engaging element to be screwed into tissue to the extent needed for optimal anchoring, without a requirement for the anchor to finish in a particular rotational orientation. It is further hypothesized that, irrespective of the type of tissue-engaging element 230 used, this independence allows eyelet 240 (and wire 212) to be in an optimal position, with respect to axis ax2 of each anchor 220, for a given application. For example, for an application in which implant 210 is used for annuloplasty, anchors 220 are often anchored in a curve around the valve annulus, and eyelets 240 and wire 212 are often disposed on the inside of the curve relative to axes ax2.

For some applications, and as shown, tube 252 is shaped to control, during delivery and anchoring, a rotational position of eyelet 240 with respect to axis ax2 and/or tissue-engaging element 230. For some such applications, tube 252 defines an internal channel 254 that defines a major channel region 254a and a minor channel region 254b (FIG. 5B). Major channel-region 254a has a larger cross-sectional area than does minor channel region 254b. Anchor 220 is slidable through channel 254 with tissue-engaging element 230 sliding (often snugly) through primary channel region 254a, and eyelet 240 sliding (often snugly) through minor channel region 254b and along wire 212. Rotational control of tube 252 thereby controls the position of eyelet 240, and therefore of wire 212, around axis ax2 of each anchor. While driver interface 282 and tissue-engaging element 230 are rotatable within tube 252, ring 284 and eyelet 240 are not. For some applications, and as shown, channel 254 has a keyhole-shaped orthogonal cross-section.

To anchor or secure anchor 220, the anchor is advanced out of a distal end of tube 252 while driver 260 rotates driver interface 282 (and thereby tissue-engaging element 230) with respect to the tube, and while minor channel region 254b typically inhibits rotation of ring 284 with respect to the tube. For some applications, it is advantageous for the distal end of the tube to be disposed (or even pressed) against tissue 10 during anchoring of the anchor, e.g, as shown in FIG. 5A. For applications in which tube 252 is used to implant an implant comprising multiple anchors on a wire, such as implant 210, interference may occur between the wire and the contact between the distal end of the tube and the tissue. For some applications, tube 252 defines a lateral slit 256 extending proximally from the distal end of the tube, such that the slit is continuous with the distal opening of the tube. For some applications, slit 256 is adjacent to (e.g, laterally outward from) minor channel region 254b, and allows wire 212, but not anchor 220, to exit tube 252 laterally, proximally from the distal end of the tube. It is believed that this facilitates implantation of implants such as implant 210, comprising multiple anchors coupled to (e.g, threaded on) a wire.

For some applications, eyelet 240 facilitates sliding of wire 212 therethrough both (i) while anchor 220 is aligned with the wire, and (ii) while the anchor is orthogonal to the wire, without aperture 246 being more than 5 percent wider than the wire is thick. Therefore, for some applications, wire 212 has a thickness that is more than 50 percent (e.g, more than 70 percent, such as more than 90 percent) as great as width d7 of aperture 246. For some such applications, the thickness of wire 212 is less than 70 percent (e.g, 30-60 percent) as great as length d6 aperture 246.

For some applications, length d6 is 0.4-0.75 mm (e.g, 0.42-0.67 mm). For some applications, width d7 is 0.15-0.5 mm (e.g, 0.25-0.5 mm). For some applications, wire 212 is 0.1-0.6 mm (e.g, 0.18-0.3 mm) thick.

Reference is again made to FIGS. 1A-5C. Both eyelet 140 and eyelet 240 are at fixed angular dispositions with respect to their respective tissue-engaging element, eyelet 140 being rigidly coupled to its tissue-engaging element, and eyelet 240 being rotationally but non-deflectably coupled. It is hypothesized by the inventors that such limiting of the movement of the eyelet advantageously reduces wear on the wire that passes therethrough.

Reference is again made to FIGS. 1A-5C. Both implant 110 and implant 210, the anchors remain threaded onto the respective wire throughout and after implantation, despite the change in orientation of the wire with respect to the anchor during implantation. It is hypothesized that this advantageously reduces a likelihood of an anchor embolizing.

For some applications, anchor 120, implant 110, anchor 220, and/or implant 210 can be used in combination with apparatuses, systems, and/or implanted using methods/techniques, described in one or more of the following references, mutatis mutandis, each of which is incorporated herein by reference in its entirety:

U.S. patent application Ser. No. 14/437,373 to Sheps et al, which published as US 2015/0272734 (now U.S. Pat. No. 9,949,828)

U.S. patent application Ser. No. 15/782,687 to Iflah et al, which published as US 2018/0049875

PCT Patent Application PCT/IL2019/050777 to Brauon et al, which published as WO/2020/012481

U.S. Provisional Patent Application 62/811,693 to Brauon et al.

Figure 13B:
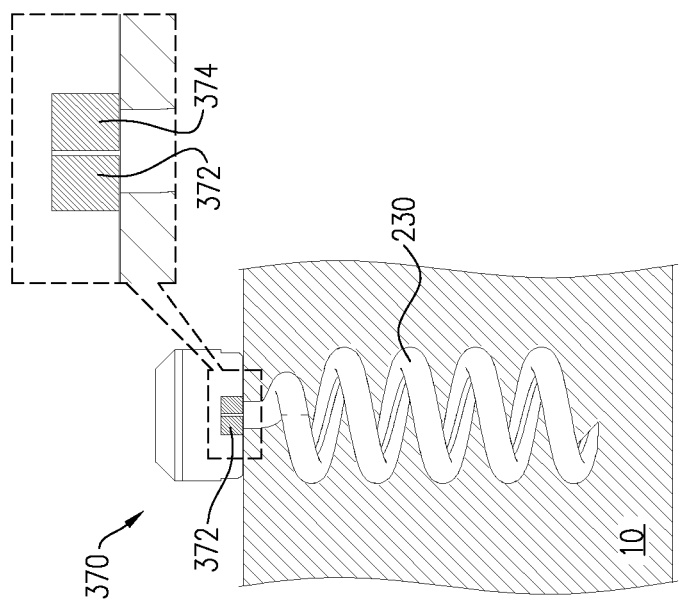
Figure 13A:
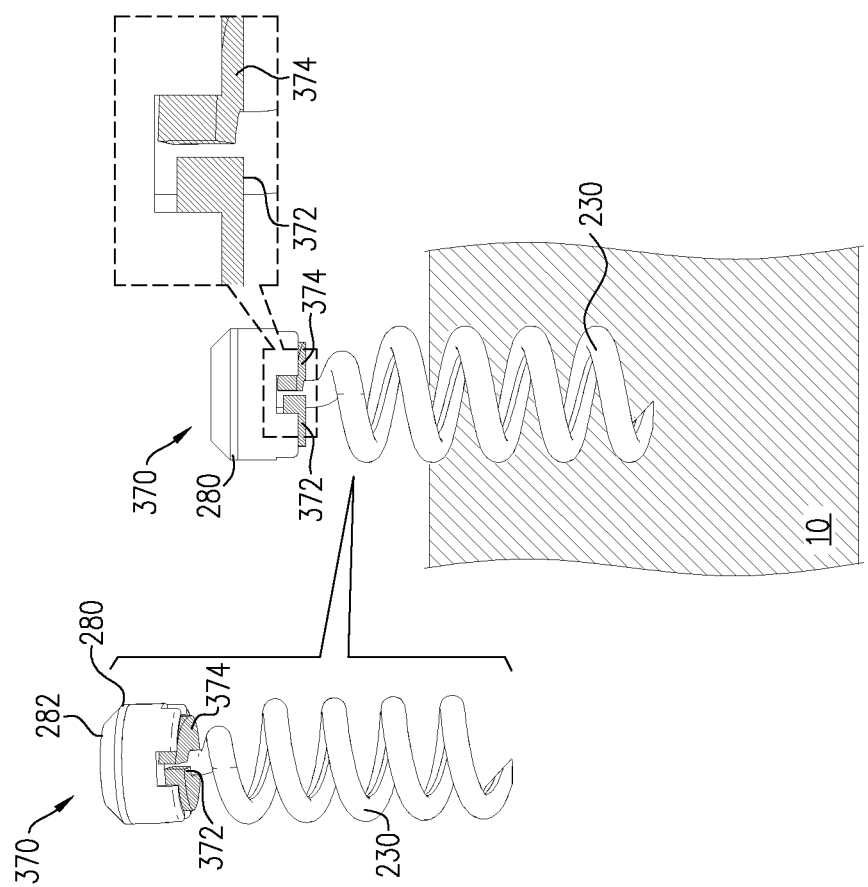

Reference is made to FIGS. 6A-E, 7A-E, 8A-E, 9A-E, 10A-E, 11A-B, 12A-B, 13A-B, and 14A-B, which are schematic illustrations of examples of tissue anchors, and techniques for use therewith, that are configured to facilitate determination of successful (e.g, complete) anchoring to a tissue that is not in line-of-sight, in accordance with some applications. For example, such tissue anchors may be useful for percutaneous (e.g, transluminal) techniques, such as those described elsewhere herein. FIGS. 6A-E show a tissue anchor 300, in accordance with some applications. FIGS. 7A-E show a tissue anchor 310, in accordance with some applications. FIGS. 8A-E show a tissue anchor 320, in accordance with some applications. FIGS. 9A-E show a tissue anchor 330, in accordance with some applications. FIGS. 10A-E show a tissue anchor 340, in accordance with some applications. FIGS. 11A-B show a tissue anchor 350, in accordance with some applications. FIGS. 12A-B show a tissue anchor 360, in accordance with some applications. FIGS. 13A-B show a tissue anchor 370, in accordance with some applications. FIGS. 14A-B show a tissue anchor 380, in accordance with some applications.

For each of tissue anchors 300, 310, 320, 330, 340, 350, 360, 370, and 380, the tissue anchor comprises:
- a tissue-engaging element that defines a central longitudinal axis of the anchor, has a sharpened distal tip, and is configured to be driven into tissue of a subject;
- a head that is coupled to a proximal end of the tissue-engaging element, and that comprises a driver interface that is configured to be reversibly engaged by the anchor driver; and
- a protrusion that protrudes distally away from the head, such that driving the tissue-engaging element into the tissue presses the protrusion against the tissue, and that is configured to move with respect to the head automatically in response to being pressed against the tissue.

In some applications, the protrusion extends distally past at least a proximal end of the tissue-engaging element (i.e., the end of the tissue-engaging element closest to the head). The movement of the protrusion with respect to the head facilitates the determination of successful anchoring. For some applications, such as for anchors 300, 310, 320, 330, 350, 360, 370, and 380 this movement is identified via imaging (e.g, fluoroscopy). For such applications, at least some parts of head 280 are radiopaque. For some applications, such as for anchor 340, this movement is identified by the protrusion pressing on a pressure sensor.

For some applications, each of anchors 300, 310, 320, 330, 340, 350, 360, 370, and 380 is similar, mutatis mutandis, to anchor 220 described hereinabove, except where noted. For example, and as shown, each of the anchors can comprise tissue-engaging element 230 and head 280, mutatis mutandis. However, other tissue-engaging elements and other heads can be used, mutatis mutandis. Similarly, each of the anchors can comprise driver interface 282. Furthermore, although an eyelet is not visible in all of FIGS. 6A-14B, each of the anchors can comprise an eyelet, such as an eyelet described herein, e.g, eyelet 240 or eyelet 640, mutatis mutandis. Similarly, each of the anchors can comprise a ring, such as a ring described herein, e.g, ring 284, mutatis mutandis.

For some applications, anchor 300 comprises a protrusion 302. Anchor 310 comprises a protrusion 312. Anchor 320 comprises a protrusion 322. Anchor 330 comprises a protrusion 332. Anchor 340 comprises a protrusion 342. Anchor 350 comprises a protrusion 352. Anchor 360 comprises a protrusion 362. Anchor 370 comprises a protrusion 372. Anchor 380 comprises a protrusion 382.

For some applications, the protrusion is configured to move elastically/reversibly with respect to the head automatically in response to being pressed against the tissue. For example, the protrusion can comprise a spring, or can be coupled to head 280 via a spring—i.e., the anchor can comprise a spring coupled functionally between the protrusion and the head. Anchor 300 comprises a spring 304. Anchor 310 comprises a spring 314. Anchor 320 comprises a spring 324. Anchor 330 comprises a spring 334. Anchor 340 comprises a spring 344. Anchor 350 may not comprise a spring. Anchor 360 comprises a spring 364. Anchor 370 comprises a spring 374. Anchor 380 comprises a spring 384.

Figure 7A:
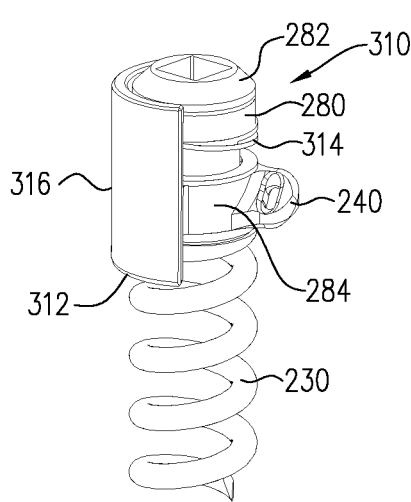
Figure 7B:
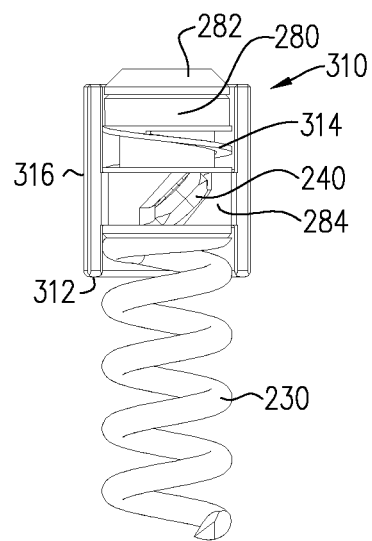
Figure 7C:
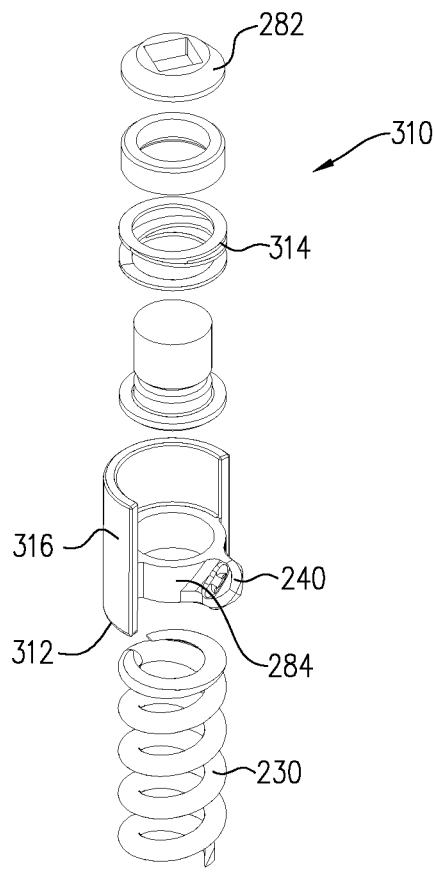
Figure 7D:
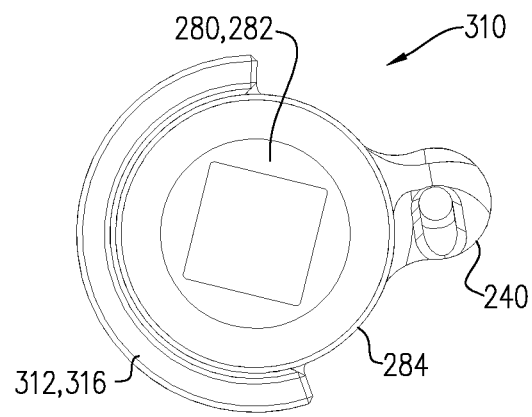
Figure 7E:
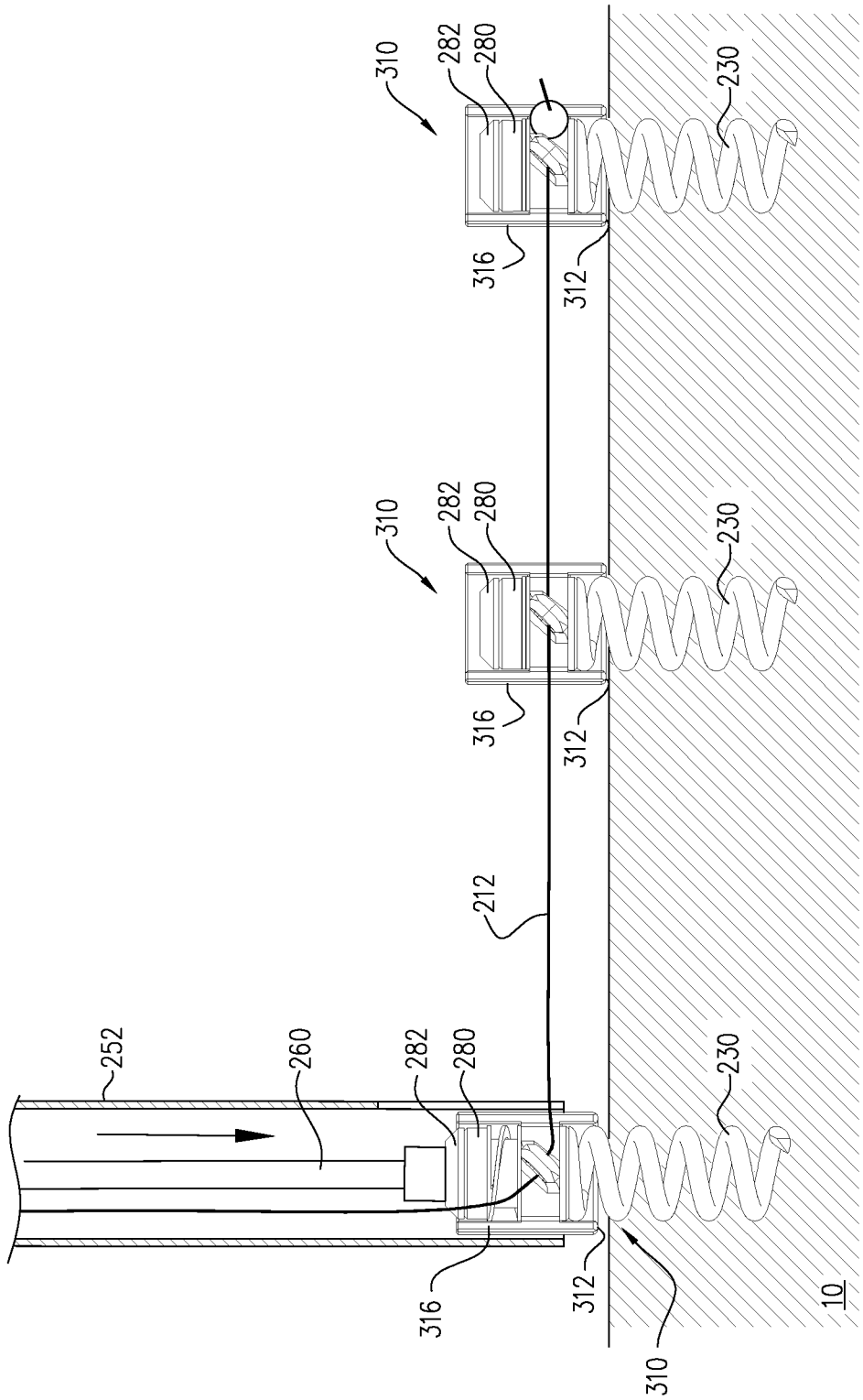
Figure 8A:
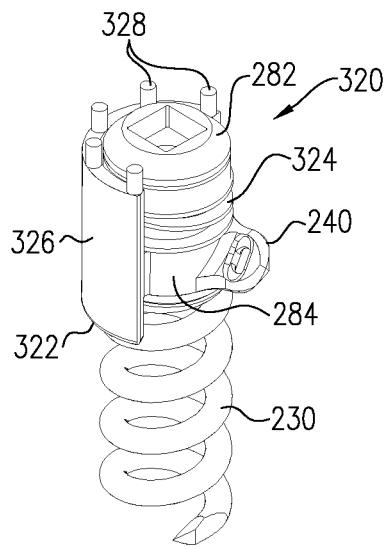
Figure 8B:
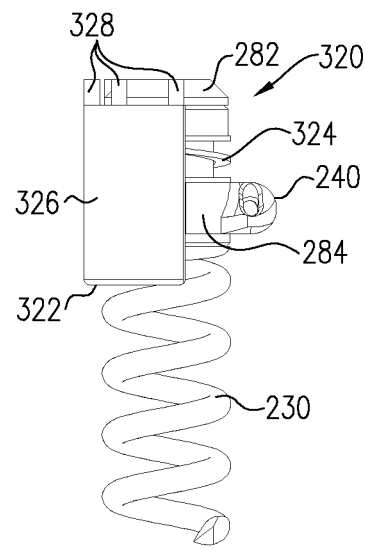
Figure 8C:
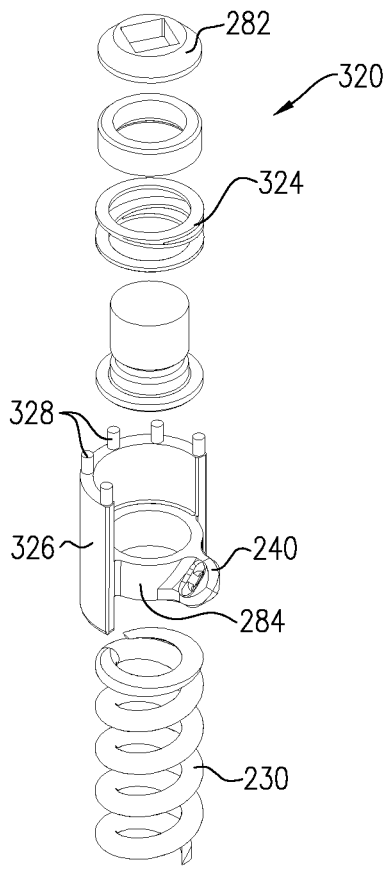
Figure 8D:
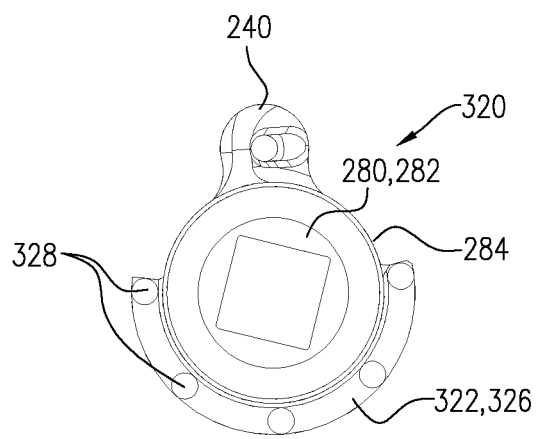
Figure 8E:
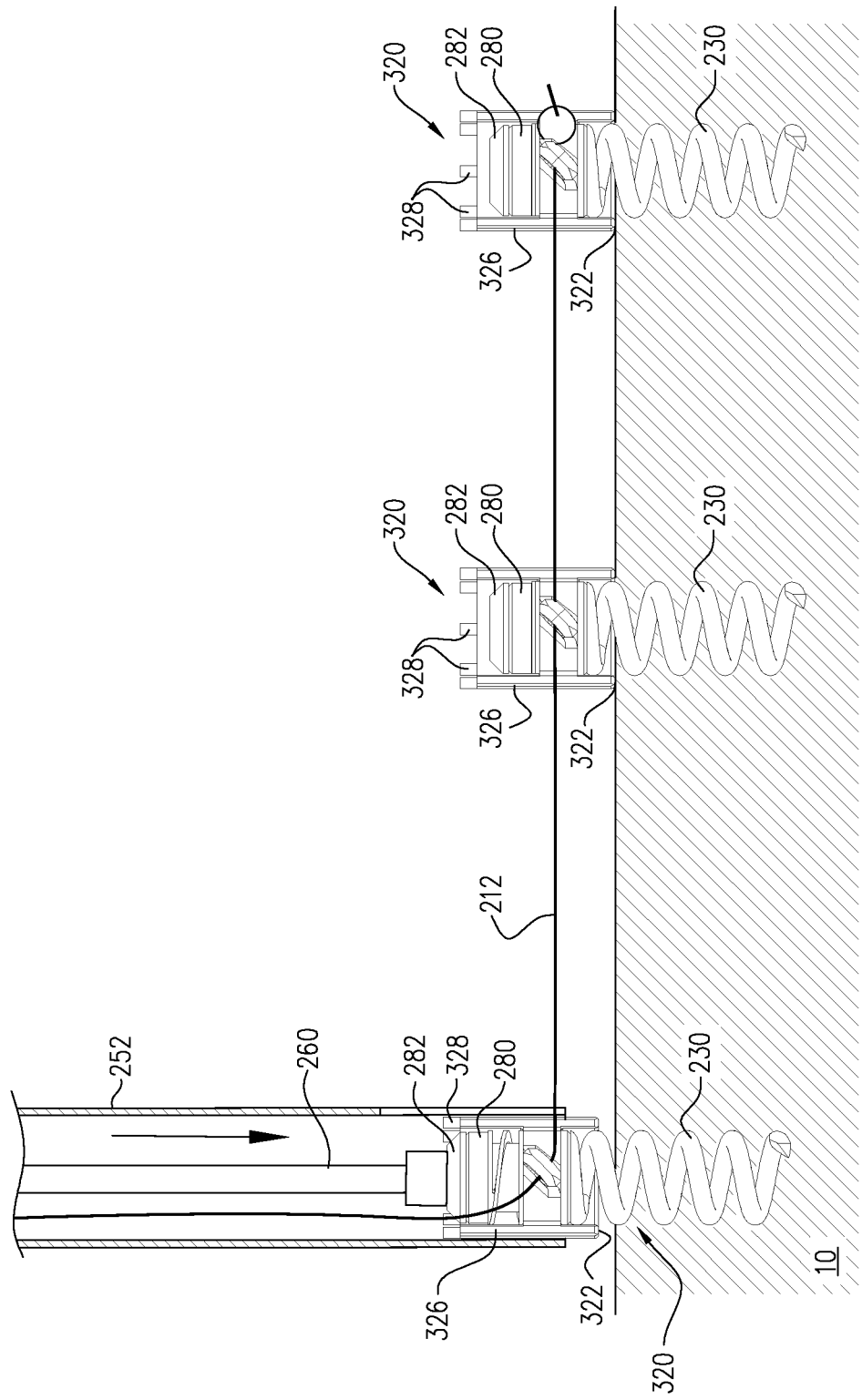
Figure 9E:
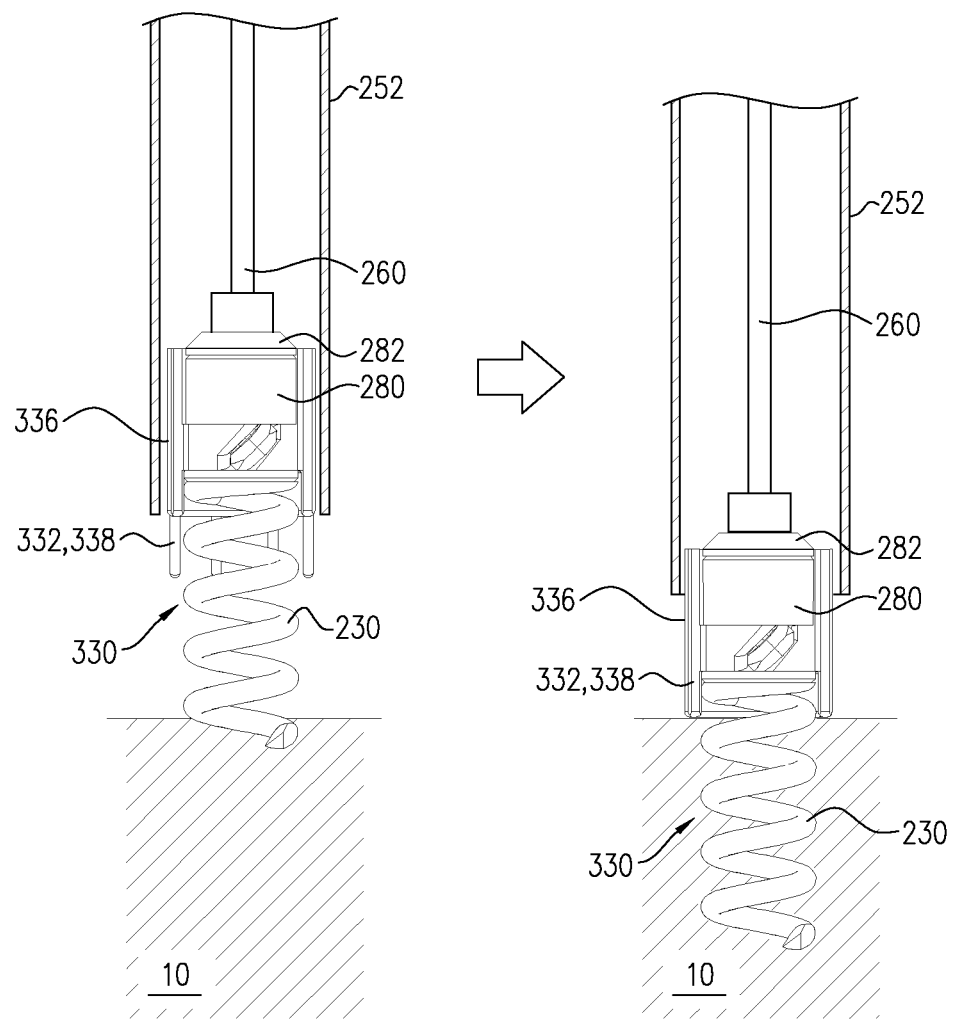
Figure 10A:
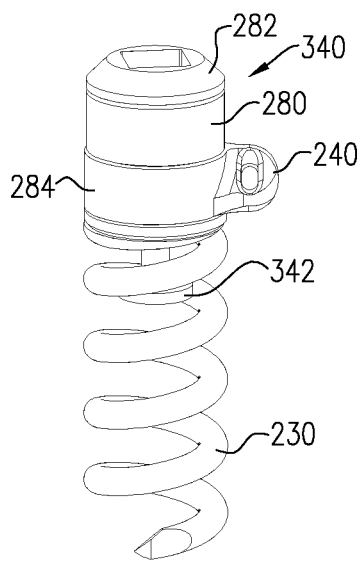
Figure 10B:
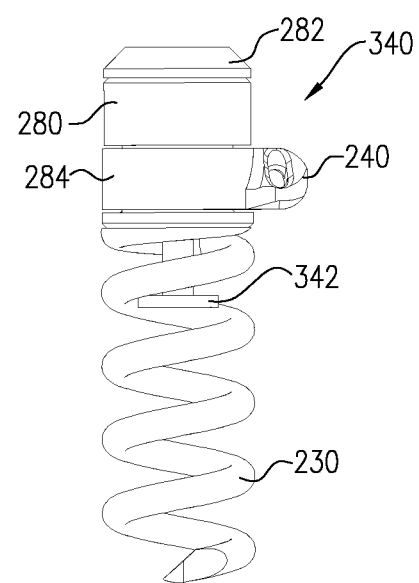
Figure 10C:
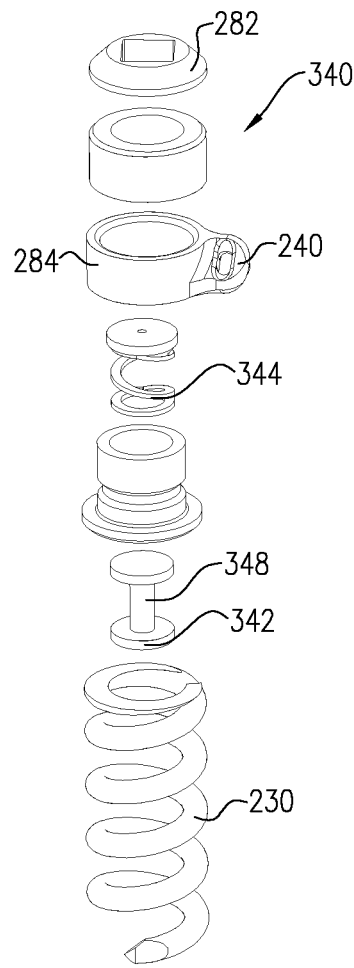
Figure 10D:
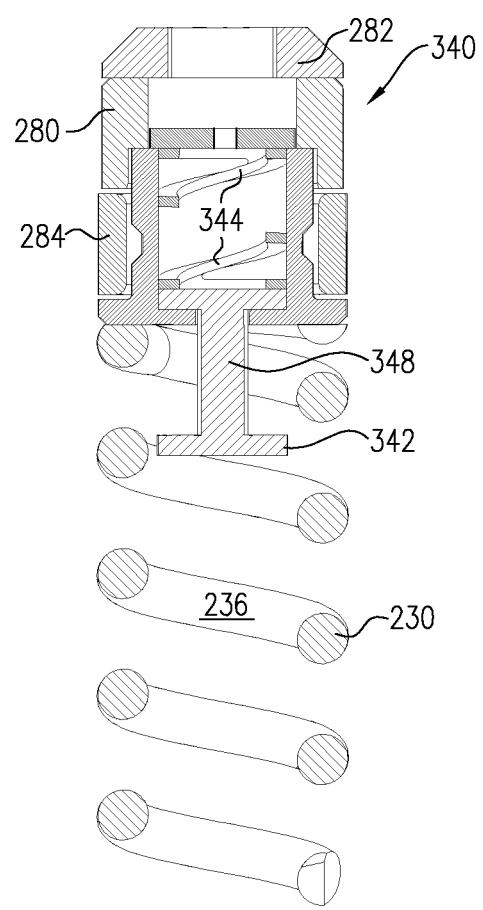
Figure 10E:
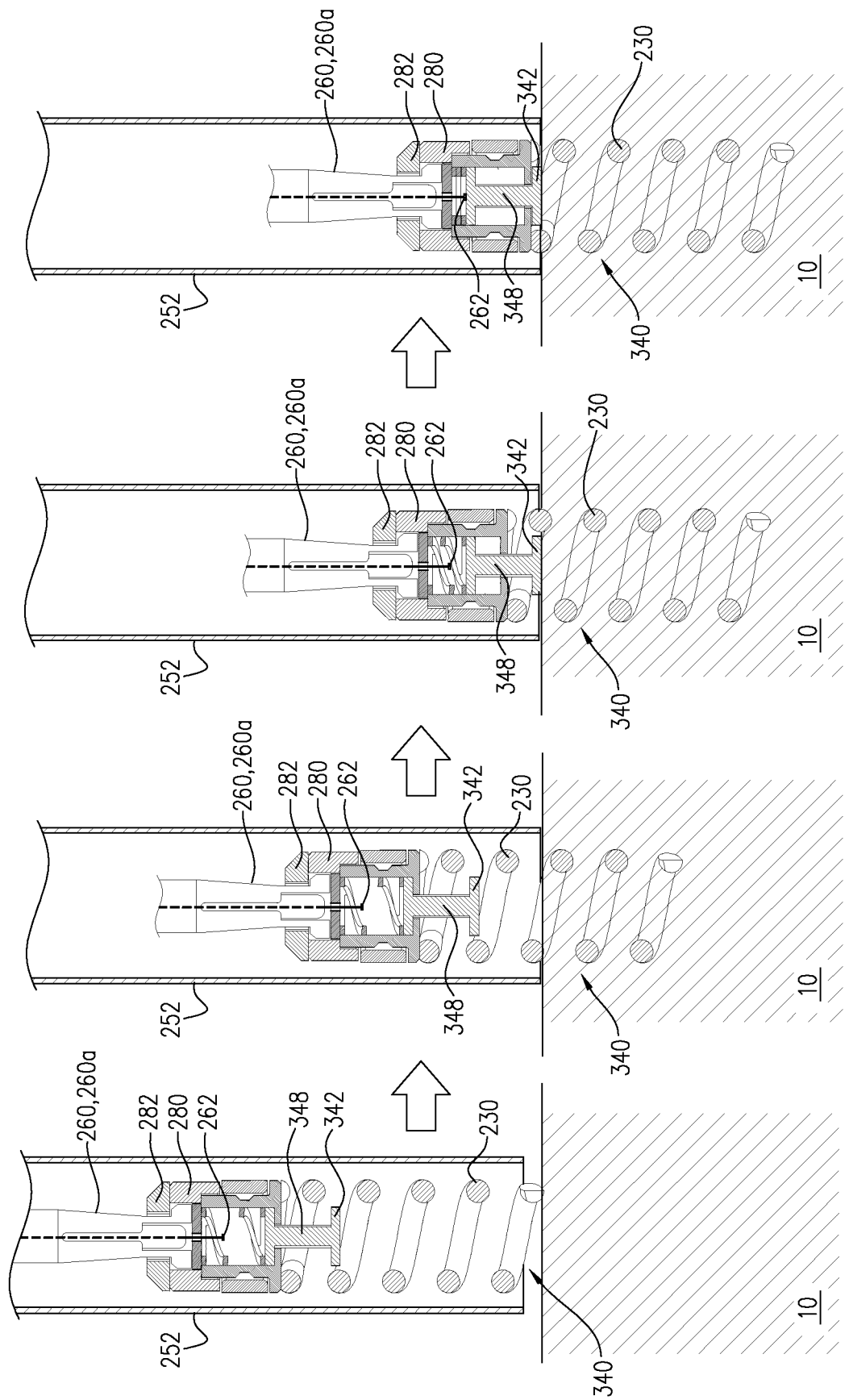

Each of FIGS. 6E, 7E, 8E, 9E, and 10E shows the respective tissue anchor being anchored to tissue, in accordance with some applications. FIGS. 6E, 7E, and 8E show the tissue anchor being a component of an implant similar to implant 210 (e.g, comprising wire 212), but such tissue anchors can also be used in various other contexts, including individually—e.g, as shown in FIGS. 9E and 10E, mutatis mutandis. Similarly, anchors 330 and 340 of FIGS. 9A-E and 10A-E can optionally be used as a component of an implant similar to implant 210 (e.g, comprising wire 212), mutatis mutandis. In each of FIGS. 6E, 7E, 8E, 9E, and 10E, at least the right-most anchor has already been successfully anchored, and the left-most anchor has not yet been successfully anchored. Therefore, the behavior of the anchors (including movement of the protrusion with respect to head 280) can be understood from these figures by comparing the left anchor to the other anchors.

FIGS. 11A, 12A, 13A, and 14A show the respective anchor prior to successful anchoring, and FIGS. 11B, 12B, 13B, and 14B show the respective anchor after successful anchoring. Therefore, the behavior of these anchors (including movement of the protrusion with respect to head 280) can be understood by comparing a given FIG. A to the corresponding FIG. B.

Often, and as shown for anchors 300, 310, 320, 330, 340, 350, 360, 370, and 380, the protrusion is configured to move proximally with respect to the head automatically in response to being pressed against the tissue. That is, as tissue-engaging element 230 moves distally into tissue 10, head 280 and the protrusion move distally toward the tissue, but because the protrusion protrudes distally away from head 280, the protrusion reaches the tissue before the head. Once the protrusion contacts the tissue it stops moving distally, while head 280 continues to move distally toward the tissue, and with respect to the protrusion.

For some applications, the protrusion is disposed laterally outward from the tissue-engaging element. For example, protrusions 302, 312, 322, 362, 372, and 382 extend circumferentially at least partway around tissue-engaging element 230. Similarly, protrusions 332 and 352 are disposed laterally outward from tissue-engaging element 230, and for applications in which the anchor comprises a plurality of protrusions 332 or 352, the protrusions are distributed circumferentially around the tissue-engaging element.

For some applications, the protrusion is disposed medially (e.g, radially inward) from the tissue-engaging element. For example, in some applications, protrusion 342 is disposed medially from tissue-engaging element 230, often on the central longitudinal axis of the tissue anchor. That is, in some applications in anchor 340, helical tissue-engaging element 230 extends helically around protrusion 342.

For some applications, the protrusion and the spring of an anchor are integrated regions of a monolithic structure, and therefore the spring can be considered to be a portion of the protrusion. For such applications, the protrusion (e.g, the spring portion thereof) can be considered to bend automatically in response to the protrusion being pressed against the tissue. Protrusions 302 and spring 304, protrusion 362 and spring 364, protrusion 372 and spring 374, and protrusion 382 and spring 384, are examples of such protrusion/spring pairs that can be integrated regions of respective monolithic structures.

Protrusion 302 of anchor 300 is a ring that can be configured to fully circumscribe tissue-engaging element 230. For some applications, and as shown, spring 304 is a helical compression spring that extends helically around tissue-engaging element 230. For some applications, spring 304 and protrusion 302 are formed from a single helical coil, e.g, with proximal turns of the coil serving as spring 304, and the distalmost turn(s) of the coil having a smaller pitch (e.g, a pitch of about zero) to form protrusion 302. For anchor 300, determination of successful (e.g, complete) anchoring to tissue 10 is often made by fluoroscopic identification of protrusion 302 approaching and/or contacting head 280. Therefore, protrusion 302 (and optionally spring 304) is often radiopaque.

For some applications, the tissue anchor comprises a cuff that extends at least partway around head 280 and the central longitudinal axis of the anchor, a distal portion of the cuff protruding distally away from the head to define the protrusion. For example, anchor 310 (FIGS. 7A-E) comprises a cuff 316, a distal portion of the cuff protruding distally away from head 280 to define protrusion 312; and anchor 320 (FIGS. 8A-E) comprises a cuff 326, a distal portion of the cuff protruding distally away from head 280 to define protrusion 322. Spring 314 is coupled functionally between cuff 316 and head 280, and spring 324 is coupled functionally between cuff 326 and head 280, each such that the respective cuff is configured to move proximally with respect to head 280 automatically in response to the distal portion of the cuff (i.e., the part that defines the protrusion) being pressed against the tissue.

As shown in FIG. 7B and by the left anchor in FIG. 7E, at least a proximal portion of head 280 (e.g, driver interface 282) protrudes proximally from cuff 316 (e.g, in a resting state of anchor 310). As shown by the middle and right anchors in FIG. 7E, cuff 316 is dimensioned such that the moving of the cuff proximally with respect to head 280 obscures the proximal portion of the head (e.g, driver interface 282) with a proximal portion of the cuff. At least the proximal portion of the cuff is radiopaque. Therefore, in a side-view fluoroscopic image, the shape of the proximal portion of head 280 is visible before anchor 310 is anchored, but is obscured after the anchor has been successfully anchored. In the particular example shown, the proximal portion of head 280 (e.g, of driver interface 282) has beveled edges, and so the apparent shape change that is visible fluoroscopically would be from a generally trapezoid shape to a generally rectangular shape. However, various other shapes and various other shape-changes are also possible.

Anchor 320 (FIGS. 8A-E) is similar to anchor 310, except that it further comprises one or more radiopaque indicators 328 (e.g, posts) extending proximally from cuff 326, and the cuff is dimensioned such that the moving of the cuff proximally with respect to head 280 moves the indicators proximally past a proximal portion of the head, such that they become visible on a side-view fluoroscopic image after the anchor has been successfully anchored.

Protrusion 332 of anchor 330 (FIGS. 9A-E) is defined by a distal portion of a post 338 that is configured to move (e.g, axially slide) proximally with respect to head 280 in response to being pressed against the tissue. Spring 334 is coupled functionally between post 338 and head 280. For some applications, and as shown, anchor 330 comprises a plurality of such posts and protrusions. For some such applications, anchor 330 comprises a respective spring for each post 338.

For some applications, and as shown, anchor 330 comprises a cuff 336 that extends at least partway around head 280 and the central longitudinal axis of the anchor, but that, unlike cuffs 316 and 326, is not configured to move proximally with respect to head 280.

Protrusion 332 is radiopaque, and as shown in FIG. 9E, prior to anchoring, is visible in a side-view fluoroscopic image, protruding distally (e.g, distally from head 280 and/or of cuff 336). As also shown in FIG. 9E, in response to being pressed against tissue 10, post 338/protrusion 332 slides axially proximally (e.g, with respect to head 280 and/or cuff 336), and becomes less visible (e.g, invisible) in the side-view fluoroscopic image, thereby indicating successful anchoring.

For some applications, post 338 is configured and dimensioned such that the axial sliding of the post proximally in response to being pressed against tissue 10 results in a proximal portion of the post extending proximally past a proximal portion of head 280, thereby indicating successful anchoring (not shown, but similarly to as described for anchor 350, mutatis mutandis).

For some applications, cuff 316, cuff 326, and/or cuff 336 is revolvable or rotatable around the central longitudinal axis of the respective anchor. For some such applications, and as shown, the cuff is coupled to a ring that is rotatable about the central longitudinal axis of the anchor. For example, and as shown, for applications in which the anchor comprises ring 284 and eyelet 240, the cuff can be coupled to ring 284 opposite eyelet 240.

Similarly to protrusion 332 of anchor 330, protrusion 342 of anchor 340 (FIGS. 10A-E) is also defined by a distal portion of a post 348 that is configured to move (e.g, axially slide) proximally with respect to head 280 in response to being pressed against the tissue. In contrast to protrusion 332, protrusion 342 is disposed medially from tissue-engaging element 230, often on the central longitudinal axis of the tissue anchor. That is, in anchor 340, helical tissue-engaging element 230 extends helically around protrusion 342. For some applications, protrusion 342 is radiopaque, and its movement with respect to head 280 can be used as a fluoroscopic indicator of successful anchoring, as described hereinabove, mutatis mutandis. Alternatively or additionally, the movement of protrusion 342/post 348 can be detected by a sensor (e.g., a pressure sensor) that is a component of the anchor driver. For example, and as shown in FIG. 10E, an anchor driver 260a can be provided as an optional embodiment of anchor driver 260, comprising a sensor (e.g., a pressure sensor) 262 at a distal end of the driver. Sensor 262 is contacted (e.g., pressed) by a proximal portion of post 348 upon proximal movement of the post with respect to head 280. Sensor 262 can be positioned on driver 260a such that, while the driver is engaged with anchor 340, the sensor is disposed within head 280, e.g., distally to interface 282. Sensor 262 is configured to provide a signal (e.g., an "anchor success" signal) in response to being pressed by post 348. For some applications, and as shown, anchor driver 260a comprises a wire extending from sensor 262 to a proximal portion of the anchor driver, and the sensor is configured to transmit the signal via the wire. Optionally, the sensor and/or system can be configured to provide a wireless signal.

Anchor 350 (FIGS. 11A-B) is similar to anchor 330, in that it comprises a protrusion 352 defined by a distal portion of a post 358 that is configured to move (e.g., axially slide) proximally with respect to head 280 in response to being pressed against the tissue. Unlike anchor 330, anchor 350 typically does not comprise a spring. For some applications, and as shown, anchor 350 comprises a plurality of such posts and protrusions.

Protrusion 332 is radiopaque, and as shown in FIG. 11A, prior to anchoring, is visible in a side-view fluoroscopic image, protruding distally (e.g., distally from head 280). As shown in FIG. 11B, in response to being pressed against tissue 10, post 358/protrusion 352 slides axially proximally (e.g, with respect to head 280), such that a proximal portion of post 358 becomes visible proximally of head 280, thereby indicating successful anchoring.

For some applications, the distal ends of posts 338, 348, and 358 (e.g., protrusions 332, 342, and 352) are blunt, in order to facilitate their pushing by the tissue, e.g., without piercing the tissue.

Anchor 360 (FIGS. 12A-B) is similar to anchor 300 in that its protrusion, protrusion 362, is a ring that can be configured to fully circumscribe tissue-engaging element 230, and in that determination of successful (e.g., complete) anchoring to tissue 10 is often made by fluoroscopic identification of protrusion 362 approaching and/or contacting head 280. Therefore, protrusion 362 is often radiopaque. Although spring 364 of anchor 360 is a compression spring, in contrast to spring 304, spring 364 is not helical. Rather spring 384 comprises a plurality of chevron-shaped beams distributed circumferentially around the central longitudinal axis of anchor 360 (e.g, distributed circumferentially around a proximal portion of tissue-engaging element 230). The chevron-shaped beams may all be in phase with each other (as shown), or some may be in antiphase with others.

Anchor 370 (FIGS. 13A-B) is similar to anchor 300 in that its spring, spring 374, is a helical compression spring that extends helically around tissue-engaging element 230. Further similarly, spring 374 and protrusion 372 are often formed from a single helical coil, with a proximal portion of the coil serving as the spring, and a distal portion of the coil serving as the protrusion. However, the helical coil of anchor 370 often defines no more than one complete turn. For example, the helical coil can define 80-100% (e.g, 90-100%, e.g, 95-100%, e.g, 95-99%) of a complete turn. For some applications, spring 374 resembles a helical split washer.

In response to being pressed against the tissue, a first end of the helical compression spring (e.g, a proximal end) becomes aligned, along the central longitudinal axis of the anchor, with a second end of the helical compression spring—e.g, a distal end, which defines protrusion 372. It is often this alignment that is detected fluoroscopically in order to determine successful anchoring of anchor 370. (It is to be noted that using a helical compression spring that has more than one complete turn would mean that a turn disposed between the distal and proximal ends of the spring would inhibit the ends from coming into alignment with each other.)

Anchor 380 (FIGS. 14A-B) is similar to anchor 300 in that its protrusion, protrusion 382, is a ring that can be configured to fully circumscribe tissue-engaging element 230, and in that determination of successful (e.g, complete) anchoring to tissue 10 is often made by fluoroscopic identification of protrusion 382 approaching and/or contacting head 280. Therefore, protrusion 382 is often radiopaque. Although spring 384 of anchor 380 is a compression spring, in contrast to spring 304, spring 384 is not helical. Rather spring 364 comprises a plurality of arches distributed circumferentially around the central longitudinal axis of anchor 380 (e.g, distributed circumferentially around a proximal portion of tissue-engaging element 230). As shown, spring 384 can comprise more than one layer (e.g, two layers) of such arches. For example, and as shown, spring 384 can comprise two layers of such arches, one layer inverted with respect to the other, such that the apex of an arch of one layer meets the apex of an arch of the other layer.

Figure 15:
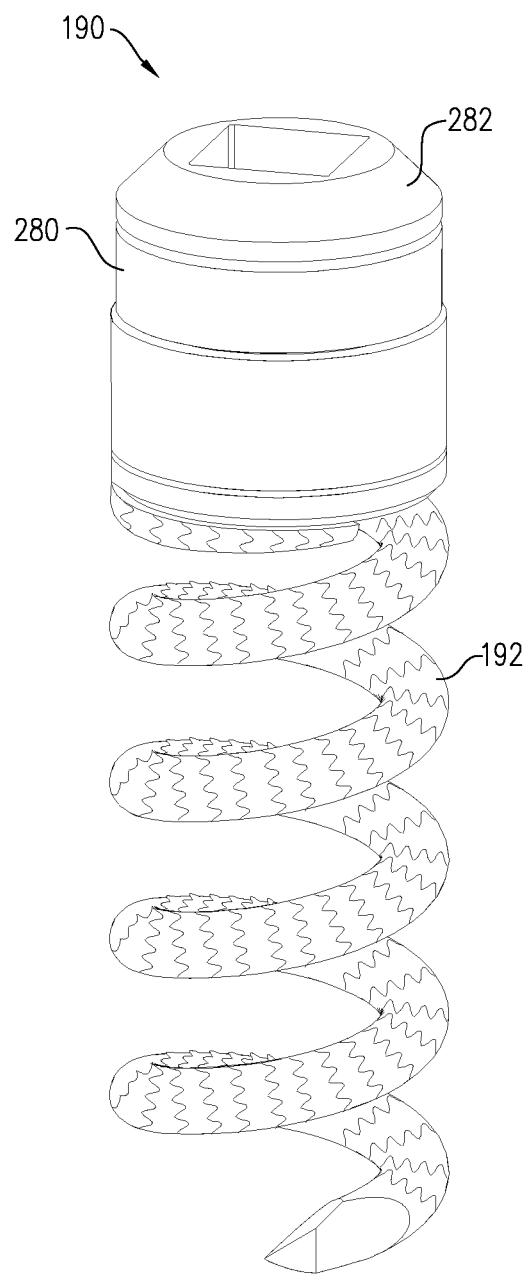
FIG. 15 is a schematic illustration of an example tissue anchor, in accordance with some applications.

Reference is made to FIG. 15, which is a schematic illustration of a tissue anchor 190, in accordance with some applications. Anchor 190 comprises a head such as head 280, and a driver interface such as driver interface 282. Anchor 190 also comprises a tissue-engaging element 192. Tissue-engaging element 192 can include a helical tissue-engaging element. Tissue-engaging element 192 can be identical to or similar to tissue-engaging element 230 except that tissue-engaging element 192 has a knurled surface. It is hypothesized that the knurling of the surface of tissue-engaging element 192 facilitates securing of the tissue-engaging element within tissue 10, e.g, by helping to inhibit the tissue-engaging element from working its way out of tissue over time.

Reference is again made to FIGS. 6A-15. The tissue anchors described with respect to FIGS. 6A-15 can be used in place of one or more tissue anchors of the systems described herein (e.g, system 100, system 200, system 400, and/or system 600) mutatis mutandis. Similarly, tissue anchors described elsewhere in this patent application can be modified to include one or more of the features of the tissue anchors described with respect to FIGS. 6A-15, such as a protrusion, a spring, and/or a knurled tissue-engaging element. Furthermore, one of the tissue anchors described with respect to FIGS. 6A-15 can be modified to include one or more features of one or more other tissue anchors described with respect to FIGS. 6A-15.

Reference is made to FIGS. 16A-C, 17A-C, 18, and 19A-C, which are schematic illustrations of systems for facilitating controlled anchoring of an anchor to tissue, in accordance with some applications. FIGS. 16A-C and 17A-C schematically illustrate a system 400, and FIGS. 18 and 19A-C schematically illustrate a system 450. Each of systems 400 and 450 comprises a flexible tube (e.g., a transluminal catheter), a tissue anchor, and an anchor driver shown and described herein as driver 260. In each case, the anchor can comprise (i) a helical tissue-engaging element defining a central longitudinal axis of the anchor by extending helically around the central longitudinal axis, having a sharpened distal tip, and configured to be driven into tissue of a subject; and (ii) an anchor head, coupled to a proximal end of the tissue-engaging element, and comprising a driver interface.

In each case, the flexible tube (e.g, a lateral wall thereof) often defines an internal channel from a proximal portion of the catheter to a distal portion of the catheter, and a distal opening at the distal portion of the catheter, the channel ending at the distal opening. The anchor driver is often configured to advance the anchor through the channel and out of the distal opening, and to drive the tissue-engaging element into the tissue, e.g, by rotating the anchor. Therefore, the tissue anchors, flexible tubes, and anchor drivers of systems 400 and 450 are similar to those for other systems described herein. However, the flexible tube (e.g, catheter) of each of systems 400 and 450 often further comprises a spur at the distal portion of the catheter. In each case, the spur protrudes (either fixedly or retractably) medially into the channel so as to (i) obstruct the tissue-engaging element from passing the spur distally in the absence of rotation of the tissue-engaging element, and (ii) allow the tissue-engaging element to screw past the spur distally. This is hypothesized by the inventors to reduce a likelihood of premature exposure of the anchor's tissue-engaging element from the tube (which might, for example, result in inadvertent snagging of tissue and/or another part of the system), and/or inadvertent excessive axial pressing of the anchor against the tissue (e.g, as opposed to helical corkscrewing of the anchor into the tissue).

System 400 (FIGS. 16A-C and 17A-C) comprises a tissue anchor 410, and a flexible tube (e.g, catheter) 420.

Tissue anchor 410 comprises a head 412 and a tissue-engaging element 414. For some applications, tissue-engaging element 414 is identical to or similar to tissue-engaging element 230 or other tissue-engaging elements described hereinabove. For some applications, other than defining a groove 416, head 412 is identical to or similar to head 280 described hereinabove, or to other heads described herein, mutatis mutandis. Tube 420 (e.g, a lateral wall 422 thereof) often defines an internal channel 424 from a proximal portion of the catheter to a distal portion of the catheter, and a distal opening 426 at the distal portion of the catheter, the channel ending at the distal opening. For some applications, tube 420 is identical to or similar to one or more other flexible tubes described herein, except that it further comprises a spur 430 that protrudes medially into the channel. In contrast to spur 480 of system 450, described hereinbelow, spur 430 often fixedly protrudes into the channel (e.g, is fixedly attached to lateral wall 422).

Figure 17C:
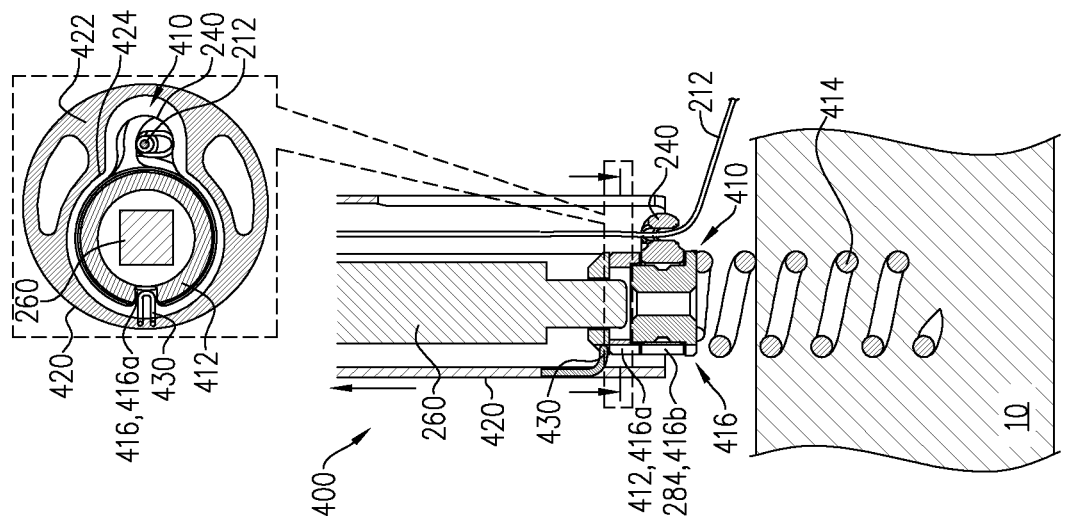
Figure 17B:
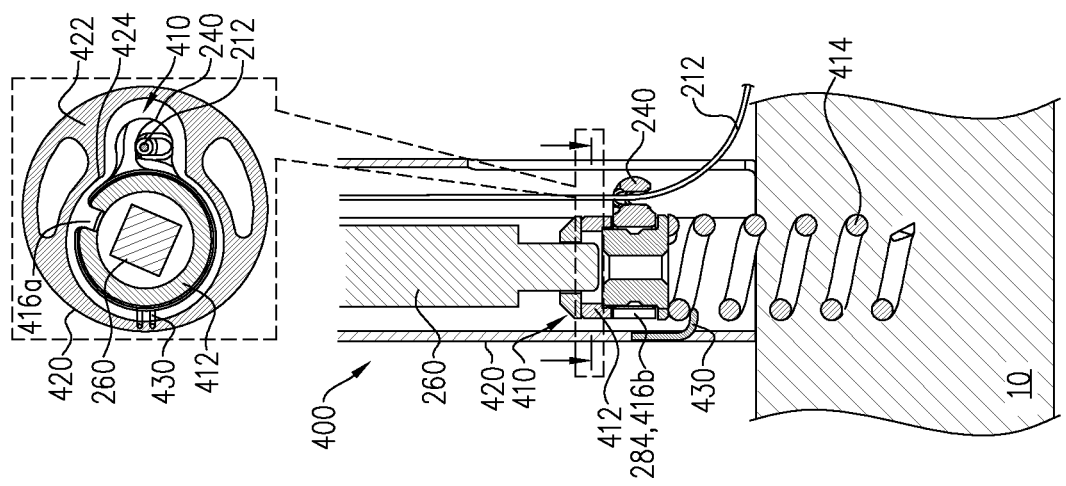
Figure 17A:
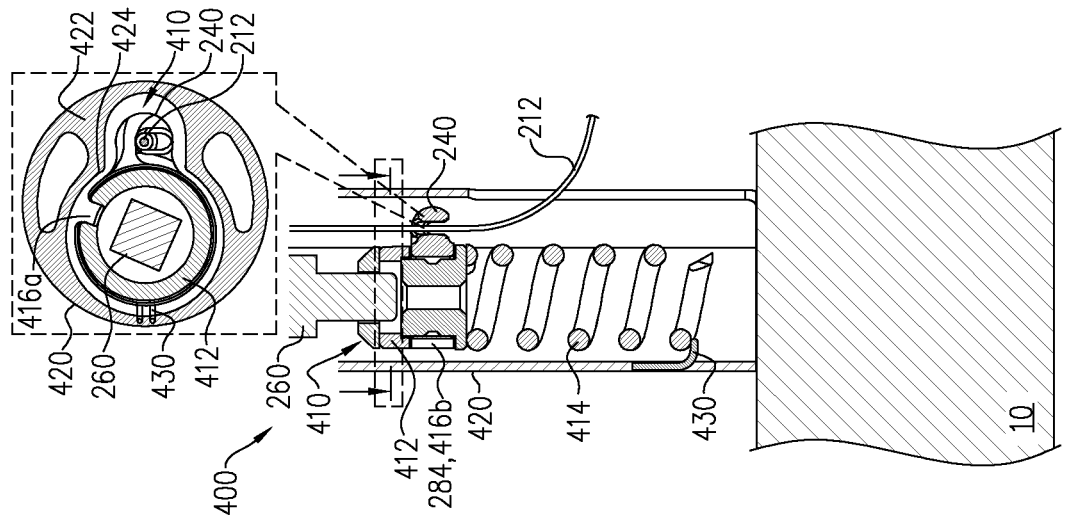

FIG. 16A is a perspective view showing anchor 410 disposed within the distal portion of tube 420, and FIGS. 16B and 16C are perspective views showing anchor 410 alone, in different states, in accordance with some applications. FIGS. 17A-C are schematic illustrations of progressive stages in the anchoring of anchor 410 using system 400, in accordance with some applications.

The dimensions of the channel of tube 420, tissue-engaging element 414, and spur 430 are such that, during axial advancement of anchor 410 distally through the catheter, when the tissue-engaging element reaches spur 430, the spur obstructs further distal advancement of the anchor in the absence of rotation of the tissue-engaging element (FIG. 17A). For some applications, and as shown, spur 430 is longitudinally positioned sufficiently proximally from distal opening 426 such that this obstruction occurs before any portion of anchor 410 (including its sharpened distal tip) is exposed from the distal opening. Optionally, spur 430 can be longitudinally positioned sufficiently distally that, when this obstruction occurs, the sharpened distal tip of tissue-engaging element 414 (but typically less than one complete turn of the helix of the tissue-engaging element) is exposed from the distal opening.

Further distal advancement of anchor 410 is achieved by rotating the anchor, e.g., using driver 260, such that helical tissue-engaging element 414 screws past spur 430 (FIG. 17B). FIGS. 17A-B show the distal opening of tube 420 being held in contact with tissue 10. Thus, the further distal advancement of anchor 410 screws tissue-engaging element 414 into tissue 10.

For some applications, head 412 is dimensioned (e.g, is sufficiently wide) such that, in at least one rotational position of the head with respect to tube 420, spur 430 inhibits the head from passing the spur axially. For such applications, head 412 is often dimensioned such that, in at least one other rotational position of the head with respect to tube 420, the head is slidable past spur 430 axially. In the example, shown, a groove 416, parallel with the central longitudinal axis of anchor 410, is defined in an outer surface of head 412. Spur 430 inhibits head 412 from passing the spur axially in most rotational positions of the head with respect to the tube, and rotational alignment of groove 416 with the spur defines the rotational position in which the head is slidable past the spur axially. Therefore, in that rotational position, the spur can slide along the groove as the head is slid past the spur axially.

Anchor 410 is configured (e.g., by the relative rotational orientation between tissue-engaging element 414 and groove 416) such that, during advancement of the anchor, once the proximal end of the tissue-engaging element has passed spur 430, the groove becomes aligned with the spur, such that head 412 can be slid past the spur axially. Such a configuration can be seen in FIG. 16B, where a transition zone 432 represents where, during advancement of anchor 410, spur 430 exits from between turns of the helix of tissue-engagement element 414 and enters groove 416. FIG. 17C shows anchor 410 having been advanced sufficiently such that the proximal end of tissue-engaging element 414 has passed spur 430, the groove has become aligned with the spur, and head 412 has slid past the spur axially, by tube 420 having been retracted proximally.

In the particular embodiment shown, the axial position of spur 430 within tube 420 is such that spur 430 exits the proximal end of tissue-engaging element 414 while more than a full turn of the tissue-engaging element remains outside of tissue 10. This remaining portion of tissue-engaging element 414 is typically then driven in the absence of the control provided by spur 430. For other applications, spur 430 is disposed closer to distal opening 426, such that less of tissue-engaging element 414 remains outside of tissue 10 at the point at which spur 430 exits the proximal end of the tissue-engaging element.

Therefore, in use, at least some of the following steps are often performed:
Anchor 410 is advanced axially with little or no rotation until tissue-engaging element 414 reaches spur 430.

At that point, further advancement is helical, requiring rotation of the anchor, e.g., such that the relationship between distal advancement and rotation is according to the helical pitch of tissue-engagement element 414. This helical advancement often includes screwing of tissue-engaging element 414 into tissue.

Once the proximal end of tissue-engaging element 414 has passed spur 430, the spur slides axially through groove 416 with little or no rotation of anchor 410.

Once spur 430 has exited the proximal end of groove 416, further helical advancement of anchor 410 is possible, in order to further screw tissue-engaging element 414 into the tissue.

For some applications, anchor 410 includes features of other anchors described herein. For example, and as shown, head 412 can comprise eyelet 240, e.g, mounted on ring 284, and thereby rotatably coupled to another component of head 412, e.g., as described for anchor 220, mutatis mutandis. Furthermore, and as shown, tube 420 can have an internal channel that defines a major channel region and a minor channel region, e.g., as described for tube 252, mutatis mutandis. For some such applications, groove 416 axially traverses ring 284 in order for the entirety of head 412 to slide axially past spur 430. That is, groove 416 has (i) at least one fixed groove-section 416a that is defined by part of head 412 that is rotationally fixed with respect to tissue-engaging element 414 (and part(s) 416a is/are thereby rotationally fixed with respect to the tissue-engaging element); and (ii) at least one revolvable groove-section 416b that is defined by ring 284, and that is therefore revolvable about the central longitudinal axis of the anchor, with respect to the tissue-engaging element (and with respect to driver interface 282).

In the example shown, groove 416 has one revolvable groove-section 41b, flanked by two fixed groove-sections 416a. FIG. 16B shows anchor 410 with fixed groove-sections 416a aligned with revolvable groove-section 41b, and FIG. 16C shows the anchor with the fixed groove-sections revolved away from the revolvable groove-section. For clarity, it is to be noted that, although FIG. 16C appears to show revolvable groove-section 416b in the same position as in FIG. 16B, and fixed groove-sections 416a in a different position to that in FIG. 16B, the fixed groove-sections remain rotationally fixed with respect to tissue-engaging element 414, while the tissue-engaging element rotates with respect to the revolvable groove-section.

In the particular example shown, groove-section 416b (and groove 416 as a whole, when groove-sections 416a and 416b are aligned) is disposed opposite eyelet 240—i.e., 180 degrees, from the eyelet, around the central longitudinal axis of anchor 410. Correspondingly, spur 430 is disposed opposite the minor channel region of tube 420. Anchor 410 and tube 420 can also be configured for different rotational orientations of groove 416, by matching the position of spur 430 relative to the minor channel region, with the position of the groove (or at least groove section 416b) relative to eyelet 240.

As described hereinabove, groove-section 416b is in a fixed rotational orientation with respect to eyelet 240, and therefore is seen in the same rotational position in FIGS. 17A, 17B, and 17C. FIG. 17A shows groove-section 416a not rotationally aligned with spur 430. FIG. 17B shows anchor 410 after three full turns of tissue-engaging element 414 have been driven into tissue 10, with groove-section 416a returned to the same rotational position as in FIG. 17A. FIG. 17C shows anchor 410 after tissue-engaging element 414 has been driven further into tissue 10, until the proximal end of the tissue-engaging element has passed spur 430. As shown, at that point, groove-section 416a becomes aligned with spur 430, and with groove-section 41b, thereby forming a complete groove 416, through which the spur can slide, e.g, such that tube 420 can be retracted, as shown.

Reference is again made to FIG. 17C. It will be appreciated that, while spur is disposed within groove-section 406*a*, driver 260 is rotationally locked to tube 420 via head 412 of anchor 410. For some applications, this state can be exploited by the operator in order to adjust a rotational orientation of tube 420 by applying torque to the tube via rotation of driver 260.

System 450 (FIGS. 18 and 19A-C) comprises a tissue anchor 460, and a flexible tube (e.g., catheter) 470 that comprises a lateral wall 472 that defines an internal channel 474 that ends at a distal opening 476. Tube 470 further comprises a spur 480. Tissue anchor 460 comprises an anchor head 462, and a helical tissue-engaging element 464 that defines a central longitudinal axis of the anchor, has a sharpened distal tip, and is configured to be driven into tissue of a subject. System 450 is similar, and has similar advantages, to system 400. However, in contrast to spur 430 of system 400, spur 480 of system 450 is at least partly retractable into lateral wall 472 of tube 470. It is hypothesized that the retractability of spur 480 reduces (e.g, obviates) the need for tissue anchor 460 to have special features (such as a groove) for passing the spur. In fact, anchor 460 can be identical to or similar to anchor 220 described hereinabove, or to anchor 620 described hereinbelow.

Spur 480 is thereby reversibly transitionable between (i) an extended state in which the spur extends medially from the lateral wall into channel 474, and (ii) a retracted state in which the spur is at least partly retracted into the lateral wall. In its extended state, spur 480 inhibits anchor head 462 from passing the spur axially. In its retracted state, spur 480 allows head to pass the spur distally.

For some applications, and as shown, tube 470 further comprises a pullwire 478 that is coupled to spur 480, and that extends proximally from the spur along lateral wall 472 (e.g, within a secondary channel 475 of tube 470), such that the spur is retractable into the lateral wall by pulling on the pullwire. For such applications, spur 480 can generally be returned to its extended state by releasing or pushing the pullwire. For some such applications, spur 480 comprises, or is coupled to another element that comprises, an elastic and/or shape-memory material that facilitates the reversible transitioning of the spur.

FIG. 19A shows anchor 460 having been axially advanced distally through tube 470, until tissue-engaging element 464 reaches spur 480, and the spur obstructs further distal advancement of the anchor in the absence of rotation of the tissue-engaging element. FIG. 19B shows anchor 460 having been advanced further distally while tissue-engaging element 464 is rotated several times, such that the tissue-engaging element screws past spur 480 and into tissue 10. FIG. 19C shows spur 480 having been retracted into secondary channel 475, enabling further advancement of anchor 460.

For some applications, spur 480 is retracted only once head 462 reaches the spur, such that retraction of the spur is necessary for further advancement of anchor 460. For some applications, spur 480 is retracted at any stage that the operator deems to be beneficial.

Systems 400 and 450, and/or features thereof, can be integrated into other systems described herein, e.g, to confer the advantages described for systems 400 and 450 on the other systems. For example, the tissue anchor, flexible tube, and anchor driver of another system described herein can be replaced by those of systems 400 and/or 450.

Reference is made to FIGS. 20A-D, which are schematic illustrations of a system 500 comprising an implant 510, in accordance with some applications. System 500 is a tissue-adjustment system and can be used for adjusting a dimension of a tissue structure. For example, system 500 can be an annuloplasty system, and implant 510 can be an annuloplasty structure (e.g., an annuloplasty ring, annuloplasty implant, etc.). System 500 (e.g., implant 510) can be used in similar ways to those described for system 100, system 200, system 400, and/or system 600, mutatis mutandis.

Implant 510 comprises at least one wire 512, a plurality of tissue anchors 520, and a plurality of connectors 540, each of the connectors slidably coupling, to the wire, a respective anchor 520. (For simplicity, only one anchor 520 and one connector 540 of implant 510 are shown). Each anchor 520 comprises a tissue-engaging element 530, a head 534, and a neck 532. Tissue-engaging element 530 defines a central longitudinal axis of the anchor, e.g, by extending helically around the axis, as described for other tissue-engaging elements hereinabove, mutatis mutandis. Tissue-engaging element has a sharpened distal tip and is configured to be driven into tissue of a subject, as described for other sharpened distal tips hereinabove, mutatis mutandis. Neck 532 couples tissue-engaging element 530 to head 534, often by extending along the central longitudinal axis of anchor 520. Head 534 comprises or defines a driver interface 536, which is configured to be reversibly engaged by an anchor driver, e.g., as described hereinabove, mutatis mutandis. Other tissue-engaging element configurations, such as described elsewhere herein, are also possible.

Each connector 540 comprises a flexible sheet (e.g., comprising a fabric and/or a polymer) that is shaped to define a hole 542 and at least one eyelet 546. Neck 532 extends through hole 542, such that (i) head 534 is disposed on a first side of the sheet, (ii) tissue-engaging element 530 is disposed on a second, opposite, side of the sheet, and (iii) the anchor 520 is rotatable, around its central longitudinal axis, with respect to the sheet, by the neck rotating within the hole.

Wire 512 is threaded through eyelet 546, thereby slidably coupling the connector to the wire. For some applications, eyelet 546 is defined by a hem stitched in the flexible sheet.

Figure 20A:
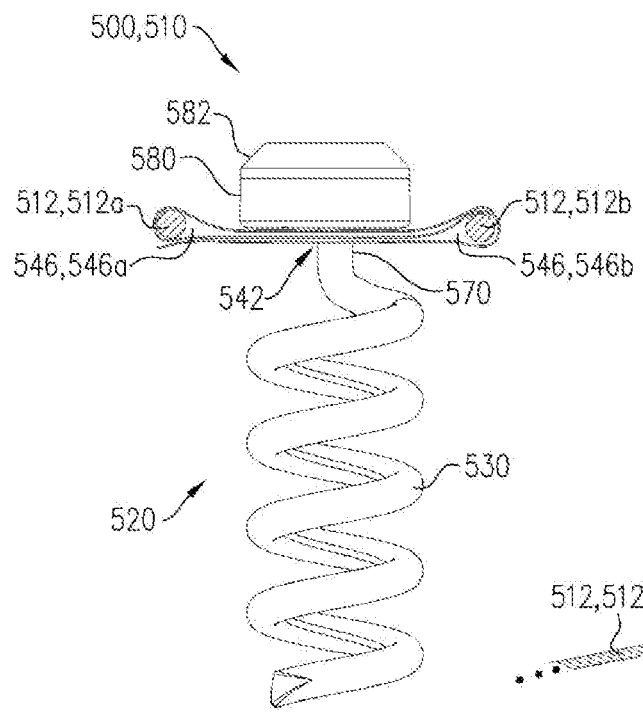
FIGS. 20A-D are schematic illustrations of examples of systems comprising an implant, in accordance with some applications.
Figure 20B:
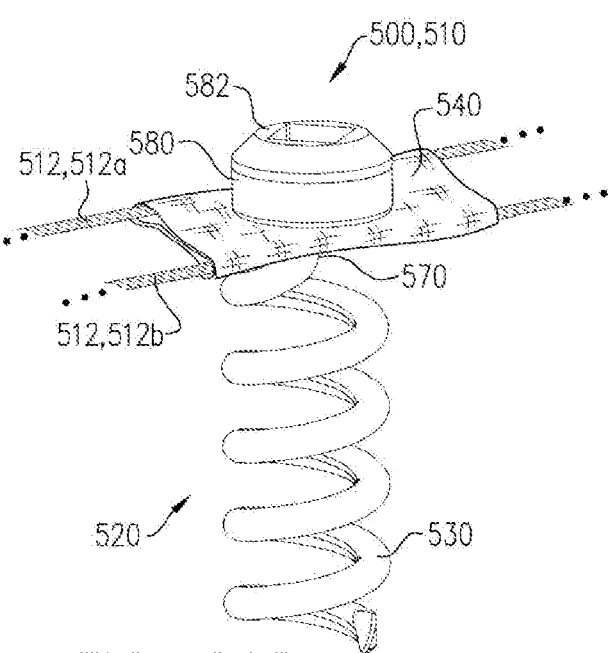
Figure 20C:
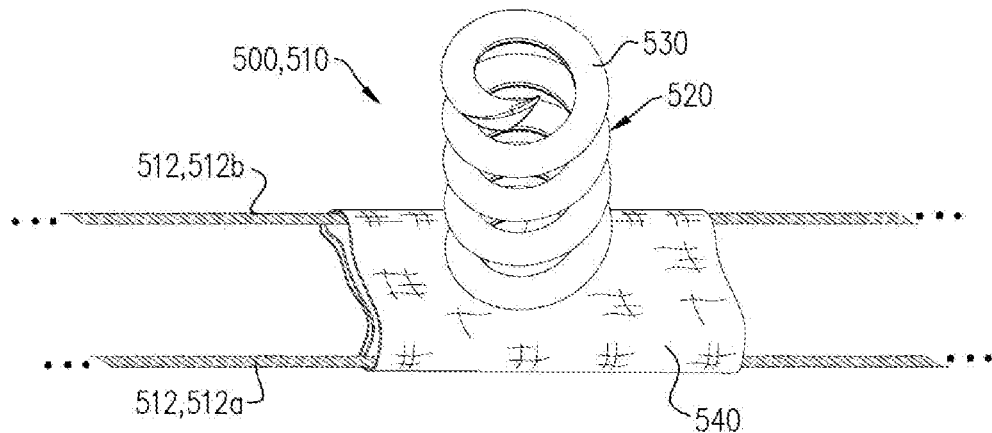

For some applications, and as shown in FIGS. 20A-C, implant 510 comprises two wires 512 (e.g., a first wire 512*a* and a second wire 512*b*), and each connector 540 (e.g, the sheet thereof) is shaped to define two eyelets 546 (e.g., a first eyelet 546*a* and a second eyelet 546*b*), with each wire being slidably coupled to the anchor by being threaded through a respective eyelet. For example, and as shown, hole 542 can be defined between first eyelet 546*a* and second eyelet 54*b*, such that anchor 520 (e.g., neck 532 thereof) is disposed between first wire 512*a* and second wire 512*b*. For some applications, and as shown, wires 512*a* and 512*b* are generally parallel with each other.

Implant 510 can be implanted and adjusted using techniques described for other systems described herein, mutatis mutandis. For example, anchors 520 can be anchored sequentially around the annulus of a heart valve, such as the mitral valve, before wire 512 is tensioned in order to contract the annulus. Further, these techniques and methods can be performed on a living animal or on a simulation, such as on a cadaver, cadaver heart, simulator (e.g. with the body parts, heart, tissue, etc. being simulated), etc.

It is hypothesized by the inventors that the flexibility of the sheet of connector 540 confers advantages on system 500 that are similar to those described for systems 100, 200, 400, and 600, mutatis mutandis. For example, the flexibility of the sheet may allow anchors 520 to be slid along the wire (i) while generally parallel to the wire (e.g, during delivery), and (ii) while generally orthogonal to the wire (e.g, after implantation, during contraction).

Figure 20D:
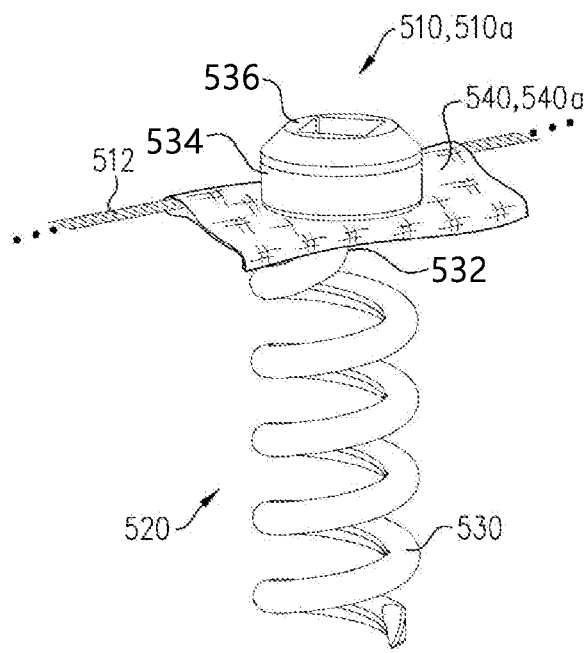

FIG. 20D shows an embodiment 510*a* of implant 510, which is different from the implant 510 illustrated in FIGS. 20A-C in that it includes a single wire 512 threaded through an eyelet 546 of connector 540, instead of two wires. For some applications, implant 510*a* comprises an embodiment 540*a* of connector 540, which includes a single eyelet 546 on one side thereof, instead of two eyelets.

Reference is made to FIGS. 70A-C, which are schematic illustrations of a system 550 comprising an implant 560, in accordance with some applications. System 550 is a tissue-adjustment system and can be used for adjusting a dimension of a tissue structure. For example, system 550 can be an annuloplasty system, and implant 560 can be an annuloplasty structure (e.g., an annuloplasty ring, annuloplasty implant, etc.). System 550 (e.g, implant 560) can be used in similar ways to those described for system 100, system 200, system 400, 500 and/or system 600, mutatis mutandis.

Implant 560 comprises at least one wire 562, a plurality of tissue anchors 570, and a plurality of flexible sleeves 590, each of the sleeves slidably coupling, to the wire, a respective anchor 570. (For simplicity, only one anchor 570 and one sleeve 590 of implant 560 are shown). Each anchor 570 comprises a tissue-engaging element 580, a head 588, and a neck 582. Tissue-engaging element 580 can be configured similar to other tissue-engaging elements herein. In some applications, tissue-engaging element 580 defines a central longitudinal axis of the anchor, e.g., by extending helically around the axis, as described for other tissue-engaging elements hereinabove, mutatis mutandis. Tissue-engaging element has a sharpened distal tip and is configured to be driven into tissue of a subject as described for other sharpened distal tips hereinabove, mutatis mutandis. Neck 582 couples tissue-engaging element 580 to head 584, often by extending along the central longitudinal axis of anchor 570. Head 584 comprises or defines a driver interface 586, which is configured to be reversibly engaged by an anchor driver, e.g, as described hereinabove, mutatis mutandis. Head 584 further defines a head circumferential surface 588 around the central axis defined by the tissue engaging element.

Each sleeve 590 can be made of a flexible fabric and/or a polymer, that is shaped to snugly cover at least a portion of the head 584, and more precisely, comprises a sleeve circumferential portion that is snugly disposed around the head circumferential surface 588. The sleeve 590 further includes a proximal opening 594 disposed over the upper surface of head 584 and dimensioned to expose the driver interface 586, so that a driver of system 550 will be able to engage with the driver interface 586 without interference of the sleeve 590. The diameter of the proximal opening 594 can be at least as large as the diameter of the driver interface 586, yet, for some applications, it can be smaller than the outer diameter of the head 584, serving as an upper boundary for holding the sleeve 590 coupled to head 584. It is to be understood that a reference to the diameter of head 584 refers to the maximal distance between opposite sides of head circumferential surface 588.

Sleeve 590 further comprises a distal opening 592 through which neck 582 can extend. The diameter of the distal opening 592 can be at least as large as the diameter of neck 582, yet, for some applications, it can be smaller than the outer diameter of the head 584, serving as lower boundary for holding the sleeve 590 coupled to head 584. The anchor 570 is rotatable, around its central longitudinal axis, with respect to the sleeve 590, wherein the neck 582 is configured to rotate within the distal opening 592.

Sleeve 590 further comprises at least one eyelet 598 disposed over at least a portion of sleeve circumferential portion 596. Wire 562 (or another line, contracting member, etc.) is threaded through eyelet 598, thereby slidably coupling the sleeve to the wire. For some applications, eyelet 598 is defined by a patch or fabric strip coupled (e.g., stitched or glued) to the sleeve 596 at upper and lower portions thereof.

For some applications, and as shown in FIGS. 70A-B, implant 560 comprises two wires, lines, contracting members 562 (e.g., a first wire 562*a* and a second wire 562*b*), and each sleeve 590 includes two eyelets 598 (e.g., a first eyelet 598*a* and a second eyelet 598*b*) defined at opposite sides of the sleeve circumferential portion 596, with each wire being slidably coupled to the anchor by being threaded through a respective eyelet. For some applications, and as shown, wires 562*a* and 562*b* are generally parallel with each other.

Implant 560 can be implanted and adjusted using techniques described for other systems described herein, mutatis mutandis. For example, anchors 570 can be anchored sequentially around the annulus of a heart valve, such as the mitral valve, before wire 562 is tensioned in order to contract the annulus. Further, these techniques and methods can be performed on a living animal or on a simulation, such as on a cadaver, cadaver heart, simulator (e.g. with the body parts, heart, tissue, etc. being simulated), etc.

It is hypothesized by the inventors that the flexibility of sleeve 590 confers advantages on system 550 that are similar to those described for systems 100, 200, 400, 500, and 600, mutatis mutandis. For example, the flexibility of the sleeve may allow anchors 570 to be slid along the wire (i) while generally parallel to the wire (e.g., during delivery), and (ii) while generally orthogonal to the wire (e.g., after implantation, during contraction).

FIG. 70C shows an embodiment 560*a* of implant 560, which is different from the implant 560 illustrated in FIGS. 70A-B in that it includes a single wire, line, contracting member 562 threaded through an eyelet 598 of the sleeve, instead of two wires. For some applications, implant 560*a* comprises an embodiment 590*a* of sleeve 590, which includes a single eyelet 598*a* on one side thereof, instead of two eyelets.

Reference is now made to FIGS. 21A-G, 22A-B, 23A-B, 24, 25, 26, and 27, which are schematic illustrations of examples of a tissue anchor 620, an implant 610 comprising the tissue anchor, a system 600 comping the implant, and techniques for use therewith, in accordance with some applications. System 600 is a tissue-adjustment system and can be used for adjusting a dimension of a tissue structure. For example, system 600 can be an annuloplasty system, and implant 610 can be an annuloplasty structure (e.g, an annuloplasty ring, annuloplasty implant, etc.).

System 600 can be identical to or similar to system 200 except where noted. Similarly, implant 610 and anchor 620 are identical to or similar to implant 210 and anchor 220, except where noted.

Like implant 210, implant 610 comprises line or wire 212 and a plurality of anchors. However, implant 610 often further comprises one or more tubular spacers 670, threaded onto wire 212. Each spacer is often disposed, on wire 212, between a pair of adjacent anchors 620. Spacer 670 limits a proximity between the pair of anchors—i.e., the amount by which the pair of anchors can become closer, e.g, when wire 212 is tensioned. This effect, and the benefits thereof, are described in more detail hereinbelow.

Figure 21B:
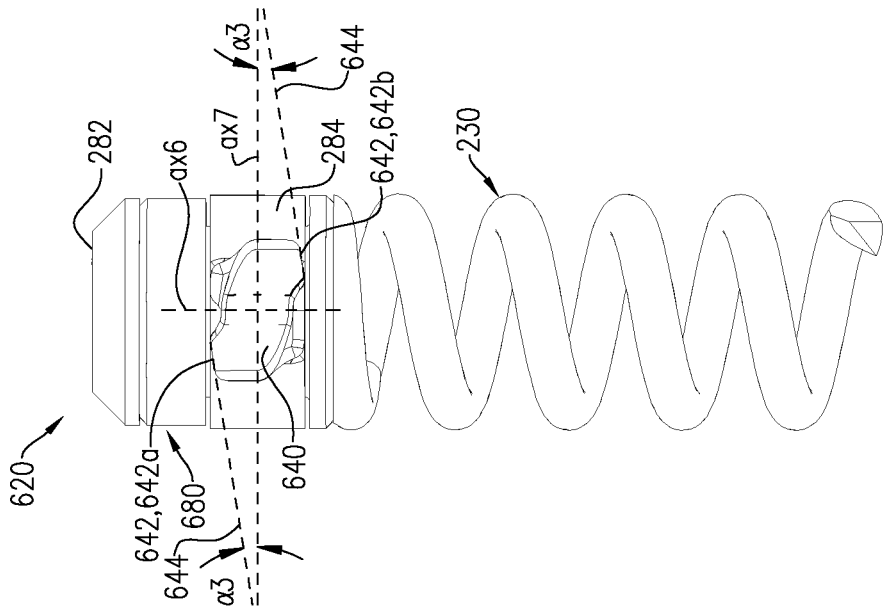
Figure 21A:
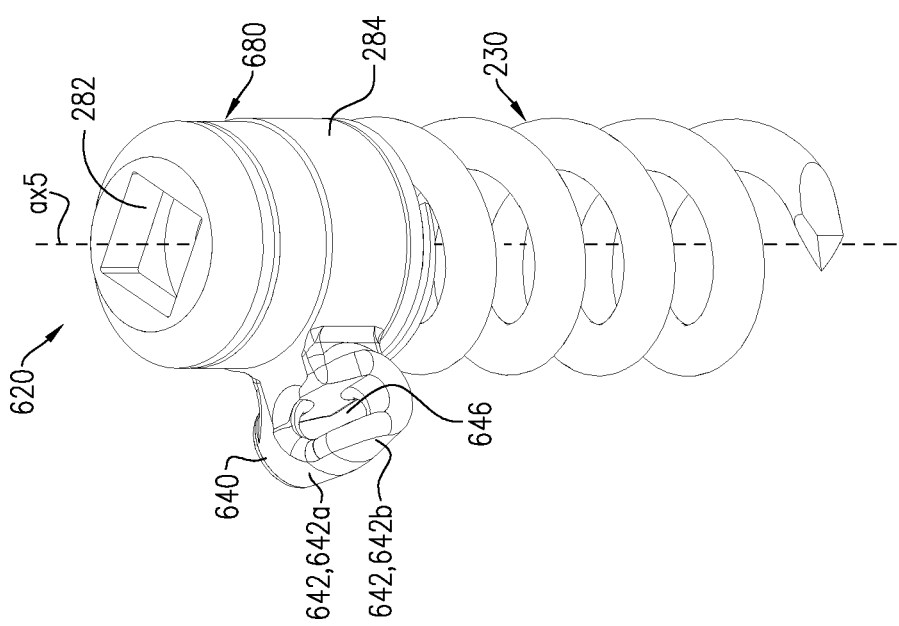
Figure 21D:
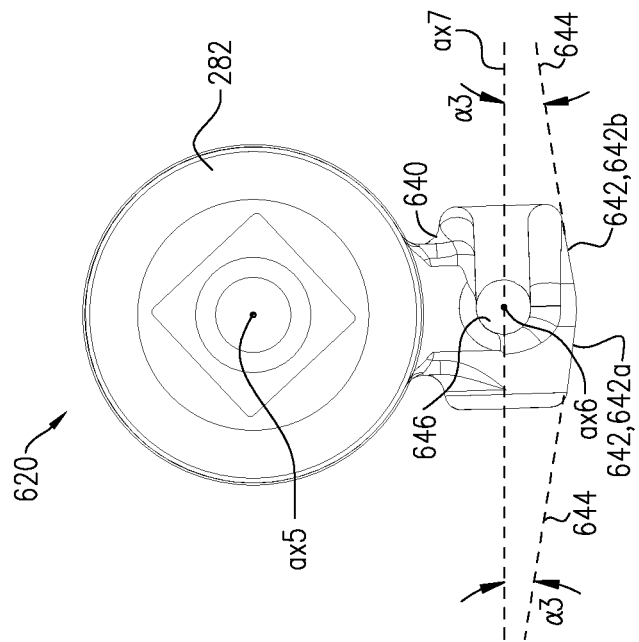
Figure 21C:
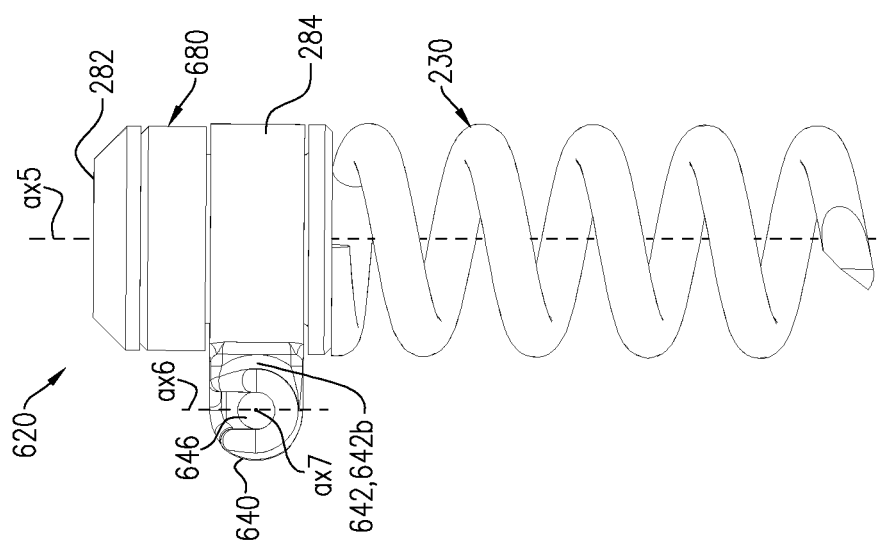
Figure 21G:
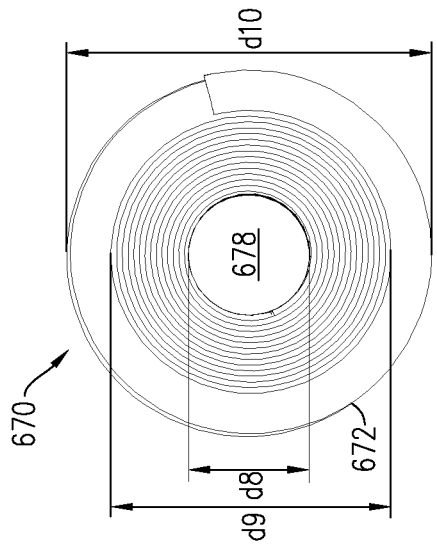
Figure 21E:
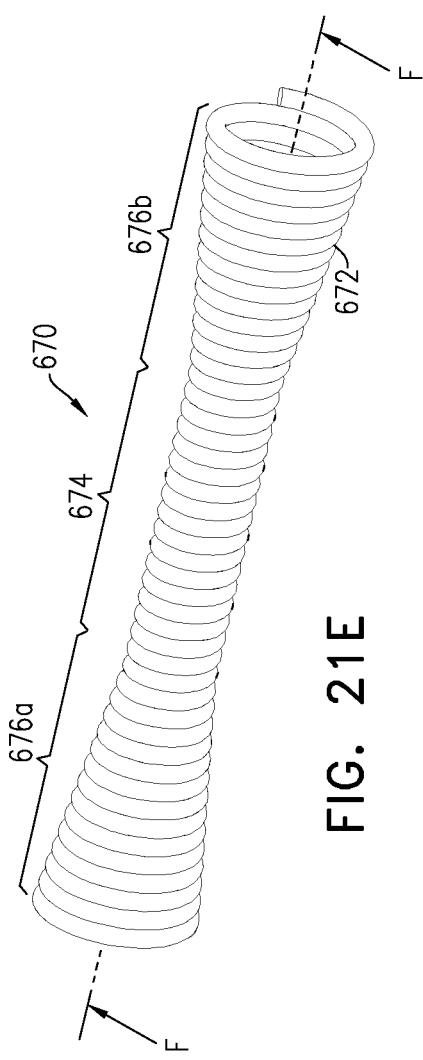
Figure 21F:
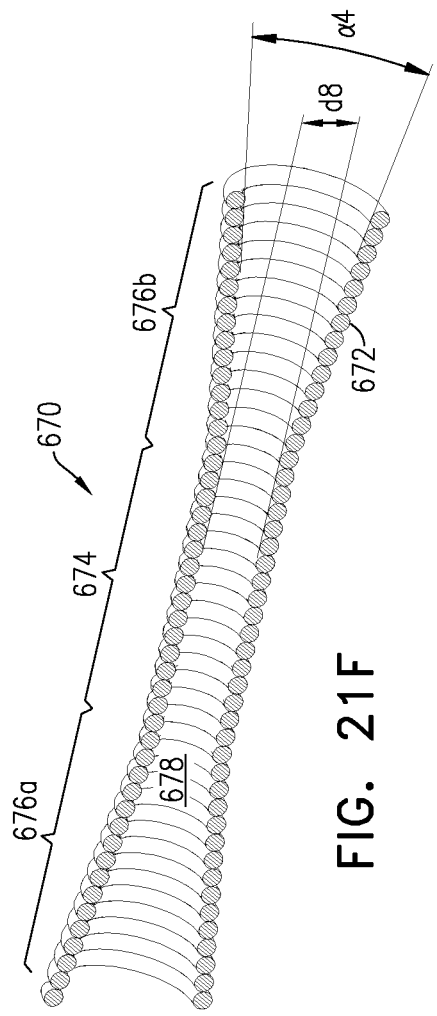

Anchor 620 can be identical to or similar to anchor 220 and comprises a head 680 that is often identical to or similar to head 280 of anchor 220, except that eyelet 640 of head 680 has a different shape (primarily a different external shape) compared to eyelet 240 of anchor 220. Nonetheless, the shape and features described with reference to aperture 246 of eyelet 240 are often also present in an aperture 646 defined by eyelet 640. For example, eyelet 640 defines an aperture through which the line or wire 212 is threaded and is disposed laterally from the central longitudinal axis ax5 of the tissue anchor, e.g., being mounted to be revolvable or rotatable, such as around axis ax5, while the aperture remains disposed (e.g., slanted) at a fixed angle with respect to axis ax5. Furthermore, like eyelet 240, eyelet 640 typically defines (i) a first clear straight pathway through aperture 646 along a first line ax6 that is parallel to axis ax5, and (ii) a second clear straight pathway through the aperture along a second line ax7 that is orthogonal to the first line (e.g., as shown in FIGS. 21C-D). As for eyelet 240, this is hypothesized by the inventors to facilitate smooth sliding along wire 212 in either of these orientations (and typically also in a continuum of orientations therebetween). Thus, line ax6 can be considered to be a first slide axis of anchor 620 (e.g., of eyelet 640 thereof), and line ax7 can be considered to be a second slide axis of the anchor (e.g., of the eyelet thereof).

Distinguishing it from eyelet 240, eyelet 640 has an external shape that defines a tapered portion 642 that tapers away from aperture 646 along slide-axis ax7. This is best seen in FIGS. 21B and 21D, where the tapering is illustrated by a line 644. Often, and as shown, each eyelet 640 has two tapered portions 642 (e.g., a tapered portion 642*a* and a tapered portion 642*b*), tapering away from aperture 646 in opposite directions along slide-axis ax7. For some applications, each tapered portion has a taper angle alpha_3, with respect to slide-axis ax7, of 5-20 degrees (e.g., 5-15 degrees, e.g., 7-12 degrees, e.g., 8-10 degrees, such as about 9 degrees). For such applications, the full taper angle between opposing sides of each tapered portion 642 is therefore twice as great as angle alpha_3—i.e., 10-40 degrees (e.g., 10-30 degrees, e.g., 14-24 degrees, e.g., 16-20 degrees, such as about 18 degrees).

Each spacer 670 has a first spacer-end and a second spacer-end, and between the spacer-ends the spacer defines a spacer-lumen 678. Each spacer 670 has a mid-portion 674, which has an internal diameter d8. Spacer-lumen 678 widens from mid-portion 674 toward the spacer-ends, e.g., defining a first flared zone 676*a* and a second flared zone 67*b*. Flared zones 676 can have an internal flare angle alpha_4 that is slightly (e.g., 1-3 degrees) smaller than the full taper angle of tapered portion 642 of eyelet 640. For some applications, internal flare angle alpha_4 is 10-40 degrees (e.g., 10-30 degrees, e.g., 12-22 degrees, e.g., 14-18 degrees, such as about 16 degrees). Each flared zone 676 is shaped to smoothly and snugly receive a tapered portion 642 of an eyelet 640.

Often, and as shown, in flared zones 676, as well as spacer-lumen 678 widening from mid-portion 674 toward the spacer-ends, an outer diameter of the spacer also increases from the mid-portion toward the spacer-ends. That is, flared zones 676 are often externally flared as well as internally flared. However, for some applications, flared zones 676 can be internally flared without being externally flared. For example, for some such applications, the outer diameter of the spacer can be roughly constant along the length of the spacer.

For some applications, spacers 670 are flexible (e.g., elastically flexible) in deflection (bending). For example, and as shown, spacers 670 can be defined by a helical wire. For some applications, despite being flexible in deflection, spacers 670 are generally not compressible axially—meaning that axially compressive forces exerted on the spacers during use (e.g., due to tensioning of wire 212) are insufficient to axially compress the spacers to a visible degree. For example, and as shown, the helical wire that defines each spacer 670 can be shaped as a closed coil—meaning that there is little if any gap between the turns of the coil.

At the spacer-ends, an inner diameter d9 of spacer 670 is sufficiently large for tapered portion 642 to enter spacer-lumen 678. For some applications, diameter d9 is 0.5-1.5 mm, e.g., as 0.7-1.1 mm, such as about 0.9 mm. For some applications, diameter d8 of mid-portion 674 is about half great as diameter d9. For some applications, diameter d8 is 0.2-0.8 mm, e.g., 0.3-0.6 mm, such as about 0.45 mm. Diameter d8 is often smaller, or at most 20% larger, than the apparent circular shape of aperture 646 (described hereinabove for aperture 246, mutatis mutandis)—e.g., the circular aperture visible in FIG. 21C.

System 600 often comprises a delivery tool 650, which comprises anchor driver 260 and often also comprises a flexible tube 652 (e.g., a transluminal catheter) via which each anchor 620, engaged with driver 260, is advanceable to the tissue to which the anchor is to be anchored. System 600 often is used generally as described for system 200, mutatis mutandis. FIG. 22A shows multiple anchors 620 having been anchored to tissue 10, with one anchor currently being advanced, by driver 260, through tube 652. In addition to being threaded through the eyelets of anchors 620, wire 212 is also threaded through spacers 670 (i.e., spacer-lumen 678 thereof), often with one spacer between adjacent anchors such that, for each spacer, one spacer-end faces one anchor and the other spacer-end faces another anchor.

As is visible in FIG. 22A, advancement of a spacer 670 along wire 212 can be achieved by pushing the spacer with the eyelet of the anchor proximal to that spacer. In system 200, tube 252 defines lateral slit 256. In system 600, tube 652 defines a lateral slit 656 that is similar in structure and function as slit 256, but is often specifically dimensioned such that spacers 670 can exit the tube laterally, proximally from the distal end of the tube, along with wire 212, e.g., as shown for the leftmost spacer in FIG. 22A.

Similarly to tube 252 of system 200, tube 652 (e.g., a lateral wall thereof) defines an internal channel 654 that defines a first channel region 654*a* and a second channel region 654*b* (FIG. 22*b*). Often, channel region 654*a* is a major channel region, and channel region 654*b* is a minor channel region, the major channel region having a larger cross-sectional area than the minor channel region. For some applications, channel 654 has a keyhole-shaped orthogonal cross-section, e.g., as described for channel 254 mutatis mutandis. For some applications, and as shown, channel 654 has an orthogonal cross-section that is double-lobed in shape, with a narrowed neck between the lobes. For some applications, and as shown, one lobe is larger than the other, the larger lobe thereby defining major channel region 654*a* and the smaller lobe thereby defining minor channel region 654*b*.

FIG. 23A shows an embodiment 610*a* of implant 610 having been implanted, with anchors 620 anchored in tissue 10, such as in an arc around the annulus of a heart valve. In embodiment 610*a*, a spacer 670 is disposed between each of the anchors. FIG. 23B shows embodiment 610*a* of implant 610 after it has been contracted by tensioning of wire 212.

Tensioning wire 212 draws anchors 620 together, reducing (e.g, eliminating) any space that may have existed between each anchor and its adjacent spacers. Further tensioning draws the tapered portions of eyelet 640 of anchor 620 into spacer-lumen 678 of spacer 670 (see inset of FIG. 23). As described hereinabove, the relative dimensions and taper/flare angles facilitate smooth entry and a snug fit. Smooth entry is often facilitated even when the spacer and the eyelet are not perfectly aligned, e.g, because implant 610 is implanted in an arc.

As described hereinabove, spacers 670 limit a proximity between pairs of anchors 620. It is hypothesized by the inventors that, in some applications, this advantageously facilitates even contraction of implant 610—e.g., by inhibiting one pair of anchors from becoming undesirably close while another pair of anchors remain undesirably far apart. Furthermore, and more generally, an amount of contraction-limitation between each pair of anchors can be pre-planned by increasing or decreasing the distance that one anchor is anchored from the other anchor, relative to the length of the spacer between those anchors.

The particular dimensions of eyelet 640 and spacer 670, and the fitting therebetween, are hypothesized to provide a continuous, smooth path for line or wire 212 through the implant (e.g., to reduce friction and/or a likelihood of snaring). For example, it is hypothesized by the inventors that the relative narrowness of spacer-lumen 678 at mid-portion 674 advantageously centers line/wire 212. It is further hypothesized by the inventors that the fitting between eyelet 640 and spacer 670 reduces a likelihood of the spacers undesirably sliding laterally, or jumping, relative to the eyelets when line/wire 212 is tensioned. It is therefore hypothesized by the inventors that the fitting between eyelet 640 and spacer 670 increases the predictability of the behavior of implant 610 when line/wire 212 is tensioned.

FIG. 24 shows a similar implant, but without spacers 670, after contraction.

FIG. 25 shows an embodiment 610b of implant 610, after contraction, in order to demonstrate a related, but somewhat different use of spacers 670. In embodiment 610b, a spacer is disposed only between the two end anchors at each end of wire 212—i.e., between anchors 620a and 620b, and between anchors 620e and 620d. FIG. 24 shows that, for some applications, in the absence of spacers, the end anchors (in this case, anchors 620a and 620e) experience greater force from tensioned wire 212 than do the anchors therebetween. This greater force may, in some circumstances, be too great for the end anchors and/or for the tissue, and therefore increases a likelihood of one of the end anchors becoming de-anchored from the tissue. The use of a spacer 670 between an end anchor and the adjacent anchor (FIG. 25) is believed to distribute force between these anchors (e.g, as the end anchor pushes the spacer against the adjacent anchor), thereby reducing the excessiveness of the force experienced by the end anchor, and thereby reducing a likelihood of the end anchor becoming de-anchored.

Figure 26:
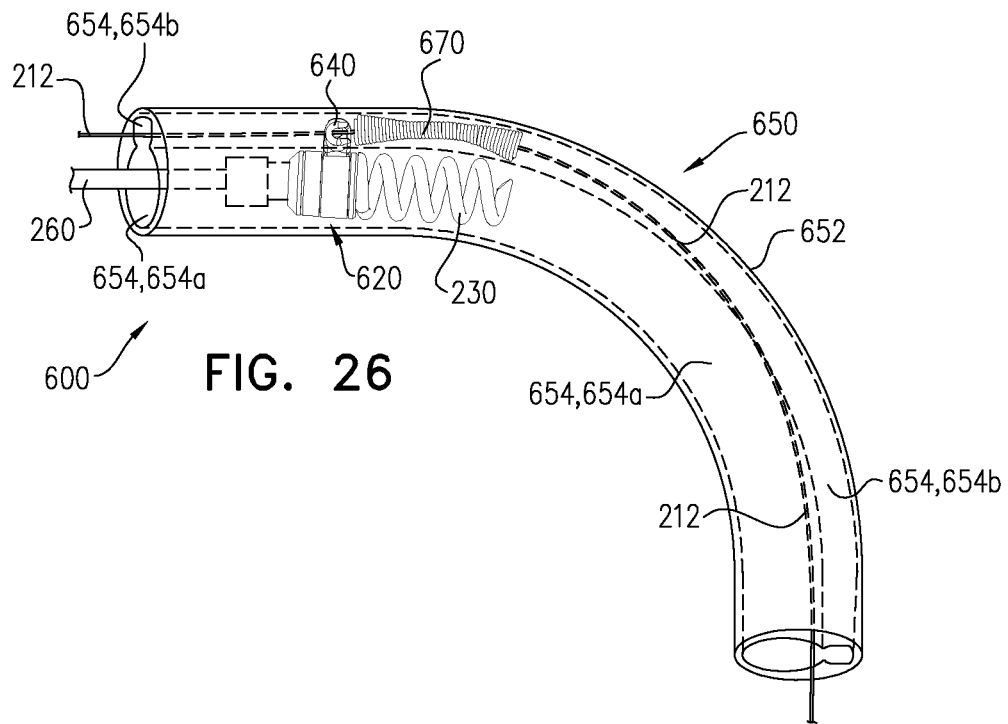

Reference is now made to FIGS. 25 and 26, which are schematic illustrations of an anchor 620 and a spacer 670 being advanced, over line or wire 212, within internal channel 654 of tube 652. As described hereinabove, for some applications, and as shown, channel 654 has an orthogonal cross-section that is double-lobed in shape, with a narrowed neck between the lobes. FIGS. 25 and 26 illustrate an advantage, hypothesized by the inventors, of such a configuration. As described hereinabove, when an anchor such as anchor 220 or anchor 620 is advanced through a catheter whose internal channel includes a dedicated channel portion for the anchor's eyelet and for the line or wire over which the eyelet slides, the shape of the channel retains the eyelet within the dedicated channel portion. However, it may be possible, in some circumstances, for regions of wire 212 distal to the eyelet to fall out of the dedicated channel portion and into the path of the tissue-engaging element of the anchor, thereby increasing a likelihood of snaring.

Figure 27:
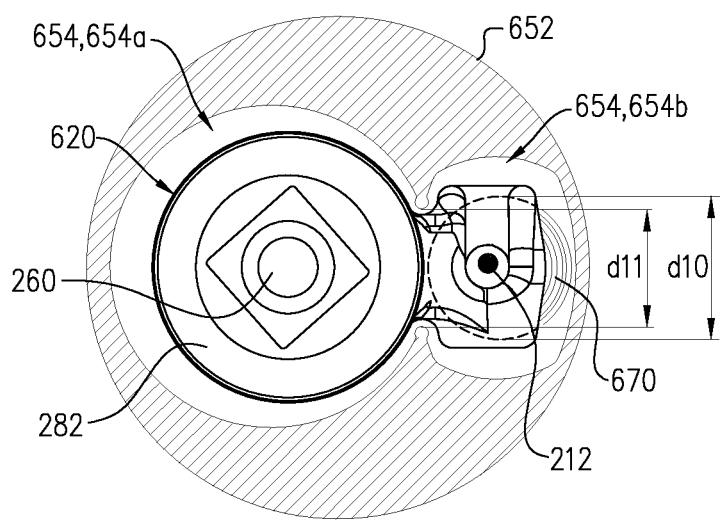

FIGS. 26 and 27 show spacer 670 within channel region 654b, being advanced by pushing the spacer with the eyelet of the anchor proximal to the spacer. FIG. 27 shows the neck of channel 654 having a width d12 that is smaller than outer diameter d10 of spacer 670. The neck is thereby dimensioned to inhibit the spacer from entering the channel region 654a. Because spacer 670 is inhibited from entering channel region 654a, and because the spacer extends distally from eyelet 640 (e.g, at least as far as the sharpened distal tip of tissue-engaging element 230), the spacer inhibits wire 212, which is threaded through the spacer, from entering the part of channel region 654a immediately distal to anchor 620. FIG. 26 shows a distal part of wire 212, far from anchor 620, falling into channel region 654a. As anchor 620 and spacer 670 are advanced distally, spacer 670 shifts progressively distal parts of wire 212 out of the way of anchor 620, and back into channel region 654b.

Reference is now made to FIGS. 28A-B, 29A-B, 30, 31A-B, 32, 33, and 34A-B, which are schematic illustrations of examples of respective systems 1000, 1020, 1030, 1040, 1050, 1060, and 1070 for facilitating a determination of successful (e.g, complete) anchoring to a tissue that is not in line-of-sight, in accordance with some applications. Systems 1000, 1020, 1030, 1040, 1050, 1060, and 1070 comprise respective tissue-indicating devices 1010 coupled to a distal tubular end portion of flexible tube 252 of delivery tool 250 used for implantation of implant 210. Device 1010 is configured to be an annulus-marking or indicating device for applications of the present invention, as device 1010 is configured to mark/indicate tissue of the annulus. Tissue-indicating device 1010 comprises radiopaque material to facilitate fluoroscopic visualization. As described hereinabove, implant 210 comprises a plurality of tissue anchors 220 and a contracting member, e.g, wire 212, a line, a suture, etc.). For some applications, the contracting member comprises a metal wire. Tool 250 is considered an anchor-delivery tool, as it facilitates delivery of anchors 220 into tissue 10. In order to properly identify when tube 252 comes into contact with tissue 10, tissue-indicating device 1010 provides such indication as it transitions from a resting state, e.g, as shown in FIGS. 28A, 29A, and 34A, to a compressed state, e.g, as shown in FIGS. 28B, 29B, and 34B.

Tissue-indicating device 1010 comprising a radiopaque material shaped to define a tubular body having a central longitudinal axis. Device 1010 is and configured for placement in contact with an annulus of a native heart valve of the subject. Device 1010 is (a) compressible into a compressed state responsively to contact with tissue of the native heart valve, and (b) expandable from the compressed state in an absence of force applied to tissue-indicating device 1010. Tissue-indicating device 1010 is configured to provide a guide for implantation of tissue anchor 220 along the annulus during implantation of tissue anchor 220. Device 1010 provides a real-time indicator of the presence of tissue in the compressed state. Once an anchor 220 is delivered, tube 252 is pulled proximally so as to transition device 1010 into its resting state, and tube 252 is moved to another location of tissue 10 in order to contact the tissue at the next location and be transitioned into the compressed state responsively to force applied thereto by tissue 10. Device 1010 is retrievable following the implantation of implant 220.

To anchor or secure anchor 220, the anchor is advanced out of a distal end of tube 252 and out of the distal end of tissue-indicating device 1010. For some applications, it is advantageous for the distal end of tissue-indicating device 1010 to be disposed (or even pressed) against tissue 10 during anchoring of the anchor, e.g, as shown in FIGS. 28B, 29B, and 34B. For some applications, device 1010 comprises a tubular stent body. For some applications, device 1010 comprises superelastic material, e.g, nitinol or stainless steel.

Reference is now made to FIGS. 28A-B, 29A-B, and 30-32. For some applications, device 1010 is manufactured from a laser-cut nitinol tube, but other manufacturing options are also available (e.g, cut from a sheet, molded, shaped, printed, etc.). Device 1010 comprises a proximal tube element (e.g, a ring or a tube) 1012, a distal tube element (e.g, a ring or a tube) 1014, and a linking element 1016 which comprises a compressible element 1018 and 1022 and coupled together tube elements 1012 and 1014. Distal tube element 1014 is spaced at a first distance from proximal tube element 1012 during a resting state of tissue-indicating device 1010. In this manner, device 1010 has a height H1 in the resting state as shown in FIGS. 28A and 29A. Distal tube element 1014 is spaced at a second distance from proximal tube element 1012 during the compressed state of tissue-indicating device 1010, the second distance being shorter than the first distance. In this manner, device 1010 has a height H2 in the compressed state as shown in FIGS. 28B and 29B.

Proximal tube element 1012 defines a static element which is often fixedly coupled to the distal end portion of tube 252, while compressible elements 1018 and 1022 and distal tube element 1014 define dynamic, moveable elements. When in contact with the tissue, compressible element 1018 and distal tube element 1014 move longitudinally proximally toward proximal, static tubular element 1012. The change in conformation of device 1010 brings the radiopaque elements closer together so that a greater concentration of radiopaque material is achieved of device 1010 in the compressed state such that it is discernable from the fluoroscopic image that there is an indication of the presence of tissue in a given area. For some applications, in order to increase radiopacity of device 1010, beads of tantalum or similar material can be added to device 1010.

For applications in which tube 252 is used to implant an implant comprising multiple anchors on a wire, such as implant 210, interference might occur, in certain situations, between the wire and the contact between the distal end of the tube and the tissue. For some applications, tube 252 defines a lateral slit 256 extending proximally from the distal end of the tube. For some applications, slit 256 allows wire 212, but not anchor 220, to exit tube 252 laterally, proximally from the distal end of the tube. It is believed that this facilitates implantation of implants such as implant 210, comprising multiple anchors coupled to (e.g, threaded on) a wire. As such, tissue-indicating device 1010 of FIGS. 28A-B, 29A-B, and 30-33 is shaped so as to define a lateral slit 1013. Device 1010 is coupled to the distal end portion of tube 252 in a manner in which lateral slit 1013 of device 1010 aligns with lateral slit 256 of tube 252. Slit 1013 extends proximally from the distal end of device 1010. For some applications, slit 1013 allows wire 212, but not anchor 220, to exit tube 252 and device 1013 laterally, proximally from the distal end of the tube.

For some applications, as shown in FIGS. 28A-B, distal tube element 1014 is longitudinally longer than proximal tube element 1012. Compressible element 1018 comprises a spring comprising a coiled element, as shown, for some applications. For some applications, proximal tube element 1012 and linking element 1016 (or compressible element 1018) surround the tubular distal end portion of tube 252, and linking element 1016 is compressible longitudinally proximally along the tubular distal end portion of the anchor-delivery tube 252 to draw distal tube element 1014 toward proximal tube element 1012. In such a configuration, the distal end portion to tube 252 provides support and stability to and a path along which linking element 1016 and distal tube element 1014 move as they are compressed proximally.

For some applications, distal tube element 1014 is shaped so as to define openings. Tube 252 comprises a pin which fits within the opening. The pin is configured to prevent rotation between tube 252 and device 1010.

As shown in FIGS. 29A-B, proximal tube element 1012 is longitudinally longer than distal tube element 1014. Compressible element 1022 comprises a spring comprising at least one strut element (e.g, first and second scaffolding elements 1024 and 1026) that is compressible along a longitudinal axis of tube 252. At least respective parts of first and second scaffolding elements 1024 and 1026 are spaced apart from each other during the resting state of tissue-indicating device 1010 (as shown in FIG. 29A), and the respective parts of first and second scaffolding elements 1024 and 1026 are moved closer together other during the compressed state of tissue-indicating device 1010 (as shown in FIG. 29B). For some applications, proximal tube element 1012 surrounds the tubular distal end portion of tube 252, and linking element 1016 (or compressible element 1018) a distal tube element 1014 are disposed distally to a distal end 1011 of tube 252. Linking element 1016 is compressible longitudinally proximally to draw distal tube element 1014 toward proximal tube element 1012.

Figure 32:
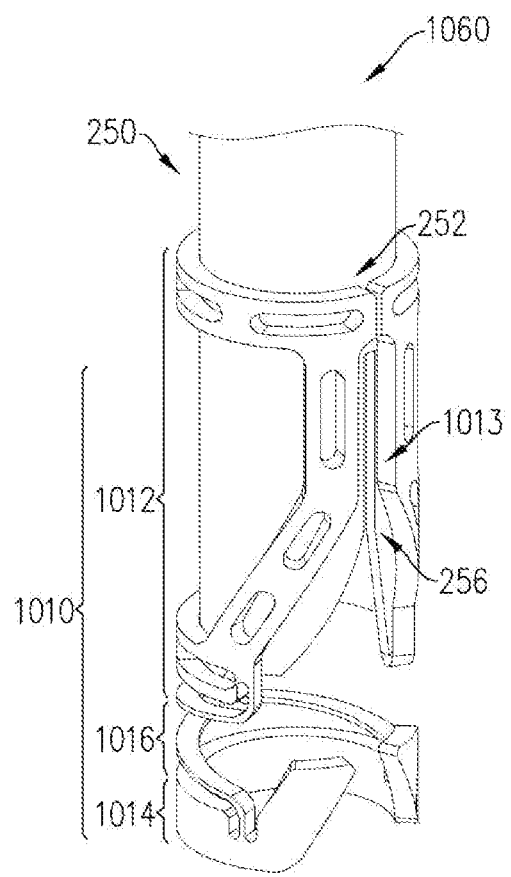

FIGS. 30, 31A-B, and 32 show tissue-indicating devices 1010, in accordance with some applications. FIG. 30 shows tissue-indicating device 1010 of system 1030, in accordance with some applications. FIG. 31A shows tissue-indicating device 1010 of system 1040, in accordance with some applications. FIG. 31B shows tissue-indicating device 1010 of system 1050, in accordance with some applications. FIG. 32 shows tissue-indicating device 1010 of system 1060, in accordance with some applications.

Each device of systems 1030, 1040, 1050, and 1060 are shown with design variations, which provide different radiopaque images. Proximal tubular elements 1012 are often longer than distal tubular elements 1014 so as to provide stability to elements 1012 as they are coupled to tube 252 and also provide increased surface-area contact between device 1010 and tube 252. Linking elements 1016 each comprise springs of strut-like or coiled elements.

While various tissue-indicating devices are described and shown herein, other-tissue indicating devices and designs of tissue-indicating devices and variations on described devices are also possible.

Figure 33:
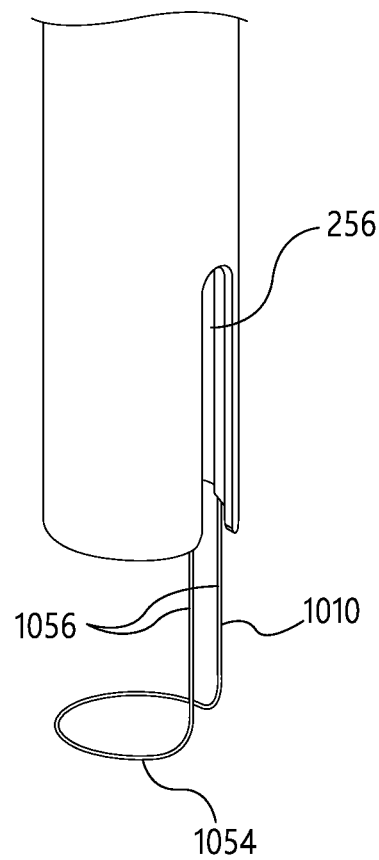

FIG. 33 shows a variation of a system, which can be the same as or similar to other systems described herein, except that the tissue indicating device 1010 shown in FIG. 33 is a wire. This is a relatively simple design that also indicates or marks contact with tissue (e.g, with an annulus). The wire can be configured to move or compress on contact with tissue. In some applications, the wire is retractable and extendable with respect to the tube or catheter, e.g, it can be configured to extend out of the catheter and compress or retract into the tube/catheter as the wire is pushed against the tissue. Movement of the wire relative to the tip (e.g., a radiopaque tip or end) of the tube/catheter can signal contact with the tissue. In some applications, an electronic signal and/or sensor on or associated with the wire can be sent to indicate contact with the tissue. The wire can take a variety of shapes and configurations. In some applications, the wire has a shaped portion 1054 at an end or tip thereof (e.g, at the distal tip or distal-most tip, etc.), which can be in a horseshoe, semicircular, partially circular shape, or other shape. In some applications, as shown in FIG. 33, the tissue-indicating device and/or wire thereof includes two parallel sections 1056 that extend into separate lumens of the tube/catheter. These sections 1056 can be parallel with each other and/or an axis of the distal end of the tube/catheter. These parallel sections 1056 can form therebetween a channel or slit, which can function similar to slit 1013 above and cooperate with a slit in the tube/catheter 256, which provides the same benefits discussed with respect to similar slits. In applications having both a shaped distal portion 1054 and parallel sections 1056, the parallel sections 1056 can be configured to extend from the tube/catheter to the shaped distal portion 1054 and can connect these together.

As another example of a tissue-indicating device, reference is now made to FIGS. 34A-B. In some applications, the compressible element is braided from a plurality of wires. In some applications, the compressible element 1018 of device 1010 comprises a plurality of struts 1072. The struts can be arranged in a braided and/or interconnected arrangement. During the resting state of tissue-indicating device 1010 (FIG. 34A), the tissue-indicating device assumes first height H1, and during the compressed state (FIG. 34B), tissue-indicating device 1010 assumes second height H2 that is shorter than first height H1. During the compressed state, tissue-indicating device 1010 shortens longitudinally and expands radially. Plurality of struts 1072 comprises a subset of rounded struts 1074 at a distal end of tissue-indicating device 1010 so as to facilitate atraumatic contact between device 1010 and tissue 10. For some applications, the plurality of rounded struts 1074 each comprise closed loops.

For some applications, the braided mesh provided by struts 1072 enables device 1010 to change its geometry in accordance with the topography of the annulus of the valve. For some applications, struts 1072 comprise an alloy. For some applications, struts 1072 comprise nitinol and/or stainless steel.

Reference is now made to FIGS. 35A-B, 36A-B, 37A-B, 38A-B, 39A-B, 44A-B, 45A-B, and 46A-B which are schematic illustrations of examples of respective systems 1080, 1090, 1100, 1200, 1300, 1800, 1820, and 1830 for covering excess contracting member after the contracting member has been cut following cinching, in accordance with some applications. Systems 1080, 1090, 1100, 1200, 1300, 1800, 1820, and 1830 comprise respective contracting-member-covering devices 1082, 1092, 1102, 1202, 1302, 1802, 1822, and 1832 that are each couplable to the contracting member (e.g, wire 212, a line, a suture, etc.) in the vicinity of a terminal tissue anchor 1220 of anchors 220 of implant 210. For some applications, the contracting-member-covering devices described herein comprise fasteners which are configured to lock in place wire 212 after annuloplasty is performed by cinching. For some applications, the contracting-member-covering devices described herein do not comprise fasteners and are advanced toward implant 210 once implant 210 has been locked by a fastener (or any suitable locking mechanism) that is separate and discrete from the contracting-member-covering device. For some applications, the contracting-member-covering devices described herein are configured to expand to cover the excess portions of wire 212 and end 213. For some applications, the contracting-member-covering devices described herein are configured to change shape to cover the excess portions of wire 212 and end 213. For some applications, the contracting-member-covering devices described herein are configured to cover the excess portions of wire 212 and end 213 by drawing the excess portions of wire 212 and end 213 within a housing of the contracting-member-covering device. For some applications, the contracting-member-covering-device is meant to cover the excess portions of wire 212 and end 213, and it is not sufficient on its own (i.e., without a fastener coupled either to wire 212 in the vicinity of a housing of the device or within the housing of the device) to facilitate locking or immobilizing of wire 212. That is, for some applications, the contracting-member-covering-device on its own does not provide sufficient force to lock or immobilize wire 212 and overcome the tension of wire 212.

Since the contracting member comprises a wire 212, once wire 212 is clipped or cut following cinching of implant 210 in order to perform annuloplasty, it is advantageous to cover a free end 213 of wire 212 and excess portions of wire 212. Covering of free end 213 of wire 212 and excess portions of wire 212 prevents any damage to tissue that can be caused by exposure of the metal of wire 212 to tissue once wire 212 is cut. Additionally, covering of free end 213 of wire 212 and excess portions of wire 212 prevents additional fibrosis around free end 213 of wire 212 and excess portions of wire 212. It is advantageous that the contracting member comprise a metal wire since metal is stronger and more durable than a fabric suture, for example. Additionally, the metal of wire 212 is radiopaque and can be viewed under fluoroscopy during the annuloplasty procedure.

Reference is now made to FIGS. 35A-B, 36A-B, 37A-B, 38A-B, and 39A-B. Contracting-member-covering devices 1082, 1092, 1102, 1202, and 1302 each comprise a housing 1430 which houses a contracting-member-fastener 1460 which defines the systems' locking mechanism. Fastener 1460 is shaped so as to define a generally-rectangular, planar clip comprising a super-elastic material, e.g, nitinol. Fastener 1460 comprises a deformable element shaped so as to define a plurality of slits which are surrounded by a plurality of flexible legs 1462 which enable the clip to transition between slanted (FIGS. 35A, 36A, 37A, 38A, and 39A) and straight (FIGS. 35B, 36B, 37B, 38B, and 39B) states. The contracting-wire-engaging surface of the clip is shaped to define a plurality of teeth (not shown for clarity of illustration). For some applications, the teeth are jagged. For some applications, the upper surface of the clip does not comprise teeth and is flat. The teeth are configured to increase friction between wire 212 and fastener 1460.

It is to be noted that fastener 1460 is used by way of illustration and not limitation and that any suitable securing means, fastener, clip, etc. can be used.

Fastener 1460 comprises a clamping structure that is (a) biased toward assuming a closed state (FIGS. 35B, 36B, 37B, 38B, and 39B). In the closed state, the clamping structure is configured to clamp onto wire 212 passed therethrough, and (b) can be flexed to an open state (FIGS. 35A, 36A, 37A, 38A, and 39A) through which wire 212 can move. In the closed state, fastener 1460 is configured to restrict movement of wire 212 with respect to the plurality of anchors 220.

Wire extends through an opening 1434 of housing 1430 and through a stop 1472 (e.g, a holder) that is disposed within an opening of housing 1430 in a vicinity of contracting-member-fastener 1460. Stop 1472 can be shaped so as to define a lumen therethrough for surrounding wire 212. Stop 1472 is engageable by tool 1502 and removable from housing 1430 via tool 1502. Stop 1472 is shaped so as to fit snugly within a channel extending from opening 1434 such that it pushes against the contracting-wire-engaging surface of the clip and maintains fastener 1460 in a slanted state, i.e., an unlocked state of fastener 1460. In the slanted state as shown in FIGS. 35A, 36A, 37A, 38A, and 39A, the clip is deformed and does not push against wire 212. In the slanted state, wire 212 is free to move with respect to fastener 1460, housing 1430, and stop 1472. Wire 212 is pulled until it sufficiently contracts the annuloplasty structure.

In FIGS. 35B, 36B, 37B, 38B, and 39B, stop 1472 has been decoupled and removed from housing 1430. In the absence of force applied to the contracting-wire-engaging surface of the clip by stop 1472, the clip returns to its resting, straight state and traps wire 212 between the contracting-wire-engaging surface of the clip and a surface 1432 of housing 1430, e.g, an inner wall. As such, fastener 1460 is now in a locked state in which the clip locks and crimps wire 212.

Once all the tissue anchors 220 have been implanted, wire 212 is threaded through a contracting-member-covering device-delivery and contracting-member-severing tool 1502 which is advanced along wire 212 to anchor 1220. The relative spatial orientation of the components of tool 1502 enable wire 212 to pass straightly and directly though the lumen of tool 1502 and along the longitudinal axis of tool 1502 without taking a winding path through tool 1502. This direct and unwinding path of wire 212 through tool 1502 reduces friction of wire 212 as it moves within tool 1502. This direct path for wire 212 is enabled due to the orientation of components of tool 1502.

Tool 1502 comprises a static cutting element 1510 and a moveable, dynamic cutting element 1520, each of cutting elements 1510 and 1520 defining a sharp edge. Dynamic cutting element 1520 slides proximally and diagonally with respect to static cutting element 1510. Tool 1502 comprises stop 1472 and is configured to facilitate movement of stop 1472 proximally in a manner in which stop 1472 is displaced from within housing 1430 through opening 1434. Once stop 1472 is displaced from within housing 1430, fastener 1460 assumes a closed position in order to trap wire 212 between the clamping surface of fastener 1460 and surface 1432 of housing 1430. Such displacement of stop 1472 also enables stop 1472 to push (e.g, by hammering) proximally on dynamic cutting element 1520 such that dynamic cutting element 1520 slides proximally diagonally along static cutting element 1510 in a manner in which elements 1510 and 1520 sever and cut wire 212. Thus, tool 1502 provides a mechanism which enables simultaneous cutting and locking of wire 212.

Thus, tool 1502 is arranged such that tool 1502 advantageously provides a safety mechanism by which wire 212 can only be severed by proximal force applied thereto by stop 1472 after fastener 1460 has been transitioned into the fastened, or locked, state and locks in place wire 212. That is, tool 1502 cannot inadvertently sever wire 212 all the while tool 1502 is not coupled to stop 1472 and all the while stop 1472 does not push against cutting element 1520. In one swift motion, tool 1502 (1) locks in place wire 212 by transitioning fastener 1460 into the locked state, and (2) severs wire 212.

Figure 35A:
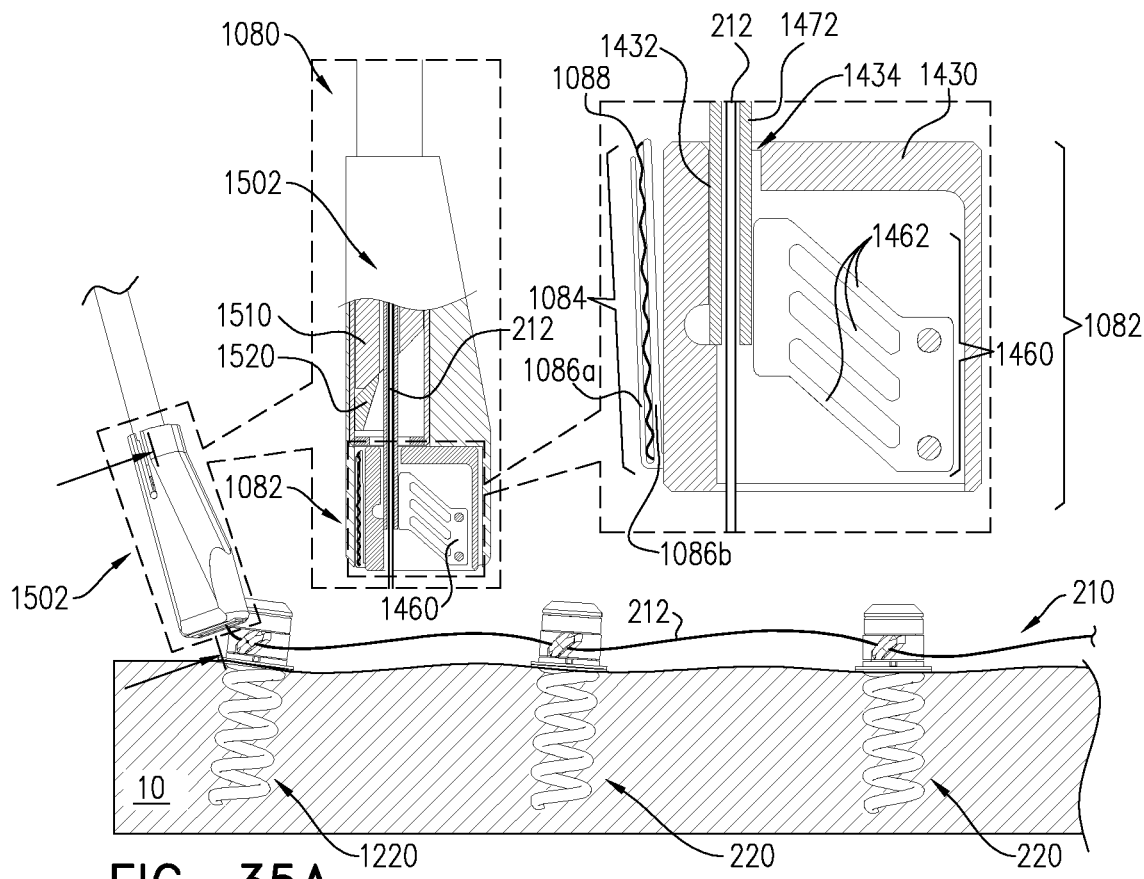
FIGS. 35A-B, 36A-B, 37A-B, 38A-B, and 39A-B are schematic illustrations of examples of respective systems for covering excess contracting member after the contracting member has been cut following cinching, in accordance with some applications.
Figure 35B:
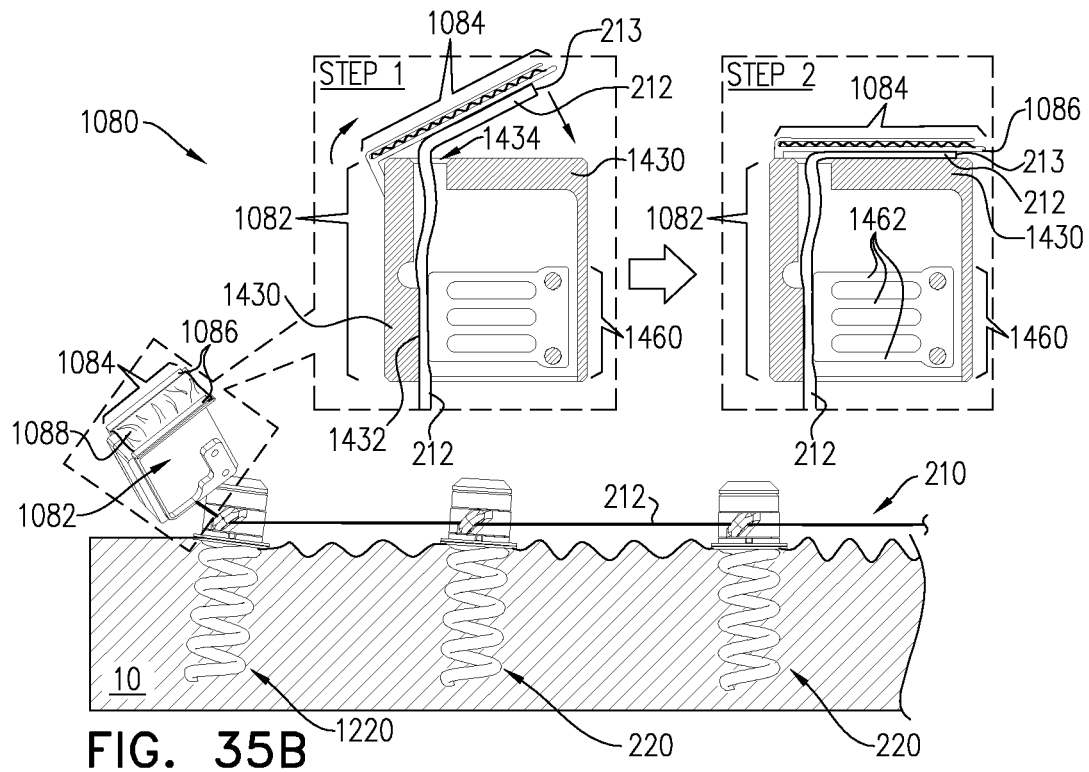

Reference is now made to FIGS. 35A-B. Contracting-member-covering device 1082 comprises a flap 1084 that is disposed external to housing 1430. Flap 1084 is moveable from (1) an open state in which flap 1084 is distanced from housing 1430, to (2) a closed state in which flap 1084 is disposed alongside housing 1430 in a manner in which flap 1084 pushes the excess portions of wire 212 exiting housing 1430 via opening 1434 and end 213 of wire 212, against an external surface of housing 1430 while also covering the excess portions of wire 212 and end 213 of wire 212. Additionally, flap 1084 covers opening 1434 of housing 1430. Flap 1084 is coupled to housing 1430 in a manner in which it swivels from a first, open position in alignment with a first lateral wall of housing 1430, as shown in FIG. 35A, to a second, closed position in alignment with a second lateral wall of housing 1430, as shown in FIG. 35B. In the second position, flap 1084 traps the excess portion of wire 212 and end 213 between flap 1084 and the second lateral wall of housing 1430. For some applications, device 1082 has a tendency to assume the second, closed position in the absence of force applied thereto. For example, device 1082 is held in the first, open position by the presence of tool 1502. Once tool 1502 has locked and severed wire 212, tool 1502 is decoupled from housing 1430 and moved proximally, allowing flap 1084 to change shape and transition to assume the second, closed position. In such applications, flap 1084 acts as a spring.

For some applications, housing 1430 is covered by a braided fabric mesh, not shown.

Flap 1084 comprises two metal scaffolding beams 1086 disposed opposite each other. A piece of fabric 1088 is coupled to and extends between the two metal scaffolding beams 1086 in a manner in which, in the closed state of flap 1084, fabric 1088 covers the excess portions of wire 212 and end 213 of wire 212 and covers opening 1434 of housing 1430. Each scaffolding beam 1086 has two sub-beams 1086*a* and 1086*b* between which fabric 1088 is coupled and held in place.

Figure 36A:
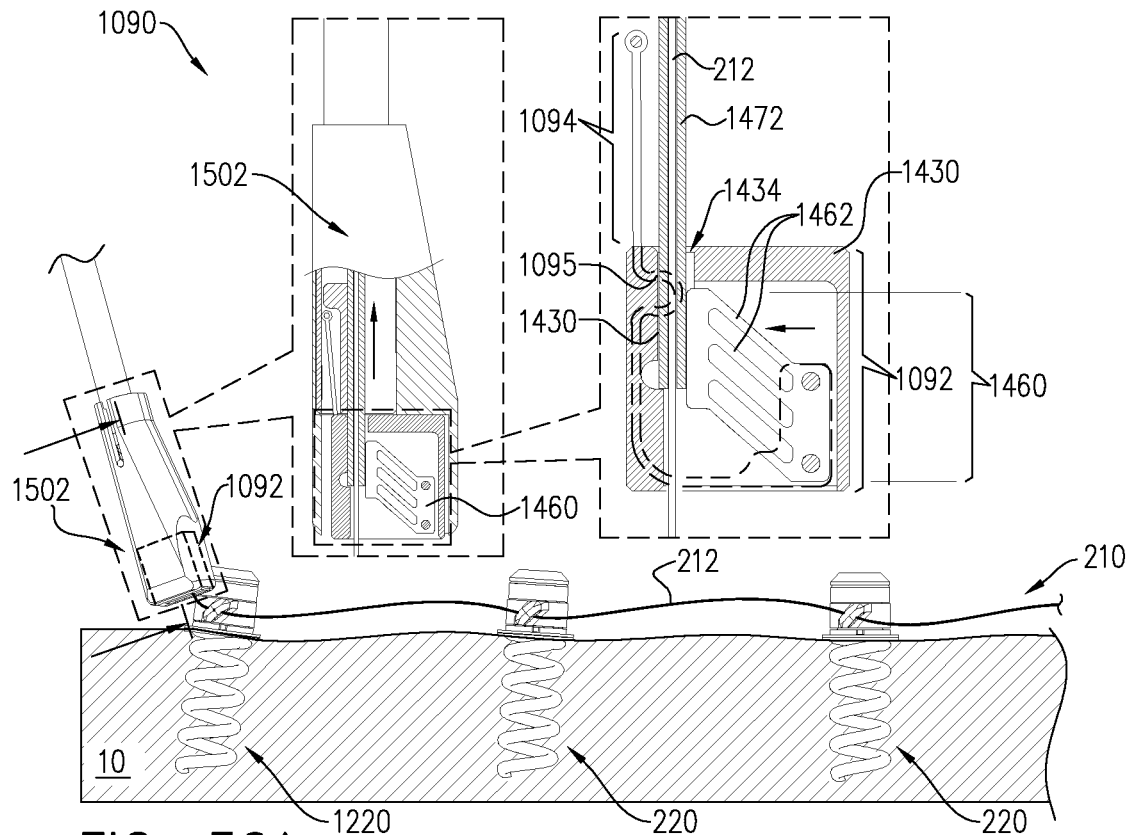
Figure 36B:
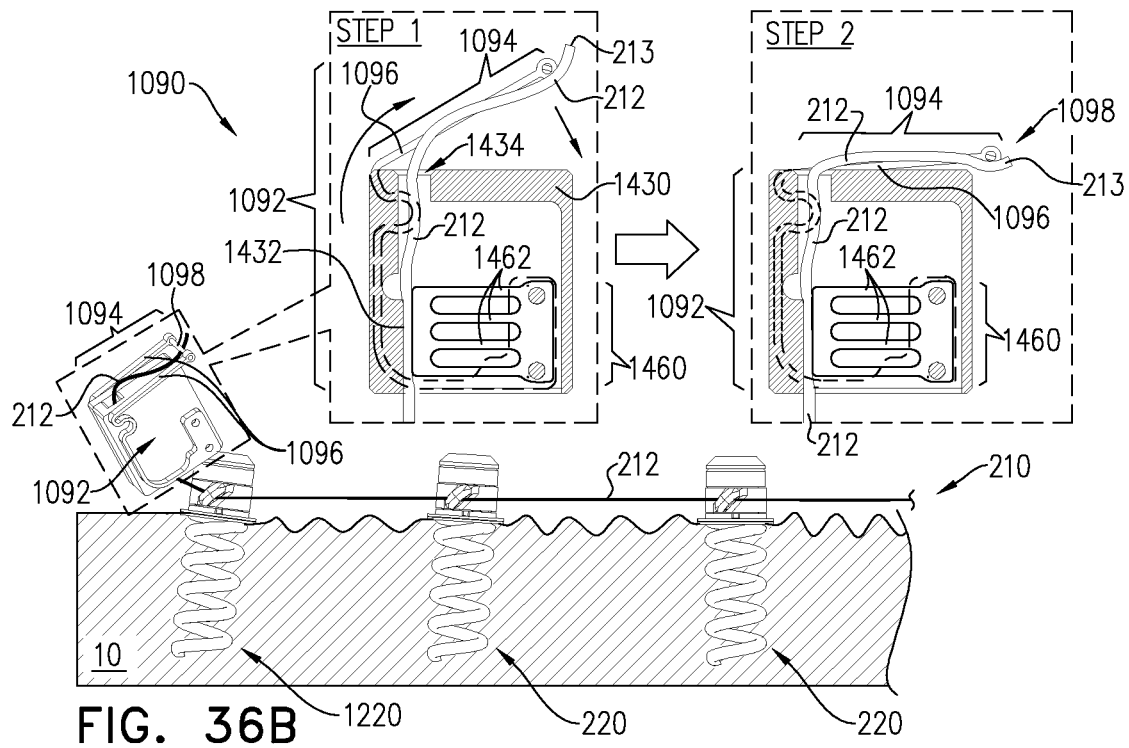

Reference is now made to FIGS. 36A-B. Contracting-member-covering device 1092 comprises a flap 1094 that is disposed external to housing 1430. Flap 1094 is moveable from (1) an open state in which flap 1094 is distanced from housing 1430, to (2) a closed state in which flap 1094 is disposed alongside housing 1430 in a manner in which flap 1094 pushes the excess portions of wire 212 exiting housing 1430 via opening 1434 and end 213 of wire 212, against an external surface of housing 1430.

Flap 1094 is coupled to housing 1430 in a manner in which it swivels from a first, open position, as shown in FIG. 36A, to a second, closed position in alignment with a lateral wall of housing 1430, as shown in FIG. 36B. In the first position, flap 1094 is aligned with a longitudinal axis of tool 1502. Flap 1094 is coupled to housing 1430 via a hinge 1095 which facilitates device 1092 to change shape and move flap 1094 from the first position to the second position. In the second position, flap 1094 traps the excess portion of wire 212 and end 213 between flap 1094 and the second lateral wall of housing 1430. For some applications, device 1092 has a tendency to assume the second, closed position in the absence of force applied thereto. For example, device 1092 is held in the first, open position by the presence of tool 1502. Once tool 1502 has locked and severed wire 212, tool 1502 is decoupled from housing 1430 and moved proximally, allowing flap 1094 to change shape and transition to assume the second, closed position. In such applications, flap 1094 acts as a spring.

For some applications, housing 1430 is covered by a braided fabric mesh, not shown.

Flap 1094 comprises two metal scaffolding beams 1096 disposed opposite each other and a cross-beam 1098 extending between the two metal scaffolding beams. During the transition between the first and second states of device 1092, cross-beam 1098 pushes the excess portions of wire 212. In the closed state, cross-beam 1098 maintains the pushed state of the excess portions of wire 212 and end 213 of wire 212 against the external surface of housing 1430.

For some applications, a piece of fabric is coupled to and extends between the two metal scaffolding beams 1096 in a manner in which, in the closed state of flap 1094, the fabric 1099 covers the excess portions of wire 212 and end 213 of wire 212 and covers opening 1434 of housing 1430.

Figure 37A:
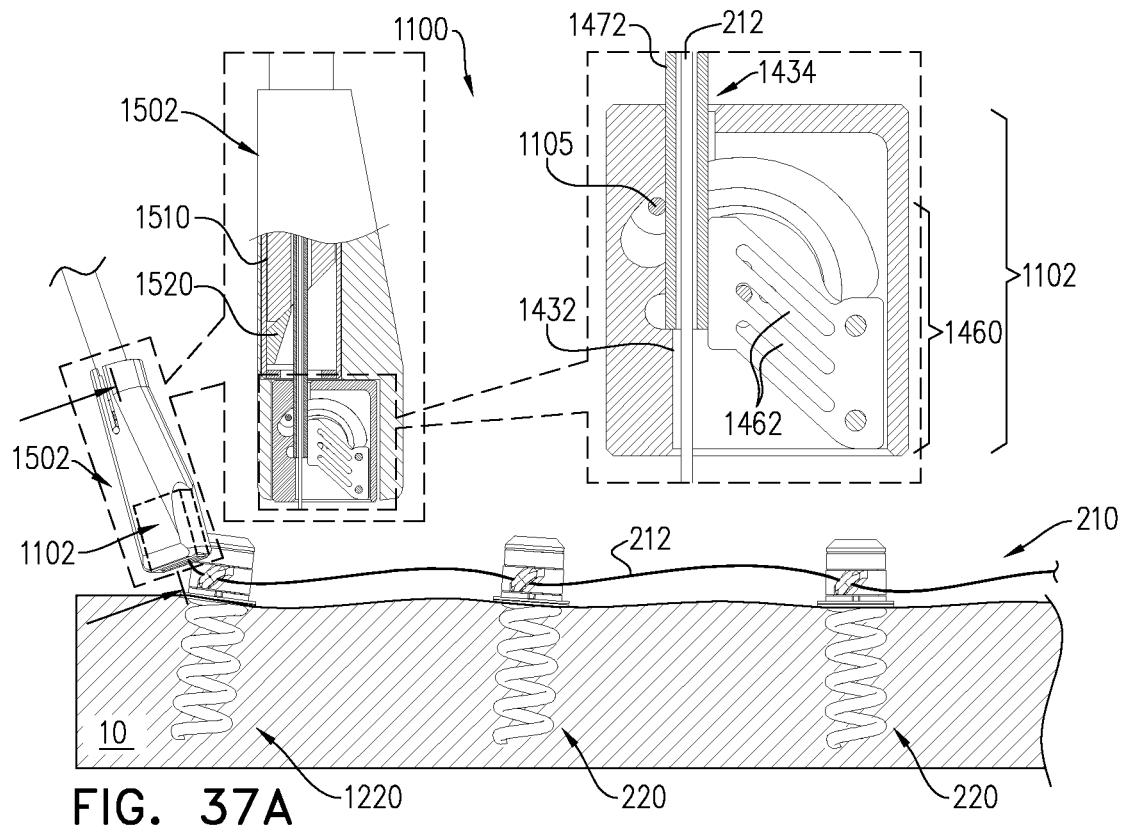
Figure 37B:
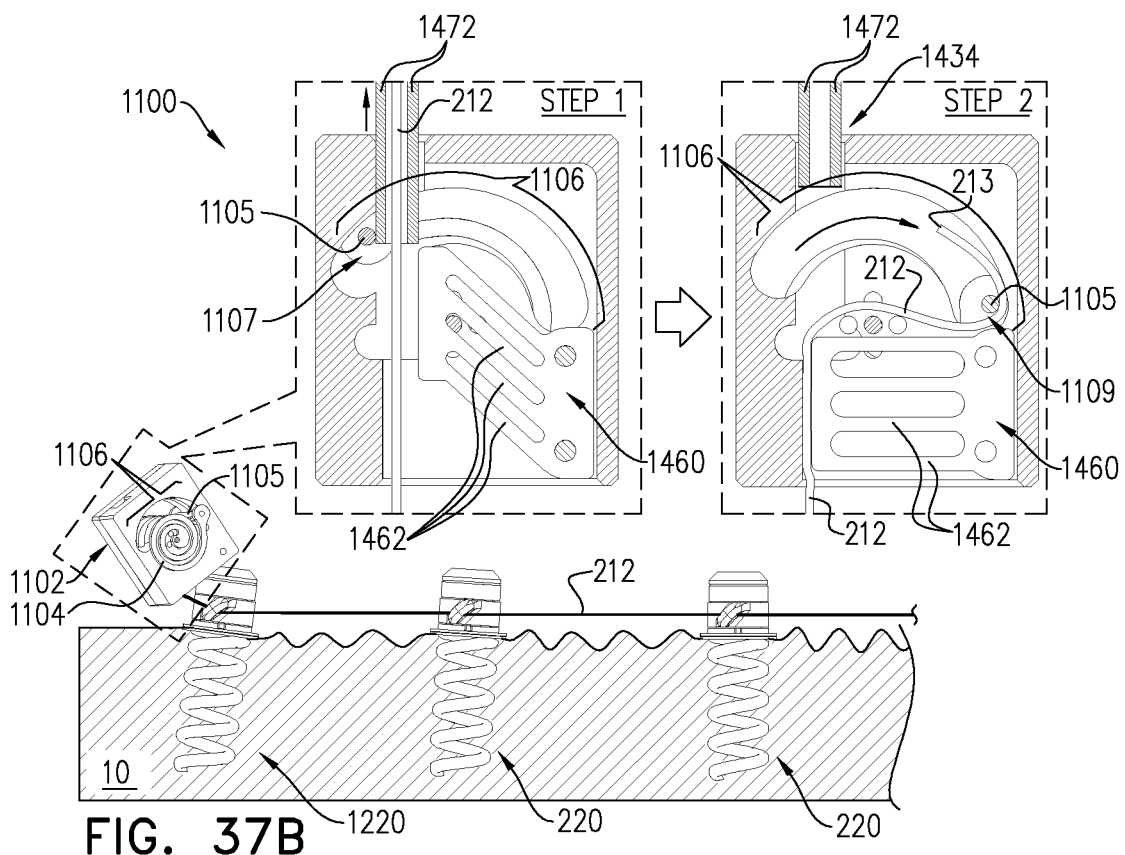

Reference is now made to FIGS. 37A-B. Contracting-member-covering device 1102 comprises a spiral spring 1104 movable along a path 1106 defined by housing 1430. Device 1102 is configured to cover the excess portions of wire 212 and end 213 of wire 212 by drawing the excess portions of wire 212 and end 213 of wire 212 within housing 1430. In such a manner, device 1102 facilitates uptake of the excess portions of wire 212 and end 213 of wire 212 into housing 1430 by pulling the excess portions of wire 212 and end 213 of wire 212 through opening 1434 and along path 1106. Wire 212 passes alongside an end of spiral spring 1104. The end of spiral spring 1104 comprises a cross-beam 1105. Spiral spring 1104 is moveable from (1) an open state in which spring 1104 is preloaded and constrained, and cross-beam 1105 is in a first position 1105 in path 1106, to (2) a closed state in which spring 1104 assumes a relaxed state in which cross-beam 1105 is in a second position 1107 in path 1106. As spring 1104 transitions from its open state (FIG. 37A) to its closed state (FIG. 37B), cross-beam 1105 pushes the excess portions of wire 212 and end 213 of wire 212 along path 1106 and away from opening 1434 of housing 1430. For some applications, opening 1434 closes automatically once wire 212 is withdrawn into housing 1430. For some applications, housing 1430 is covered by a braided fabric mesh, not shown, and the mesh closes over opening 1434 once wire 212 is withdrawn into housing 1430.

Spring 1104 is made of superelastic material, e.g, nitinol.

For some applications, device 1102 has a tendency to assume the closed state in the absence of force applied thereto. For example, device 1102 is held in the open state by the presence of tool 1502. Once tool 1502 has locked and severed wire 212, tool 1502 is decoupled from housing 1430 and moved proximally drawing stop 1472 proximally. As shown, in the open state of device 1102, stop 1472 is disposed in part within the path 1106 and thereby (a) maintains fastener 1460 in the open state when tool 1052 is coupled to housing 1430 and (b) maintain cross-beam 1105 in a position in which cross-beam 1105 does not engage wire 212, thereby restricting movement of cross-beam 1105 and of spring 1104. Upon proximal movement of stop 1472 from within path 1106 and the absence of stop 1472, movement of cross-beam 1105 is no longer restricted, and cross-beam 1105 is allowed to move along path 1106 and, as it moves, push wire 212 along path 1106 such that the excess portions of wire 212 and end 213 of wire 212 are pulled, collected, and covered within housing 1430 and along path 1106.

Figure 38A:
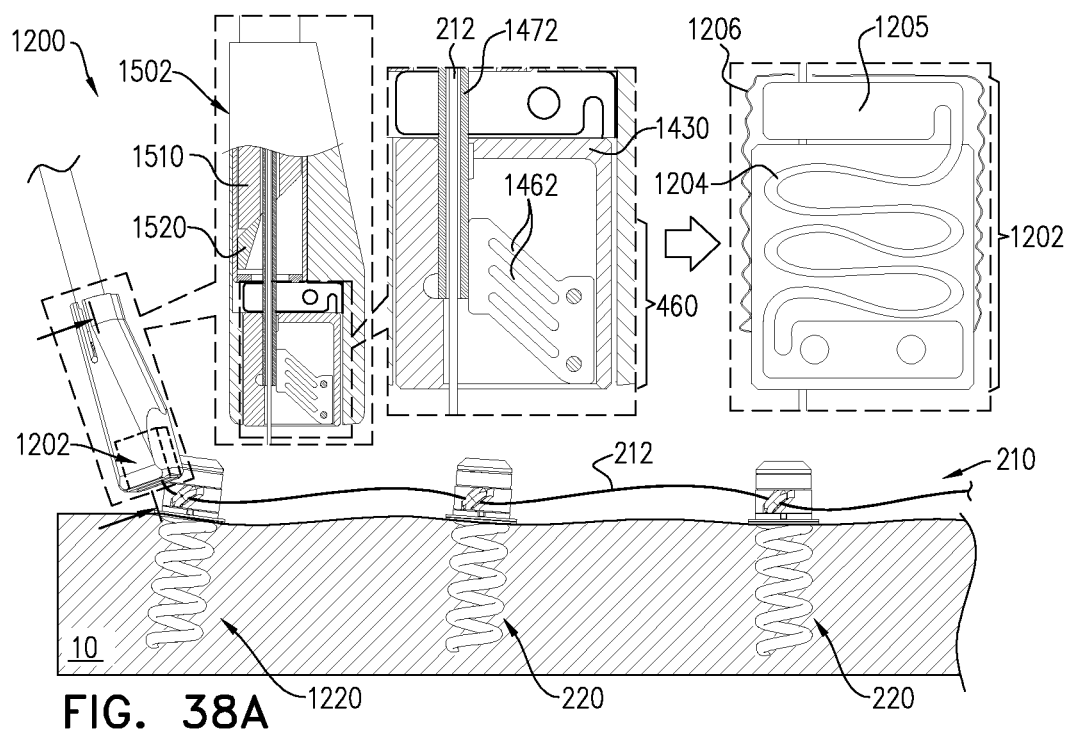
Figure 38B:
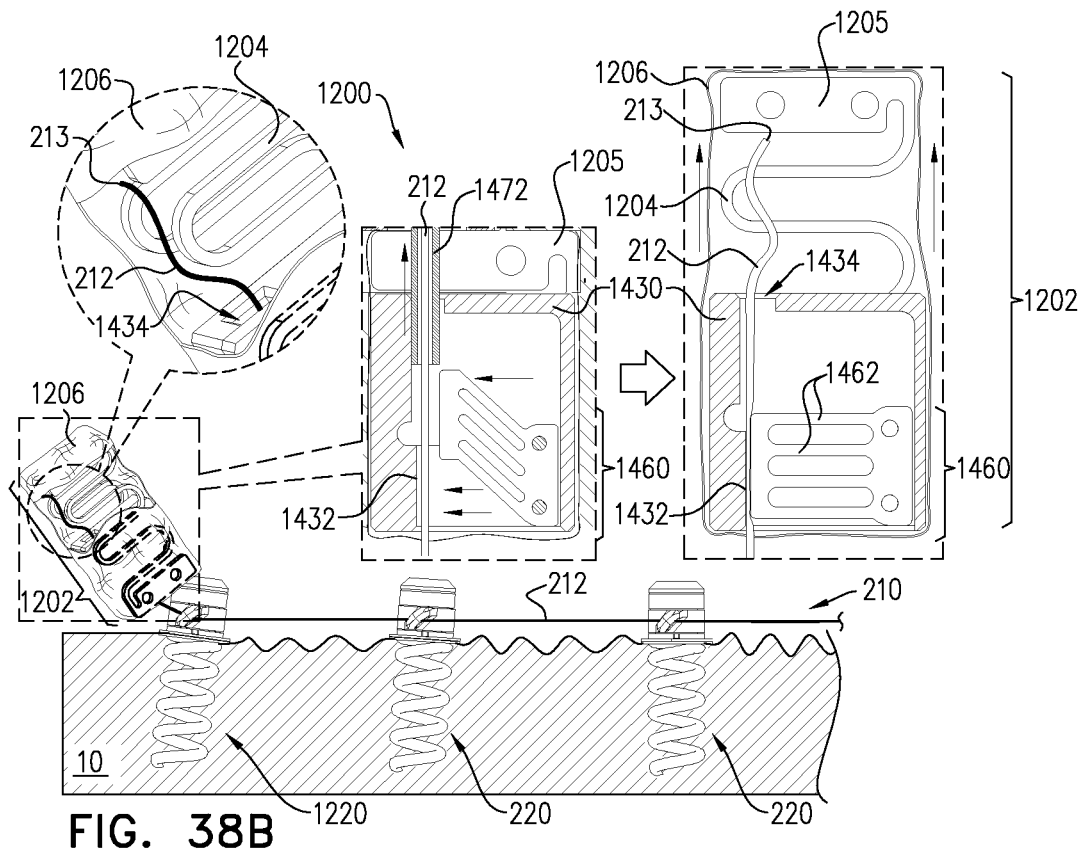

Reference is now made to FIGS. 38A-B. Contracting-member-covering device 1202 comprises a spring 1204 coupled to housing 1430 in a vicinity of opening 1434. Spring 1204 is configured to expand to cover the excess portions of wire 212 and end 213 of wire 212 exiting the housing via opening 1434. Spring 1204 comprises a superelastic material, e.g, nitinol, and comprises a pushing element 1205 which is configured to push against the fabric 1206 surrounding housing 1430 and spring 1204. Device 1202 is moveable from (1) a compressed state in which spring 1204 is longitudinally compressed and fabric 1206 is slack, to (2) an expanded state in which spring 1204 longitudinally expands in a manner in which pushing element 1205 pushes against fabric 1206 in order to expand fabric 1206 such that excess portions of wire 212 exiting housing 1430 via opening 1434 and end 213 of wire 212 are enveloped by device 1202 and covered thereby.

For some applications, device 1202 has a tendency to assume the expanded state in the absence of force applied thereto. For example, device 1202 is held in the compressed state by the presence of tool 1502. Once tool 1502 has locked and severed wire 212, tool 1502 is decoupled from housing 1430 and moved proximally, allowing spring 1204 to change shape and transition to assume the expanded position.

Spring 1204 comprises two metal compressible, scaffolding elements disposed opposite each other. The scaffolding elements are configured to expand laterally away from a wall of housing 1430 that defines opening 1434. As shown, the scaffolding elements comprise a sinusoidal pattern. It is to be noted that the scaffolding elements can assume any suitable pattern.

For some applications, fabric 1206 is configured to encourage tissue growth.

Figure 39A:
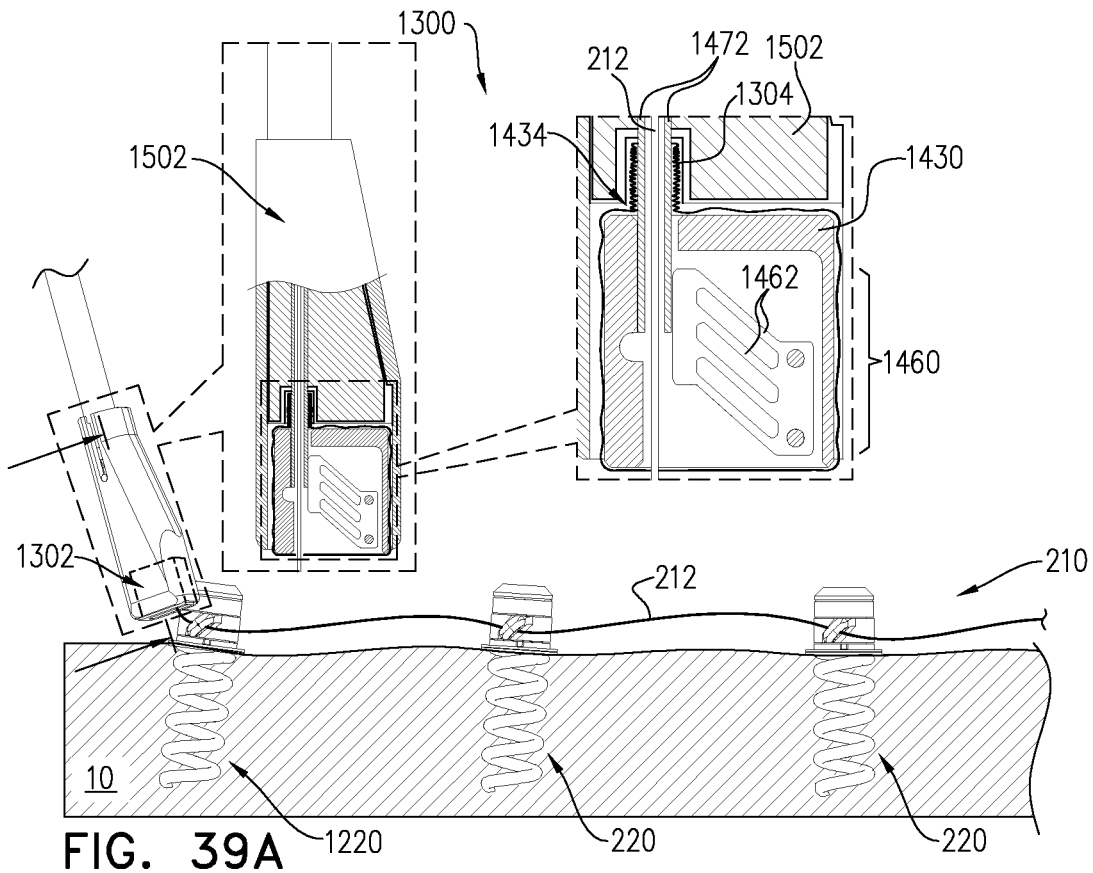
Figure 39B:
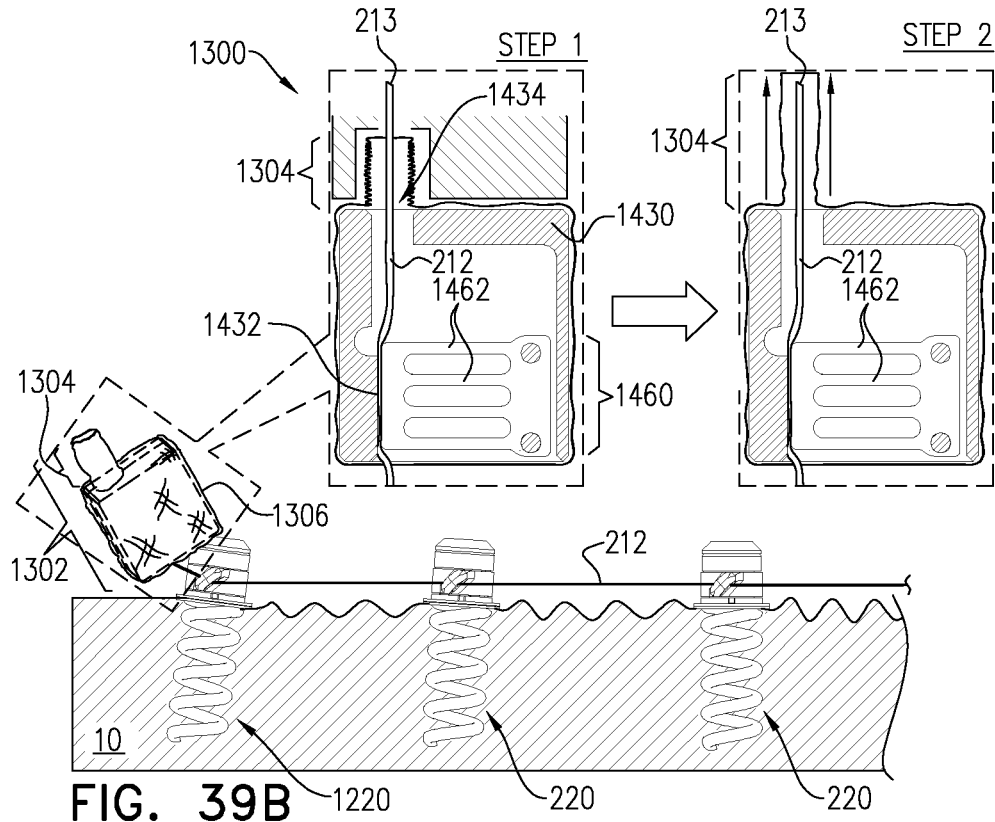

Reference is now made to FIGS. 39A-B. Contracting-member-covering device 1302 comprises an expandable fabric tube 1304 coupled to housing 1430 in a vicinity of opening 1434. Expandable fabric tube 1304 is configured to expand to cover the excess portions of wire 212 and end 213 of wire 212 exiting the housing via opening 1434. Device 1302 is moveable from (1) a compressed state in which expandable fabric tube 1304 is longitudinally compressed, to (2) an expanded state in which expandable fabric tube 1304 longitudinally expands in a manner in which tube 1304 covers excess portions of wire 212 exiting housing 1430 via opening 1434 and end 213 of wire 212.

For some applications, device 1302 has a tendency to assume the expanded state in the absence of force applied thereto. For example, device 1302 is held in the compressed state by the presence of tool 1502. Once tool 1502 has locked and severed wire 212, tool 1502 is decoupled from housing 1430 and moved proximally, allowing expandable fabric tube 1304 to change shape and transition to assume the expanded position.

For some applications, device 1302 is surrounded by fabric 1306 which is configured to encourage tissue growth.

Figure 40A:
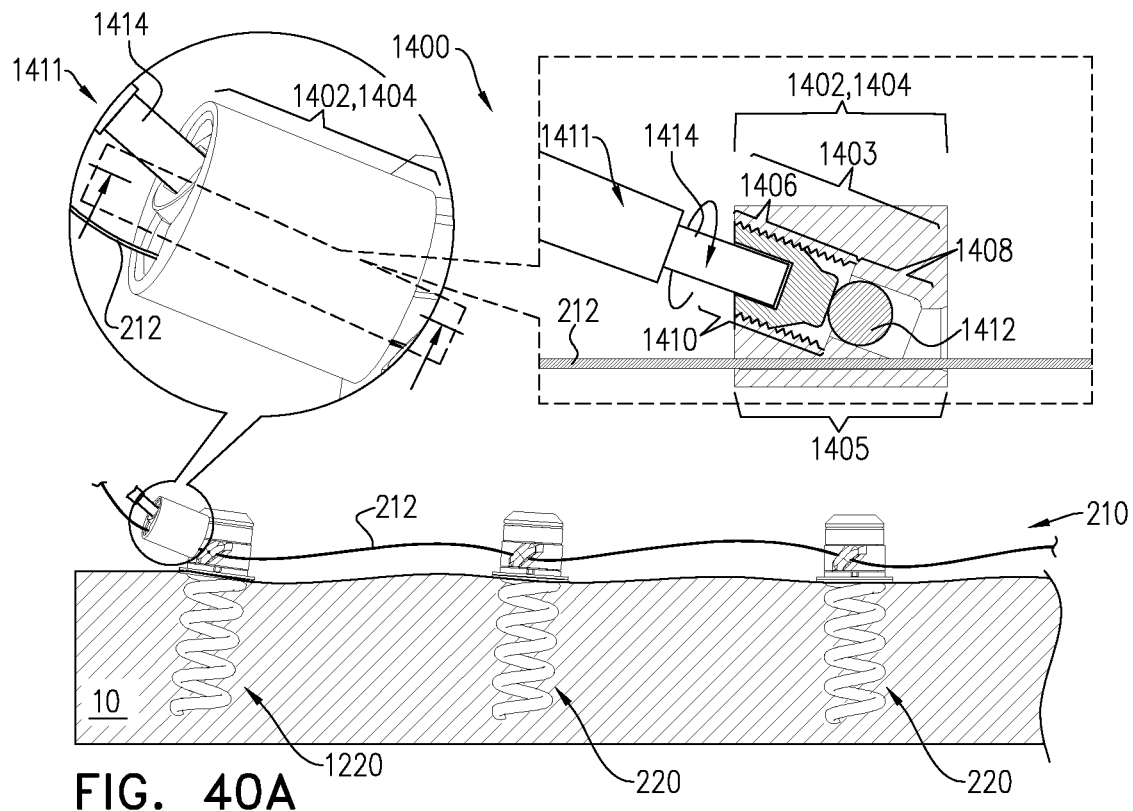
FIGS. 40A-B, 41A-B, 42A-B, and 43A-B are schematic illustrations of examples of respective systems comprising respective locking mechanisms comprising fasteners configured to be couplable to the contracting member, in accordance with some applications.
Figure 40B:
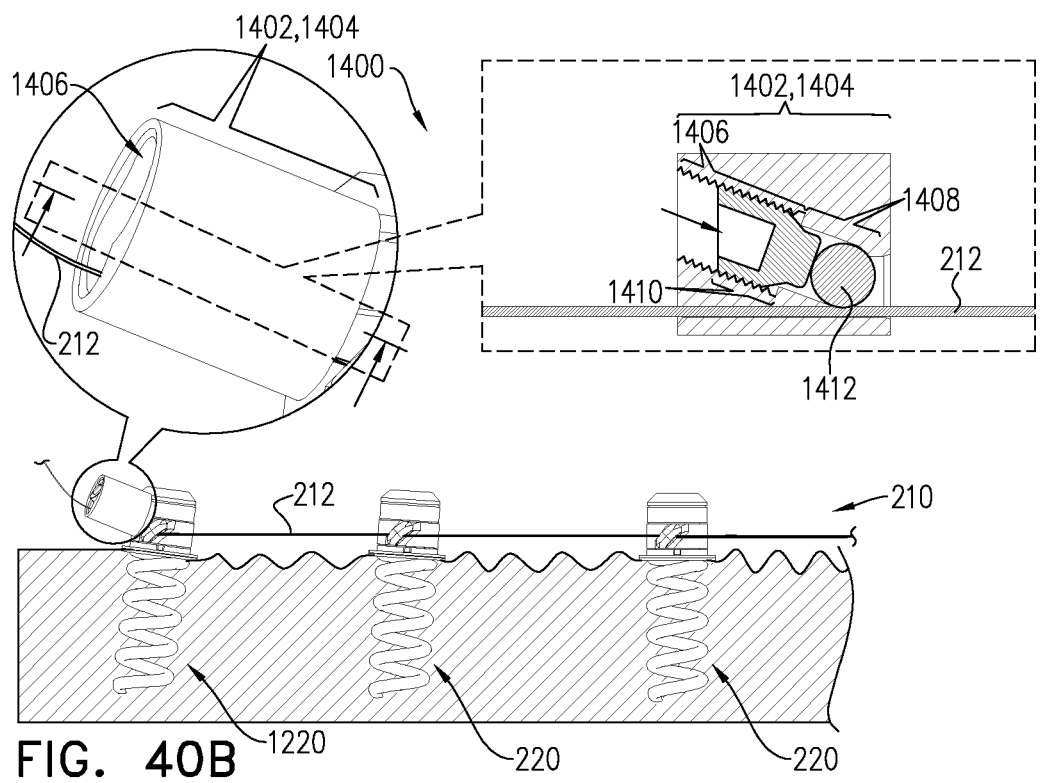

Reference is now made to FIGS. 40A-B, which are schematic illustrations of an example of a system 1400 comprising a locking mechanism comprising a fastener 1402 configured to be couplable to wire 212 (i.e., the contracting member) in a vicinity of terminal tissue anchor 1220 of the plurality of tissue anchors 220, in accordance with some applications. Fastener 1402, in a closed state thereof (FIG. 40B), is configured to restrict movement of wire 212 with respect to the plurality of tissue anchors 220. Fastener 1402 comprises a housing 1404 shaped so as to define (a) a first lumen 1405 for passage therethrough of wire 212, and (b) a second lumen 1403 disposed at a nonzero angle with respect to the lumen 1405. For some applications, second lumen 1403 is in fluid communication with a portion of first lumen 1405. First lumen 1405 runs along a longitudinal axis of housing 1404.

Fastener 1402 comprises a locking ball 1412 moveable within second lumen 1403 from a first position (FIG. 40A)

in which locking ball 1412 does not apply pressure to wire 212, to a second position (FIG. 40B) in which locking ball 1412 applies pressure to contracting member 212 either via direct contact of ball 1412 with a portion of wire 212 or by applying pressure to an inner wall of second lumen 1403, which applies pressure to first lumen 1405 and to wire 212 running therethrough. Application of pressure to wire 212 either directly or indirectly by locking ball 1412 to wire 212 restricts movement of wire 212. An advancement pin 1410 is disposed within second lumen 1403 proximally to locking ball 1412. Advancement pin 1410 is configured to advance locking ball 1412 from the first position to the second position such that pressure is applied to wire 212 by ball 1412 and wire 212 is locked between ball 1412 and an inner wall of first lumen 1405.

Second lumen 1403 has a first sublumen 1406 sized to accommodate advancement pin 1410, and a second sublumen 1408 sized to accommodate locking ball 1412. First sublumen 1406 is disposed proximally to second sublumen 1408. Often, second lumen 1403, or at least first sublumen 1406 is has a threaded surface. Advancement pin 1410 has a threaded outer surface. The threaded surfaces facilitate locking of locking ball 1412 in the second position. The threaded surfaces have a thread pitch of 1.5 mm.

A delivery tool 1411 is configured to deliver fastener 1402 along wire 212. Tool 1411 comprises a torque-delivering tool 1414 reversibly coupled to advancement pin 1410 and is configured to apply torque to advancement pin 1410. Tool 1411 can facilitate (a) locking of wire 212 by the rotating of tool 1414 in a first rotational direction in order to advance pin 1410 linearly distally such that it pushes against ball 1412 and keeps ball 1412 in a pushed position in which ball 1412 applies pressure to wire 212, and (b) unlocking of wire 212 by the rotating of tool 1414 in a second rotational direction in order to advance pin 1410 linearly proximally such that ball 1412 does not apply pressure to wire 212.

Use of ball 1412 provides less friction to wire 212 which helps prevent fraying of wire 212 over time.

For some applications, fastener 1402 can be used in combination with any one of contracting-member-covering devices 1082, 1092, 1102, 1202, 1302, 1802, 1822, and 1832 described hereinabove with or without fastener 1460.

While particular examples of fasteners are described at various locations herein, other securing means, fasteners, clips, etc. can also be used even if not described in a particular example herein.

Wire 212, for some applications, has an outer diameter of 0.2-0.4 mm, e.g, 0.3 mm. First lumen 1405 has an outer diameter of 0.8-1.2 mm, e.g, 1.0 mm. Housing 1404 has an outer diameter of 2.8-3.2 mm, e.g, 3.0 mm, and a length of 3.3-3.7 mm, e.g, 3.5 mm.

For some applications, locking ball 1412 is advanced from second lumen 1403 within first lumen 1405. Locking ball 1412 has an outer diameter of 1.0-1.1 m, e.g, 1.05 mm, which is slightly larger than the diameter of first lumen 1405 which helps facilitate application of pressure to wire 212 by ball 1412 as it is compressed within first lumen 1405.

Figure 41A:
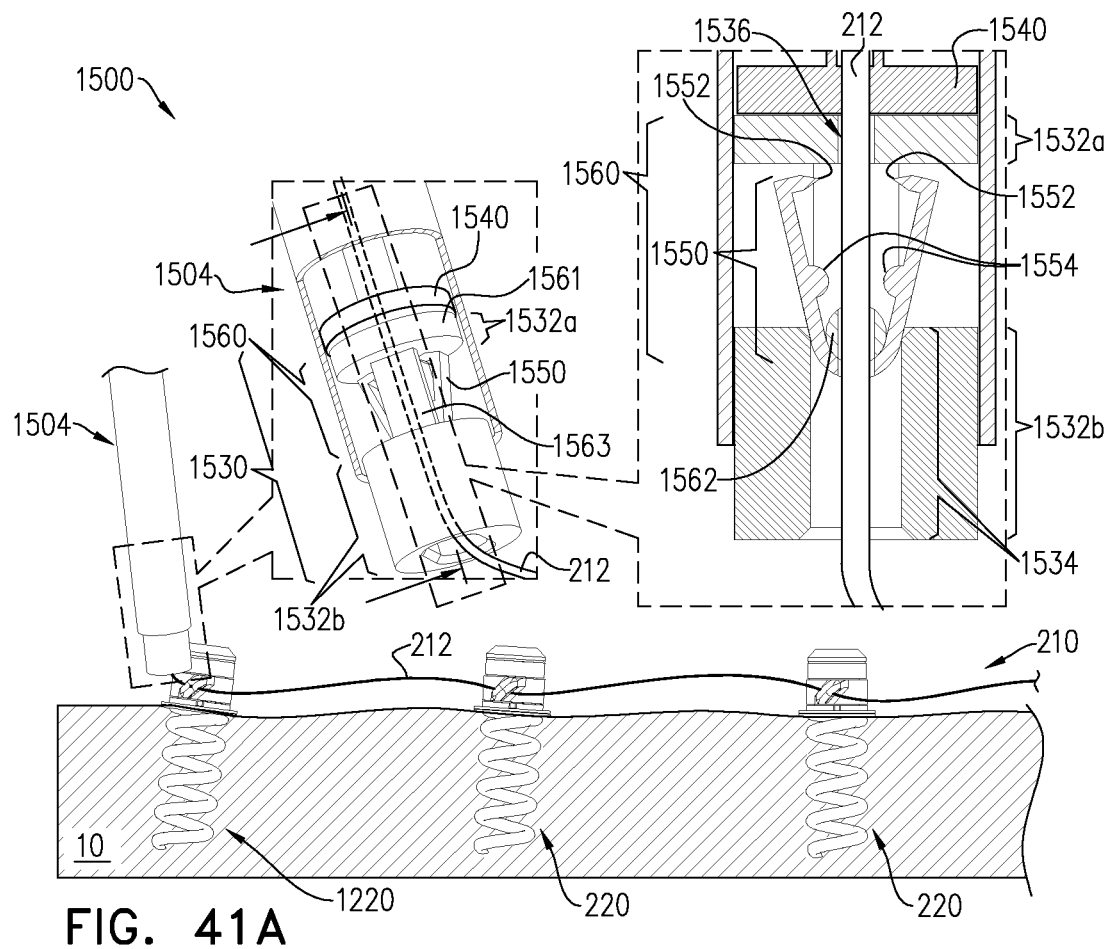
Figure 41B:
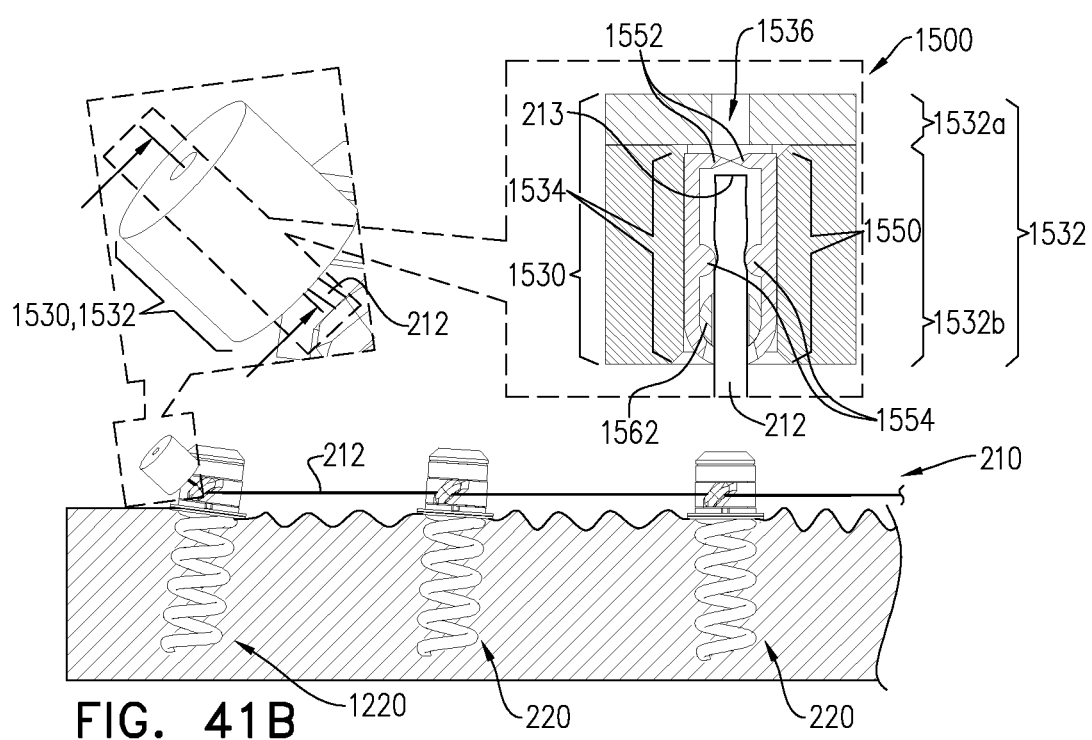

Reference is now made to FIGS. 41A-B, which are schematic illustrations of an example of a system 1500 comprising a locking mechanism comprising a fastener 1530 configured to be couplable to wire 212 (i.e., the contracting member) in a vicinity of terminal tissue anchor 1220 of the plurality of tissue anchors 220, in accordance with some applications. Fastener 1530, in a closed state thereof (FIG. 41B), is configured to restrict movement of wire 212 with respect to the plurality of tissue anchors 220. Fastener 1530 comprises a housing 1532 shaped so as to define a lumen 1534 therethrough. Housing 1532 comprises first and second housing subcomponents 1532*a* and 1532*b* which are separate during delivery of fastener 1530 toward implant 210 (FIG. 41A) and fit together during the closed state of fastener 1530 (FIG. 41B).

A contracting-member-lock-and-cutter element 1550 is slidable within lumen 1534 of housing 1532. Contracting-member-lock-and-cutter element 1550 comprising first and second arms coupled together at respective distal portions thereof at a distal portion of contracting-member-lock-and-cutter element 1550. The first and second arms of element 1550 are compressible toward each other when contracting-member-lock-and-cutter element 1550 is advanced within lumen 1534 of housing 1532 (FIG. 41B) such that contracting-member-lock-and-cutter element 1550 assumes a closed state. The first and second arms are each shaped to as to define respective cutting elements 1552 at respective proximal ends of the first and second arms, and respective protrusions 1554 at respective middle portions of the first and second arms. Protrusions 1554 are often rounded and project radially inwardly from the arms toward a central longitudinal axis of housing 1532.

A pusher 1560 is shaped so as to push contracting-member-lock-and-cutter element 1550 within lumen 1532 of housing 1532. Pusher 1560 comprises a round proximal pushing element 1561 which is engageable by a pushing tool 1540 of a delivery tool 1504 used to deliver housing 1532. Round proximal pushing element 1561 of pusher 1560 serves as housing element 1532*a*. Round pushing element 1561 is coupled to a distally-extending pushing column 1563 that is shaped to define a pushing bar 1562. Bar 1562 is removably coupled to element 1550 and slides within lumen 1534 in order to push element 1550 within lumen 1534. Once element 1550 is disposed within lumen 1534, the arms are compressed by the wall defining lumen 1534, and pusher 1560 remains within lumen 1534, often due to frictional force.

Prior to delivery of fastener 1530, wire 212 is threaded through fastener 1530 by being threaded through an opening in the distal surface of housing 1530, through lumen 1534 of second housing component 1532*b*, through an opening defined by the distal portion of contracting-member-lock-and-cutter element 1550, through an opening defined by pushing bar 1562 of pusher 1560, and through an opening 1536 at first housing component 1532*a*.

As element 1550 is pushed within lumen 1534, the wall of lumen 1534 of housing 1532 pushes against the first and second arms of element 1550 such that they compress toward each other. In the closed state of contracting-member-lock-and-cutter element 1550 (FIG. 41B), (a) protrusions 1554 of contracting-member-lock-and-cutter element 1550 come together in order to compress wire 212 therebetween and facilitate locking of wire 212 by restricting movement of the contracting member, and (b) cutting elements 1552 of contracting-member-lock-and-cutter element 1550 come together in order to cut wire 212. Since element 1550 remains within the body of the patient, cutting elements 1552 remain within the body of the patient.

Since housing 1532 of fastener 1530 covers free end 213 of wire 212, fastener 1530 functions as a contracting-member-covering device.

Figure 42A:
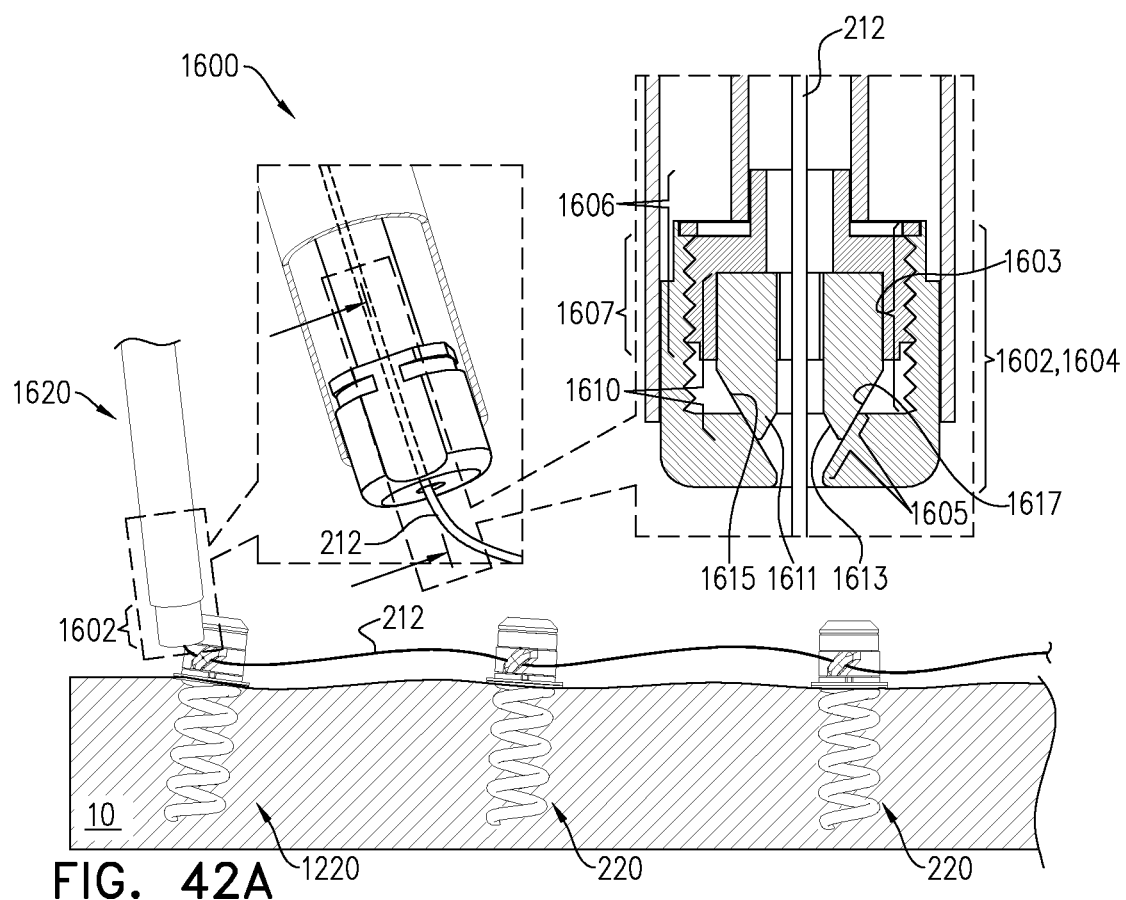
Figure 42B:
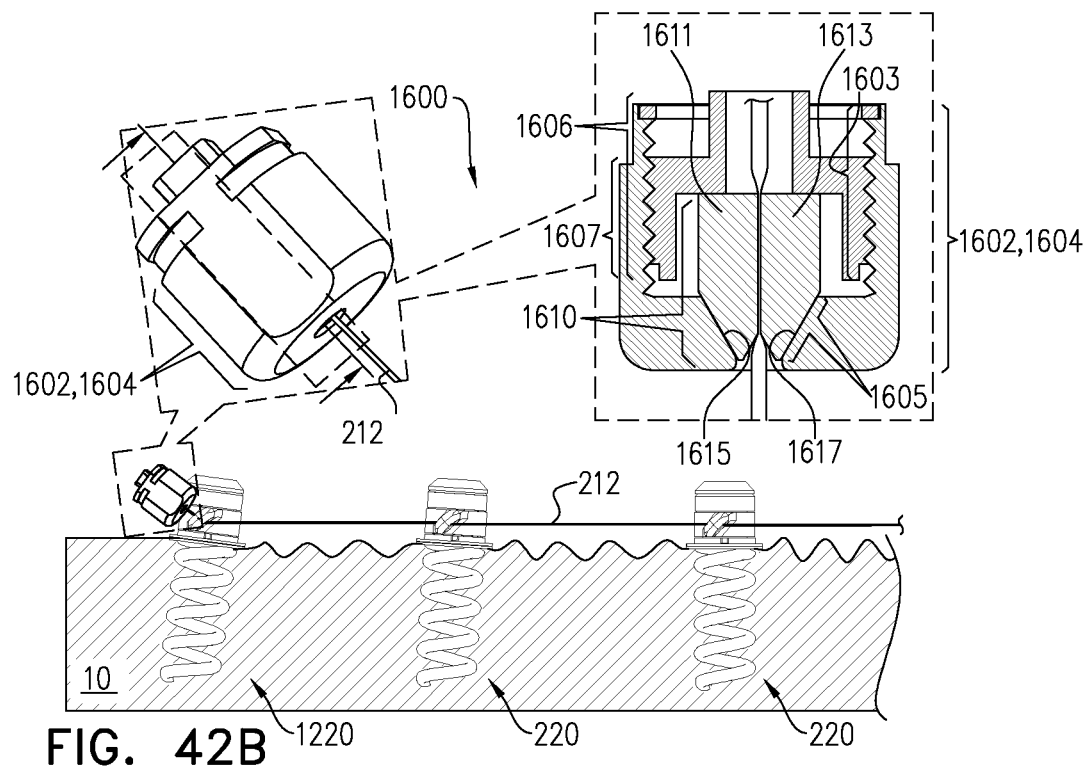

Reference is now made to FIGS. 42A-B, which are schematic illustrations of a system 1600 comprising a locking mechanism comprising a fastener 1602 configured to be couplable to wire 212 (i.e., the contracting member) in a vicinity of terminal tissue anchor 1220 of the plurality of tissue anchors 220, in accordance with some applications.

Fastener 1602, in a closed state thereof (FIG. 42B), is configured to restrict movement of wire 212 with respect to the plurality of tissue anchors 220. Fastener 1602 comprises a housing 1604 comprising an inner wall shaped so as to define (a) a lumen for passage therethrough of wire 212, and (b) a distal conical surface 1605, and (c) a proximal portion 1603 of the inner wall that is threaded.

Fastener 1602 comprises a threaded screwing element 1606 having a threaded surface 1607 that is engageable with the threaded proximal portion 1603 of the inner wall of housing 1604.

A lock or wire lock 1610 is coupled to threaded screwing element 1606 and moveable within the lumen of housing 1604 responsively to screwing of threaded screwing element 1606. Wire lock 1610 comprises first and second gripping elements 1611 and 1613 disposed on either side of wire 212. Each of first and second gripping elements 1611 and 1613 defines a tapered surface 1615 and 1617, respectively, configured to (1) fit within distal conical surface 1605 of housing 1604 responsively to pushing of contracting-member lock 1610 distally by distal screwing of threaded screwing element 1606, and thereby (2) compress wire 212 passing through first and second gripping elements 1611 and 1613.

Using a tool, fastener 1602 is delivered toward anchor 1220 and element 1606 is longitudinally screwed distally within the lumen of housing 1604.

Prior to delivery of fastener 1602, wire 212 is threaded through fastener 1602 by being threaded through an opening in the distal surface of housing 1602, between gripping elements 1611 and 1613 of wire lock 1610, and through threaded screwing element 1606.

For some applications, housing 1604 of fastener 1602 covers the free end of wire 212, thereby functioning as a contracting-member-covering device.

For some applications, fastener 1602 can be used in combination with any one of contracting-member-covering devices 1082, 1092, 1102, 1202, 1302, 1802, 1822, and 1832 described hereinabove with or without fastener 1460.

Figure 43A:
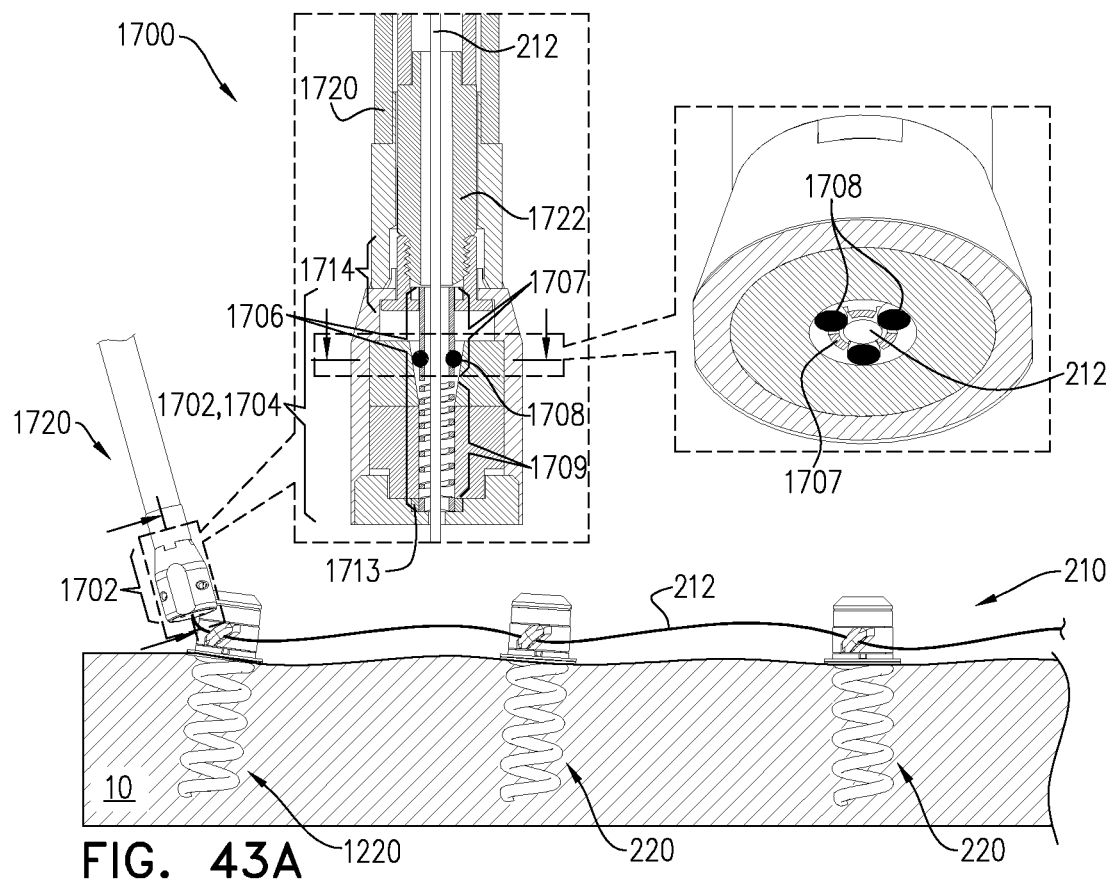
Figure 43B:
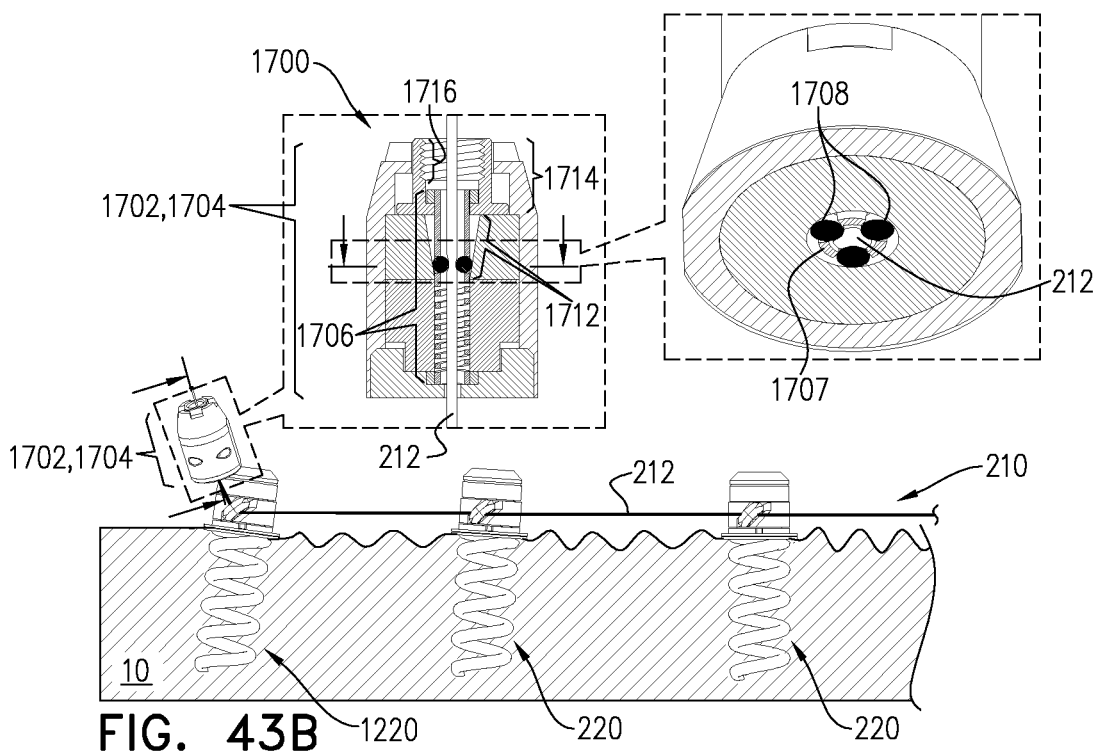

Reference is now made to FIGS. 43A-B, which are schematic illustrations of a system 1700 comprising a locking mechanism comprising a fastener 1702 configured to be couplable to wire 212 (i.e., the contracting member) in a vicinity of terminal tissue anchor 1220 of the plurality of tissue anchors 220, in accordance with some applications. Fastener 1702, in a closed state thereof (FIG. 43B), is configured to restrict movement of wire 212 with respect to the plurality of tissue anchors 220. Fastener 1702 comprises a housing 1704 comprising an inner wall shaped so as to define a lumen for passage therethrough of wire 212. The lumen is shaped in part so as to define a conical surface 1712 having a wide proximal portion and a narrow distal portion having a narrow surface at a distal end of conical surface 1712.

Housing 1704 comprises a distal spring-coupling element 1713, e.g, a washer, at a distal end of the lumen and a proximal spring-coupling element 1714 at a proximal end of the lumen and disposed proximally to conical surface 1712. A longitudinal spring 1706 is coupled at each respective end to proximal and distal spring-coupling elements 1714 and 1713, respectively. Spring 1706 comprises a superelastic material. e.g., nitinol, and comprises a coiled distal subcomponent 1709 and a proximal cylindrical subcomponent 1707. Often, the proximal and distal subcomponents 1707 and 1709 of spring 1706 are fabricated from a single piece. The coiled element of distal subcomponents 1707 is shown in an expanded state in FIG. 43A and is configured to compress (FIG. 43B) in a manner which draws proximal cylindrical subcomponent 1707 distally. The proximal subcomponent 1707 of spring 1706 is coupled to at least one (e.g, three, as shown by way of illustration and not limitation) inwardly-compressible element 1708. As shown, inwardly-compressible elements 1708 comprise compressible spheres that are coupled to spring 1706 at a site along spring 1706 that is disposed within a space defined by conical surface 1712. For some applications, spring 1706 is shaped so as to define at least one slit or any suitable opening for inward movement of inwardly-compressible elements 1708. Inwardly-compressible elements 1708 are disposed alongside wire 212. In an open state of fastener 1702 (FIG. 43A), elements 1708 do not apply pressure to wire 212, and wire 212 slides freely with respect to fastener 1702.

Proximal spring-coupling element 1714 comprises a cylindrical element coupled to a distal washer. Element 1714 is movable distally within a space defined by housing 1704 at a proximal portion thereof. The washer of proximal spring-coupling element 1714 surrounds and is fixedly coupled to the proximal end of spring 1706. In the open state of fastener 1702 (FIG. 43A), proximal spring-coupling element 1714 is in a proximal position in which spring 1706 is pulled into a stretched state between proximal and distal spring-coupling elements 1714 and 1713, respectively, in which inwardly-compressible elements 1708 are disposed in a space defined by the wide portion of conical surface 1712 and do not apply inward pressure to wire 212. Proximal spring-coupling element 1714 is held in this proximal position by a delivery tool 1720 that is reversibly coupled to proximal spring-coupling element 1714. Proximal spring-coupling element 1714 defines a threaded surface 1716 that is engaged by a rotation tool 1722. Proximal spring-coupling element 1714 remains in the proximal position when tool 1722 remains coupled to element 1714 and applies a proximal force to element 1714.

Once anchors 220 are implanted in tissue 10, wire 212 is pulled in order to perform annuloplasty on the valve. In order to maintain tension on wire 212, fastener 1702 is locked in place with respect to wire 212 by decoupling tool 1720 from fastener 1702. Rotation tool 1722 of tool 1720 is rotated in order to unscrew tool 1720 from housing 1704 of fastener 1702. Once rotation tool 1722 is unscrewed, tool 1720 no longer applies a proximal force to proximal spring-coupling element 1714, and spring 1706 is allowed to relax and compress distally drawing proximal spring-coupling element 1714 distally, as shown in FIG. 43B such that fastener 1702 assumes the closed state.

In a closed state of fastener 1702, proximal spring-coupling element 1714 is in the distal position in which spring 1706 assumes the relaxed state in which inwardly-compressible elements 1708 are disposed in the narrow portion of conical surface 1712 and apply inward pressure to wire 212 responsively to pressure applied to element 1708 by the narrow surface of conical surface 1712.

For some applications, housing 1704 of fastener 1702 covers the free end of wire 212, thereby functioning as a contracting-member-covering device.

For some applications, fastener 1702 can be used in combination with any one of contracting-member-covering devices 1082, 1092, 1102, 1202, 1302, 1802, 1822, and 1832 described hereinabove with or without fastener 1460.

Reference is now made to FIGS. 44A-B, 45A-B, and 46A-B, which are schematic illustrations of systems 1800, 1820, and 1830 each comprising respective contracting-member-covering devices 1802, 1822, and 1832. Each of contracting-member-covering devices 1802, 1822, and 1832 comprises a respective housing. Devices 1802 and 1822 comprise housing 1804 and device 1832 comprises housing 1834.

Wire 212 passes longitudinally through each housing of devices 1802, 1822, and 1832.

Reference is now made to FIGS. 44A-B. Housing 1804 comprises first and second deflectable wires 1806 and 1808 passing transversely through housing 1804 and alongside a portion of wire 212. Wires 1806 and 1808 comprise a superelastic material, e.g, nitinol. For some applications, wires 1806 and 1808 are rectangular in cross-section. It is to be noted that any number of deflectable wires can be used, e.g, three. First and second wires 1806 and 1808 are in a first position (FIG. 44A) in which first and second deflectable wires 1806 and 1808 do not engage wire 212. As shown, in the first position, wires 1806 and 1808 are in a loaded configuration in which each of the first and second deflectable wires assumes a curved configuration. In the first position shown in FIG. 44A, at least a majority of first deflectable wire 1806 is disposed above the portion of wire 212, and at least a majority of second deflectable wire 1808 is disposed below the portion of wire 212. In order to maintain wires 1806 and 1808 in the first position, a tube 1810 is positionable between wire 212 and first and second deflectable wires 1806 and 1808. Tube 1810 restricts first and second deflectable wires 1806 ad 1808 from transitioning into a second, activated position shown in FIG. 44B.

As shown in FIG. 44B, tube 1810 is removed from within housing 1804 to allow for first and second deflectable wires 1806 and 1808 to transition to the second, activated position in which first and second wires 1806 and 1808 deflect to assume a configuration which changes a conformation of the portion of wire 212 in a manner which draws additional portions of the wire 212 into housing 1804. In the second position, device 1802 uptakes into housing 1804 and covers excess portions of wire 212 and end 213 of wire 212 following cutting of wire 212. In the second position, first deflectable wire 1806 pushes down on the portion of wire 212, and second deflectable wire 1808 pushes upwardly against the portion of wire 212. In the second position, first and second deflectable wires 1806 and 1808 assume a straight configuration. In the second position, first and second deflectable wires 1806 and 1808 each assume a length (measured along an axis that is transverse to the longitudinal axis of housing 1804) that is greater than a width of housing 1804. In order to accommodate the length of wires 1806 and 1808 in the second position in FIG. 44B, housing 1804 is shaped so as to define openings 1805. Respective ends of wires 1806 and 1808 protrude from housing 1804 through openings 1805.

Figure 45A:
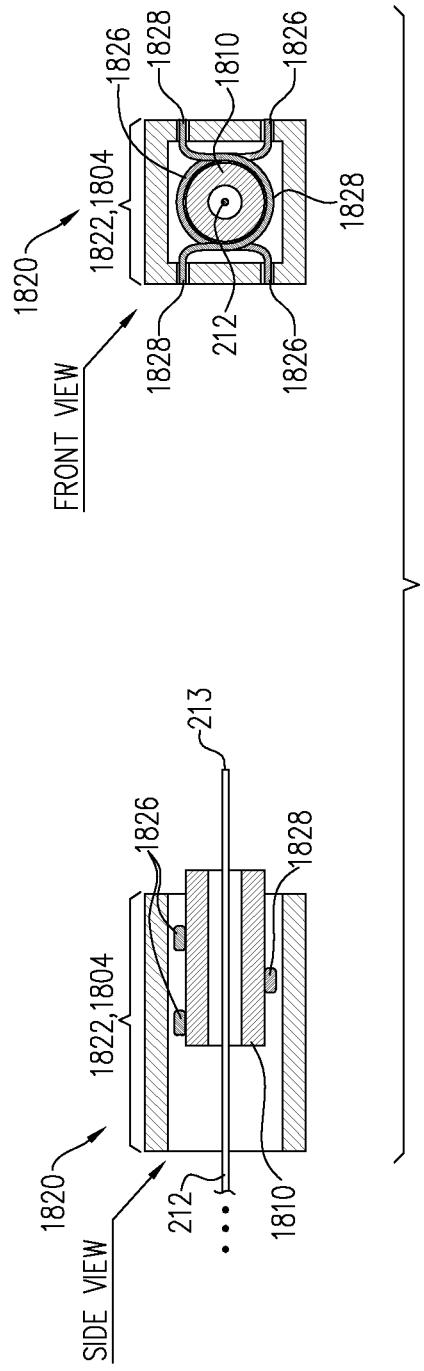
Figure 45B:
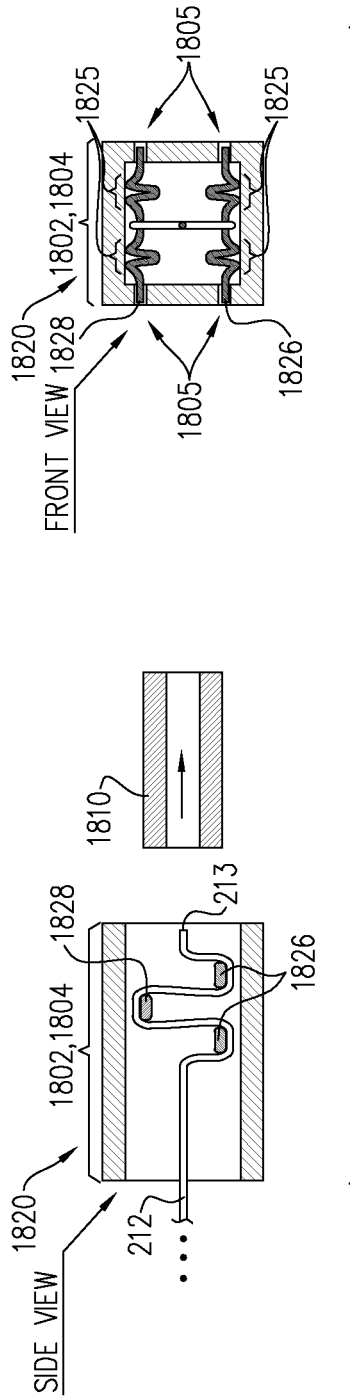

Reference is now made to FIGS. 45A-B. Housing 1804 comprises first and second deflectable wires 1826 and 1828 passing transversely through housing 1804 and alongside a portion of wire 212. Wires 1826 and 1828 comprise a superelastic material, e.g, nitinol. For some applications, wires 1826 and 1828 are rectangular in cross-section. It is to be noted that any number of deflectable wires can be used, e.g, three. First and second wires 1826 and 1828 are in a first position (FIG. 45A) in which first and second deflectable wires 1826 and 1828 do not engage wire 212. As shown, in the first position, wires 1826 and 1828 are in a loaded configuration in which each of the first and second deflectable wires assumes a curved configuration. In the first position shown in FIG. 45A, at least a majority of first deflectable wire 1826 is disposed above the portion of wire 212, and at least a majority of second deflectable wire 1828 is disposed below the portion of wire 212. In order to maintain wires 1826 and 1828 in the first position, a tube 1810 is positionable between wire 212 and first and second deflectable wires 1826 and 1828. Tube 1810 restricts first and second deflectable wires 1826 ad 1828 from transitioning into a second, activated position shown in FIG. 45B.

As shown in FIG. 45B, tube 1810 is removed from within housing 1804 to allow for first and second deflectable wires 1826 and 1828 to transition to the second, activated position in which first and second wires 1826 and 1828 deflect to assume a configuration which changes a conformation of the portion of wire 212 in a manner which draws additional portions of the wire 212 into housing 1804. In the second position, device 1822 uptakes into housing 1804 and covers excess portions of wire 212 and end 213 of wire 212 following cutting of wire 212. In the second position, first deflectable wire 1826 pushes down on the portion of wire 212, and second deflectable wire 1828 pushes upwardly against the portion of wire 212. In the second position, first and second deflectable wires 1826 and 1828 assume a straight configuration. In the second position, first and second deflectable wires 1826 and 1828 each assume a length (measured along an axis that is transverse to the longitudinal axis of housing 1804) that is greater than a width of housing 1804. In order to accommodate the extended lengths of wires 1826 and 1828 in the second position in FIG. 45B, housing 1804 is shaped so as to define openings 1805. Respective ends of wires 1826 and 1828 protrude from housing 1804 through openings 1805. First and second deflectable wires 1826 and 1828 each define at least one crimping region 1825 configured to shorten the length of first and second deflectable wires 1826 and 1828 in the second position such that the ends of wires 1826 and 1828 do not protrude from within housing 1804.

Reference is now made to FIGS. 46A-B. Housing 1834 comprises first and second deflectable wires 1836 and 1838 passing transversely through housing 1834 and alongside a portion of wire 212. Wires 1836 and 1838 comprise a superelastic material, e.g, nitinol. For some applications, wires 1836 and 1838 are rectangular in cross-section. It is to be noted that any number of deflectable wires can be used, e.g, three. First and second wires 1836 and 1838 are in a first position (FIG. 46A) in which first and second deflectable wires 1836 and 1838 do not engage wire 212. As shown, in the first position, wires 1836 and 1838 are in a loaded configuration in which each of the first and second deflectable wires assumes a curved configuration. In the first position shown in FIG. 46A, a portion of first deflectable wire 1836 is disposed above the portion of wire 212, and a portion second deflectable wire 1838 is disposed below the portion of wire 212. In order to maintain wires 1836 and 1838 in the first position, a tube 1810 is positionable between wire 212 and first and second deflectable wires 1836 and 1838. Tube 1810 restricts first and second deflectable wires 1836 ad 1838 from transitioning into a second, activated position shown in FIG. 46B.

Wires 1836 and 1838 have a length (measured along an axis that is transverse to the longitudinal axis of housing 1834) that is smaller than a width of housing 1834.

As shown in FIG. 46B, tube 1810 is removed from within housing 1834 to allow for first and second deflectable wires 1836 and 1838 to transition to the second, activated position in which first and second wires 1836 and 1838 deflect to assume a configuration which changes a conformation of the portion of wire 212 in a manner which pushes aside wire 212 and draws additional portions of the wire 212 into housing 1834. In the second position, device 1832 uptakes into housing 1834 and covers excess portions of wire 212 and end 213 of wire 212 following cutting of wire 212. In the second position, second deflectable wire 1838 (by way of example) pushes upwardly against the portion of wire 212. In the second position, first and second deflectable wires 1836 and 1838 assume a generally straight configuration.

Reference is now made to FIGS. 44A-B, 45A-B, and 46A-B. It is to be noted that contracting-member-covering devices 1802, 1822, and 1832 can be used in combination with any of fasteners 1402, 1460, 1530, 1602, and 1702 described herein and any other suitable securing means, fastener, clip, etc.

Figure 47A:
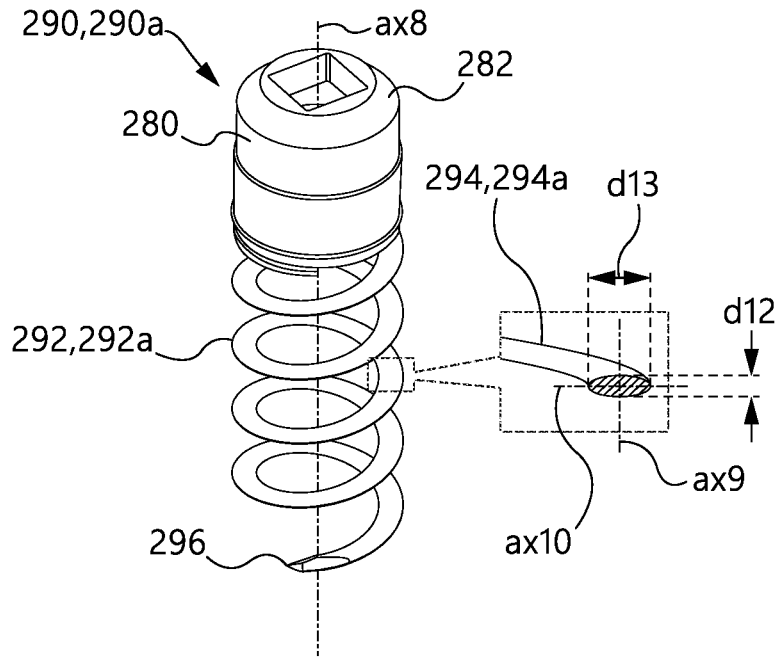
FIGS. 47A-B are schematic illustrations of embodiments of a tissue anchor, in accordance with some applications.
Figure 47B:
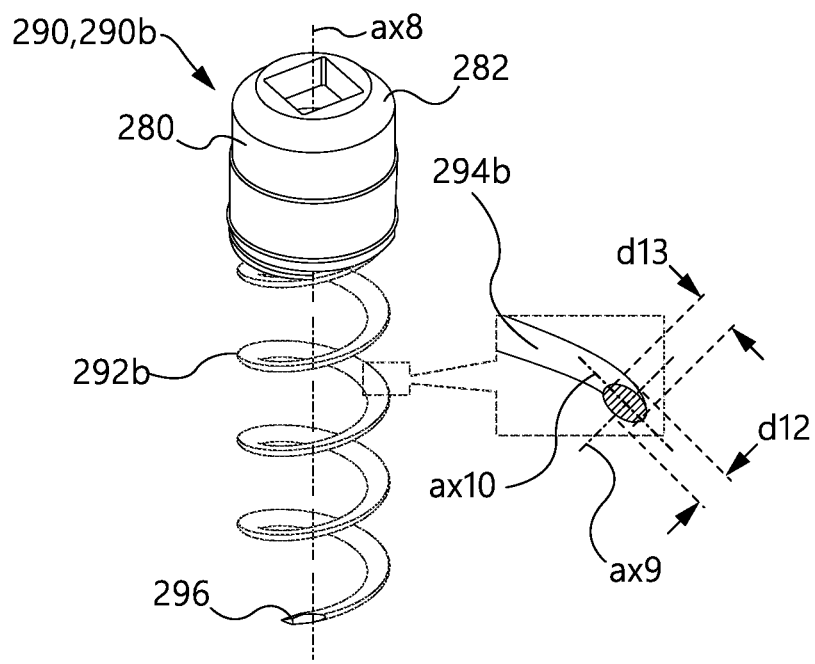

Reference is made to FIGS. 47A-B, which are schematic illustrations of embodiments of a tissue anchor 290, in accordance with some applications. Anchor 290 comprises a head such as head 280, and a driver interface such as driver interface 282. Anchor 290 also comprises a tissue-engaging element 292, which can be a helical tissue-engaging element as shown, and which can be identical to or similar to tissue-engaging element 230 or other tissue-engaging elements herein, except that tissue-engaging element 292 is made of a rod 294 that is shaped as a noncircular ellipse, or any other shape having non-identical dimensions across two orthogonal axes of its cross-section. Tissue-engaging element 292 defines a central longitudinal axis ax8 of the anchor 290 and terminates with a sharpened distal tip 296 which is similar to the sharpened distal tip 238 of tissue-engaging element 230.

The cross-sectional profile of the rod 294 defines a height d12 along a first sectional axis ax9 thereof, and a width d13 along a second sectional axis ax10 that is orthogonal of the first major axis ax9. The width d13 is greater than the height d12. For example, width d13 can be at least 1.3 times as great as height d12. For example, width d13 can be 1.3-5 times as great as height d12, e.g, 1.4-3 times as great, e.g, 1.5-2.5 times as great, e.g, 1.5-2.3 times as great, e.g, 1.5-2.1 times as great, such as 1.6-2 times as great. It is hypothesized by the inventors that the greater surface contact offered by the enlarged cross-sectional width d13 of the rod 294 facilitates securing of the tissue-engaging element 290 within tissue 10, e.g, by providing higher resistance to unintentional extraction of the tissue-engaging element from the tissue.

FIG. 47A shows an embodiment 290a of tissue-engaging element 290, wherein the first sectional axis ax9 is parallel to the central longitudinal axis ax8, such that the width d13 defines a higher contact area with tissue 10 in a manner that may increase resistance to spontaneous pulling force applied to the tissue-engaging element 292a in the axial direction (i.e., in the direction of central longitudinal axis ax8).

FIG. 47B shows another embodiment 290b of tissue-engaging element 290, wherein first sectional axis ax9 is angled with respect to the central longitudinal axis ax8, such that the width d13 defines a higher contact area with tissue 10 in a manner that may increase resistance to spontaneous forces applied to the tissue-engaging element 292b with components either in the axial and/or lateral directions, depending on the dimensions of the wide d13 and the angle between axes ax9 and ax8.

It is to be understood that other than the non-circular cross-sectional profile of the rod 294, tissue engaging element 292 can be similar to any other tissue-engaging elements, and while shown in combination with head 280, any other heads can be used, mutatis mutandis. Furthermore, although an eyelet is not visible in FIGS. 47A-B, anchor 290 can comprise an eyelet, such as an eyelet described herein, e.g, eyelet 240 or eyelet 640, mutatis mutandis.

Reference is made to FIGS. 48-49, which are schematic illustrations of a system 700 comprising an implant 710, in accordance with some applications. System 700 is a tissue-adjustment system and can be used for adjusting a dimension of a tissue structure. For example, system 700 can be an annuloplasty system, and implant 710 can be an annuloplasty structure (e.g, an annuloplasty ring, annuloplasty implant, etc.). System 700 (e.g, implant 710) can be used in similar ways to those described for system 100, system 200, and/or system 400.

System 700 can be identical to or similar to system 200 except where noted. Similarly, implant 710 and anchor 720 are identical to or similar to implant 210 and anchor 220, except where noted.

Like implant 210, implant 710 comprises line or wire 212 and a plurality of anchors. Anchor 720 can be similar to anchor 220 and comprises a tissue engaging element 230 defining a central longitudinal axis ax11, and a head 730. Distinguishing it from head 280, head 730 generally does not include a protruding eyelet. Instead, head 730 comprises a ring 736 that includes a channel 740 extending between two openings 742a and 742b along channel axis ax12, which is orthogonal to the central longitudinal axis ax11 or to an axis parallel to the longitudinal axis ax11. The channel 740 is configured to accommodate wire 212 that may extend therethrough. For some applications, channel 740 can be considered to be an internal eyelet. For some applications, openings 742 have rounded or chamfered edges, so as to reduce likelihood of cutting or otherwise damaging the wire 212 that may contact them.

Head 730 further comprises a driver interface 738, which can be identical or similar to driver interface 282. For some applications, head 730 comprises a proximal head segment 732, provided with the driver interface 738, and a distal head segment 734, wherein the ring 736 is disposed there-between. The proximal head segment 732 and the distal head segment 734 can be immovable with respect to the tissue engaging element 230. Ring 790 circumscribes and is rotatable about axis ax11, e.g, by being rotatably coupled to tissue-engaging element 230, such as by being rotatably coupled to another component of head 730 (e.g, proximal head segment 732 and/or distal head segment 734) that is fixedly coupled to the tissue-engaging element.

FIG. 49 shows implant 710 with anchors 720 anchored in tissue 10, such as in an arc around the annulus of a heart valve. The implant 710 is shown in FIG. 49 after it has been contracted by tensioning of wire 212. Since the ring 736 is rotatable about axis ax11 of the tissue engaging element 230, such that the rotational position of the channel 740 is independent of that of tissue-engaging element 230. It is hypothesized that, for applications in which tissue-engaging element 230 is helical, this independence advantageously allows the tissue-engaging element to be screwed into tissue to the extent needed for optimal anchoring, without a requirement for the anchor to finish in a particular rotational orientation. It is further hypothesized that, irrespective of the type of tissue-engaging element 230 used, this independence allows channel 740 (and wire 212) to be in an optimal position, with respect to axis ax11 of each anchor 720, for a given application. For example, for an application in which implant 710 is used for annuloplasty, anchors 720 are often anchored in a curve around the valve annulus, and channels 740 and wire 212 are often disposed on the inside of the curve relative to axes ax11.

For some applications, channel 740 facilitates sliding of wire 212 therethrough while the anchor is orthogonal to the wire, without the diameter d14 of channel 740 and openings 742 thereof being more than 5 percent wider than the thickness of the wire.

For some applications, channel axis ax12 is offset from central axis ax11. For some applications, channel 740 is offset from central axis ax11, forming a gap of at least 0.1 mm between the innermost edge of the channel 740 (defined as the edge closest to the central axis ax11) and the central axis ax11. For example, the gap can be greater than 0.2 mm, e.g, greater than 0.5 mm, e.g, greater than 1 mm.

Figure 50A:
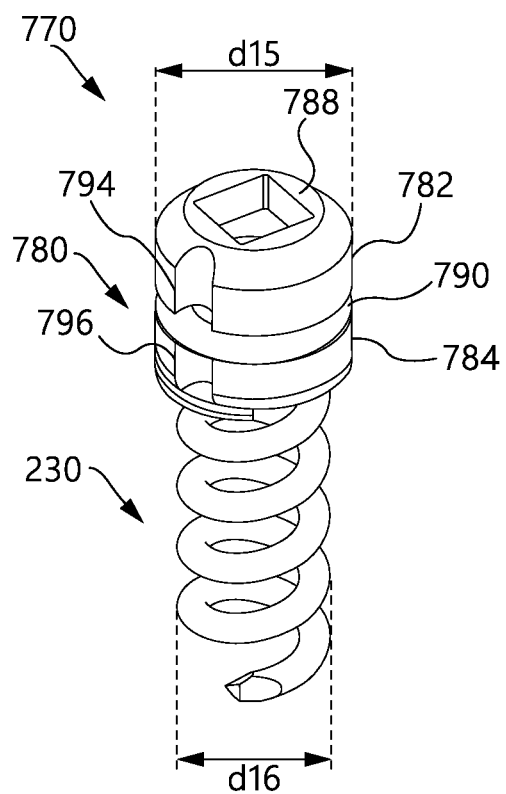
FIGS. 50A-B and 51 are schematic illustrations of an example tissue anchor, an implant comprising the tissue anchor, and a system comprising the implant, in accordance with some applications.
Figure 50B:
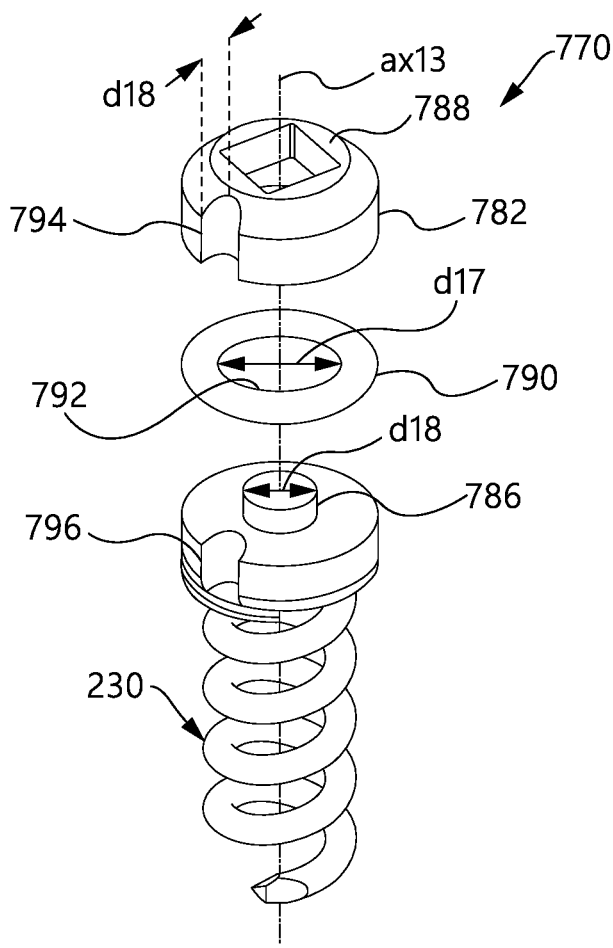
Figure 51:
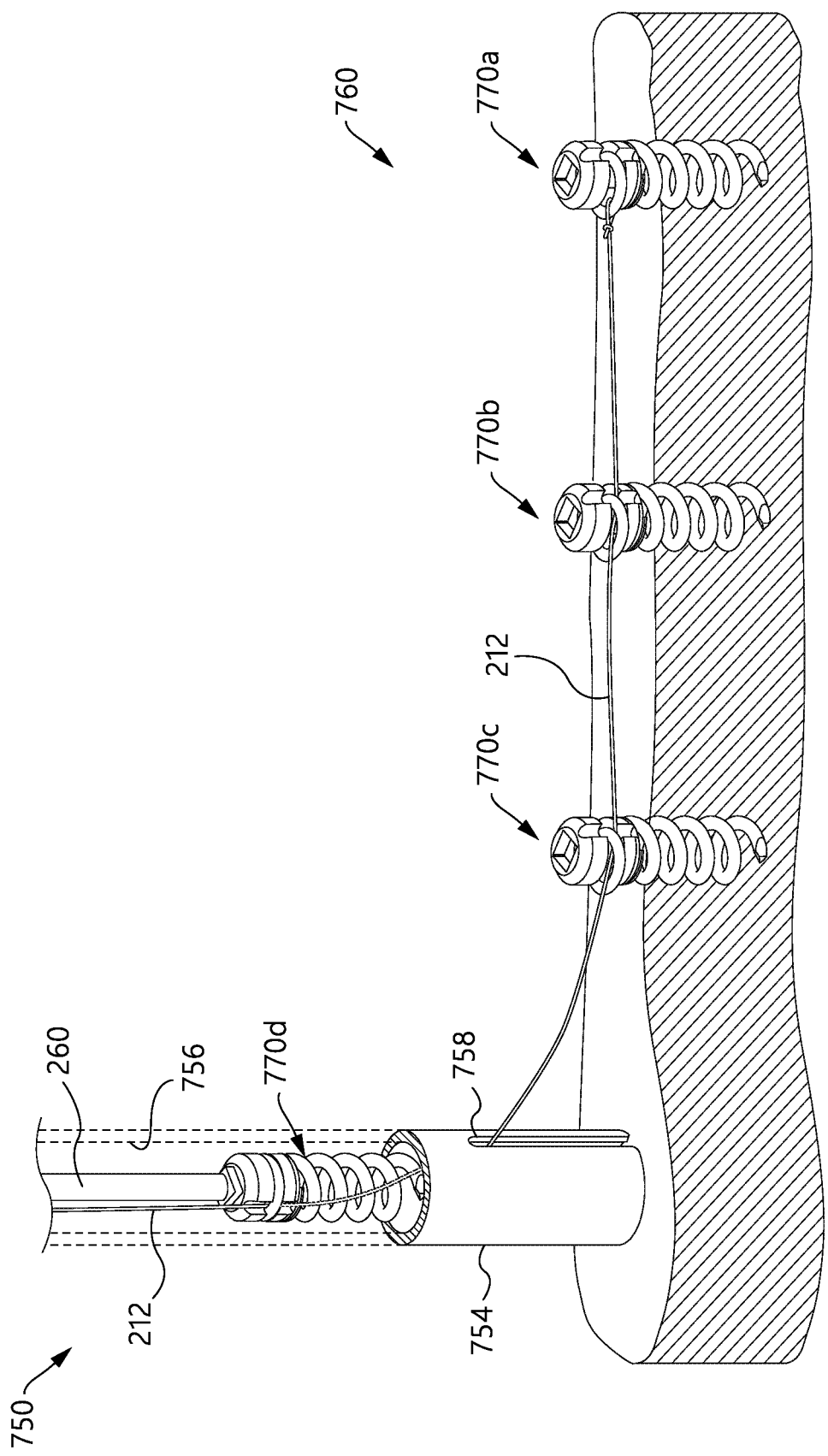

Reference is made to FIGS. 50A-51, which are schematic illustrations of a system 750 comprising an implant 760, in accordance with some applications. System 750 is a tissue-adjustment system and can be used for adjusting a dimension of a tissue structure. For example, system 750 can be an annuloplasty system, and implant 760 can be an annuloplasty structure (e.g., an annuloplasty ring, annuloplasty implant, etc.). System 750 (e.g., implant 760) can be used in similar ways to those described for system 100, system 200, system 400, and/or system 700.

System 750 can be identical to or similar to system 200 except where noted. Similarly, implant 760 and anchor 770 are identical to or similar to implant 210 and anchor 220, except where noted.

Like implant 210, implant 760 comprises line or wire 212 and a plurality of anchors. Anchor 770 can be similar to anchor 220 and comprises a tissue engaging element 230 defining a central longitudinal axis ax13, and a head 780. Distinguishing it from head 280, head 780 usually does not include a protruding eyelet. Instead, head 780 comprises a ring 790 that disposed around the central axis ax13, and that can move radially so as have its center offset from the central axis ax13.

Head 790 further comprises a driver interface 788, which can be identical or similar to driver interface 282. For some applications, head 790 comprises a proximal head segment 782, provided with the driver interface 788, and a distal head segment 784, wherein the ring 790 is disposed there-between. The proximal head segment 782 and the distal head segment 784 can be immovable with respect to the tissue engaging element 230. For some applications, head 780 further comprises a stem 786 having a diameter d18, which extends between the proximal head segment 782 and the distal head segment 784. Stem 786 can be integrally formed with any of the proximal head segment 782 and/or the distal head segment 784. Ring 790 is disposed around stem 786 and can be both rotatably and laterally movable with respect to stem 786 and/or the central axis ax13 thereof.

Head 780 has an outer diameter d15, and tissue-engaging element 230, that when implemented as a helical tissue-engaging element, has an outer diameter of the helix d16. For some applications, the outer diameter of head 780 is the outer diameter of both the proximal head segment 782 and the distal head segment 784. For some applications, the outer diameter of ring 790 is identical to the outer diameter d15 of the proximal head segment 782 and/or the distal head segment 784.

Ring 790 has an inner diameter d17 that is greater than the diameter d18 of stem 786. For example, diameter d17 can be at least 1.3 times as great as diameter d18. For example, diameter d17 can be 1.3-5 times as great as diameter d18, e.g, 1.4-3 times as great as diameter d18, e.g, 1.5-2.5 times as great as diameter d18, e.g, 1.5-2.3 times as great as diameter d18, e.g, 1.5-2.1 times as great as diameter d18, such as 1.6-2 times as great as diameter d18.

For some applications, the proximal head segment 782 comprises a proximal groove 794, and the distal head segment 784 comprises a distal groove 796, wherein both grooves 794 and 796 are aligned with each other parallel to the central axis ax13, and are configured to accommodate wire 212 that my extend through and along the grooves. Each groove, defined at the external surface of the respective head portion, can have a radial depth d18, dimensioned to accommodate wire 212. For example, the radial depth d18 can be at least as great as the diameter of the wire 212.

System 750 comprises delivery tool 752, which is similar to implant delivery tool 250, except where noted. Delivery tool 752 comprises a flexible tube 754 (e.g., a transluminal catheter) via which each anchor 770, engaged with driver 260, is advanceable to the tissue to which the anchor is to be anchored.

FIG. 51 shows multiple anchors 770a, 770b and 770c having been anchored to tissue 10, with one anchor 770d currently being advanced, by driver 260, through tube 652. Flexible tube 754 can include a lateral slit 758 that can be identical to lateral slit 256 of tube 252. Unlike flexible tube 252, flexible tube 754 defines an internal channel 756 that does not necessarily include major and minor channel regions, but may rather define a single circular cross-sectional profile. For some applications, the internal channel 756 has a diameter that is no more than 20 percent greater than the diameter d15 of the head 780 and/or the ring 790, e.g., no more than 10 percent greater than diameter d15, e.g., no more than 5 percent greater than diameter d15. The close similarity between the inner diameter of the internal channel 756 and the outer diameter d15 of the head 780 and its ring 790, result in the ring 790 being generally coaxial with the head 780 in a delivery state through the tube 754.

When an anchor is delivered through the flexible tube 754, as shown for anchor 770d, wire 212 extends generally parallel with the central axis ax13 through the ring 790, and optionally along both grooves 794 and 796. The grooves help in retaining wire 212 in a relatively straight orientation, parallel with central axis ax13, reducing bends that could have been formed in the absence of such grooves. For some applications, outer diameter d15 of head 780 is greater than outer diameter d16 of the helix of tissue-engaging element 230. For example, diameter d15 can be greater than diameter d16 by at least the thickness of wire 212, and more preferably, by at least twice the thickness of wire 212. This difference in diameters between the head diameter d15 and the tissue-engaging element diameter d16 can allow wire 212 to extend from the distal groove 796 along tissue-engaging element 230, while avoiding or at least minimizing bending of the wire 212.

As subsequent anchors 770 are anchored to the tissue 10, wire 212 becomes oriented laterally with respect to the anchors. Due to the ability of the ring 790 to move laterally to assume an offset position relative to the central axis ax13 of the respective anchor 770, the wire can still take a clear straight path through the plurality of rings 790 of the anchored anchors. A first stopper 214a and a second stopper 214b can be used, e.g, as described for implant 110 hereinabove, mutatis mutandis. For some applications, as shown for anchor 770a, the wire can be coupled to the ring 790 of the first anchor, such as by being looped there-around, instead of utilizing a stopper 214a such as a bead. Nevertheless, a stopper 214a can be still used in the same manner described hereinabove, instead of the wire 212 being looped over the ring 790.

Reference is made to FIGS. 52A-54C, which are schematic illustrations of a system 800 comprising an implant 810, in accordance with some applications. System 800 is a tissue-adjustment system and can be used for adjusting a dimension of a tissue structure. For example, system 800 can be an annuloplasty system, and implant 810 can be an annuloplasty structure (e.g, an annuloplasty ring, annuloplasty implant, etc.). System 800 (e.g, implant 810) can be used in similar ways to those described for system 100, system 200, and/or system 400.

System 800 can be identical to or similar to system 200 except where noted. Similarly, implant 810 and anchor 820 are identical to or similar to implant 810 and anchor 820, except where noted.

Like implant 210, implant 810 comprises line or wire 212 and a plurality of anchors, wherein the plurality of anchors can be either of the same anchor type, of composed of more than one anchor type, as will be elaborated further below. Anchor 820 can be similar to anchor 220 and comprises a tissue engaging element 230 defining a central longitudinal axis ax14, and a head 840. Distinguishing it from head 280, head 840 usually does not include an eyelet. Instead, head 840 comprises a wire tensioning mechanism 830 that includes a spool disposed within a housing.

Reference is made to FIGS. 52A, 52B and 52C, showing a view in perspective, an exploded view and a cross-sectional view, respectively, of an example tissue anchor 820, in accordance with some applications. Head 840 comprises a stem 842 with a driver interface 844, and a wire tensioning mechanism 830. Driver interface 844 can be identical or similar to driver interface 282. Stem 842 can be integrally formed with tissue engaging element 230 and extend therefrom. Optionally, stem 842 can be a distinct component, which is affixed to tissue engaging element 230, such that rotational movement applied to driver interface 844 and stem 842, rotates the tissue engaging element 230 therewith.

Wire tensioning mechanism 830 comprises a housing 850 defining an inner chamber 860 having a diameter d21, and a spool 840 disposed within the inner chamber 860, and coaxial therewith around central axis ax14. The spool has an outer diameter d23 which is smaller than the inner chamber diameter d21. Housing 850 has a housing base portion 852, a sidewall 854 that can be, for some applications, defined in a circular manner around the chamber 860, and a housing top portion 856 defining a top opening 864 having a diameter d22, which is smaller than the spool outer diameter d23.

The housing 850 further comprises at least one side opening 858 extending through the sidewall 854. For some applications, side opening 858 can be a circular opening having a diameter d19. For some applications, side opening can have an oval, elliptic, or rectangular shape, having a height in a direction parallel with axis ax14 and a width that is orthogonal to the height, wherein the height can have the value d19 while the width can be at least as great as d19, and optionally larger than d19.

Spool 870 includes a channel 880 extending between two openings 882a and 882b along channel axis ax15, which is orthogonal to an axis parallel to the longitudinal axis ax14. The channel 880 has a diameter d20 and is configured to accommodate wire 212 that may extend therethrough. For some applications, openings 882 have rounded or chamfered edges, so as to reduce likelihood of cutting or otherwise damaging the wire 212 that may contact them.

For some applications, both the side opening 858 and the channel 880 facilitate sliding of wire 212 therethrough while the anchor is orthogonal to the wire, without the diameter or height d19 of side opening 858, and/or the diameter d20 of channel 880 and/or openings 882 thereof being more than 5 percent wider than the thickness of the wire.

For some applications, channel axis ax15 is offset from central axis ax14. For some applications, channel 880 is offset from central axis ax14, forming a gap of at least 0.1 mm between the innermost edge of the channel 880 (defined as the edge closest to the central axis ax14) and the central axis ax14. For example, the gap can be greater than 0.2 mm, e.g, greater than 0.5 mm, e.g, greater than 1 mm.

Spool 870 has a spool base 872 facing the housing base portion 852, and a spool top portion 874 facing the housing top portion 856. For some applications, spool 870 further comprises a spool central lumen 871 having a diameter d24, configured to accommodate stem 842 that may extend therethrough, wherein the stem 842 has a diameter d25 that is smaller than spool lumen diameter d24. Stem 842 may extend through spool central lumen 871, such that driver interface 844 is positioned proximal to the spool 870.

For some applications, housing 850 is affixed to tissue engaging element 230, such that when tissue engaging element 230 rotates, housing 850 rotates therewith. For other applications, housing 850 is rotatably attached to tissue engaging element 230, such that it cannot move axially relative to tissue engaging element 230, but can rotate about central axis ax14 independently of tissue engaging element 230. For some applications, housing base portion 852 define an opening with a diameter greater than the stem diameter d25, configured to allow stem 842 to extend therethrough and into spool central lumen 871. For some applications, anchor 820 further comprises a flange 822 disposed around the proximal end of the tissue engaging element 230 and configured to support the housing 850. The flange 822 can be integrally formed with the tissue engaging element 230 and extend radially therefrom, or can be a disc or a washer attached to the tissue engaging element 230, and can optionally serve as a bearing supporting the housing base portion 852.

The wire tensioning mechanism 830 is configured to move between a locked configuration, in which the spool 870 is engaged with the housing 850 and/or with the stem 842, and therefore cannot rotate with respect to the housing 850 and/or to the tissue engaging element 230, respectively, and an unlocked configuration, in which the spool 870 is free to rotate with respect to the housing 850 and/or to the tissue engaging element 230. The spool 870 is biased to the locked configuration of the mechanism 830, in the absence of an external force acting there-against to force it to an unlocked configuration.

For some applications, spool top portion 874 comprises spool locking interface 878, that can include a plurality of teeth or protrusions extending upward toward the housing top portion 856, and the housing top portion 856 comprises complementary locking interface 866, that can be in the form of notches or recesses facing the spool locking interface 878, and are aligned with, and configured to engage with, the spool locking interface 878. For example, the recesses of the complementary locking interface 866 are dimensioned and configured to receive the teeth of the spool locking interface 878 in the locked configuration, as shown in FIG. 52C.

It is to be understood that the spool locking interface 878 is shown with a plurality of teeth extending upward, and the complementary locking interface 866 is shown with corresponding recesses, by way of illustration and not limitation, and that other applications can include a spool locking interface 878 with a single protrusion received within a single recess of the complementary locking interface 866, and that still other applications can include one or more teeth or protrusions extending from the housing top portion 856 downward, configured to engage, in a similar manner, with corresponding recesses formed at the spool locking interface 878.

For some applications, the stem comprises a protrusion 846 which can be in the form of a pin, extending radially outward therefrom, and the spool comprises a spool side recess 876, configured to engage with the protrusion 846 in a locked configuration. For example, the spool side recess 876 can be defined at the spool top portion 874, and can be open ended at its upper side, enabling the protrusion to move into the side recess 876 in a locked configuration, and out of the recess—such as being position above the spool top portion 874, in an unlocked configuration. For applications that include a protrusion 846 and a spool side recess 876, the protrusion 846 extends beyond the spool lumen diameter d24.

Spool top portion 874 further comprises spool driving interface 884, which can include a plurality of teeth or protrusions extending upward toward the housing top opening 864. The spool driving interface 884 is positioned radially closer to the central axis ax14, relative to the spool locking interface 878.

For some applications, housing top portion 856 further comprises housing top interface 868, which can include a plurality of teeth or protrusions extending upward (i.e., opposite to the side of the inner chamber 860), or at least one threaded engagement feature (not shown).

For some applications, wire tensioning mechanism 830 further comprises a spring 824, such as a spring disc or a spring washer, configured to bias the spool 870 to a locked configuration of the mechanism 830 in a free state thereof. It is to be understood that the spring is illustrated as a spring disc 824 by way of illustration and not limitation, and that other types of springs, such as a spring washer, leaf spring, finger disc spring, extension springs and the like, are contemplated. A spring disc 824, as well as spring washer of finger disc spring, are advantageous due to their relatively small side and relatively flat profile.

The spring disc 824 can be positioned between the housing base portion 852 and the spool base 872, configured to press against the spool base 872 to bias the spool 870 upward in a free state of the spring. For some applications, the housing base portion 852 comprises a base groove 853 configured to accommodate the spring disc 824.

Figure 53A:
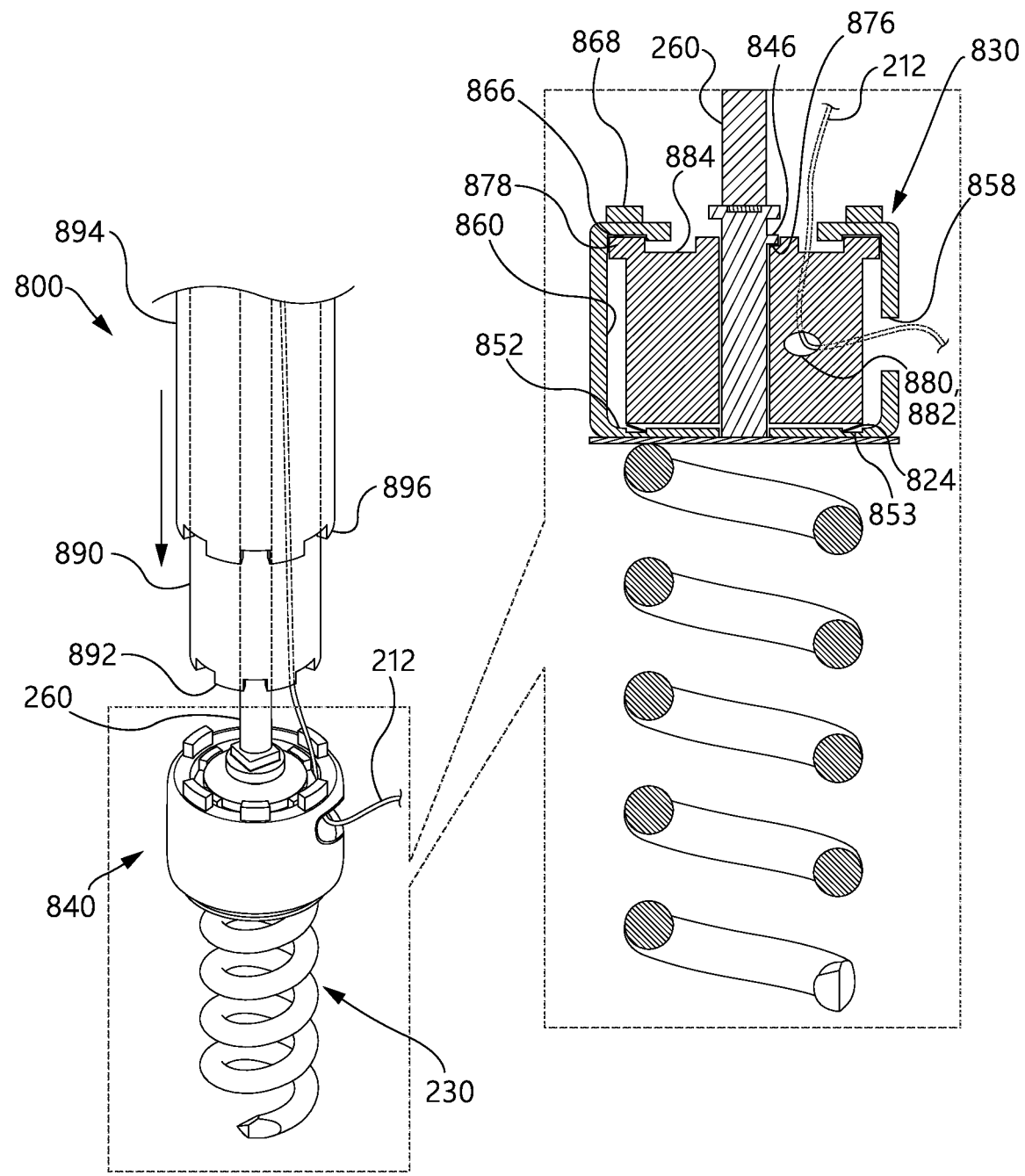
Figure 53B:
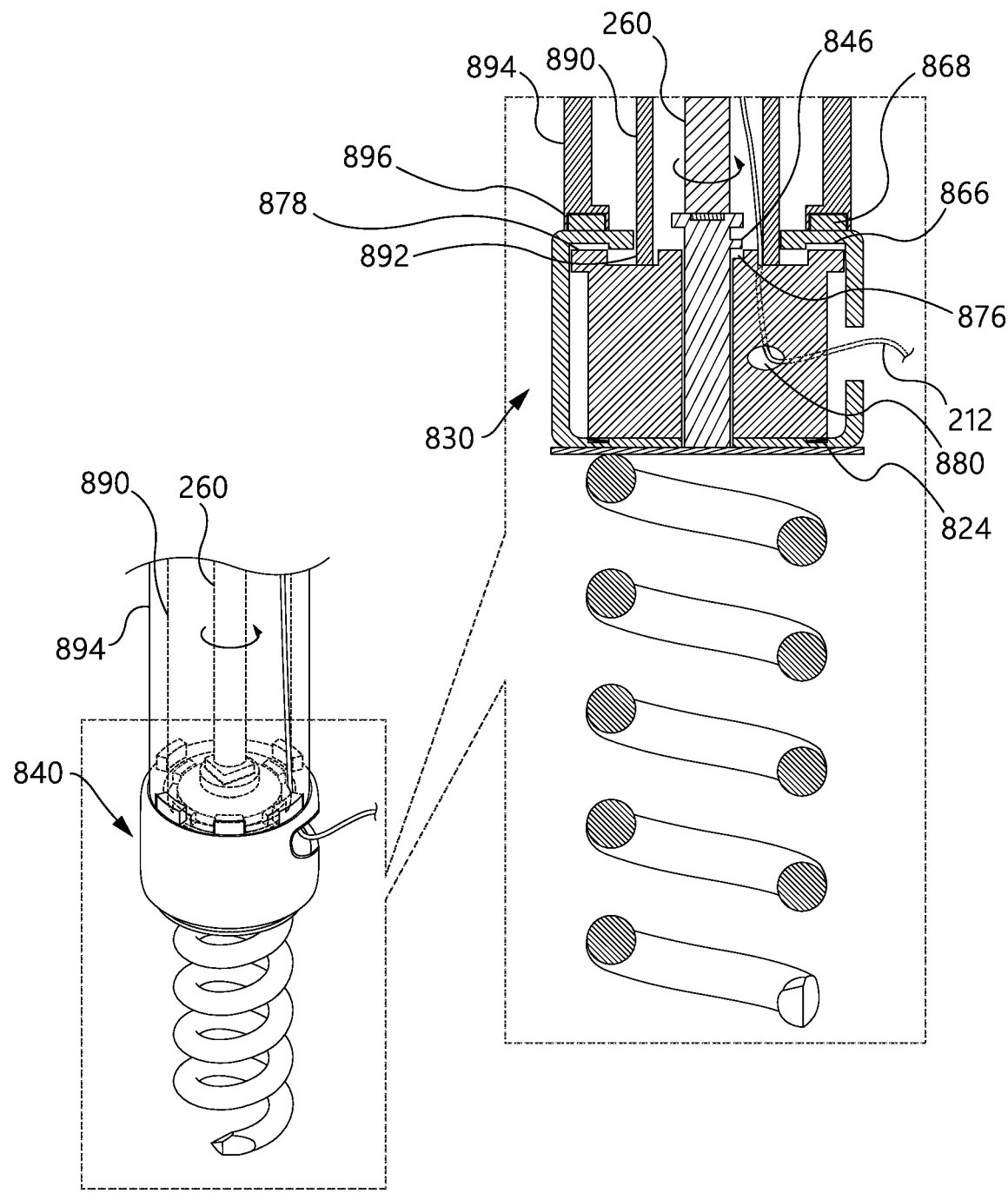
Figure 53C:
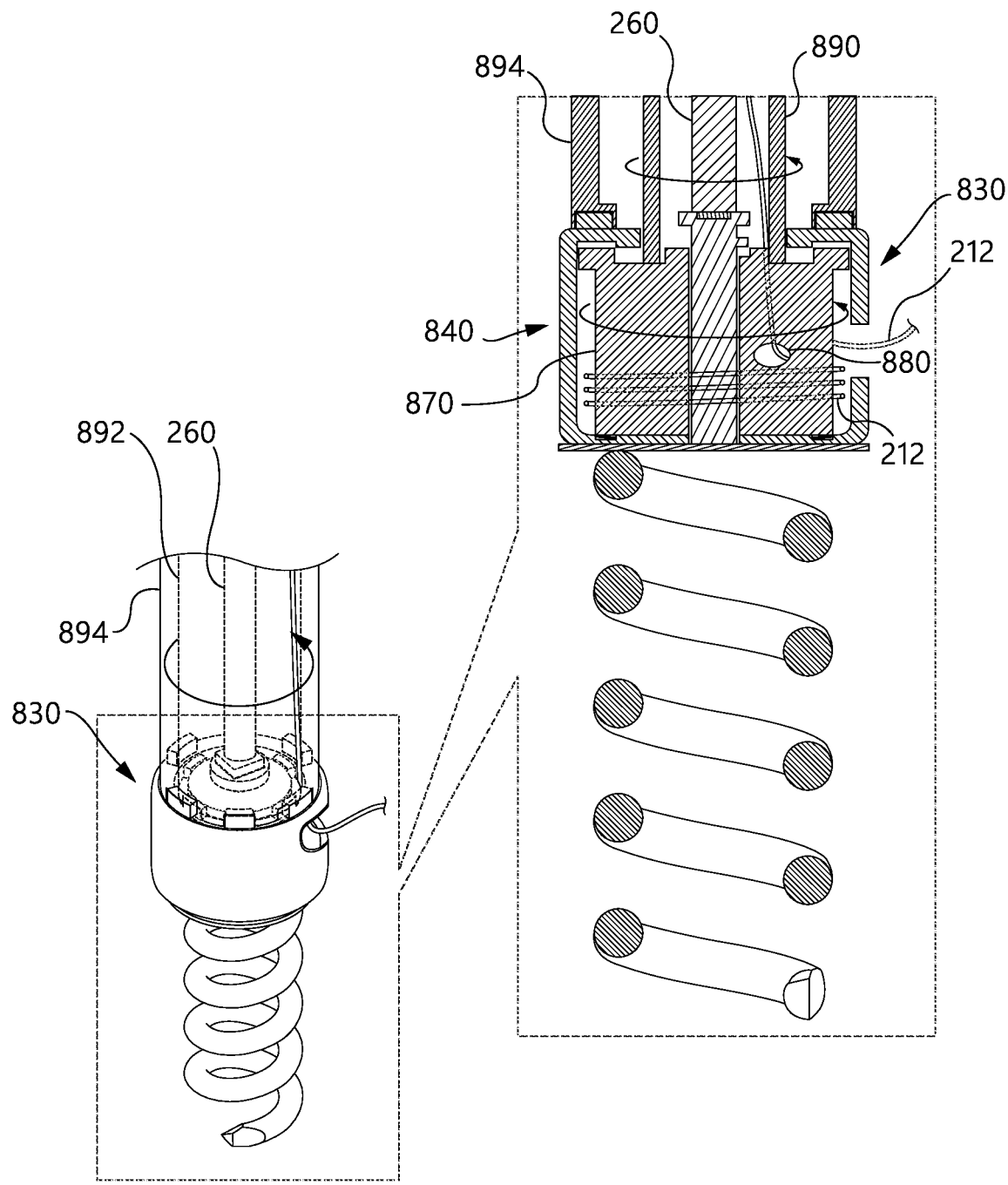

FIGS. 53A-C are schematic illustrations of progressive stages in utilization of the wire tensioning mechanism 830. in accordance with some applications. System 800 can include driver 260 advanceable to the tissue to which the anchor is to be anchored, for example through a flexible tube (e.g, transluminal catheter) as described hereinabove. For some applications, system 800 further comprises an adjustment tool 890 that can be formed with a substantially tubular profile, optionally disposed around driver 260 and similarly advanceable toward the wire tensioning mechanism 830. Adjustment tool 890 comprises an adjustment interface 892, dimensioned and configured to engage with spool driving interface 884. For example, adjustment interface 892 can be shaped in a complementary manner to that of spool driving interface 884, as shown.

For some applications, system 800 further comprises a retainment tool 894 that can be formed with a substantially tubular profile, optionally disposed around adjustment tool 890 and similarly advanceable toward the wire tensioning mechanism 830. Retainment tool 894 comprises a retainment interface 896, dimensioned and configured to engage with housing top interface 868. For example, retainment interface 896 can be shaped in a complementary manner to that of housing top interface 868, as shown, or can be configured to be threadedly engaged with housing top interface 868.

The anchor 820 is delivered toward the target tissue while the wire tensioning mechanism 830 is in a locked configuration. Once the anchor reaches the tissue and is ready to be anchored thereto, driver 260 can be advanced toward anchor 820, until it is engaged with driver interface 844, as shown in FIG. 53A. The adjustment tool 890 can be advanced concurrently with, or following, the advancement of the driver 260, and is configured to engage with spool driving interface 884. Once the adjustment interface 892 is engaged with the spool driving interface 894, further push force applied by the adjustment tool 890 in the distal direction, serves to forcibly press the spool 870 distally against the disc spring 824, which moves the spool 890 distally with respect to the housing 850, as shown in FIG. 53B. Pushing the spool 870 serves to disengage the spool locking interface 878 from the complementary locking interface 866 of the housing 850, as well as to disengage the protrusion 846 from the spool side recess 876, resulting in the unlocked configuration of the mechanism 830.

As shown, wire 212 extends through the side opening 858 into the inner chamber 860, extends further through channel 880, and may exit channel 880 through one of the openings 882 to extends upward, generally in parallel with driver 260.

Once the protrusion 846 is no longer placed within the spool side recess 876, the driver 260 can be rotated, thereby rotating the tissue-engaging element 230 in order to anchor it into the tissue, while the adjustment tool 890 can hold the spool 870 in place, so as to prevent it from rotating along with the stem 842 and the tissue-engaging element 230 during the phase of anchoring.

For applications in which the housing 850 is freely rotatable with respect to the tissue-engaging element 230, it can freely rotate about central axis ax14 so as to allow the wire 212 to be oriented toward the neighboring anchor, in a similar manner to that described for ring 284 of head 280 hereinabove.

When tensioning of wire 212 is desired, for example, to facilitate contraction of implant 810, adjustment tool 890, which remains engaged with spool driving interface 884 and pressing the spool 870 to an open configuration of the mechanism 830, can rotate about central axis ax14, thereby rotating the spool 870 therewith. During this rotational movement, the tissue-engaging element 230 and the housing 850 are retained in a fixed, immovable state. For example, driver 260 can be utilized, while still engaged with the driver interface 844, to keep the stem 842 and tissue-engaging element 230 affixed thereto, immovable with respect to spool 870.

For some applications, retainment tool 894 can be advanced concurrently with, or following, the advancement of adjustment tool 890, and is configured to engage with housing top interface 868. Once the retainment interface 896 is engaged with the housing top interface 868, it may be utilized to keep the housing 850 from rotating about axis ax14.

For applications in which housing 850 is affixed to tissue-engaging element 230, it can be sufficient to hold both tissue-engaging element 230 and housing 850 and prevent rotation thereof, during spool rotation, either via driver 260 without retainment tool 894, or via retainment tool 894 without driver 260. For applications in which housing 850 is rotationally coupled to tissue-engaging element 230, it may be required to utilize both driver 260 to prevent rotation of tissue-engaging element 230, and retainment tool 894 to prevent rotation of housing 850.

As shown in FIG. 53C, rotation of the adjustment tool 890, rotates the spool 870 therewith, which serves to wind wire 212 around the spool, thereby tensioning it and contracting implant 810. For some applications, the inner chamber diameter d21 is greater than the spool outer diameter d23, configured to allow wire 212 to wind around spool 870. For example, the difference between d21 and d23 can be at least 200% greater than the diameter of wire 212, for example greater than 250% of the diameter of wire 212, for example greater than 300% of the diameter of wire 212, for example greater than 400% of the diameter of wire 212.

For some embodiments, spool 870 can define a plurality of circumferential grooves (not shown) extending from the channel opening 882 and around its outer surface, configured to at least partially accommodate wire 212, thereby enabling the difference between d21 and to be smaller than 200% of the diameter of wire 212.

Once wire 212 is tensioned to a satisfying degree, some or all of driver 260, adjustment tool 890, and retainment tool 894, may be retrieved, and a stopper, such as second stopper 214*b*, can be utilized to lock the wire against head 840. Similarly, any of the assemblies and mechanisms described hereinabove for cutting excess portions of wire 212, as well as covering excess portions of the wire, can be used in combination with anchor 820 and/or mechanism 830, including systems such as system 1080, 1090, 1100, 1200, 1300, 1800, 1820, and 1830.

While described as part of a head 840 of an implant anchor 820, it is to be understood that the wire tensioning mechanism 830, comprising the housing 850 and the spool 870, can be utilized according to any of the embodiments and configurations described hereinabove as a stand-alone mechanism, that can be incorporated in other devices and systems, for tensioning any a wire that may extend through a side opening 858 of the housing and a channel 880 of the spool 870, mutatis mutandis, wherein the inner chamber 860 of housing 850 defines the central longitudinal axis ax14. For example, wire tensioning mechanism 830 can be utilized without tissue-engaging element 230, and potentially without a stem 842 and/or a driver interface 844. For example, wire tensioning mechanism 830 can be utilized as an alternative to an adjustment mechanism for an annuloplasty ring structure disclosed in U.S. patent application Ser. No. 15/782,687 to Iflah et al, which published as US 2018/0049875, which is incorporated herein by reference in its entirety.

Figure 54A:
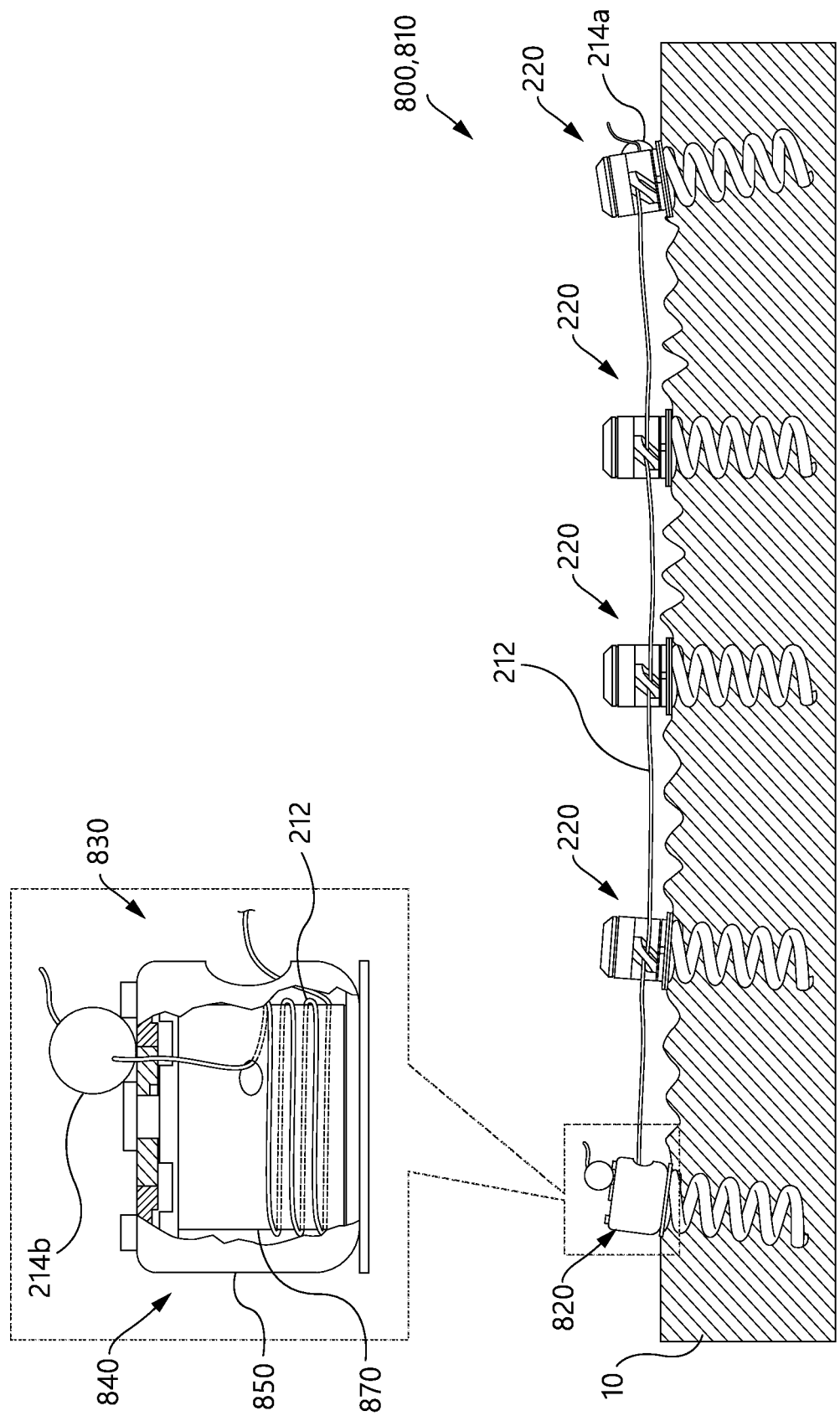

FIG. 54A shows an embodiment 810*a* of implant 810 having been implanted, with at least two types of anchors anchored in tissue 10, such as in an arc around the annulus of a heart valve. In embodiment 810*a*, a plurality of anchors that do not necessarily include a wire tensioning mechanism 830 with a spool 870, such as anchors 220 (that may be also termed "secondary anchors"), are anchored to the tissue 10, wherein the final anchor is an anchor 820 (that may be also termed "primary anchor") with a wire tensioning mechanism 830. While wire 212 extends between the anchors 220 and toward anchor 820, the wire tensioning mechanism 830 of the final anchor 820 is utilized to apply tension to wire 212 in any manner described hereinabove, thereby contracting implant 810*a*.

Figure 54B:
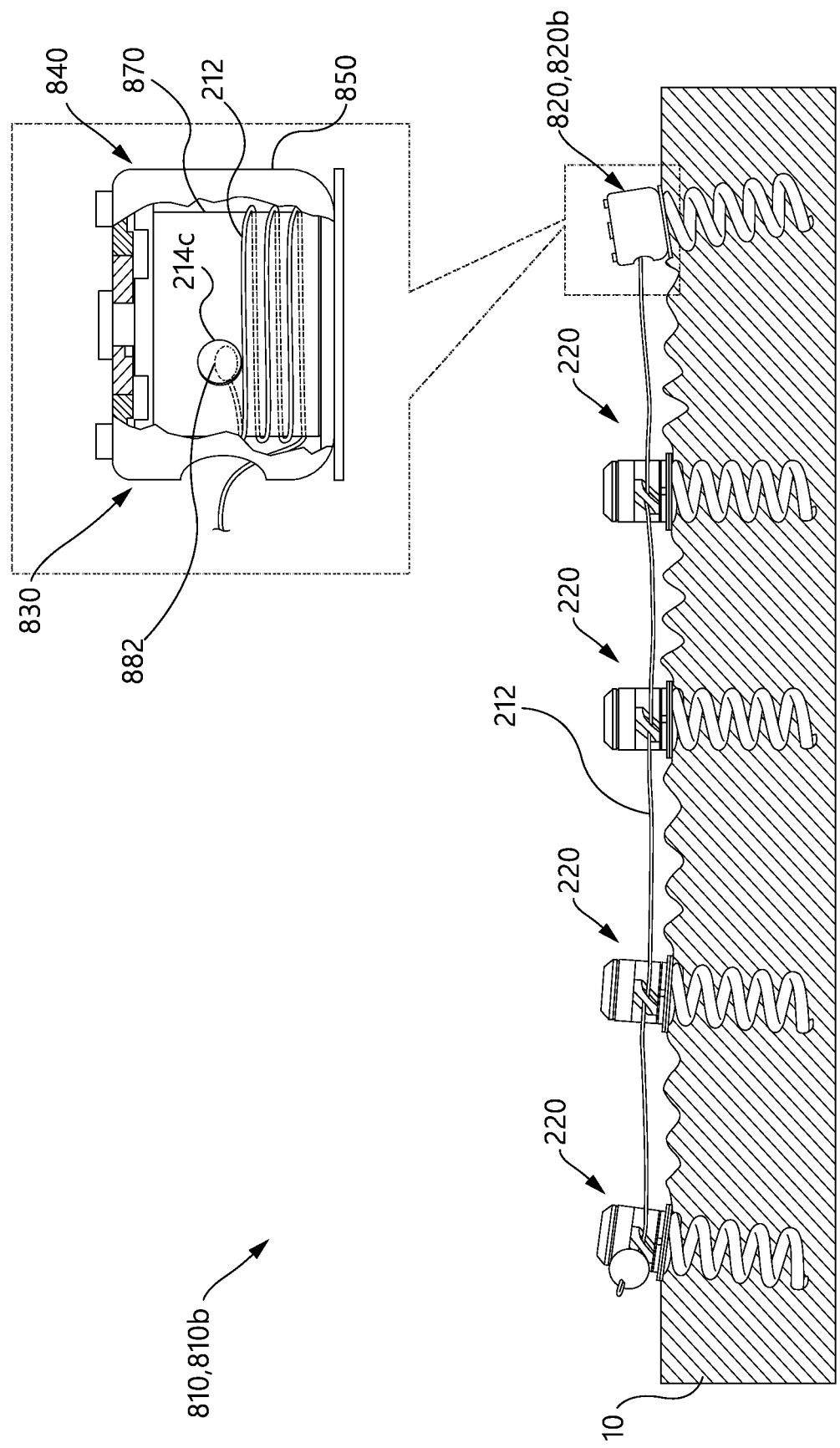

FIG. 54B shows an embodiment 810*b* of implant 810 having been implanted in tissue 10. In embodiment 810*b*, the first anchor anchored into tissue 10 is an anchor with a wire tensioning mechanism 830, such as an embodiment 820*b* of anchor 820, while the rest of the anchors, including the final anchor, can be of another type of anchor that does not necessarily include a wire tensioning mechanism 830, such as anchors 220. In embodiment 820*b*, wire 212 can be coupled to spool 870 at one end thereof, for example by including a lock or stopper 214, such as lock or stopper 214*b* or 214*c*. For some applications, stopper 214 can be a relatively flat stopper, such as a disc member having a diameter larger than channel diameter d20, and having a thickness configured to fit between the spool 870 and the sidewall 854. Optionally, a thicker stopper, for example in the form of a bid, are also contemplated, when used with a channel 880 having a widened recess (not shown), for example on the form of a tapering widening portion extending toward a respective channel opening 882, which is dimensioned to accommodate at least a portion of the stopper therein.

When the anchor having a wire tensioning anchor mechanism 830 is the first anchor, such as the case with anchor 820*b* of implant 810*b* shown in FIG. 54B, a flexible tube (e.g, catheter) for delivering adjustment tool 890, optionally with retainment tool 894, toward the head 840, should be maneuvered after anchoring the last anchor of implant 810*b* back to the first anchor 820*b*. It may be preferable, in such applications, to have an additional guiding wire extending from the first anchor 820*b* toward and into the catheter, or another shaft disposed around the implantation catheter used for delivery the anchors. Such guiding wire (not shown) can be utilized to guide the catheter back toward the first anchor 820*b*, after which the series of step described above can be implemented to apply tension to the wire 212 during rotation of the spool 870, mutatis mutandis, for example while using a stopper 214*b* to halt movement of the opposite end of wire 212 against the last anchor.

FIG. 54C shows an embodiment 810*c* of implant 810 having been implanted in tissue 10. In embodiment 810*c*, at least one of the intermediate anchors, between the first anchor and the last anchor, is an anchor that includes with a wire tensioning mechanism 830, such as an embodiment 820*c* of anchor 820. For some applications, the last anchor of implant 810*c* can be an anchor 820 with a wire tensioning mechanism 830, such as described with respect to FIG. 54A above. For some applications, the first anchor of implant 810*c* can be an anchor 820*b* with a wire tensioning mechanism 830, such as described with respect to FIG. 54B above. For some applications, implant 810 includes at least one intermediate anchor 820*c*, and at least one anchor of another type that does not include a wire tensioning mechanism 830, such as anchor 220. For some applications, all of the anchors of implant 810*c* include a wire tensioning mechanism 830, and can include anchors 820 of different types, including anchor 820*b* and at least one anchor 820*c*.

In embodiment 820*c*, the anchor serves as an intermediate anchor disposed between two other anchors, such that wire 212 extends to both sides of the anchor 820*c*. Thus, anchor 820*c* comprises an embodiment 850*c* of housing 850, provided with two side openings 858 that can be opposite to each other, enabling wire 212 to extend through a side opening 858 on one side of the sidewall 854*c*, toward and through channel 880, and then toward and out of the opposite side opening 858.

For some embodiments, an anchor with a wire tensioning mechanism 830 can be utilized as a single anchor within a system that does not include a plurality of anchors. While FIGS. 53A-C demonstrate various annuloplasty implant configurations, that include a plurality of anchors with a wire 212 extending therebetween, FIG. 54D shows an embodiment 820*d* of anchor 820 used as a single anchor, having a wire, such as wire 212, couple at one end thereto.

For some applications, a single tissue anchor, such as anchor 820*d*, can be utilized for anchoring a wire serving as an artificial chord, that may function as a replacement for chordae tendineae, wherein a distal end of the wire, such as wire 212 or any other wire, is coupled to the anchor 820*d*, and wherein the anchor 820*d* may be anchored to a papillary muscle or to another muscle tissue along the wall of the left ventricle.

As shown for the example of embodiment 820*d* in FIG. 54D, wire 212 can extend, for example, from an attachment point to a native mitral leaflet, or to another component coupled to a native mitral leaflet, at one end of the wire, toward head 840 of anchor 820*d*, such that the wire 212 enters through side opening 858 into the internal chamber 860, and is looped through channel 880 and around a portion of spool 870, forming a closed loop 216 with a knot or other means of enclosing the loop at the gap between the spool 870 and the sidewall 854. The spool 870 may be rotated according to any of the above-mentioned techniques to wind the wire 212 over the spool 870, so as to tension the wire 212 between the anchor 820*d* and the native mitral leaflet, for example. While shown for an anchor 820*d* having the wire attached to the spool 870 via a loop 216, it is to be understood that other types of anchors 820, such as anchor 820*b* having an internal stopper 214*c*, can be utilized in the same manner for single anchor implementations, mutatis mutandis.

Systems 750 and 800, and/or features thereof, can be integrated into other systems described herein, e.g, to confer the advantages described for systems 750 and 800 on the other systems. For example, the tissue anchor, flexible tube, and anchor driver of another system described herein can be replaced by those of systems 750 and/or 800.

For some applications, anchor 290, anchor 720, implant 710, anchor 770, implant 760, anchor 820, and/or implant 810 can be used in combination with apparatuses, systems, and/or implanted using methods/techniques, described in one or more of the following references, mutatis mutandis, each of which is incorporated herein by reference in its entirety:

U.S. patent application Ser. No. 14/437,373 to Sheps et al, which published as US 2015/0272734 (now U.S. Pat. No. 9,949,828)

U.S. patent application Ser. No. 15/782,687 to Iflah et al, which published as US 2018/0049875

PCT Patent Application PCT/IL2019/050777 to Brauon et al, which published as WO/2020/012481

U.S. Provisional Patent Application 62/811,693 to Brauon et al.

Reference is now made to FIGS. 55-59C which are schematic illustrations of examples of an uptake assembly 920 (which can also be referred to as a gripping assembly, wire uptake assembly, contracting member uptake assembly, snare, snare assembly, etc.), that can be used in combination with a system 900 equipped with a handle 910 and a catheter 912. System 900 and handle 910 can be utilized to facilitate contraction of an implant, such as implant 110, 210, 510, 610, 710, 760, 810, and for advancing assemblies for cutting and locking excess portions of the wire, line, contracting member, etc, including advancing systems 1080, 1090, 1100, 1200, 1300, 1800, 1820, and 1830 for covering excess wire, line, contracting member, etc. In some applications, the uptake assembly 920 comprises a gripper 930 and a sleeve 922, axially movable relative to each other, configured to facilitate gripping and pulling an extracorporeal portion of the wire. It is to be understood that while a specific wire 212 is shown in FIGS. 55-59C and often referred to as "wire" for ease of illustration and discussion, the references to "wire" or "wire 212" can also be any other type of wire, line, or contracting member disclosed herein, such as wire 112, wire 212, wire 512, wire 562, wire assembly 2100, as well as other wires, lines, sutures, members, etc. that can be comprised in other systems and assemblies.

Figure 55:
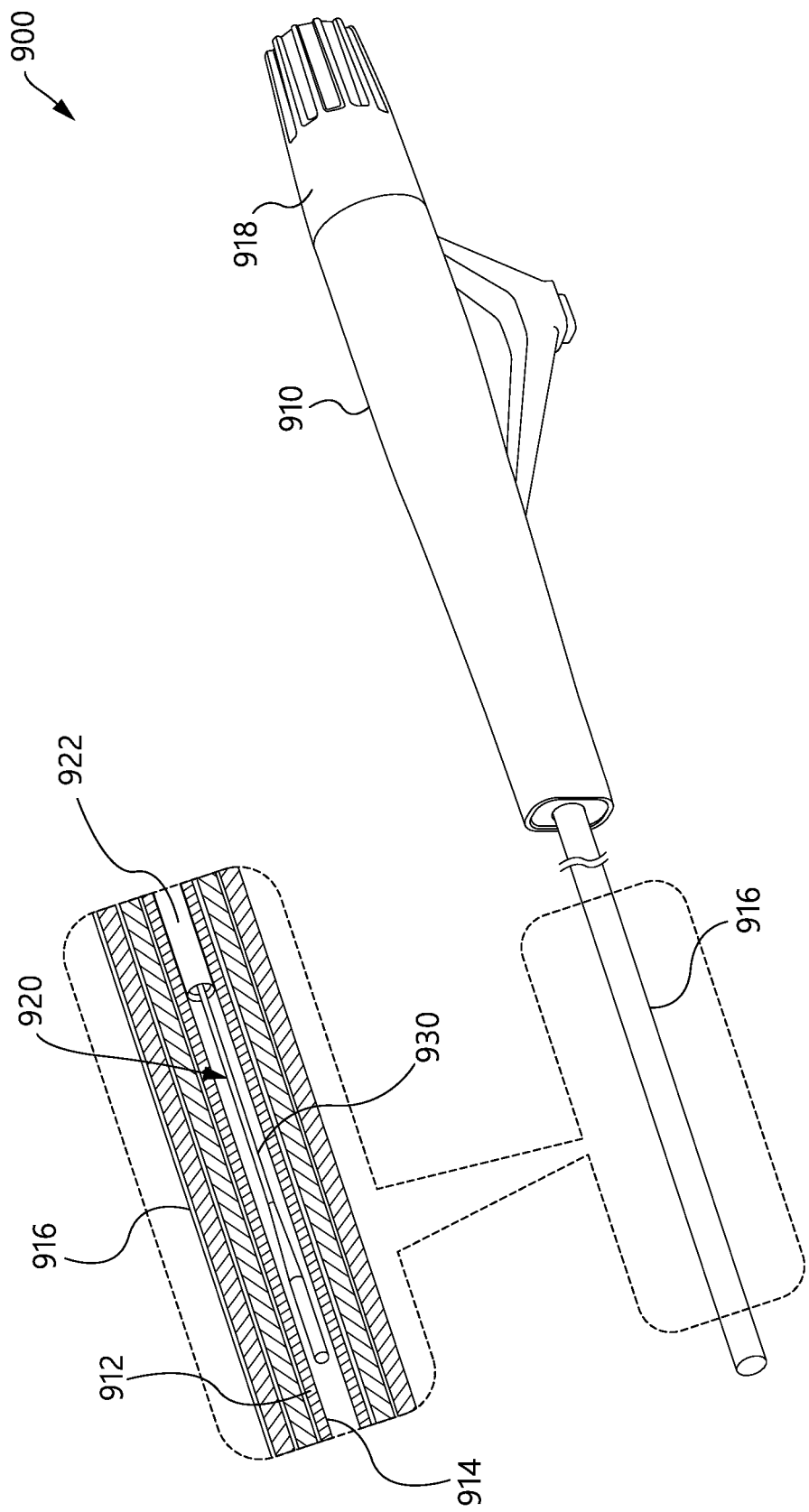

FIG. 55 shows a system 900 that includes a catheter 912 extending distally from a handle 910. The catheter 912 defines a catheter lumen 914 through which the sleeve 922 of the uptake assembly 920 at least partially extends. The catheter 912 can be disposed coaxially within an outer shaft 916, or within a plurality of outer shafts disposed coaxially over catheter 912. The handle 910 can include a removable segment 918, for example at a rear portion thereof.

It is to be noted that a system 900 with a handle 910 is used by way of illustration and not limitation and that uptake assembly 920 can be used independently, can be used in with or without a handle, can be used with or without a catheter, and can be used with or without one or more outer shafts. For some applications, at least some components of uptake assembly 920 are attached to, and/or operably movable by, removable segment 918. For some applications, removable segment 918 is removable coupled to handle 910. Alternatively or additionally, removable segment 918 can be removable coupled, directly or indirectly, to catheter 912, and can be utilized with or without a handle 910. For some applications, removable segment 918 can be decoupled from at least one component of the uptake assembly 920.

FIGS. 56A-C are schematic illustrations of progressive stages in utilization of the uptake assembly 920 for gripping a wire 212 (or other line, contracting member, etc.), in accordance with some applications. Sleeve 922 can be any tube or catheter defining a sleeve lumen 924 that has an internal lumen diameter d31.

Gripper 930 includes a gripper distal portion 932 having a maximal outer diameter d33, and a gripper narrow portion 936 having an outer diameter d32. For some applications, gripper 930 includes a distal transitioning portion 940, defined, for example in a tapering manner, between the gripper distal portion 932 and the gripper narrow portion 936.

For some applications, gripper 930 further includes a gripper proximal portion 938 having an outer diameter d30. For some applications, gripper 930 includes a proximal transitioning portion 942, defined, for example in a tapering manner, between the gripper narrow portion 936 and the gripper proximal portion 938.

Sleeve 922 defines a central longitudinal axis ax30, which for some applications, can also be a central axis of the gripper proximal portion 938 when the gripper 930 extends therethrough. Sleeve 922 terminates at sleeve distal end 926, defining a distal opening through which gripper 920 can extend out of the lumen 924. In an initial state of the uptake assembly 920, as shown in FIG. 56A, gripper 930 is partially disposed within the sleeve 922, such that (a) the gripper narrow portion 936 is partially disposed within the sleeve lumen 924 and partially extends out of the sleeve 922, and (b) the gripper distal portion 932 is exposed out of the sleeve 922, distal to the sleeve distal end 926, wherein the distal transitioning portion can be also partially or fully positioned distal to the sleeve distal end 926.

As shown, for applications in which the gripper 930 includes a gripper proximal portion 938, it can be at least partially disposed, potentially along with proximal transitioning portion 942, within the sleeve lumen 924 in the initial state shown in FIG. 56A.

In a follow up stage, shown in FIG. 56B, a wire 212 (or other line, contracting member, etc.) is inserted into the lumen 924, over the neck portion 936. For some applications, the wire 212 can be inserted further in the proximal direction 90 until a proximal end 216 thereof can no longer advance in this direction and is stopped proximal to the gripper proximal portion 938. The wire 212 can be prevented from further advancement within the lumen 924 in a proximal direction 90 either due to contract with the gripper proximal portion 928 or the proximal transitioning portion 942.

The lumen diameter d31 is at least as great as the gripper proximal diameter d30, so as to allow the gripper proximal portion 938 to extend therethrough and to axially move relative thereto. However, the difference between the lumen diameter d31 and the gripper diameter d30 is smaller than the diameter of the wire 212, so as to prevent it from extending there-between. For example, the difference between d31 and d30 is smaller than 90% of the diameter of wire 212, for example smaller than 70% of the diameter of wire 212, for example smaller than 50% of the diameter of wire 212, for example smaller than 30% of the diameter of wire 212, for example smaller than 20% of the diameter of wire 212, for example smaller than 10% of the diameter of wire 212.

The wire 212 can be provided as a radially compressible wire, that can be compressed to some extent relative to its free-state diameter. In such cases, it is to be understood that any reference to a diameter of the wire 212 refers to its free state diameter, in the absence of external forces acting to compress it.

The narrow diameter d32 is smaller than the gripper proximal diameter d30 and the lumen diameter d31, and is dimensioned to allow wire 212 (or other line, member, etc.) to extend over it within the lumen 924, between the neck portion 936 and the inner walls of the sleeve 922. For example, the difference between the lumen diameter d31 and the narrow diameter d32 can be at least as great as the diameter of wire 212, for example greater than 110% of the diameter of wire 212, for example greater than 120% of the diameter of wire 212, for example greater than 130% of the diameter of wire 212, for example greater than 150% of the diameter of wire 212, for example greater than 200% of the diameter of wire 212.

In a follow up stage, shown in FIG. 56C, the gripper 930 is pulled in a proximal direction 90 such that at least a portion the gripper distal portion 932 extends into the lumen 924, until it can be no longer pulled due to the frictional forces acting there-against by the wire 212 pressed between the gripper distal portion 932 and the sleeve 922. As stated above, the wire 212 can be somewhat compressible, for example up to 95% of its free state diameter, for example up to 90% of its free state diameter, for example up to 80% of its free state diameter, for example up to 60% of its free state diameter.

The gripper distal diameter d33 is greater than the neck diameter d32, but smaller than the lumen diameter d31 and for applications that include a proximal portion 938, also smaller than the proximal portion diameter d30. The gripper distal portion 932 is dimensioned to press-lock the wire 212 between its outer surface and the inner surface of the sleeve 922. Thus, when the gripper 930 is pulled proximally, the distal transitioning portion 940 and the gripper distal portion 932 can slide over the wire 212, wherein the higher diameter d33 of the distal portion 932, relative to the diameter d32 of the narrow portion 936, serves to press the wire 212 against the sleeve 212, potentially compressing it to some extent, until the wire is press-locked and is immovable relative to any component of the assembly 920.

For some applications, the series of steps shown in FIGS. 56A-C can be implemented while the uptake assembly 920 is disposed within a catheter 912, such that both the sleeve distal end 926 and the gripper distal portion 932 are disposed within the catheter lumen 914 in an initial state (FIG. 56A), in which case the wire 212 can be inserted into catheter lumen 914 and follow the series of step described hereinabove.

For some applications, the series of steps shown in FIGS. 56A-C can be implemented while a portion of the uptake assembly 920 is disposed within a catheter 912, yet at least partially extends out of the catheter lumen 914, for example such that the gripper distal portion 932 is exposed distal to the catheter 912 in an initial state. For some applications, the series of steps shown in FIGS. 56A-C can be implemented while the uptake assembly 920 is exposed and does not extend through any other catheter.

FIG. 57A shows a follow-up step in the utilization of the uptake assembly 920, in accordance with some applications. Once the wire 212 (or other contracting member) is gripped and press-locked by the assembly 920, the assembly 920 can be pulled proximally, for example—with respect to a patient's body from which an extracorporeal section of the wire 212 extends, wherein the wire 212 is pulled along with the assembly 920 to any desired length. For example, the assembly 920 and wire 212 can be pulled so as to expose an extracorporeal length of the wire 212 which is sufficient for further utilization thereof with system 900 or any other system, such as for the sake of winding wire 212 over a spool (not shown).

For some applications, the difference between the lumen diameter d31 and the gripper distal diameter d33 is smaller than the diameter of wire 212. For example, the difference between the lumen diameter d31 and the gripper distal diameter d33 can be no greater than 95% of the diameter of wire 212, e.g, no greater than 90% of the diameter of wire 212, e.g, no greater than 85% of the diameter of wire 212, e.g, no greater than 80% of the diameter of wire 212.

As mentioned above, for some applications, at least one component of the assembly 920, including the sleeve 922, the gripper 930, or both, can be coupled, optionally in a releasable manner, to a removable segment 918. According to some applications, pulling the assembly 920 along with the wire 212 can be facilitated by pulling the removable segment 918. The removable segment 918, as also mentioned above, can be releasably coupled to a handle 910. In such implementations, the removable segment can be first released from the handle 910, and then pulled proximally 90 to facilitate pulling of the assembly 920 and the wire 212 there-along.

As further shown in FIG. 57A, the assembly 920 can be pulled proximally so as to expose at least a portion of wire 212 or other contracting member out of the handle 910, such as out of a rear end 917 of the handle 910. It is to be noted that this configuration of pulling the wire 212 away from handle 910 is shown by way of illustration and not limitation, and that the wire 212 can extend from other regions of the handle instead of its rear end, that the wire 212 can be pulled so as to expose it from a rear end (or a side opening) of a catheter 912 and/or outer shaft 916, and that the wire 212 can be pulled proximally in the absence of either a handle, a catheter, or any outer shaft.

FIGS. 57B-D are schematic illustrations of progressive stages in utilization of the uptake assembly 920 for releasing wire 212 or other contracting member, in accordance with some applications. Once a sufficient length of wire 212 has been pulled and exposed, as shown in FIG. 57B, the gripper 930 can be pushed in a distal direction 92 relative to the sleeve 922, such that the gripper distal portion 932 moves distally with respect to the sleeve distal end 926, therefore releasing its grip against wire 212, which in turn allow wire 212 to be released from the assembly 920 and out of lumen 924, as shown in FIG. 57D wherein the assembly 920 is pulled away from wire 212.

Moving the assembly 920 from a gripping state shown in FIG. 57B to a releasing state shown in FIG. 57C can be facilitated either by pushing the gripper 930 in a distal direction 92 while the sleeve 922 is kept in a fixed position, by pulling the sleeve 922 in a proximal direction 90 while the gripper 930 is kept in a fixed position, or by simultaneously pushing the gripper 930 and pulling the sleeve 922. If any of the sleeve 922 or the gripper 930 are attached to the removable segment 918 at proximal portions thereof (not shown), they can be released therefrom to facilitate the above-mentioned relative movement.

For some applications, wire 212, shown in FIG. 57B gripped by the assembly 920, can be cut distally to the assembly 920 instead of maneuvering the assembly 920 to a releasing state, as described hereinabove with respect to FIG. 57C.

Figure 58A:
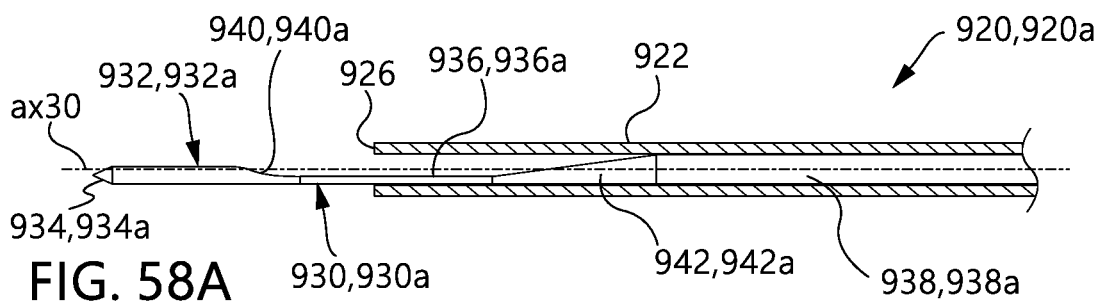
Figure 58B:
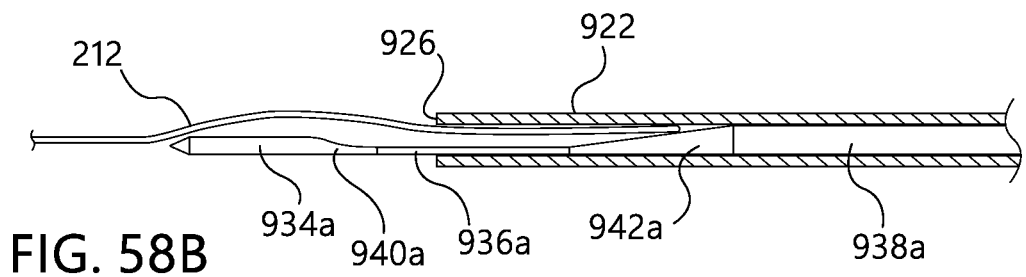
Figure 58C:
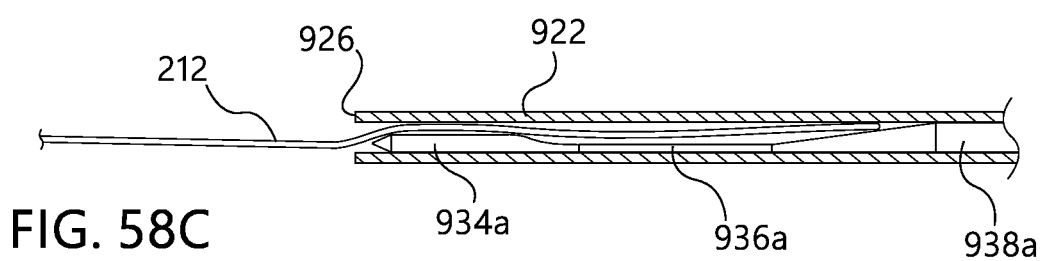

For some applications, the gripper proximal portion 938, gripper narrow portion 936 and gripper distal portion 932 are symmetrically disposed around central longitudinal axis ax30, as shown throughout FIGS. 56A-57D. FIGS. 58A-C show another embodiment of a gripping assembly or uptake assembly 920a, in which gripper narrow portion 936a and gripper distal portion 932a are asymmetrically disposed around axis ax30. The steps shown in FIGS. 58A-C are similar to the steps described above with respect to FIGS. 57B-D, and it is to be understood that any other steps and applications described hereinabove for gripping assembly 920 with respect to FIGS. 56A-57D are similarly applicable for gripping assembly 920a, mutatis mutandis. It is to be understood that various shapes for narrow portion 936 and gripper distal portion 932, as well as transition portions 940 and 942, are contemplated. The asymmetrical configuration of gripper narrow portion 936a and gripper distal portion 932a shown in FIGS. 58A-C, in which the narrow portion 936a and gripper distal portion 932a are offset from central axis ax30 and toward an internal wall of sleeve 922, can facilitate easier insertion of the wire 212 into lumen 924 of sleeve 922.

For some applications, gripper distal portion 932 comprises a gripper distal end 934 that can be shaped to facilitate easier insertion of wire 212 into lumen 924 over the distal portion 932. For example, gripper distal end 934 can be rounded, as shown throughout FIGS. 56A-57D. Optionally, gripper distal end 934 can be shaped as a tapering end portion, as shown for gripper distal end 934a in FIGS. 58A-C. It is to be understood that the rounded and tapering shapes of gripper distal end 934 are shown by way of illustration and not limitation, and that other shapes for gripper distal end 934 are contemplated. A rounded or tapering gripper distal end 934, 934a can facilitate easier movement of wire 212, especially for configurations in which the assembly 920, 920a is disposed within a catheter 912 in an initial state, allowing the wire proximal end 216 to easily slide over the gripper distal end 934, in order to advance over the gripper distal portion 932 toward the lumen 924 of the sleeve 922.

Figure 59A:
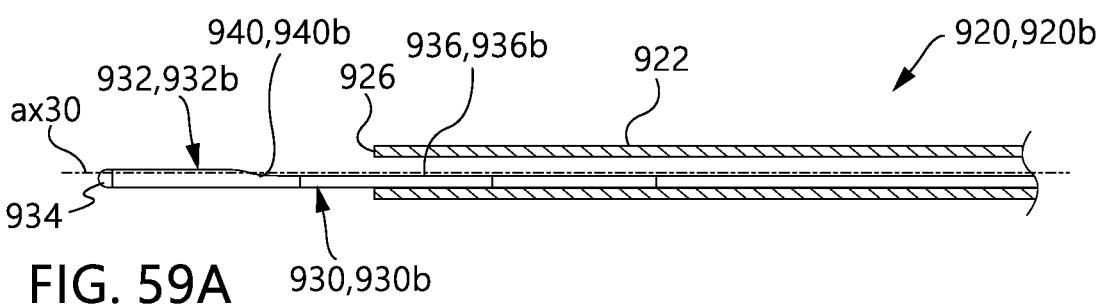
Figure 59B:
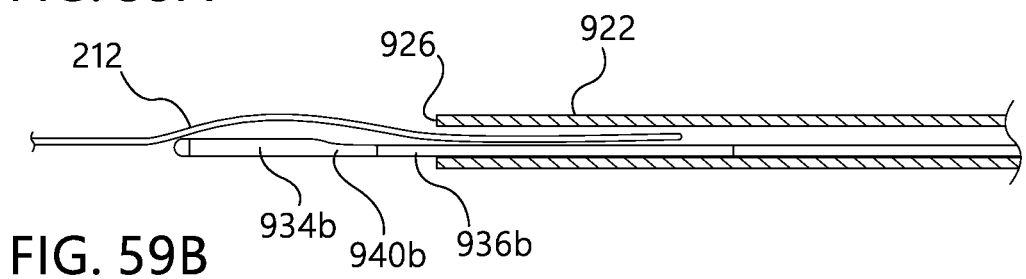
Figure 59C:
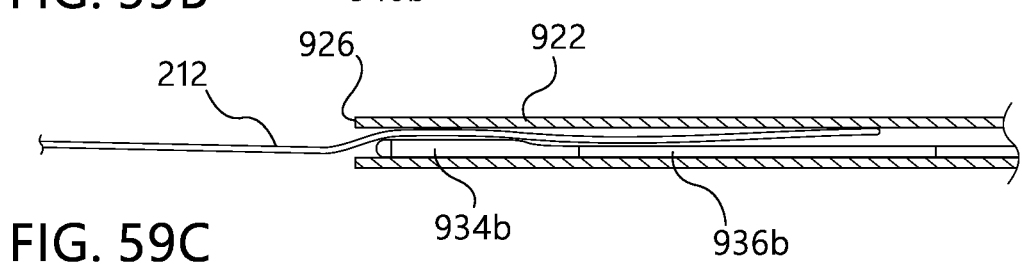

FIGS. 59A-C show another embodiment 920b of a gripping assembly 920, in which gripper 930a includes gripper distal portion 932b and gripper narrow portion 93b, but does not include a wider proximal portion. In this case, wire 212 (or other line, contracting member, etc.) can be inserted into sleeve lumen 924 to some extent, positioned between the narrow portion 936b and the inner walls of the sleeve 922, without being physically stopped by any obstacle such as a wider proximal portion of the gripper. The steps shown in FIGS. 59A-C are similar to the steps described above with respect to FIGS. 57B-D, and it is to be understood that any other steps and applications described hereinabove for gripping assembly 920 with respect to FIGS. 56A-58C are similarly applicable for gripping assembly 920b, mutatis mutandis. While gripper 930b is shown with an asymmetrical configuration, it is to be understood that this is shown by way of illustration and not limitation, and that symmetrical configurations are similarly applicable.

The implants described herein, such as implants 110, 210, 510, 610, 710, 760, 810, can also be used as docking apparatuses or systems for facilitating receiving a prosthetic heart valve or replacement heart valve at a native valve. The implants can be used initially to repair a native heart valve (e.g, as described above), but if the repair is insufficient for any reason or if the native valve worsens over time (for example, becoming more regurgitant in the months or years following the repair), then the implant has still created a better location and environment for receiving or docking a prosthetic heart valve replacement. In some instances, the prosthetic valve, when implanted, can contact the implant directly. In some instances, the prosthetic valve, when implanted, only contacts the native valve tissue, but the implant has reshaped and strengthened the native annulus sufficiently to improve placement and retention of the prosthetic heart valve.

Figure 60:
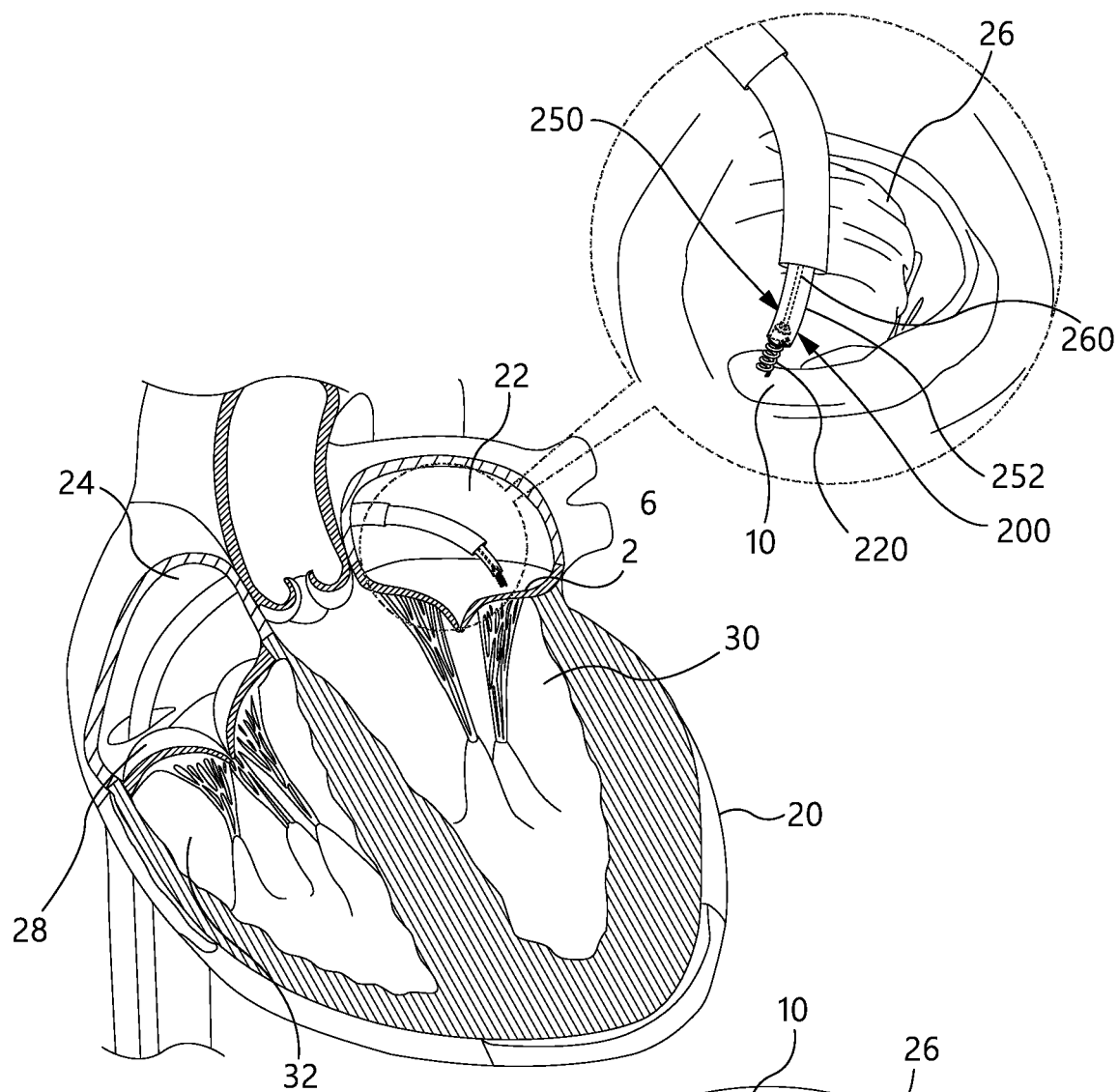
FIGS. 60, 61, and 62A-C are schematic illustrations of techniques for using an implant for contracting an annulus of a native valve, followed by prosthetic valve implantation, in accordance with some applications.

As an example, reference is now made to FIGS. 60-62C which are schematic illustrations of an implant for contracting an annulus of a native valve, which is also usable as a docking apparatus/system to allow a prosthetic valve to be mounted within the native valve against the implant or docking apparatus/system, in accordance with some applications. FIG. 60 shows a schematic cross-sections view of a heart 20 of a patient, into which a multi-component implantation system can be advanced, for delivering and anchoring an implant, such as implant 210 described hereinabove. In the illustrated example, a system 200 can be advanced toward the annulus of a mitral valve 26, but another valve such as the tricuspid valve is also possible.

The mitral valve 26 controls the flow of blood between the left atrium 22 and the left ventricle 30 of the heart 20. After the left atrium 22 receives oxygenated blood from the lungs via the pulmonary veins, the mitral valve 26 permits the flow of the oxygenated blood from the left atrium 22 into the left ventricle 30. When the left ventricle 30 contracts, the oxygenated blood that was held in the left ventricle 30 is delivered through the aortic valve and the aorta to the rest of the body. Meanwhile, the mitral valve 26 should close during ventricular contraction to prevent any blood from flowing back into the left atrium 22.

Various complications of the mitral valve 26 can potentially cause fatal heart failure. One form of valvular heart disease is mitral valve leak or mitral regurgitation, characterized by abnormal leaking of blood from the left ventricle through the mitral valve 26 back into the left atrium 22. This can be caused, for example, by dilation of the left ventricle 30 causing the native mitral leaflets to not coapt completely, resulting in a leak. In these circumstances, it may be desirable to repair the mitral valve, e.g, by annuloplasty procedures, such as implanting an implant of the types disclosed throughout the current specification, around the annulus of the mitral valve 26, and contracting the implant to reduce the diameter or size of the annulus, to improve coaptation between the leaflets. Other procedures can include replacement of the functionality of the mitral valve with that of a prosthetic heart valve.

With respect to valve replacement, while open heart surgical procedures may be more readily available, there has been much less development in terms of commercially available ways to replace a mitral valve through percutaneous or transcatheter implantation and/or other minimal or less invasive procedures. Replacement of a mitral valve is more difficult than aortic valve replacement in many respects, for example, due to the non-circular physical structure of the mitral valve, its sub-annular anatomy, and more difficult access to the valve.

One of the most prominent obstacles for mitral valve replacement is effective anchoring or retention of the valve at the mitral position, due to the valve being subject to a large cyclic load. As noted above, another issue with mitral valve replacement is the size and shape of the native mitral annulus. Aortic valves are more circular or cylindrical in shape than mitral valves. Also, the mitral and tricuspid valves are both larger than the aortic valve, and more elongate in shape, making them more difficult and unconventional sites for implanting a replacement valve with a generally circular or cylindrical valve frame. A circular prosthetic valve that is too small can result in leaking around the implant (i.e., paravalvular leakage) if a good seal is not established around the valve, while a circular prosthetic valve that is too large can stretch out and damage the narrower parts of the native mitral annulus. Further, in many cases, the need for aortic valve replacement arises due, for example, to aortic valve stenosis, where the aortic valve narrows due to calcification or other hardening of the native leaflets. Therefore, the aortic annulus generally forms a more compact, rigid, and stable anchoring site for a prosthetic valve than the mitral annulus, which is both larger than the aortic annulus and non-circular. Instances of mitral valve regurgitation are less likely to provide such a good anchoring site. Also, with the large cyclic loads the mitral valve undergoes, there is a need to establish a sufficiently strong and stable anchoring and retention. Also, even a slight shift in the alignment of the valve can still lead to blood flow through the valve or other parts of the heart being obstructed or otherwise negatively impacted.

Many of the challenges described above with respect to effective anchoring or retention of a prosthetic valve at the mitral position, are similarly applicable to the tricuspid position. This, it is to be understood that while the method illustrated in FIGS. 60-62C is described with respect to the mitral valve 26, the same method can be implemented, mutatis mutandis, for any other heart valve or bodily opening, including the tricuspid valve 28 shown in FIG. 60 positioned between the right atrium 24 and the right ventricle 32.

As shown in FIG. 60, a method of delivering and anchoring an implant, which can also be used as a docking apparatus/system, around the annulus of a valve, can include: advancing a system, such as system 200, toward the annulus. For applications in which system 200 is used to deliver an implant 210 to the mitral valve 26 of the patient, an outer catheter can be typically advanced through the patient's vasculature into the right atrium 22 until its distal end is positioned in the left atrium 22. A steerable distal end portion of the outer catheter can then be steered such that it is positioned in a desired spatial orientation within the left atrium 44. The steering procedure is typically performed with the aid of imaging, such as fluoroscopy, transesophageal echo, and/or echocardiography.

The outer catheter 12 can be advanced through the vasculature into the right atrium 22 using a suitable point of origin typically determined for a given patient. For example, the outer catheter can be introduced into the femoral vein of the patient, through the inferior vena cava, into the right atrium 24, and into the left atrium 22 transseptally, typically through the fossa ovalis, as shown in FIG. 60. Optionally, the outer catheter can be introduced into the basilic vein, through the subclavian vein to the superior vena cava, into the right atrium 24 for treating the tricuspid valve, and/or into the left atrium 22 transseptally, typically through the fossa ovalis (not shown), for treating the mitral valve. Optionally, the outer catheter can be introduced into the external jugular vein, through the subclavian vein to the superior vena cava, into the right atrium 24, and/or into the left atrium 22 transseptally, typically through the fossa ovalis (not shown).

Following the steering of the distal end portion of the outer catheter, a guide catheter can be advanced through the outer catheter in order to guide the delivery tool 250 toward the annulus of the mitral valve 26. The guide catheter can be a steerable catheter configured to guide the tool 250, and in particular, the flexible tube 252 of the tool 250, to the tissue of the annulus. In some implementations, no outer catheter is used, and the guide catheter and/or delivery tool 250 is/are used to access and treat the native valve independently.

Following the steering of the guide catheter, the flexible tube 252 is advanced through the guide catheter in order to facilitate delivery and implantation of docking apparatus 210, which is implemented as implant 210 described hereinabove, along the annulus of the mitral valve 26. During the delivery, at least a portion of a potentially steerable distal end of the flexible tube 252 is exposed from the distal end of the guide catheter and is thus free for steering toward an annulus of the mitral valve 26.

Figure 61:
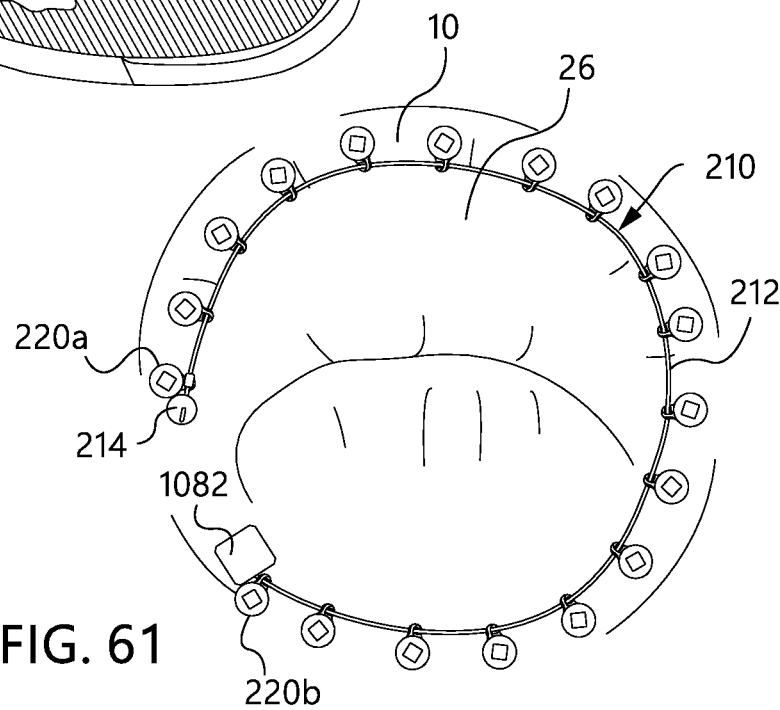

Implant 210 can be implanted into the tissue 10 of the annulus of the mitral valve 26 and adjusted using techniques described for other system 200 or any other systems described herein, mutatis mutandis. For example, anchors 220 can be anchored sequentially around the all or part (e.g, 40-90%, 50-70%, etc.) of an annulus of a native heart valve, such as the mitral valve 26, followed by tensioning the wire 212 (or other line, contracting member, etc.) in order to contract the annulus, as shown in FIG. 61. For some applications, tensioning the wire 212 will be sufficient to adequately reduce or eliminate regurgitation through the native valve, in which case, the method/procedure may be concluded. For some applications, if there is still a significant amount of regurgitation at the native valve (e.g, shortly after the initial procedure steps/tensioning or after the passage of more time, such as months or years later), a replacement prosthetic valve can be deployed in the native annulus. Such prosthetic valve deployment/implantation will be strengthened and improved by having the implant (e.g, implant 210) previously attached to the native annulus (e.g, (1) by reshaping and/or strengthening the annulus and/or (2) by allowing the prosthetic valve to interact with the implant).

It is to be understood that system 200, implant 210 and anchors 220 are shown and described with respect to FIGS. 60-62C by way of illustration and not limitation, and can in fact be replaced with any other system, implant and anchors described throughout the specification, to serve as a docking apparatus/system and components thereof.

Figure 62A:
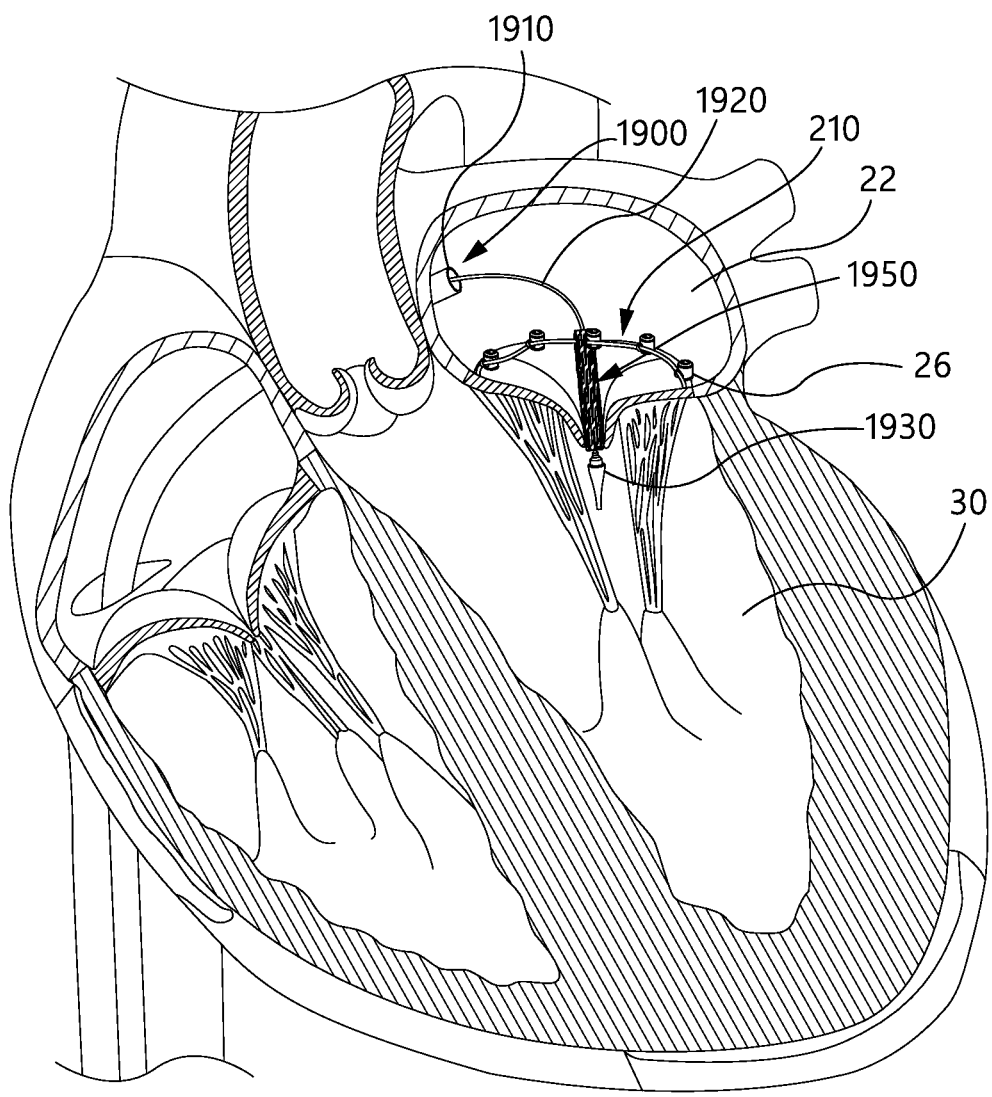
Figure 62B:
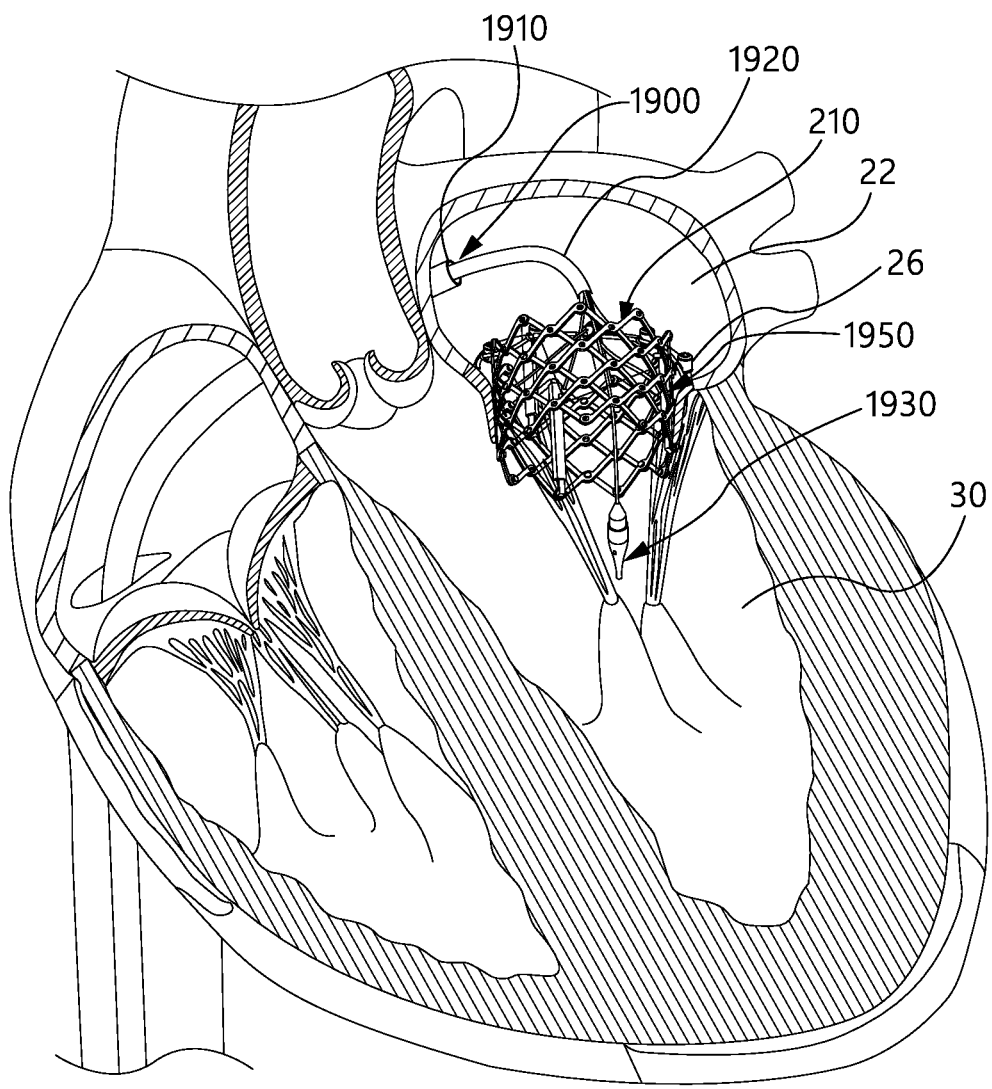
Figure 62C:
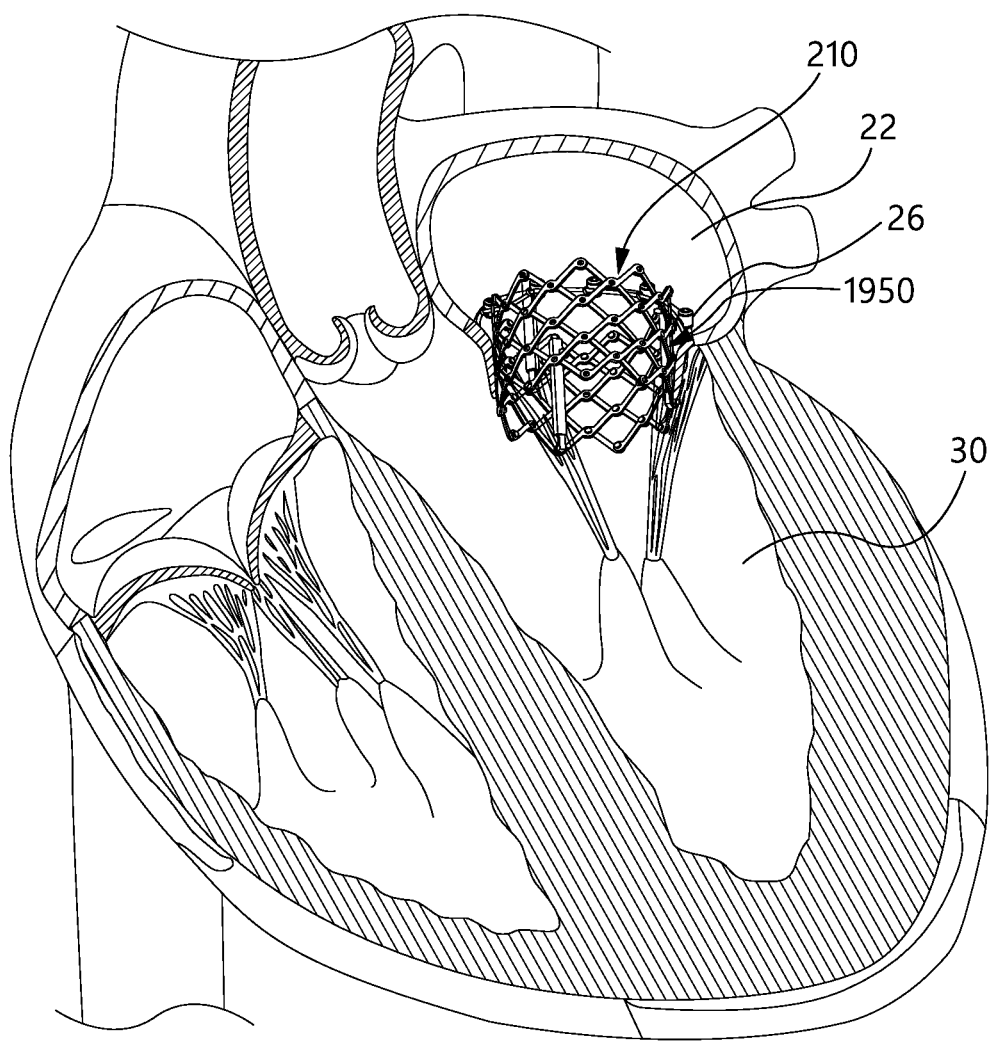

FIGS. 62A-C schematically show progressive steps of a method for implanting a prosthetic valve 1950 within a native valve, such as the mitral valve 26, against an implant acting as a docking apparatus/system, in accordance with some applications. Once the docking apparatus/system, such as implant 210, is anchored, tensioned, and locked in a contracted state, as shown for example in FIG. 61, the delivery tool 250 can be retracted. As indicated above, the procedure may be completed for a period of time (e.g, months or years) or can be followed shortly or immediately by a prosthetic valve replacement.

When a decision has been made to implant a replacement prosthetic valve, a prosthetic valve 1950 can be advanced toward the mitral valve. The delivery apparatus 1900 of prosthetic valve 1950 can include at least one outer catheter 1910 through which the prosthetic valve 1950 is advanced in a crimped state thereof. For some applications, the outer shaft utilized for advancing the delivery tool 250 of the implant 210, can be utilized for advancing the prosthetic valve 1950 as well.

A prosthetic valve 1950 can be crimped or retained by a delivery apparatus 1900 in a compressed state during delivery, and then expanded to the expanded state once the prosthetic valve 1950 reaches the implantation site.

A prosthetic valve 1950 can include a frame (visible in FIGS. 60A-60B) movable between a compressed configuration (FIG. 62A) and an expanded configuration (FIGS. 62B-C), and a leaflet structure (not shown for the sake of clarity) mounted within the frame, and comprising a plurality of prosthetic leaflets configured to regulate blood flow through the prosthetic valve.

The prosthetic valve 1950 can be delivered to the site of implantation via the delivery apparatus 1910 in a radially compressed or crimped state, toward the target site, to be mounted against the native anatomy, by expanding the valve 1950 via various expansion mechanisms.

Balloon expandable valves generally involve a procedure of inflating a balloon within a prosthetic valve, thereby expanding the prosthetic valve within the desired implantation site. Once the valve is sufficiently expanded, the balloon is deflated and retrieved along with the delivery apparatus. Self-expandable valves include a frame that is shape-set to automatically expand as soon an outer retaining capsule, which may be also defined as the distal portion of a delivery shaft, is withdrawn proximally relative to the prosthetic valve.

Mechanically expandable valves are a category of prosthetic valves that rely on a mechanical actuation mechanism for expansion. The mechanical actuation mechanism can include a plurality of expansion and locking assemblies, releasably coupled to respective actuation assemblies of the delivery apparatus, controlled via a handle (not shown) of the delivery apparatus for actuating the expansion and locking assemblies to expand the prosthetic valve to a desired diameter. The expansion and locking assemblies can optionally lock the valve's diameter to prevent undesired recompression thereof, and the actuation assemblies can be then disconnected from the expansion and locking assemblies, to enable retrieval of the delivery apparatus once the prosthetic valve is properly positioned at the desired site of implantation.

The delivery apparatus 1900 can include a nosecone 1930 attached to a distal end of a nosecone shaft 1920, which is coaxially advanced through the outer catheter 1910 toward the mitral valve 26, and is further advanced through the leaflets of the valve 26, for example into the left ventricle 30. The prosthetic valve 1950 can be advanced, for example over the nosecone shaft 1920, through the leaflet of the mitral valve 26, such that a distal portion of the prosthetic valve is disposed within the left ventricle 30, and a proximal portion thereof is disposed within the left atrium 22, as shown in FIG. 62A.

In a follow-up step shown in FIG. 62B, the prosthetic valve can be expanded against the annulus of the mitral valve 26, utilizing any frame expansion technique known in the art and described hereinabove, such as balloon inflation, self-expansion of the frame to a free expanded state, or mechanically-assisted frame expansion. Once the prosthetic valve 1950 is expanded to the desired expansion diameter, the delivery apparatus can be decoupled therefrom and retrieved from the patient's body, leaving only the prosthetic valve 1950 anchored against the annulus, as shown in FIG. 62C.

It is hypothesized that the contracted state of the annulus, achieved by anchoring and contracting a an implant, such as implant 210, as described hereinabove and illustrated in FIGS. 62A-C, facilitates improved retention of the prosthetic valve 1950 within the annulus of the native valve, by (a) reducing the size of the native valve to allow conventional prosthetic valve, such as possibly one dimensioned for implantation within smaller native valves, such as aortic valves, to be properly pressed and anchored against the surrounding tissue, and/or (b) reshaping the native annulus to a more circular shape during implant contraction, to better match a circular contour of the prosthetic valve.

The various types of implants disclosed hereinabove are typically implanted in a curved configuration (e.g, a semi-circle, partial circle, or a complete or near complete circle) around the annulus of a native heart valve, such that the contraction reduces the size of the annulus, thereby improving coaptation of the valve leaflets. To optimize the procedure, it is often important to space the anchors appropriately to allow for better contraction and reshaping of the implant and annulus. To help improve spacing of the anchors, there is a need to identify the distance between sequential anchors. For some applications, this is optionally done during implantation of the implant in real time, in order to measure the distance between anchors as they are placed. This can also be done to observe or measure the change in distance between anchors following contraction of the wire, line, contracting member, etc. extending through the anchors. For some applications, the spacing between anchors (e.g, between sequential anchors) can be indicated by utilizing a wire, line, contracting member, etc. having radiopaque markers or materials attached thereto or coated thereon.

As used herein, the term "radiopaque" refers to a material that inhibits/prevents/blocks the passage of electromagnetic radiation therethrough, and therefore is detectable by an imaging device using an x-ray or other penetrating wave or particle technologies, such as neutron beams or gamma rays, fluoroscopy, MRI, infrared, near-infrared, laser, electromagnetic or radio waves technologies, and the like.

As used herein, the term "radiolucent" refers to materials that allow/enable the passage of electromagnetic radiation therethrough, and therefore are transparent, or at least partially transparent, to scanning devices using an x-ray or other penetrating wave or particle technologies as presented herein above.

The utilization of an implant comprising a wire, line, contracting member, etc. which extends between sequential anchors, wherein the wire, line, member, etc. comprises a combination of radiopaque and radiolucent materials which are detectable by imaging devices, enables estimation and/or determination of the distance and/or change in distance, between sequential anchors, prior to, during and following contraction of the wire, line, member, etc. extending thought the anchors, during annuloplasty procedure described hereinabove.

Figure 63:
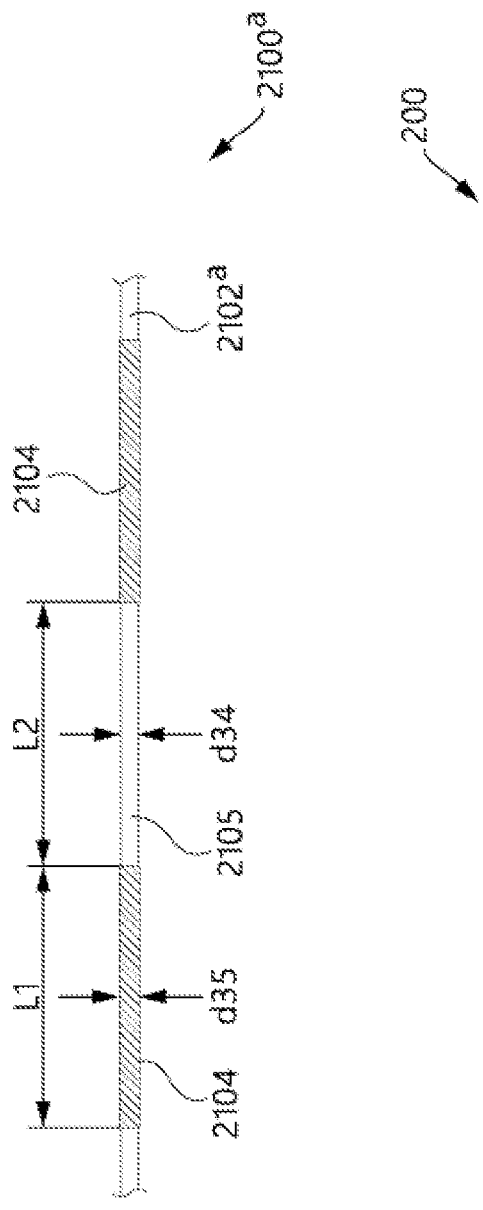
Figure 64:
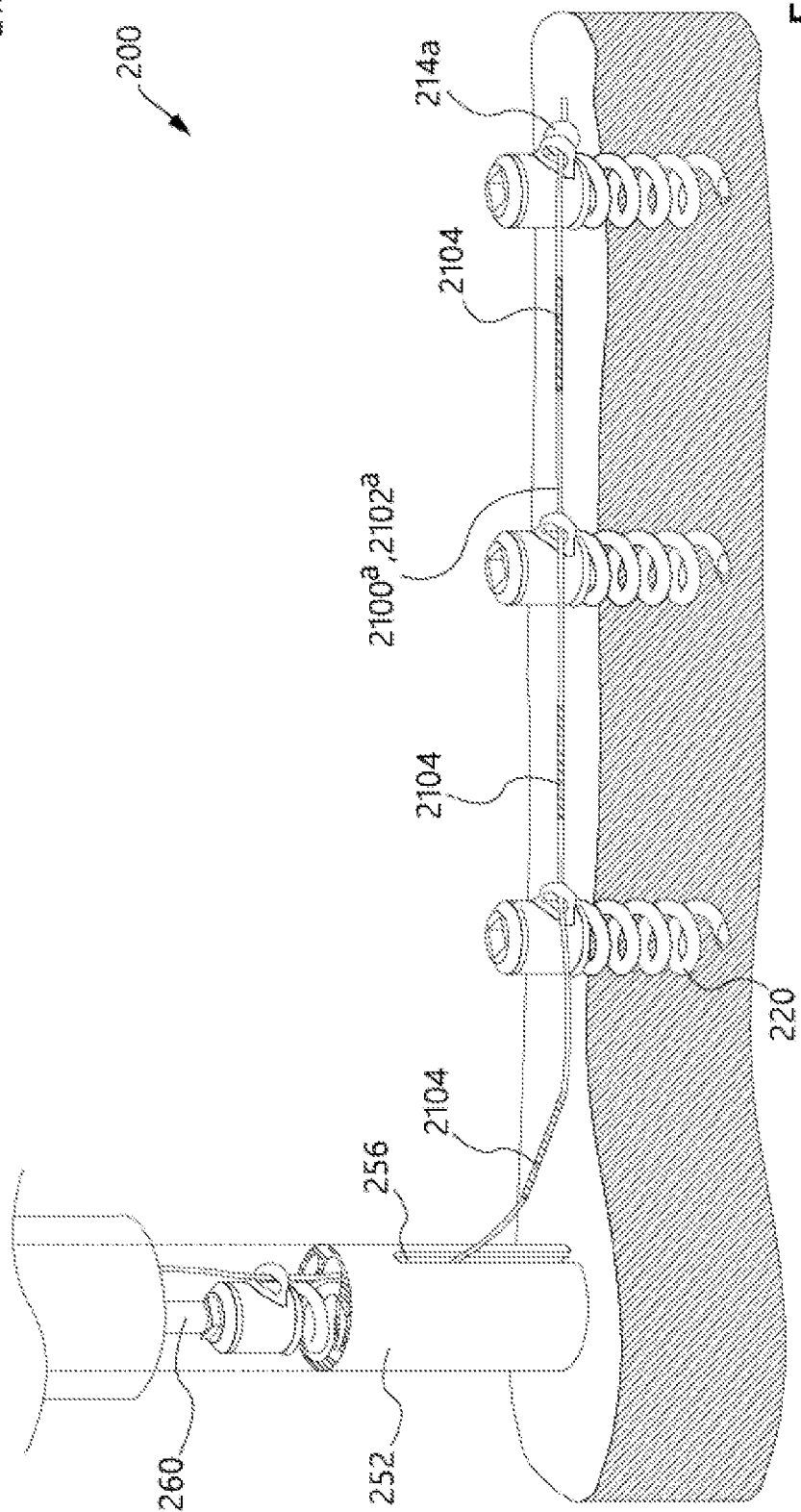
Figure 67A:
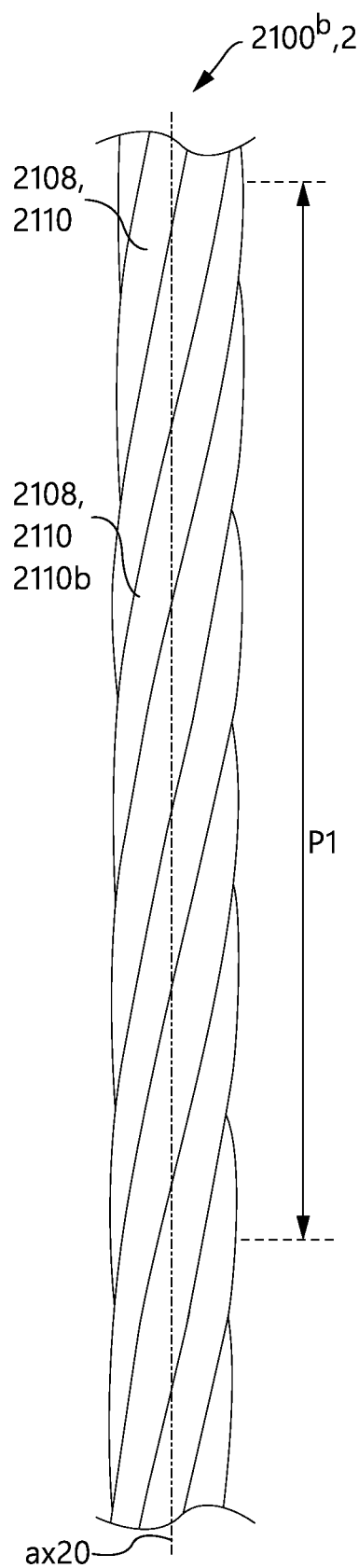
Figure 67B:
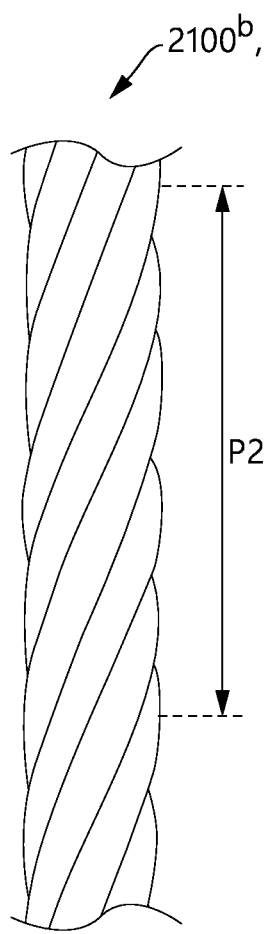
Figure 67C:
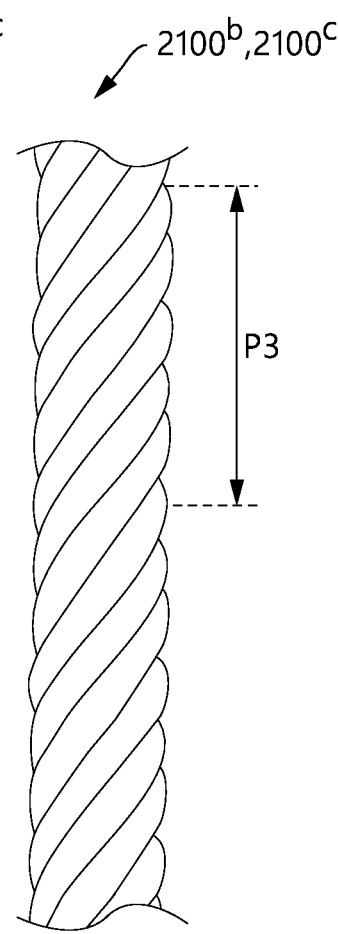
Figure 68A:
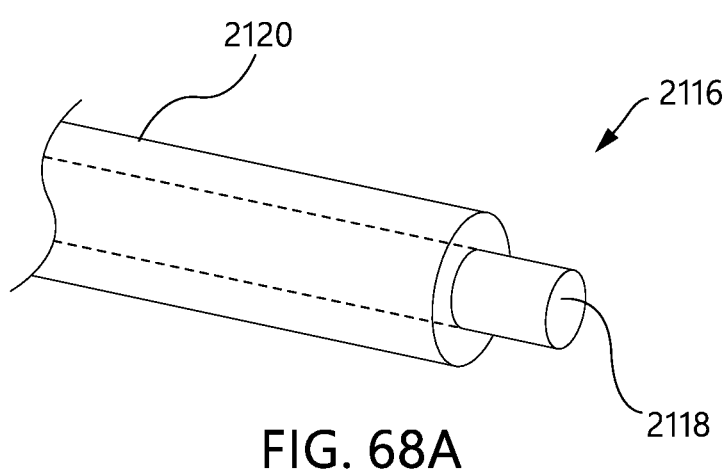
Figures 68B, 68C:
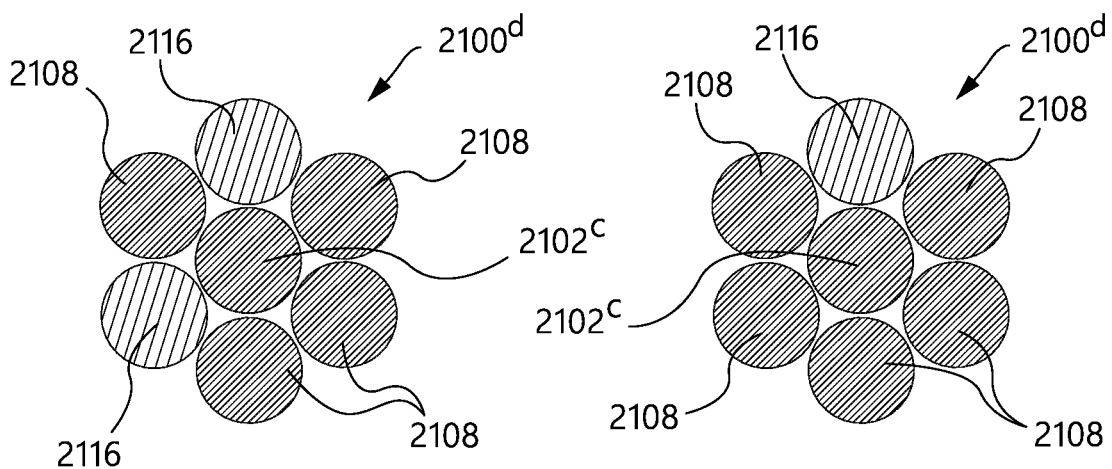
Figure 69A:
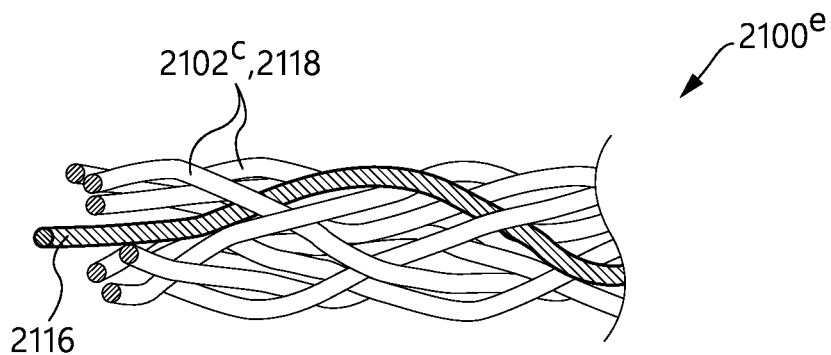
Figure 69B:
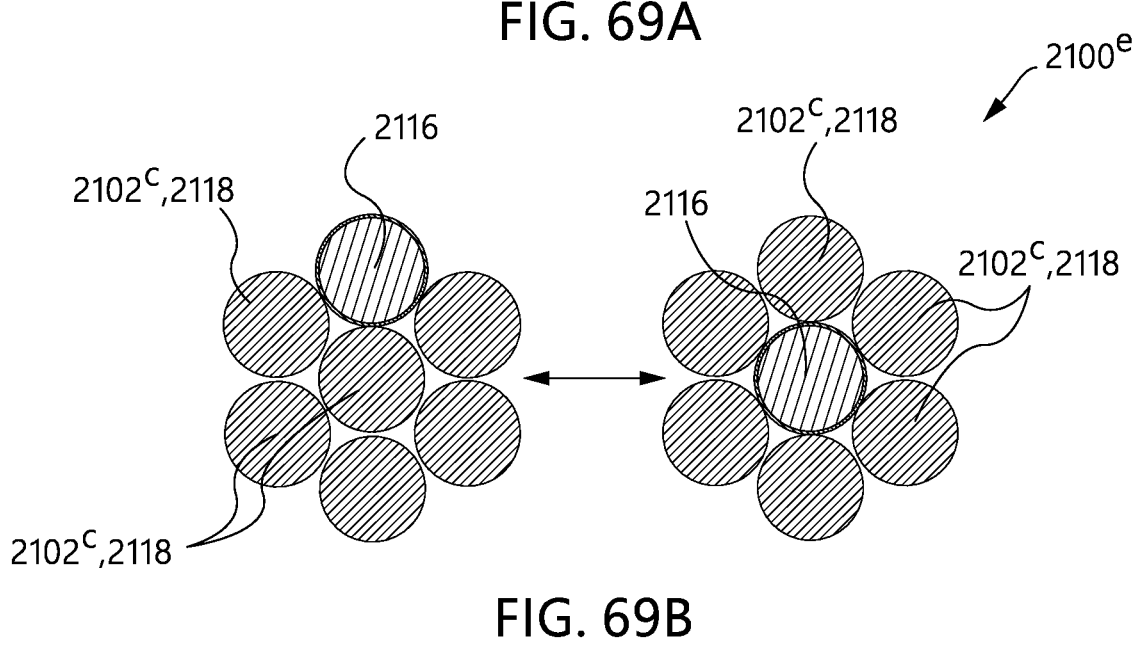

Reference is now made to FIGS. 63-69B. FIG. 63 is a view in perspective of an assembly 2100a, e.g, wire assembly, line assembly, contracting member assembly, etc, in accordance with some applications. FIG. 64 is a schematic illustration of an example of system 200 comprising the implant and wire, line, or contracting member assembly 2100a, in accordance with some applications. FIGS. 65A-65C are cross-sectional views of examples of an assembly 2100b, in accordance with some applications. FIG. 66A is a cross-sectional view of an example of assembly 2100b, in accordance with some applications. FIG. 66B is a schematic illustration of a cross-sectional view of an example of a wire, line, contracting member assembly 2100c, in accordance with some applications. FIGS. 67A-67C are views in perspective of examples of assemblies 2100b and/or 2100c, in accordance with some applications. FIG. 68A is a view in perspective of a composite tube 2116, in accordance with some applications. FIGS. 68B-68C are cross-sectional views of examples of an assembly 2100d, in accordance with some applications. FIG. 69A is a view in perspective of an example of an assembly 2100e, in accordance with some applications. FIG. 69B is a schematic illustration of cross-sectional views of an example assembly 2100e, in accordance with some applications.

It is to be understood that any of the wire, line, contracting member assemblies 2100a, 2100b, 2100c, 2100d, and/or 2100e, can be utilized instead of, or implemented as specific embodiments of, any wire, line, contracting member, etc. disclosed hereinabove, such as wire 112, wire 212, wire 512 and/or wire 562, mutatis mutandis. In other words, the wires, lines, contracting members, etc. described above can be implemented as and/or include the features of any of assemblies 2100a, 2100b, 2100c, 2100d, and/or 2100e. Furthermore, it is to be understood that any of the assemblies 2100a, 2100b, 2100c, 2100d, and/or 2100e, can be utilized in combination with any of the implants described hereinabove, such as implant 110, implant 210, implant 510, implant 610, implant 710, implant 760, and/or implant 810. Stated otherwise, any of the assemblies 2100a, 2100b, 2100c, 2100d, and/or 2100e, can extend through openings formed in any head of a tissue anchor disclosed herein, wherein an opening of the head can be either an eyelet, such as eyelets 140, 240, 546, and/or 640, a channel, such as channels 740 and/or 880, or an opening of a ring, such as ring 790.

For some applications, a wire, line, contracting member assembly 2100a comprises a main wire 2102a, wherein at least a portion of main wire 2102a is coated by a radiopaque coating 2104. For some applications, wire assembly 2100a is configured to extend thought various eyelets of the various anchors as presented herein above, such as for example, wire assembly 2100a is configured to extend through eyelet 240 of anchors 220 as illustrated at FIG. 5A. It is to be understood that wire assembly 2100a can extend thought or be connected to other types of anchors disclosed hereinabove, such as anchor 120, anchor 410, anchor 520, anchor 620, anchor 720, anchor 770, and anchor 820.

For some applications, wire assembly 2100a comprises main wire 2102a having a plurality of alternating portions coated by radiopaque coating 2104 and a plurality of alternating portions which are not coated by radiopaque coating 2104, as illustrated at FIGS. 63-64. For some applications, wire assembly 2100a comprises wire 2102a having a plurality of alternating portions coated by radiopaque coating 2104 and a plurality of alternating portions which are radiolucent portions 2105, wherein the radiolucent portions 2105 are segments of wire 2102a which are not coated by radiopaque coating 2104.

For some applications, wire assembly 2100a is configured to extend thought various eyelets or channels of the various anchors as described hereinabove, in order to facilitate contraction of the implant and perform annuloplasty. It is contemplated that during the deployment of the anchors during implantation and/or during contraction of the implant, the wire extending thought the eyelets and/or channels of the anchors can graze or grind against the eyelet or channels, thereby forming friction therebetween. Such friction can cause wear or damage to any coating which may cover the wire. Advantageously, the plurality of alternating portions of relatively thin radiopaque coating 2104 covering wire 2102a of wire assembly 2100a, as will be further elaborated hereinbelow, may reduce the risk of grinding or wearing the radiopaque coating 2104 against the eyelets of the anchors during implantation and/or contraction procedures.

For some applications, wire 2102a is formed of at least one material, selected from a metal material, synthetic polymers, natural fibers, and combinations thereof. For some applications, the wire 2102a is formed of a metal material, selected from titanium, nitinol, platinum, stainless steel, and alloys and combinations thereof. Each possibility represents a different embodiment. For some applications, the wire 2102a is made of stainless steel.

For some applications, wire 2102a is alternately coated by radiopaque coating 2104 utilizing coating technologies such as electroplating, sputtering, or evaporation. Each possibility represents a different embodiment.

For some applications, radiopaque coating 2104 comprises at least one biocompatible metal material, selected from: gold, platinum, titanium, silver, tantalum, barium, bismuth, iridium, tungsten, rhenium, osmium, iridium, palladium, and biocompatible oxides and combinations thereof. Each possibility is a separate embodiment.

For some applications, radiopaque coating 2104 comprises gold. For some applications, radiopaque coating 2104 comprises gold having a purity of at least 99%. The radiopaque coating 2104 may be coated with a biocompatible material, such as for example, a resin. Advantageously, utilizing biocompatible metal materials, such as gold, for the radiopaque coating 2104, enables enhanced attachment between a metallic wire 2102a and the radiopaque coating 2104. This may be advantageous over synthetic polymeric materials that may not form adequate attachment to a metallic wire 2102a.

For some applications, the diameter d34 of the uncoated portions of wire 2102a, as illustrated at FIG. 60, is in the range of 0.05 to 1 mm. For example, the diameter d34 of wire 2102a is in the range of 0.1 to 0.8 mm, such as in the range of 0.15 to 0.5 mm, such as in the range of 0.2 to 0.4 mm. For some applications, the diameter d34 of wire 2102a is about 0.3 mm.

For some applications, the diameter d35 of the portions of wire 2102a coated by radiopaque coating 2104 is in the range of 0.1 to 1.1 mm. For example, the diameter d35 is in the range of 0.15 to 0.85 mm, such as in the range of 0.2 to 0.55 mm, such as in the range of 0.35 to 0.65 mm, such as in the range of 0.5 to 0.7 mm, such as in the range of 0.25 to 0.45 mm. For some applications, the diameter d35 is about 0.35 mm. Advantageously, the dimensions of diameter d35 enable wire assembly 2100a to extend thought various eyelets of the various anchors as presented hereinabove.

For some applications, the length L1 of each alternating portion coated by radiopaque coating 2104 of wire 2102a is in the range of 0.01 to 20 mm. For example, the length L1 is in the range of 1 to 10 mm, such as in the range of 3.5 to 4.5 mm.

For some applications, the length L2 of each alternating radiolucent portion 2105 of wire 2102a is in the range of 0.1 to 20 mm. For example, the length L2 is in the range of 1 to 10 mm, such as in the range of 3.5 to 4.5 mm.

Reference is not made to FIGS. 65A-65C. For some applications, there is provided a wire assembly 2100b comprising a main wire 2102b, wherein at least one portion of main wire 2102b is coated by a radiopaque coating 2106, and at least two additional wires 2108, wherein the and at least two additional wires 2108 are woven around main wire 2102b. For some applications, wire assembly 2100b is configured to extend thought various eyelets of various anchors, in a similar to that described for assembly 2100a. For some applications, a plurality of additional wires 2108 are woven or interlaced radially in an in-and-out fashion around wire 2102b in order to form the wire assembly 2100b.

As used herein, the terms "woven", "interweave" and "interlace" are interchangeable, and refer to interlacing/intermixing or braiding or winding a plurality of distinct wires in order to form a single complex pattern. The act of weaving can be performed utilizing various weaving or braiding techniques or patterns known in the art.

For some applications, wire assembly 2100b comprises main wire 2102b having a plurality of alternating portions coated by radiopaque coating 2106 and a plurality of alternating portions which are radiolucent portions, similar to wire assembly 2100a. For some applications, radiopaque coating 2106 is identical to radiopaque coating 2104.

For some applications, each one of the at least two additional wires 2108 is identical to wire 2102b. For some applications, each one of the at least two additional wires 2108 is not coated by radiopaque coating 2106. For some applications, each one of the at least two additional wires 2108 is radiolucent.

For some applications, the wire 2102b and/or each additional wire 2108 is formed of a metal material, selected from titanium, nitinol, platinum, stainless steel, and alloys and combinations thereof. Each possibility represents a different embodiment. For some applications, the wire 2102b is made of stainless steel.

For some applications, the diameter d36 of wire 2102b without coating and/or each additional wire 2108 is in the range of 0.01 to 0.8 mm. For example, the diameter d36 is in the range of 0.05 to 0.3 mm, such as in the range of 0.05 to 0.15 mm. For some applications, the diameter d36 is about 0.1 mm.

For some applications, the diameter d37 of wire 2102b coated by radiopaque coating 2106 is in the range of 0.01 to 1 mm. For example, the diameter d15 is in the range of 0.05 to 0.6 mm, such as in the range of 0.1 to 0.3 mm. For some applications, the diameter d14 is about 0.15 mm. For some applications, the diameter of wire assembly 2100b is identical to the diameter d35 of the portions of wire 2102a coated by radiopaque coating 2104.

For some applications, wire assembly 2100b comprises wire 2102b coated by radiopaque coating 2106 along at least one portion thereof, and a plurality of additional wires 2108, wherein the plurality of additional wires 2108 are woven around wire 2102b. For some applications, wire assembly 2100b comprises wire 2102b coated by radiopaque coating 2106 along at least one portion thereof, and at least four additional wires 2108, wherein the at least four additional wires 2108 are woven around wire 2102b, as illustrated at FIG. 65C. For some applications, wire assembly 2100b comprises wire 2102b coated by radiopaque coating 2106 along at least one portion thereof, and at least five additional wires 2108, wherein the at least five additional wires 2108 are woven around wire 2102b, as illustrated at FIG. 65B. For some applications, wire assembly 2100b comprises wire 2102b coated by radiopaque coating 2106 along at least one portion thereof, and at least six additional wires 2108, wherein the at least six additional wires 2108 are woven around wire 2102b, as illustrated at FIG. 65A.

Advantageously, the plurality of additional wires 2108 woven around wire 2102b of wire assembly 2100b may reduce the risk of grinding or wearing the radiopaque coating 2106 against the eyelets of various anchors during implantation and/or contraction procedures, thereby enabling to safely mark and identify the distance between sequential anchors during implantation, in order to measure the distance change therebetween following contraction of the wire assembly 2100b extending therethrough, utilizing x-ray or other penetrating wave or particle technologies.

Reference is now made to FIGS. 66A-66B. For some applications, each one of the plurality of additional wires 2108 comprise an inner wire assembly 2110, wherein each inner wire assembly 2110 comprise a plurality of inner wires 2112. For some applications, wire assembly 2100b comprises wire 2102b coated by radiopaque coating 2106 along at least one portion thereof, and a plurality of inner wire assemblies 2110, wherein each inner wire assembly 2110 comprises a plurality of inner wires 2112. For some applications, the plurality of inner wire assemblies 2110 are woven around wire 2102b. For some applications, each plurality of inner wires 2112 of each inner wire assembly 2110 is woven around itself in order to form a woven inner wire assembly 2110, wherein a plurality of woven inner wire assemblies 2110 is woven around wire 2102b.

For some applications, wire assembly 2100b comprises wire 2102b coated by radiopaque coating 2106 along at least one portion thereof, and at least four inner wire assemblies 2110 are woven around the wire 2102b (not shown). For some applications, wire assembly 2100b comprises wire 2102b coated by radiopaque coating 2106 along at least one portion thereof, and at least five inner wire assemblies 2110 are woven around the wire 2102b (not shown). For some applications, wire assembly 2100b comprises wire 2102b coated by radiopaque coating 2106 along at least one portion thereof, and at least six inner wire assemblies 2110 are woven around the wire 2102b, as illustrated at FIG. 66A. For some applications, each plurality of inner wires 2112 comprise at least five inner wires 2112 (not shown). For some applications, each plurality of inner wires 2112 comprise at least six inner wires 2112 (not shown). For some applications, each plurality of inner wires 2112 comprise at least seven inner wires 2112, as illustrated at FIG. 66A.

For some applications, wire assembly 2100b comprises wire 2102b coated by radiopaque coating 2106 along at least one portion thereof, and at least six inner wire assemblies 2110, wherein each inner wire assembly 2110 comprises at least seven inner wires 2112, as illustrated at FIG. 66A, wherein the at least six inner wire assemblies 2110 are woven around wire 2102b.

For some applications, each inner wire assembly 2110 is radiolucent. For some applications, each one of the inner wires 2112 is radiolucent. For some applications, each one of the inner wires 2112 is formed of a metal material, selected from titanium, nitinol, stainless steel, and combinations thereof. Each possibility represents a different embodiment. For some applications, each one of the inner wires 2112 is made of stainless steel.

For some applications, the diameter d38 of each one of the inner wires 2112 is in the range of about 0.001 to about 0.1 mm. For example, the diameter d16 is in the range of 0.01 to 0.08 mm, such as in the range of 0.02 to 0.04 mm. For some applications, the diameter d16 is about 0.03 mm. For some applications, the diameter of each inner wire assembly 2110 is identical to the diameter of each one of the plurality of additional wires 2108.

Reference is now made to FIG. 66B. For some applications, there is provided a wire assembly 2100c comprising a central inner wire assembly 2110a comprising a plurality of central inner wires 2112a, wherein at least one portion of the central inner wire assembly 2110a is coated by radiopaque coating 2106 along the outer diameter thereof; and a plurality of a peripheral inner wire assemblies 2110b, wherein each one of the peripheral inner wire assemblies 2110b comprises a plurality of peripheral inner wires 2112b. For some applications, wire assembly 2100c is configured to extend thought various eyelets of various anchors, in a similar manner to that described for wire assembly 2100a and/or wire assembly 2100b.

For some applications, wire assembly 2100c comprises a central inner wire assembly 2110a comprising at least seven central inner wires 2112a, wherein at least one portion of the central inner wire assembly 2110a is coated by radiopaque coating 2106 along the outer diameter thereof, and at least six peripheral inner wire assemblies 2110b, wherein each one of the peripheral inner wire assemblies 2110b comprises at least seven peripheral inner wires 2112b, as illustrated at FIG. 66B.

For some applications, each one of the plurality of central inner wires 2112a and/or each one of the plurality of peripheral inner wires 2112b is identical to each one of the inner wires 2112 as described hereinabove.

For some applications, central inner wire assembly 2110a is coated by radiopaque coating 2106 along the outer diameter thereof, as illustrated at FIG. 66B. For some applications, central inner wire assembly 2110a comprises a plurality of alternating portions coated by radiopaque coating 2106 along the outer diameter thereof, and a plurality of alternating portions which are radiolucent portions.

For some applications, each one of the plurality of central inner wires 2112a comprises a plurality of alternating portions coated by radiopaque coating 2106 along the diameter thereof, and a plurality of alternating portions which are radiolucent portions. For some applications, each one of the plurality of central inner wires 2112a is coated by radiopaque coating 2106 along its entire length.

For some applications, the diameter of each peripheral inner wire assembly 2110b is identical to the diameter of each inner wire assembly 2110 and/or to the diameter of each one of the plurality of additional wires 2108. For some applications, the diameter of wire assembly 2100c is identical to the diameter d35 of the portions of wire 2102a coated by radiopaque coating 2104.

Reference is now made to FIGS. 67A-67C. For some applications, a plurality of additional wires 2108 are woven or interlaced radially in an in-and-out fashion around wire 2102b in order to form the wire assembly 2100b. For some applications, a plurality of inner wire assemblies 2110 are woven or interlaced radially in an in-and-out fashion around wire 2102b in order to form the wire assembly 2100b. For some applications, a plurality of a peripheral inner wire assemblies 2110b are woven or interlaced radially in an in-and-out fashion around central inner wire assembly 2110a in order to form the wire assembly 2100c. The weaving patterns of wire assemblies 2100b and 2100c may vary according to the weaving techniques and/or weaving characteristics, such as the weaving pitch.

As used herein, the terms "weaving pitch" or "pitch" are interchangeable, and refer to the distance, along a longitudinal axis ax20 extending through a wire assembly (such as wire assemblies 2100b and/or 2100c), between repeating segments of the same interlaced additional wire or peripheral assembly along the same plane.

Each one of wire assemblies 2100b and 2100c may be characterized by various pitches (such as for example P1, P2, and P3) resulting in various interlacing densities, as illustrated at FIGS. 67A-67C, which can affect the resulting wire assembly characteristics.

Reference is now made to FIGS. 68A-68C. For some applications, there is provided a wire assembly 2100d comprising a main wire 2102c, at least one additional wire 2108, and at least one composite tube 2116, wherein the at least one additional wire 2108 and the at least one composite tube 2116 are woven around the main wire 2102c. For some applications, wire assembly 2100d is configured to extend thought various eyelets of various anchors, similar to wire assembly 2100a and/or wire assembly 2100b.

For some applications, the at least one composite tube 2116 comprises an inner core 2118 comprising at least one first material, and an outer sheath 2120 comprising at least one layer comprising at least one second material, wherein said inner core 2118 is disposed within a lumen of the outer sheath 2120. For some applications, the at least one composite tube 2116 is formed by inserting the inner core 2118 into the lumen of the outer sheath 2120, and inflicting extreme compressive forces in opposite directions thereto along a longitudinal axis, thereby forming a strong mechanical bond and attachment therebetween, resulting in the formation of a composite tube having enhanced physical and mechanical attributes. It is contemplated that the outer sheath 2120 is configured to provide strength, durability and biocompatibility to the composite tube 2116, while the inner core 2118 is configured to provide enhanced resiliency and radiopaque functionalities thereto.

For some applications, the first material is selected from: gold, platinum, titanium, silver, tantalum, palladium, nitinol, and combinations and alloys thereof. Each possibility is a separate embodiment. For some applications, the first material is radiopaque. For some applications, the first material comprise gold.

For some applications, the second material is selected from: titanium, stainless steel, gold, platinum, nitinol, and combinations and alloys thereof. Each possibility is a separate embodiment. For some applications, the second material comprises at least one metal alloy. For some applications, the second material is radiolucent. For some applications, the outer sheath 2120 comprises a plurality of layers, wherein each layer comprises the at least one second material.

It is to be understood that the second material is not identical to the first material, and that the first material is chosen to be more radiopaque than the second material. For some applications, the composite tube 2116 comprise at least one drawn filled tube (DFT®).

Advantageously, the structure of the at least one composite tube 2116 woven around the main wire 2102c of wire assembly 2100d may significantly reduce the risk of grinding or wearing the radiopaque materials against the eyelets of various anchors during implantation and/or contraction procedures, thereby enabling to safely mark and identify the distance between sequential anchors during implantation, in order to measure the distance or change in distance therebetween following contraction of the wire assembly 2100d extending therethrough, utilizing x-ray or other penetrating wave or particle technologies.

For some applications, the at least one composite tube 2116 has a diameter identical to the diameter d36 of wire 2102b without coating and/or each additional wire 2108.

For some applications, main wire 2102c is formed of a metal material, selected from titanium, nitinol, platinum, stainless steel, and alloys and combinations thereof. Each possibility represents a different embodiment. For some applications, the wire 2102c is made of stainless steel. For some applications, wire 2102c does not comprise a radiopaque coating or a radiopaque material. For some applications, wire 2102c is radiolucent. For some applications, wire 2102c is identical to additional wire 2108. For some applications, the diameter of wire 2102c is identical to the diameter d36 of wire 2102b without coating and/or to the diameter of each additional wire 2108 as presented herein above.

For some applications, wire assembly 2100d comprises the main wire 2102c, a plurality of additional wires 2108, and at least one composite tube 2116, wherein the plurality of additional wires 2108 and the at least one composite tube 2116 are woven around the main wire 2102c. For some applications, wire assembly 2100d comprises: the wire 2102c, a plurality of additional wires 2108, and a plurality of composite tubes 2116, wherein the plurality of additional wires 2108 and the plurality of composite tubes 2116 are woven around wire 2102c. For some applications, the plurality of additional wires 2108 and the plurality of composite tubes 2116 are woven or interlaced radially in an in-and-out fashion around wire 2102c in order to form the wire assembly 2100d.

For some applications, wire assembly 2100d comprises a wire 2102c, at least five additional wires 2108, and at least one composite tube 2116, wherein the at least five additional wires 2108 and the at least one composite tube 2116 are woven around wire 2102c, as illustrated at FIG. 68C. For some applications, wire assembly 2100d comprises a wire 2102c, at least four additional wires 2108, and at least two composite tubes 2116, wherein the at least four additional wires 2108 and the at least two composite tubes 2116 are woven around wire 2102c, as illustrated at FIG. 68B.

For some applications, the diameter of wire assembly 2100d is identical to the diameter d35 of the portions of wire 2102a coated by radiopaque coating 2104.

For some applications, the interlaced/woven structure of wire assembly 2100d, comprising the plurality of radiolucent additional wires 2108 and at least one composite tube 2116 comprising radiopaque inner core 2118, woven around radiolucent wire 2102c, enables to form an interlaced structure of repeating segments having radiopaque functionalities extending along the entire diameter of the wire assembly 2100d. Advantageously, the interlaced structure of repeating segments having radiopaque functionalities of wire assembly 2100d may enhance detection by scanning devices, since such a structure has a larger radiopaque cross-section in comparison to a wire assembly having radiopaque functionalities extending along a narrow main wire (such as, for example, wire assembly 2100b).

For some applications, wire assembly 2100d is characterized by various pitches (such as, for example, P1, P2, and P3 of FIGS. 67A-67C) resulting in various interlacing densities, which can affect the resulting wire assembly characteristics.

Reference is now made to FIGS. 69A-69B. For some applications, there is provided a wire assembly 2100e comprising a plurality of main wires 2102c (or additional wires 2108) and at least one composite tube 2116, wherein the plurality of main wires 2102c (or additional wires 2108) and the at least one composite tube 2116 are woven or interlaced around each other. For some applications, the main wires 2102c and the composite tube 2116 are randomly woven or interlaced around each other, thereby forming a random interlaced structure.

For some applications, wire assembly 2100e comprises at least six main wires 2102c and at least one composite tube 2116, wherein the at least six main wires 2102c and at least one composite tube 2116 are woven or interlaced around each other, as illustrated at FIG. 69B. For some applications, wire assembly 2100e comprises at least five main wires 2102c and at least two composite tubes 2116, wherein the at least five main wires 2102c and at least two composite tubes 2116 are woven or interlaced around each other (not shown).

For some applications, the plurality of main wires 2102c and the at least one composite tube 2116 are woven or interlaced around each other so that the composite tube 2116 is alternately positioned in the center of the wire assembly 2100e (as illustrated at FIG. 69B, right illustration), and alternately positioned in a peripheral position adjacent to one of the plurality of main wires 2102c which is positioned in the center of the wire assembly 2100e (as illustrated at FIG. 69B, left illustration). FIG. 69B schematically shows two cross-sections taken at different positions along the length of the same wire assembly 2100e.

For some applications, the interlaced/woven structure of wire assembly 2100e, comprising the plurality of radiolucent main wires 2102c and at least one composite tube 2116 comprising radiopaque inner core 2118, woven around each other, enables to form an interlaced structure of repeating segments having radiopaque functionalities extending alone the entire diameter of the wire assembly 2100d and along the center thereof. Advantageously, the interlaced structure of repeating segments having radiopaque functionalities of wire assembly 2100d may enhance detection by scanning devices, since such a structure has a bigger radiopaque cross-section than compared to a wire assembly having radiopaque functionalities extending along a narrow central wire (such as, for example, wire assembly 2100b).

For some applications, wire assembly 2100e comprises main wire 2102c, a plurality of additional wires 2108, and at least one composite tube 2116, wherein the plurality of additional wires 2108, the at least one composite tube 2116, and main wire 2102c, are woven or interlaced around each other, wherein the main wire 2102c is identical to each one of the plurality of additional wires 2108, as illustrated at FIG. 69B. For some applications, the wire assembly 2100e comprises main wire 2102c, at least five additional wires 2108, and at least one composite tube 2116. For some applications, the wire assembly 2100e comprises main wire 2102c, at least four additional wires 2108, and at least two composite tubes 2116.

For some applications, apparatus, systems, and/or techniques described herein can be used in combination with apparatus, systems, and/or techniques described in one or more of the following references, mutatis mutandis, each of which is incorporated herein by reference in its entirety for all purposes:

- U.S. patent application Ser. No. 14/437,373 to Sheps et al, which published as US 2015/0272734 (now U.S. Pat. No. 9,949,828)
- U.S. patent application Ser. No. 15/782,687 to Iflah et al, which published as US 2018/0049875
- PCT Patent Application PCT/IL2019/050777 to Brauon et al, which published as WO/2020/012481
- U.S. Provisional Patent Application 62/811,693 to Brauon et al.

The present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, the techniques, methods, operations, steps, etc. described or suggested herein can be performed on a living animal or on a non-living simulation, such as on a cadaver, cadaver heart, simulator (e.g. with the body parts, tissue, etc. being simulated), etc.

Although the operations of some of the disclosed embodiments are described in a particular, sequential order for convenient presentation, it should be understood that this manner of description encompasses rearrangement, unless a particular ordering is required by specific language set forth above. For example, operations or steps described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are discernible by one of ordinary skill in the art.

The invention claimed is:

1. An apparatus comprising a tissue anchor for use with an anchor driver, the anchor comprising:
   a tissue-engaging element defining a central longitudinal axis of the anchor, having a sharpened distal tip, and configured to be driven into tissue of a subject; and
   a head, coupled to a proximal end of the tissue-engaging element, the head comprising:
      a driver interface, configured to be reversibly engaged by the anchor driver, and an eyelet:
         defining an aperture on an aperture plane, the aperture having a length along a long axis of the aperture and a width along a short axis of the aperture, the long axis and the short axis disposed on the aperture plane, and the length being greater than the width,
         disposed laterally from the central longitudinal axis,
         mounted such that the aperture plane is slanted at a fixed angle with respect to the central longitudinal axis, and
         mounted to be revolvable around the central longitudinal axis while the aperture plane remains slanted at the fixed angle with respect to the central longitudinal axis.

2. The apparatus according to claim 1, wherein:
   the apparatus comprises an implant that comprises the anchor, and a wire threaded through the aperture,
   the eyelet defines the aperture such that the eyelet has a first slide-axis that is parallel with the central longitudinal axis, and a second slide-axis that is orthogonal to the first slide-axis, and
   the eyelet is shaped to facilitate smooth sliding of the eyelet (i) over the wire along the first slide-axis while the wire is aligned with the first slide-axis, and (ii) over the wire along the second slide-axis while the wire is aligned with the second slide-axis.

3. The apparatus according to claim 2, wherein the eyelet has an external shape that defines a tapered portion that tapers away from the aperture along the second slide-axis.

4. The apparatus according to claim 3, wherein:
   the implant further comprises a spacer that:
      is tubular,
      has a first spacer-end, a second spacer-end, and a mid-portion therebetween, and
      defines a spacer-lumen between the first spacer-end and the second spacer-end,
   the wire is threaded through the spacer-lumen, and
   the spacer-lumen widens from the mid-portion toward the first spacer-end, thereby being shaped to snugly receive the tapered portion of the eyelet.

5. The apparatus according to claim 4, wherein the spacer is elastically flexible in deflection.

6. The apparatus according to claim 4, wherein the spacer is not compressible axially.

7. The apparatus according to claim 4, wherein the spacer is defined by a helical wire shaped as a closed coil that defines the spacer-lumen.

8. The apparatus according to claim 4, wherein:
   the anchor is a first anchor of the implant,
   the implant further comprises a second anchor that comprises an eyelet that defines an aperture and has an external shape that defines a tapered portion,
   the wire is threaded through the aperture of the eyelet of the second anchor such that the spacer is disposed, on the wire, between the tapered portion of the eyelet of the first anchor and the tapered portion of the eyelet of the second anchor, with the first spacer-end facing the first anchor, and the second spacer-end facing the second anchor.

9. The apparatus according to claim 8, wherein the spacer-lumen widens from the mid-portion toward the second spacer-end, thereby being shaped to snugly receive the tapered portion of the eyelet of the second anchor.

10. The apparatus according to claim 8, wherein the spacer is configured to limit a proximity between the first anchor and the second anchor.

11. The apparatus according to claim 1, wherein the eyelet is shaped and oriented such that both (i) when viewed along a first view-line that is parallel with the central longitudinal axis, and (ii) when viewed along a second view-line that is orthogonal to the first view-line, the aperture appears circular.

12. The apparatus according to claim 1, wherein the aperture is shaped as a stadium.

13. The apparatus according to claim 1, wherein the eyelet is mounted such that the aperture plane is slanted at 30-60 degrees with respect to the central longitudinal axis.

14. The apparatus according to claim 1, wherein the head comprises a ring that circumscribes the central longitudinal axis, and is rotatably coupled to the tissue-engaging element, and wherein the eyelet is mounted on the ring, and is revolvable around the central longitudinal axis by rotation of the ring about the central longitudinal axis.

15. The apparatus according to claim 1, further comprising the anchor driver.

16. The apparatus according to claim 15, wherein:
the apparatus comprises a delivery tool that comprises the anchor driver and a percutaneously-advanceable tube, and
while the anchor driver is engaged with the anchor, the anchor driver and the anchor are slidable through the tube.

17. The apparatus according to claim 16, wherein:
the tube defines an internal channel that has a keyhole-shaped orthogonal cross-section that defines a major channel region and a minor channel region,
the major channel region has a larger cross-sectional area than does the minor channel region, and
the anchor is slidable through the channel with the tissue-engaging element sliding snugly through the major channel region, and the eyelet sliding snugly through the minor channel region.

18. The apparatus according to claim 17, wherein:
the apparatus comprises an implant that comprises a wire and the tissue anchor,
the eyelet is shaped to facilitate smooth sliding of the eyelet simultaneously (i) snugly though the minor channel region, and (ii) over the wire, while the wire is disposed within the minor channel region and is parallel with the central longitudinal axis.

19. The apparatus according to claim 18, wherein the eyelet is shaped to facilitate smooth sliding of the eyelet over the wire while the wire is oriented orthogonal to the central longitudinal axis.

20. The apparatus according to claim 18, wherein:
the anchor is advanceable out of a distal end of the tube,
the tube defines a lateral slit extending proximally from the distal end of the tube,
the lateral slit is adjacent to the minor channel region, and
the lateral slit allows the wire, but not the anchor, to exit the tube laterally, proximally from the distal end of the tube.

21. The apparatus according to claim 1, wherein:
the apparatus comprises an implant comprising a wire and the tissue anchor, and
the eyelet is shaped to facilitate smooth sliding of the wire through the aperture both (i) while the wire is parallel with the central longitudinal axis, and (ii) while the wire is oriented orthogonal to the central longitudinal axis.

22. An apparatus comprising an implant that comprises:
a tissue anchor for use with an anchor driver, the anchor comprising:
a tissue-engaging element defining a central longitudinal axis of the anchor, having a sharpened distal tip, and configured to be driven into tissue of a subject; and
a head, coupled to a proximal end of the tissue-engaging element, the head comprising:
a driver interface, configured to be reversibly engaged by the anchor driver, and an eyelet:
defining an aperture on an aperture plane, the aperture having a length along a long axis of the aperture and a width along a short axis of the aperture, the long axis and the short axis disposed on the aperture plane, the length being greater than the width, the wire threaded through the aperture,
disposed laterally from the central longitudinal axis,
mounted such that the aperture plane is slanted at a fixed angle with respect to the central longitudinal axis,
defining the aperture such that the eyelet has a first slide-axis that is parallel with the central longitudinal axis, and a second slide-axis that is orthogonal to the first slide-axis,
shaped to facilitate smooth sliding of the eyelet (i) over the wire along the first slide-axis while the wire is aligned with the first slide-axis, and (ii) over the wire along the second slide-axis while the wire is aligned with the second slide-axis, and
having an external shape that defines a tapered portion that tapers away from the aperture along the second slide-axis, and
a tubular spacer that has a first spacer-end, a second spacer-end, and a mid-portion therebetween, the spacer defining a spacer-lumen between the first spacer-end and the second spacer-end, and widening from the mid-portion toward the first spacer-end, thereby being shaped to snugly receive the tapered portion of the eyelet, and a wire, threaded through the spacer-lumen.

23. The apparatus according to claim 22, wherein the spacer is elastically flexible in deflection.

24. The apparatus according to claim 22, wherein the spacer is not compressible axially.

25. The apparatus according to claim 22, wherein the spacer is defined by a helical wire shaped as a closed coil that defines the spacer-lumen.

26. The apparatus according to claim 22, wherein:
the anchor is a first anchor of the implant,
the implant further comprises a second anchor that comprises an eyelet that defines an aperture and has an external shape that defines a tapered portion,
the wire is threaded through the aperture of the eyelet of the second anchor such that the spacer is disposed, on the wire, between the tapered portion of the eyelet of the first anchor and the tapered portion of the eyelet of the second anchor, with the first spacer-end facing the first anchor, and the second spacer-end facing the second anchor.

27. The apparatus according to claim 26, wherein the spacer-lumen widens from the mid-portion toward the second spacer-end, thereby being shaped to snugly receive the tapered portion of the eyelet of the second anchor.

28. The apparatus according to claim 26, wherein the spacer is configured to limit a proximity between the first anchor and the second anchor.

29. An apparatus, comprising:
a delivery tool that comprises:
an anchor driver, and
a percutaneously-advanceable tube that defines an internal channel that has a keyhole-shaped orthogonal cross-section that defines a major channel region and a minor channel region, the major channel region having a larger cross-sectional area than the minor channel region, and
a tissue anchor for use with the anchor driver, the anchor comprising:

a tissue-engaging element defining a central longitudinal axis of the anchor, having a sharpened distal tip, and configured to be driven into tissue of a subject; and a head, coupled to a proximal end of the tissue-engaging element, the head comprising:

a driver interface, configured to be reversibly engaged by the anchor driver, and an eyelet:
- defining an aperture on an aperture plane, the aperture having a length along a long axis of the aperture and a width along a short axis of the aperture, the long axis and the short axis disposed on the aperture plane, and the length being greater than the width,
- disposed laterally from the central longitudinal axis, and
- mounted such that the aperture plane is slanted at a fixed angle with respect to the central longitudinal axis, wherein:
while the anchor driver is engaged with the anchor, the anchor driver and the anchor are slidable through the tube, and the anchor is slidable through the channel with the tissue-engaging element sliding snugly through the major channel region, and the eyelet sliding snugly through the minor channel region.

30. The apparatus according to claim 29, wherein:
the apparatus comprises an implant that comprises a wire and the tissue anchor,
the eyelet is shaped to facilitate smooth sliding of the eyelet simultaneously (i) snugly though the minor channel region, and (ii) over the wire, while the wire is disposed within the minor channel region and is parallel with the central longitudinal axis.

31. The apparatus according to claim 30, wherein the eyelet is shaped to facilitate smooth sliding of the eyelet over the wire while the wire is oriented orthogonal to the central longitudinal axis.

32. The apparatus according to claim 30, wherein:
the anchor is advanceable out of a distal end of the tube,
the tube defines a lateral slit extending proximally from the distal end of the tube,
the lateral slit is adjacent to the minor channel region, and
the lateral slit allows the wire, but not the anchor, to exit the tube laterally, proximally from the distal end of the tube.

* * * * *